United States Patent
Xin et al.

(10) Patent No.: US 10,961,583 B2
(45) Date of Patent: Mar. 30, 2021

(54) INHIBITION OF HSD17B13 IN THE TREATMENT OF LIVER DISEASE IN PATIENTS EXPRESSING THE PNPLA3 I148M VARIATION

(71) Applicant: Regeneron Pharmaceuticals, Inc., Tarrytown, NY (US)

(72) Inventors: Yurong Xin, Tarrytown, NY (US); Jesper Gromada, Tarrytown, NY (US); Xiping Cheng, Tarrytown, NY (US); Frederick Dewey, Tarrytown, NY (US); Tanya Teslovich Dostal, Tarrytown, NY (US); Claudia Schurmann, Tarrytown, NY (US); Aris Baras, Tarrytown, NY (US); Noura Abul-Husn, Tarrytown, NY (US)

(73) Assignee: Regeneron Phramaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/157,503

(22) Filed: Oct. 11, 2018

(65) Prior Publication Data

US 2019/0106749 A1    Apr. 11, 2019

Related U.S. Application Data

(60) Provisional application No. 62/570,985, filed on Oct. 11, 2017.

(51) Int. Cl.
C12Q 1/6883    (2018.01)

(52) U.S. Cl.
CPC ..... *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 10,577,630 B2 | 3/2020 | Zhang et al. | |
| 10,767,175 B2 | 9/2020 | Dellinger et al. | |
| 10,787,647 B2 | 9/2020 | Abul-Husn et al. | |
| 2003/0004102 A1 | 1/2003 | Ashkenazi | |
| 2007/0219169 A1 | 9/2007 | Becourt et al. | |
| 2010/0028879 A1 | 2/2010 | Labrie et al. | |
| 2010/0056384 A1* | 3/2010 | Hobbs | C12Q 1/6883 506/7 |
| 2018/0179553 A1 | 6/2018 | Watson et al. | |
| 2018/0185516 A1 | 7/2018 | Ansell et al. | |
| 2018/0216084 A1 | 8/2018 | Abul-Husn et al. | |
| 2018/0216104 A1 | 8/2018 | Abul-Husn et al. | |
| 2019/0002869 A1 | 1/2019 | Yin et al. | |
| 2019/0316121 A1 | 10/2019 | Smith et al. | |
| 2019/0365924 A1 | 12/2019 | Conway et al. | |
| 2019/0390195 A1 | 12/2019 | Tondera et al. | |
| 2020/0354693 A1 | 11/2020 | Abul-Husn et al. | |

FOREIGN PATENT DOCUMENTS

| | | |
|---|---|---|
| CN | 104698108 | 6/2015 |
| CN | 103520724 B | 5/2016 |
| EP | 3011032 | 10/2019 |
| EP | 3620524 | 3/2020 |
| EP | 3011031 | 9/2020 |
| WO | 1995029255 | 11/1995 |
| WO | 9720942 | 6/1997 |
| WO | 2004110459 | 12/2004 |
| WO | 2005108415 | 11/2005 |
| WO | 2010028110 | 3/2010 |
| WO | 2013177060 | 11/2013 |
| WO | 2013190075 | 12/2013 |
| WO | 2017048620 | 3/2017 |
| WO | 2018107026 | 6/2018 |
| WO | 2018107028 | 6/2018 |
| WO | 2018136702 | 7/2018 |
| WO | 2018136758 | 7/2018 |
| WO | 2018220211 | 12/2018 |
| WO | 2019183164 | 9/2019 |
| WO | 2019183329 | 9/2019 |
| WO | 2019237069 | 12/2019 |
| WO | 2019246203 | 12/2019 |

OTHER PUBLICATIONS

Zhang et al. (Protein Cell. Available online Oct. 18, 2016. 8(1): 4-13 (Year: 2016).*
Business Wire. "Arrowhead Pharmaceuticals Initiates Phase 1/2 Study of ARO-HSD in Normal Healthy Volunteers and Patients with NASH or Suspected NASH." Mar. 3, 2020, p. 1-2. Available via URL: <.businesswire.com/news/home/20200303005396/en/Arrowhead-Pharmaceuticals-Initiates-Phase-12-Study-ARO-HSD>(Year: 2020).*
Official Action dated Jun. 12, 2019 issued in related U.S. Appl. No. 15/875,192.
RefSNP cluster report rs72613567 (printed Jun. 6, 2019 from ncbi.nlm.nih.gov).
GenBank accession DR004209 (submitted Jan. 2011, printed Jun. 10, 2019, from ncbi.nlm.nih.gov).

(Continued)

*Primary Examiner* — Carla J Myers
(74) *Attorney, Agent, or Firm* — Stradley Ronon Stevens & Young, LLP

(57) ABSTRACT

The disclosure provides methods of identifying a human subject as a candidate for treating or inhibiting a liver disease by inhibiting HSD17B13. The disclosure also provides methods of treating a subject who is PNPLA3 Ile148Met+ by administering an inhibitor of HSD17B13. The disclosure also provides method of detecting a PNPLA3 Ile148Met variant and functional HSD17B13 in a subject. The disclosure also provides method of identifying a subject having a protective effect against liver disease. The disclosure also provides inhibitors of HSD17B13 for use in the treatment of a liver disease.

29 Claims, 48 Drawing Sheets

Specification includes a Sequence Listing.

(56) References Cited

OTHER PUBLICATIONS

Ghanbari, et al., "Genetic Variations in MicroRNA-Binding Sites Affect MicroRNA-Mediated Regulation of Several Genes Associated With Cardio-metabolic Phenotypes," Circ. Cardiovasc. Genet., 2015, 8(3), pp. 473-486.

Gieger, et al., "New gene functions in megakaryopoiesis and platelet formation," Nature,2012, 480(7376), pp. 201-208 plus Supplementary Information.

Haapaniemi et al., "CRISPR-Cas9 genome editing induces a p53-mediated DNA damage response," Nat. Med. doi: 10.1038/s41591-018-0049-z, (Jun. 11, 2018, epub ahead of print).

Ihry et al., "p53 inhibits CRISPR-Cas9 engineering in human pluripotent stem cells," Nat. Med. doi: 10.1038/s41591-018-0050-6 (Jun. 11, 2018, epub ahead of print).

Jiang et al., "Structural Biology. A Cas9-guide RNA complex preorganized for target DNA recognition," Science, 2015, 348(6242), pp. 1477-1481.

Jinek et al., "RNA-programmed genome editing in human cells," eLife, 2013, 2:e00471.

Komor et al., "CRISPR-Based Technologies for the Manipulation of Eukaryotic Genomes," Cell, 2017, 168(1-2), pp. 20-36.

Kosicki et al., "Repair of double-strand breaks induced by CRISPR-Cas9 leads to large deletions and complex rearrangements," Nat. Biotechnol., 2018, 36(8), pp. 765-771.

Nishimasu et al., "Crystal Structure of Cas9 in Complex with Guide RNA and Target DNA," Cell, 2014, 156(5), pp. 935-949.

PubMed NCBI Search Results for ((CRISPR[Title] or Cas9[Title]) and ("Jan. 1, 2012"[PDATE] : "Jan. 22, 2017")), https://www.ncbi.nlm.nih.gov/pubmed, retrieved on Sep. 22, 2019.

Quadri, et al., "Mutations in SLC30A10 Cause Parkinsonism and Dystonia with Hypermanganesemia, Polycthemia, and Chronic Liver Disease," The American Journal of Human Genetics, 2012, 90, pp. 467-477 plus Supplemental Material.

Ratziu, et al., "Current efforts and trends in the treatment of NASH," Journal of Hepatology, 2015, 62, pp. S65-S75.

Santa Cruz Biotechnology, "17ß-HSD13 Antibody (K-14): sc-161285" [Retrieved from the Internet Jun. 1, 2016: www.scbt.com/datasheet-161285-17betahsd13-k-14-antibody.html].

Santa Cruz Biotechnology, "17ß-HSD13 siRNA (m), shRNA and Lentiviral Particle Gene Silencers" [Retrieved from the Internet Jun. 1, 2016: www.scbt.com/datasheet-108263-17beta-hsd13-sima-m.html].

Tang, et al., "A mouse knockout library for secreted and transmembrane proteins," Nature Biotechnology, 2010, 28(7), pp. 749-755 plus Online Methods and Supplementary Information.

Non-Final Office Action dated Jul. 10, 2019 for U.S. Appl. No. 15/875,514.

Notice of Allowance dated Jan. 22, 2020 in U.S. Appl. No. 15/875,514.

International Search Report and Written Opinion of the International Searching Authority dated Jun. 6, 2018 for WIPO Application No. PCT/US2018/014454.

UniProtKB-Q7Z5P4-1, "17-beta-hydroxysteroid dehydrogenase 13", 2003, pp. 6.

UniProtKB-Q7Z5P4-2, "17-beta-hydroxysteroid dehydrogenase 13", 2003, pp. 6-7.

Van Der Meer, A. J., et al., "Association Between Sustained Virological Response and All-Cause Mortality Among Patients With Chronic Hepatitis C and Advanced Hepatic Fibrosis", JAMA, 2012. pp. 2584-2593, 308(24).

Victor, R. G., et al., "The Dallas Heart Study: A Population-Based Probability Sample for the Multidisciplinary Study of Ethnic Differences in Cardiovascular Health", Am J Cardiol, 2004, pp. 1473-1480, 93.

Willer, C. J., et al., "METAL: fast and efficient meta-analysis of genomewide association scans", Bioinformatics, 2010, pp. 2190-2191, 26(17).

Williams, C. D., et al., "Clinical Advances in Liver, Pancreas, and Biliary Tract", Gastroenterology, 2011, pp. 124-131, 140.

Wong, R. J., et al., "Nonalcoholic Steatohepatitis is the Second Leading Etiology of Liver Disease Among Adults Awaiting Liver Transplantation in the United States", Gastroenterology, 2015, pp. 547-555, 148.

Yang, J., et al., "GCTA: A Tool for Genome-wide Complex Trait Analysis", The American Journal of Human Genetics, 2011, pp. 76-82, 88.

Younossi, Z. M., et al., "Changes in the Prevalence of the Most Common Causes of Chronic Liver Diseases in the United States From 1988 to 2008", Clinical Gastroenterology and Hepatology, 2011, pp. 524-530, 9.

Yuan, X. et al., "Population-Based Genome-wide Association Studies Reveal Six Loci Influencing Plasma Levels of Liver Enzymes", The American Journal of Human Genetics, 2008, pp. 520-528, 83.

Zhang, J., et al., "PowerBLAST: A New Network BLAST Application for Interactive of Automated Sequence Analysis and Annotation", Genome Research, 1997, pp. 649-656, 7.

Abul-Husn et al., "A Protein-Truncating HSD17B13 Variant and Protection from Chronic Liver Disease", N Engl J Med, 2018, 378, pp. 1096-1106.

Adam, M., et al., "Hydroxysteroid (17b) dehydrogenase 13 deficiency triggers hepatic steatosis and inflammation in mice", The FASEB Journal, 2018, pp. 1-14.

Altschul, S. F., et al., "Basic Local Alignment Search Tool", J. Mol. Biol., 1990, pp. 403-410, 215.

Altschul, S. F., et al., "Gapped BLAST and PSI-BLAST: a new generation of protein database search programs", Nucleic Acids Research, 1997, pp. 3389-3402, 25 (17).

Brantly et al., "Crystal RG. Molecular basis of alpha-1-antitrypsin deficiency", Am J Med, 1988, pp. 13-31, 84.

Brasaemle, D. L, et al., "Isolation of Lipid Droplets from Cells by Density Gradient Centrifugation", Current Protocols in Cell Biology, 2005, 3.15.1-3.15.12.

Browning, J. D. et al., "Prevalence of Hepatic Steatosis in an Urban Population in the United States: Impact of Ethnicity", Hepatology, 2004, pp. 1387-1395, 40(6).

Chambers, J. C., et al., "Genome-wide association study identifies loci influencing concentrations of liver enzymes in plasma" Nat Genet, 2011, pp. 1131-1138, 43(11).

Cohen, J. C., et al., "Human Fatty Liver Disease: Old Questions and New Insights", Science, 2011, pp. 1519-1523, 332.

Denny, J. C., et al., "PheWAS: demonstrating the feasibility of a phenome-wide scan to discover gene-disease associations", Bioinformatics, 2010, pp. 1205-1210, 26(9).

Denny, J. C., et al., "Systematic comparison of phenome-wide association study of electronic medical record data and genome-wide association study data", Nat Biotechnol, 2013, pp. 1102-1110, 31(12).

Dewey, F. E., et al., "Distribution and clinical impact of functional variants in 50,726 whole-exome sequences from the DiscovEHR Study", Science, 2016, pp. aaf6814, 354(6319).

Ding, Y., et al., "Isolating lipid droplets from multiple species", Nature Protocols, 2013, pp. 43-51, 8(1).

Feitosa et al., "The ERLIN1-CHUK-CWF19L1 gene cluster influences liver fat deposition and hepatic inflammation in the NHLBI Family Heart Study", Atherosclerosis, 2013, pp. 175-180, 228.

Ford et al., "A New Assay for Picomole Levels of Androsterone and Testosterone Using Co-immobilized Luciferase, Oxidoreductase, and Steroid Dehydrogenase", Analytical Biochemistry, 1981, 110, pp. 43-48.

Huang et al., "Expression and Characterization of a PNPLA3 Protein Isoform (I148M) Associated with Nonalcoholic Fatty Liver Disease", J Biol Chem, 2011, pp. 37085-37093, 286.

International Search Report and Written Opinion for PCT Application PCT/US2018/014357.

Kampf, C., et al., "The human liver-specific proteome defined by transcriptomics and antibody-based profiling", The FASEB Journal, 2014, pp. 2901-2914, 28(7).

Kitamoto et al., "Genome-wide scan revealed that polymorphisms in the PNPLA3, SAMM50, and PARVB genes are associated with development and progression of nonalcoholic fatty liver disease in Japan", Hum Genet, 2013, pp. 783-792, 132.

(56) References Cited

OTHER PUBLICATIONS

Kleiner, D. E., et al., "Design and Validation of a Histological Scoring System for Nonalcoholic Fatty Liver Disease", Hepatology, 2005, pp. 1313-1321, 41(6).
Kochanek, K. D., et al., "Deaths: Final Data for 2014", National Viral Statistics Reports, 2016, pp. 1-122, 65(4).
Kozlitina, J., et al., "Exome-wide association study identifies a TM6SF2 variant that confers susceptibility to nonalcoholic fatty liver disease", Nat Genet, 2014, pp. 352-356, 46(4).
Krazeisen et al., "Phytoestrogens inhibit human 17β-hydroxysteroid dehydrogenase type 5", Molecular and Cellular Endocrinology, 2001, 171, pp. 151-162.
Lazo, M. et al., "Prevalence of Nonalcoholic Fatty Liver Disease in the United States: The Third National Health and Nutrition Examination Survey, 1988-1994", Am J Epidemiol, 2013, pp. 38-45, 178(1).
Li, H., et al., "Fast and accurate short read alignment with Burrows—Wheeler transform", Bioinformatics, 2009, pp. 1754-1760, 25(14).
Li, P., et al., "LTB4 causes macrophage—mediated inflammation and directly induces insulin resistance in obesity", Nat Med, 2015, pp. 239-247, 21(3).
Liu, S., et al., "Molecular cloning and expression analysis of a new gene for shortchain dehydrogenase/reductase 9", Acta Biochimica Polonica, 2007, pp. 213-218, 54(1).
Liu, Y.-L., et al., "TM6SF2 rs58542926 influences hepatic fibrosis progression in patients with non-alcoholic fatty liver disease", Nature Communications, 2014, pp. 1-6, 5(4309).
Mahdessian et al., "TM6SF2 is a regulator of liver fat metabolism influencing triglyceride secretion and hepatic lipid droplet content", PNAS, 2014, pp. 8913-8918, 111.
McKenna, A., et al., "The Genome Analysis Toolkit: A MapReduce framework for analyzing next-generation DNA sequencing data", Genome Research, 2010, pp. 1297-1303, 20.
Moeller, G., et al. "Integrated view on 17betahydroxysteroid dehydrogenases", Molecular and Cellular Endocrinology, 2009, pp. 7-19, 301.
Morgan, R. L., et al., "Eradication of Hepatitis C Virus Infection and the Development of Hepatocellular Carcinoma", Annals of Internal Medicine, 2013, pp. 329-337 and W-158-W-160, 158(5)(Part 1).
NCBI Reference Sequence: NM_178135, "*Homo spiens* hydroxysteroid 17-beta dehydrogenase 13 (HSD17B13), transcript variant A, mRNA" 2017, pp. 1-5.
NCBI Reference Sequence: NM_001136230, "*Homo sapiens* hydroxysteroid 17-beta dehydrogenase 13 (HSD17B13), transcript variant B, mRNA" 2017, pp. 1-5.
NCBI Reference Sequence: NP_835236, "17-beta-hydroxysteroid dehydrogenase 13 isoform A precursor [*Homo sapiens*]", 2017 pp. 1-4.
NCBI Reference Sequence: NP_001129702, "17-beta-hydroxysteroid dehydrogenase 13 isoform B [*Homo sapiens*]", 2017, pp. 1-4.
Pirazzi et al., "Patatin-like phospholipase domain-containing 3 (PNPLA3) I148M (rs738409) affects hepatic VLDL secretion in humans and in vitro", J Hepatol, 2012, pp. 1276-1282, 57.
Promega "Technical Manual: NAD(P)H-Glo Detection System", 2017, TM398, pp. 1-15.
Pruim, R. J., et al., "LocusZoom: regional visualization of genome-wide association scan results", Bioinformatics, 2010, pp. 2336-2337, 26(18).
Reid, J. G., et al., "Launching genomics into the cloud: deployment of Mercury, a next generation sequence analysis pipeline", BMC Bioinformatics, 2014, pp. 1-11, 15(30).
Romeo, S., et al., "Genetic variation in PNPLA3 confers susceptibility to nonalcoholic fatty liver disease", Nat Genet, 2008, pp. 1461-1465, 40(12).
Rotman Y. et al., "The Association of Genetic Variability in PNPLA3 with Histological Severity of Non-Alcoholic Fatty Liver Disease", Hepatology, 2010, pp. 894-903, 52(3).
Shen et al., "The rs738409 (I148M) variant of the PNPLA3 gene and cirrhosis: a meta-analysis", J Lipid Res, 2015, pp. 167-175, 56.

Smagris et al., "Inactivation of Tm6sf2, a Gene Defective in Fatty Liver Disease, Impairs Lipidation but Not Secretion of Very Low Density Lipoproteins", J Biol Chem, 2016, pp. 10659-10676, 291.
Smith, T. F., et al., "Comparsion of Biosequences", Advances in Applied Mathematics, 1981, pp. 482-489, 2.
Sookoian, S., et al., "A nonsynonymous gene variant in the adiponutrin gene is associated with nonalcoholic fatty liver disease severity", Journal of Lipid Research, 2009, pp. 2111-2116, 50.
Sookoian, S., et al., "Genetic Variation in Transmembrane 6 Superfamily Member 2 and the Risk of Nonalcoholic Fatty Liver Disease and Histological Disease Severity", Hepatology, 2015, pp. 515-525, 61(2).
Speliotes, E. K., et al., "Genome-Wide Association Analysis Identifies Variants Associated with Nonalcoholic Fatty Liver Disease That Have Distinct Effects on Metabolic Traits", PLoS Genetics, 2011, e1001324, 7(3).
Su, W., et al., "Comparative proteomic study reveals 17!-HSD13 as a pathogenic protein in nonalcoholic fatty liver disease", PNAS, 2014, pp. 11437-11442, 111(31).
Trepo, E., et al., "PNPLA3 gene in liver diseases", Journal of Hepatology, 2016, pp. 399-412, 65.
Office Action dated Feb. 4, 2020 in related U.S. Appl. No. 15/913,366.
Leippe et al., "Bioluminescent Nicotinamide Adenine Dinucleotide Detection Assays Part 1: Technology and Features", 2014, hhttp://www.promega.com/resources/pubhub/bioluminescent-nicotinamide-adenine-dinucleotide-detection-assays/.
New England Biolabs Catalog, "Nucleic Acids, Linkers and Primers", 1998/199, pp. 121 and 284.
Schiavinato et al., "EMILIN-3, Peculiar Member of Elastin Microfibril Interface-located Protein (EMILIN) Family, Has Distinct Expression Pattern, Forms Oligomeric Assemblies, and Serves as Transforming Growth Factor B (TGF-B) Antagonist", Journal of Biological Chemistry, 2012, 187(14), pp. 11498-11515.
SNP(ss) Report in Submission Format for NCBI Assay Id (ss#): ss557289122, 2012, www.ncbi.nlm.gov/.
Non-Final Office Action dated Mar. 12, 2020 in related U.S. Appl. No. 15/875,192.
Edelman et al., "Genetic analysis of nonalcoholic fatty liver disease within a Caribbean-Hispanic population", Molecular Genetics & Genomic Medicine, 2015, 3(6), pp. 558-569.
Hotta et al., "R association of the rs738409 polymorphism in PNPLA3 with liver damage and the development of nonalcoholic fatty liver disease", BMC Medical Genetics, 2010, 11(172), pp. 1-10.
Kahali et al., "Insights from Genome-Wide Association Analyses of Nonalcoholic Fatty Liver Disease", Seminars in Liver Disease, 2015, 35(4), pp. 375-391.
Oniki et al., "Influence of the PNPLA3 rs738409 Polymorphism on Non-Alcoholic Fatty Liver Disease and Renal Function among Normal Weight Subjects", PLOS ONE, 2015, 10(7), pp. e0132640.
Shen et al., "The rs738409 (I148M) variant of the PNPLA3 gene and cirrhosis: a meta-analysis", Journal of Lipid Research, 2015, 56(1), pp. 167-175.
Wong, R. J., et al., "Nonalcoholic Steatohepatitis is the Second Leading Etiology of Liver Disease Among Adults Waiting Liver Transplantation in the United States", Gastroenterology, 2015, pp. 547-555, 148.
Notice of Allowance dated May 1, 2020 in U.S. Appl. No. 15/875,514.
International Search Report/Written Opinion dated Jun. 26, 2019 received in application No. PCT/US19/23079.
G. Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBIO, 2015, 6(4):e01122-15.
S.Q. Tsai and K. Young, "Defining and improving the genome-wide specificities of CRISPR-Cas9 nucleases", Nature Reviews Genetics, 2016, 17:300-312.
Moeller et al., "Multifunctionality of human 17ß-hydroxysteriod dehydrogenases", Molecular and Cellular Endocrinology, 2006, 248, pp. 47-55.
Final Office Action dated Sep. 22, 2020 for U.S. Appl. No. 15/913,366.
Final Office Action dated Dec. 3, 2020 for U.S. Appl. No. 15/875,192.

* cited by examiner

| Characteristic | GHS Discovery Cohort (N = 46,544) | GHS Bariatric Surgery Cohort (N = 2,644) | Dallas Heart Study (N = 1,357) | Penn Medicine Biobank (N = 8,526) |
|---|---|---|---|---|
| Age (years) – median (IQR) | 63 (50 - 74) | 53 (44 - 61) | 46 (38 - 54) | 68 (60 - 76) |
| Female sex – number (%) | 26,875 (58) | 2,119 (80) | 724 (53) | 3,242 (38) |
| Body mass index – median (IQR) | 30 (25 - 45) | 47 (42 - 54) | 28 (25 - 32) | 30 (25 - 32) |
| Transaminase level (U/L) – median (IQR) | | | | |
| Alanine aminotransferase (ALT) | 22.0 (17.0 - 29.0) | 23.0 (17.5 - 29.5) | 20.0 (15.0 - 27.0) | 22.0 (17.0 - 30.0) |
| Aspartate aminotransferase (AST) | 23.0 (20.0 - 27.5) | 23.0 (20.0 - 27.0) | 21.0 (18.0 - 25.0) | 24.0 (20.0 - 30.5) |
| Presence of liver disease – N (%) | | | | |
| Alcoholic liver disease | 197 (0.4) | 7 (0.3) | - | - |
| Alcoholic cirrhosis | 130 (0.3) | 3 (0.1) | - | - |
| Nonalcoholic (non-viral) liver disease | 1,938 (4.2) | 1,543 (58.4) | - | - |
| Nonalcoholic cirrhosis | 382 (0.8) | 24 (0.9) | - | - |
| Hepatocellular carcinoma | 76 (0.2) | 1 (0.04) | - | - |
| No liver disease | 30,628 (65.8) | 1 (0.04) | - | - |

Figure 1

| Trait | Chr | BP | Ref | Alt | rsID | Gene | Annotation | AA Substitution | Beta (SE) | P | AAF | N |
|---|---|---|---|---|---|---|---|---|---|---|---|---|
| ALT | 1 | 220970028 | A | G | rs2642438 | MARC1 | missense | p.Thr165Ala | 0.008 (0.001) | 4.67E-08 | 0.7067 | 40,834 |
| | 4 | 88231392 | T | TA | rs72613567 | HSD17B13 | splice donor | | -0.009 (0.001) | 4.16E-12 | 0.2634 | 40,834 |
| | 8 | 144997604 | C | T | rs371119003 | PLEC | missense | p.Ala2302Thr | -0.160 (0.026) | 1.30E-09 | 0.0005 | 40,833 |
| | 8 | 145008502 | G | A | | PLEC | missense | p.Arg522Cys | -0.268 (0.032) | 3.26E-17 | 0.0003 | 40,834 |
| | 8 | 145692918 | G | A | rs35968570 | KIFC2 | missense | p.Glu174Lys | -0.033 (0.005) | 1.40E-11 | 0.0139 | 40,834 |
| | 8 | 145730072 | G | A | rs143408057 | GPT | missense | p.Arg83His | -0.314 (0.036) | 3.28E-18 | 0.0003 | 40,834 |
| | 8 | 145730161 | C | T | rs201815297 | GPT | missense | p.Ala87Val | -0.224 (0.014) | 6.28E-59 | 0.0018 | 40,834 |
| | 8 | 145730221 | G | A | rs112574791 | GPT | missense | p.Arg107Lys | -0.033 (0.005) | 4.25E-11 | 0.0136 | 40,834 |
| | 8 | 145731636 | T | G | rs145155876 | GPT | stop gained | p.Tyr326* | -0.235 (0.031) | 1.76E-14 | 0.0004 | 40,814 |
| | 8 | 145732114 | G | C | rs141505249 | GPT | missense | p.Glu430Gln | -0.224 (0.013) | 8.84E-64 | 0.0019 | 40,795 |
| | 8 | 145732151 | G | A | rs143462595 | GPT | missense | p.Arg442His | -0.077 (0.013) | 1.18E-09 | 0.0021 | 40,826 |
| | 8 | 145732180 | G | C | rs147998249 | GPT | missense | p.Val452Leu | -0.225 (0.013) | 8.19E-65 | 0.0019 | 40,833 |
| | 8 | 145732305 | G | GC | | GPT | frameshift | p.Glu475fs | -0.271 (0.031) | 1.00E-18 | 0.0004 | 40,834 |
| | 8 | 145748532 | A | G | rs567402720 | LRRC24 | missense | p.Leu290Ser | -0.185 (0.028) | 3.42E-11 | 0.0004 | 40,813 |
| | 9 | 117122202 | C | T | rs3748177 | AKNA | synonymous | p.Glu755Glu | -0.007 (0.001) | 9.51E-09 | 0.5232 | 40,834 |
| | 9 | 117124731 | G | A | rs3748176 | AKNA | missense | p.Pro624Leu | -0.007 (0.001) | 4.31E-09 | 0.5230 | 40,832 |
| | 10 | 101595996 | T | A | rs17222773 | ABCC2 | missense | p.Val1188Glu | -0.015 (0.003) | 2.97E-08 | 0.0608 | 40,834 |
| | 10 | 101606861 | G | T | rs1137968 | ABCC2 | synonymous | p.Val1430Val | -0.015 (0.003) | 2.71E-08 | 0.0608 | 40,834 |
| | 10 | 101610533 | C | T | rs8187707 | ABCC2 | synonymous | p.His1496His | -0.015 (0.003) | 2.77E-08 | 0.0608 | 40,834 |
| | 10 | 101611294 | G | A | rs8187710 | ABCC2 | missense | p.Cys1515Tyr | -0.015 (0.003) | 2.15E-08 | 0.0611 | 40,834 |
| | 10 | 101912064 | T | C | rs2862954 | ERLIN1 | missense | p.Ile291Val | 0.012 (0.001) | 2.43E-21 | 0.4755 | 40,834 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error;

Figure 2

| Trait | Chr | BP | Ref | Alt | rsID | Gene | Annotation | AA Substitution | N Ref/Ref | N Ref/Alt | N Alt/Alt | Mean ALT or AST level (U/L) Ref/Ref | Ref/Alt | Alt/Alt |
|---|---|---|---|---|---|---|---|---|---|---|---|---|---|---|
| ALT | 1 | 2.2E+08 | A | G | rs2642438 | MARC1 | missense | p.Thr165Ala | 3,515 | 17,262 | 20,637 | 23.88 | 24.52 | 24.92 |
| | 4 | 8.8E+07 | T | TA | rs72613567 | HSD17B13 | splice donor | | 22,441 | 16,130 | 2,843 | 25.02 | 24.26 | 24.1 |
| | 8 | 1.4E+08 | C | T | rs371119Q03 | PLEC | missense | p.Ala2302Thr | 41,373 | 40 | 0 | 24.67 | 18.1 | NA |
| | 8 | 1.5E+08 | G | A | | PLEC | missense | p.Arg522Cys | 41,387 | 27 | 0 | 24.67 | 13.8 | NA |
| | 8 | 1.5E+08 | G | A | rs35968570 | KIFC2 | missense | p.Glu174Lys | 40,271 | 1,133 | 10 | 24.67 | 12.07 | NA |
| | 8 | 1.5E+08 | G | A | rs143408057 | GPT | missense | p.Arg83His | 41,393 | 21 | 0 | 24.67 | 12.07 | NA |
| | 8 | 1.5E+08 | C | T | rs201815297 | GPT | missense | p.Ala87Val | 41,270 | 144 | 0 | 24.7 | 14.68 | NA |
| | 8 | 1.5E+08 | G | A | rs112574791 | GPT | missense | p.Arg107Lys | 40,293 | 1,111 | 10 | 24.71 | 23.09 | 18.35 |
| | 8 | 1.5E+08 | T | G | rs145155876 | GPT | stop gained | p.Tyr326* | 41,364 | 30 | 0 | 24.67 | 14.07 | NA |
| | 8 | 1.5E+08 | G | C | rs141505249 | GPT | missense | p.Glu430Gln | 41,223 | 150 | 2 | 24.7 | 14.48 | 13.75 |
| | 8 | 1.5E+08 | G | A | rs143462595 | GPT | missense | p.Arg442His | 41,232 | 174 | 0 | 24.68 | 20.87 | NA |
| | 8 | 1.5E+08 | G | C | rs147998249 | GPT | missense | p.Val452Leu | 41,254 | 159 | 0 | 24.7 | 14.74 | NA |
| | 8 | 1.5E+08 | G | GC | | GPT | frameshift | p.Glu475fs | 41,385 | 29 | 0 | 24.67 | 14.24 | NA |
| | 8 | 1.5E+08 | A | G | rs567402720 | LRRC24 | missense | p.Leu290Ser | 41,358 | 35 | 0 | 24.67 | 17.71 | NA |
| | 9 | 1.2E+08 | C | T | rs3748177 | AKNA | synonymous | p.Glu755Glu | 9,414 | 20,645 | 11,355 | 25.12 | 24.72 | 24.18 |
| | 9 | 1.2E+08 | G | A | rs3748176 | AKNA | missense | p.Pro624Leu | 9,427 | 20,634 | 11,351 | 25.12 | 24.73 | 24.17 |
| | 10 | 1E+08 | T | A | rs17222723 | ABCC2 | missense | p.Val1188Glu | 36,543 | 4,704 | 167 | 24.77 | 23.97 | 22.12 |
| | 10 | 1E+08 | G | T | rs1137968 | ABCC2 | synonymous | p.Val1430Val | 36,543 | 4,704 | 167 | 24.77 | 23.97 | 22.04 |
| | 10 | 1E+08 | C | T | rs8187707 | ABCC2 | synonymous | p.His1496His | 36,542 | 4,706 | 166 | 24.77 | 23.97 | 22.03 |
| | 10 | 1E+08 | G | A | rs8187710 | ABCC2 | missense | p.Cys1515Tyr | 36,519 | 4,726 | 169 | 24.77 | 23.97 | 21.99 |
| | 10 | 1E+08 | T | C | rs2862984 | ERLIN1 | missense | p.Ile291Val | 11,318 | 20,819 | 9,277 | 25.32 | 24.71 | 23.77 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error;

Figure 2 (cont.)

| Trait | Chr | BP | Ref | Alt | rsID | Gene | Annotation | AA Substitution | Beta (SE) | P | AAF | N |
|---|---|---|---|---|---|---|---|---|---|---|---|---|
| | 10 | 101977883 | C | T | rs2230804 | CHUK | missense | p.Val268Ile | -0.009 (0.001) | 1.93E-13 | 0.5072 | 40,834 |
| | 10 | 113917085 | T | A | rs2254537 | GPAM | synonymous | p.Pro683Pro | -0.008 (0.001) | 4.61E-10 | 0.7073 | 40,834 |
| | 10 | 113940329 | T | C | rs2792751 | GPAM | missense | p.Ile43Val | -0.008 (0.001) | 2.54E-10 | 0.7097 | 40,832 |
| | 14 | 94844947 | C | T | rs28929474 | SERPINA1 | missense | p.Glu366Lys | 0.042 (0.005) | 9.28E-21 | 0.0171 | 40,834 |
| | 19 | 19379549 | C | T | rs58542926 | TM6SF2 | missense | p.Glu167Lys | 0.014 (0.002) | 4.76E-09 | 0.0759 | 40,833 |
| | 22 | 44324727 | C | G | rs738409 | PNPLA3 | missense | p.Ile148Met | 0.023 (0.002) | 1.34E-50 | 0.2351 | 40,834 |
| | 22 | 44324730 | C | T | rs738408 | PNPLA3 | synonymous | p.Pro149Pro | 0.023 (0.002) | 1.11E-50 | 0.2349 | 40,834 |
| | 22 | 44342116 | A | G | rs2294918 | PNPLA3 | missense | p.Lys434Glu | 0.007 (0.001) | 8.26E-08 | 0.5986 | 40,832 |
| | 22 | 44368122 | A | G | rs3761472 | SAMM50 | missense | p.Asp110Gly | 0.019 (0.002) | 8.85E-30 | 0.1682 | 40,833 |
| | 22 | 44395451 | T | C | rs1007863 | PARVB | missense | p.Trp37Arg | 0.011 (0.001) | 7.98E-16 | 0.3963 | 40,834 |
| AST | 4 | 88231392 | T | TA | rs72613567 | HSD17B13 | splice donor | | -0.005 (0.001) | 6.24E-10 | 0.2638 | 40,193 |
| | 10 | 18242311 | A | G | rs10764176 | SLC39A12 | missense | p.Ser36Gly | -0.006 (0.001) | 1.09E-10 | 0.2881 | 40,193 |
| | 10 | 101157378 | CGTT | C | | GOT1 | inframe indel | p.Asn389del | -0.221 (0.024) | 1.96E-20 | 0.0002 | 40,193 |
| | 10 | 101165533 | G | C | rs374966349 | GOT1 | missense | p.Gln208Glu | 0.271 (0.027) | 2.43E-24 | 0.0002 | 40,193 |
| | 10 | 101912064 | T | C | rs2862954 | ERLIN1 | missense | p.Ile291Val | -0.005 (0.001) | 4.82E-09 | 0.4754 | 40,193 |
| | 11 | 22271870 | A | T | rs7481951 | ANO5 | missense | p.Leu322Phe | 0.004 (0.001) | 9.61E-08 | 0.5833 | 40,162 |
| | 14 | 94844947 | C | T | rs28929474 | SERPINA1 | missense | p.Glu366Lys | 0.027 (0.003) | 2.44E-20 | 0.0172 | 40,193 |
| | 19 | 19379549 | C | T | rs58542926 | TM6SF2 | missense | p.Glu167Lys | 0.008 (0.002) | 6.54E-08 | 0.0760 | 40,192 |
| | 22 | 44324727 | C | G | rs738409 | PNPLA3 | missense | p.Ile148Met | 0.014 (0.001) | 8.31E-46 | 0.2343 | 40,193 |
| | 22 | 44324730 | C | T | rs738408 | PNPLA3 | synonymous | p.Pro149Pro | 0.014 (0.001) | 8.93E-46 | 0.2341 | 40,193 |
| | 22 | 44368122 | A | G | rs3761472 | SAMM50 | missense | p.Asp110Gly | 0.011 (0.001) | 1.22E-22 | 0.1680 | 40,192 |
| | 22 | 44395451 | T | C | rs1007863 | PARVB | missense | p.Trp37Arg | 0.006 (0.001) | 1.31E-13 | 0.3961 | 40,193 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error.

Figure 2 (cont.)

| Trait | Chr | BP | Ref | Alt | rsID | Gene | Annotation | AA Substitution | N Ref/Ref | N Ref/Alt | N Alt/Alt | Mean ALT or AST level (U/L) Ref/Ref | Ref/Alt | Alt/Alt |
|---|---|---|---|---|---|---|---|---|---|---|---|---|---|---|
| | 10 | 101977883 | C | T | rs2230804 | CHUK | missense | p.Val268Ile | 10,048 | 20,733 | 10,633 | 25.18 | 24.75 | 24.01 |
| | 10 | 113917085 | T | A | rs2254537 | GPAM | synonymous | p.Pro681Pro | 3,627 | 16,984 | 20,803 | 25 | 24.97 | 24.36 |
| | 10 | 113940329 | T | C | rs2792751 | GPAM | missense | p.Ile43Val | 3,567 | 16,910 | 20,935 | 25 | 24.98 | 24.35 |
| | 14 | 94844947 | C | T | rs28929474 | SERPINA1 | missense | p.Glu366Lys | 40,006 | 1,399 | 9 | 24.58 | 16.91 | 43.89 |
| | 19 | 19379549 | C | T | rs58542926 | TM6SF2 | missense | p.Glu167Lys | 35,388 | 5,780 | 245 | 24.52 | 25.46 | 26.84 |
| | 22 | 44324727 | C | G | rs738409 | PNPLA3 | missense | p.Ile148Met | 24,257 | 14,837 | 2,320 | 24.06 | 24.99 | 28.91 |
| | 22 | 44324730 | C | T | rs738408 | PNPLA3 | synonymous | p.Pro149Pro | 24,273 | 14,824 | 2,317 | 24.06 | 24.98 | 28.92 |
| | 22 | 44342116 | A | G | rs2294918 | PNPLA3 | missense | p.Lys434Glu | 6,691 | 19,833 | 14,888 | 24.15 | 24.47 | 25.15 |
| | 22 | 44368122 | A | G | rs3761472 | SAMM50 | missense | p.Asp108Gly | 28,626 | 11,618 | 1,169 | 24.23 | 25.36 | 28.45 |
| | 22 | 44395451 | T | C | rs1007863 | PARVB | missense | p.Trp37Arg | 15,036 | 19,920 | 6,458 | 24.15 | 24.6 | 26.09 |
| AST | 4 | 88231392 | T | TA | rs72813567 | HSD17B13 | splice donor | | 22,068 | 15,870 | 2,815 | 24.47 | 24.1 | 23.96 |
| | 10 | 18242311 | A | G | rs10764176 | SLC39A12 | missense | p.Ser36Gly | 20,645 | 16,738 | 3,370 | 24.47 | 24.15 | 23.85 |
| | 10 | 101157378 | CGTT | C | rs374966349 | GOT1 | inframe indel | p.Asn389del | 40,733 | 20 | 0 | 24.29 | 14.7 | NA |
| | 10 | 101165533 | G | C | rs2862954 | GOT1 | missense | p.Gln208Glu | 40,736 | 17 | 0 | 24.28 | 44.5 | NA |
| | 10 | 101910064 | T | C | rs2862954 | ERLIN1 | missense | p.Ile291Val | 11,139 | 20,486 | 9,129 | 24.59 | 24.26 | 23.99 |
| | 11 | 22271870 | A | T | rs7481951 | ANO5 | missense | p.Leu322Phe | 7,123 | 19,686 | 13,913 | 24.03 | 24.22 | 24.53 |
| | 14 | 94844947 | C | T | rs28929474 | SERPINA1 | missense | p.Glu366Lys | 39,361 | 1,384 | 8 | 24.24 | 25.76 | 34.5 |
| | 19 | 19379549 | C | T | rs58542926 | TM6SF2 | missense | p.Glu167Lys | 34,811 | 5,698 | 243 | 24.21 | 24.74 | 25.43 |
| | 22 | 44324727 | C | G | rs738409 | PNPLA3 | missense | p.Ile148Met | 23,889 | 14,622 | 2,242 | 23.96 | 24.48 | 26.62 |
| | 22 | 44324730 | C | T | rs738408 | PNPLA3 | synonymous | p.Pro149Pro | 23,905 | 14,609 | 2,239 | 23.96 | 24.47 | 26.63 |
| | 22 | 44368122 | A | G | rs3761472 | SAMM50 | missense | p.Asp108Gly | 28,170 | 11,450 | 1,132 | 24.07 | 24.64 | 26.24 |
| | 22 | 44395451 | T | C | rs1007863 | PARVB | missense | p.Trp37Arg | 14,761 | 19,678 | 6,314 | 24.02 | 24.23 | 25.1 |

Gray shading indicates variants having exome-wide-significant associations with both ALT and AST.
Abbreviations: AAF, alternate allele frequency; Alt, alternate allele; ALT, alanine aminotransferase; AST, aspartate aminotransferase; Ref, reference allele; SE, standard error.

Figure 2 (cont.)

| Trait | Chr | BP | Ref | Alt | RSID | Gene | Annotation | AA Substitution | GHS Discovery Cohort Beta (SE) | GHS Discovery Cohort P discovery | N |
|---|---|---|---|---|---|---|---|---|---|---|---|
| ALT | 1 | 220970028 | A | G | rs2642438 | MARC1 | missense | p.Thr165Ala | 0.008 (0.001) | 4.67E-08 | 40834 |
| | 4 | 88233192 | T | TA | rs72613567 | HSD17B13 | splice donor | | -0.049 (0.001) | 4.16E-12 | 40834 |
| | 8 | 144997604 | C | T | rs371119003 | PLEC | missense | p.Ala2302Thr | -0.160 (0.026) | 1.30E-09 | 40833 |
| | 8 | 145608502 | G | A | | PLEC | missense | p.Arg522Cys | -0.268 (0.032) | 3.26E-17 | 40834 |
| | 8 | 145662918 | G | A | rs35968570 | KIFC2 | missense | p.Glu174Lys | -0.033 (0.005) | 1.40E-11 | 40834 |
| | 8 | 145730072 | G | A | rs1434208057 | GPT | missense | p.Arg83His | -0.314 (0.036) | 3.28E-18 | 40834 |
| | 8 | 145730161 | C | T | rs201815297 | GPT | missense | p.Ala87Val | -0.224 (0.014) | 6.28E-59 | 40834 |
| | 8 | 145730221 | G | A | rs112574791 | GPT | missense | p.Arg107Lys | -0.033 (0.005) | 4.25E-11 | 40834 |
| | 8 | 145731636 | T | G | rs145155876 | GPT | stop gained | p.Tyr326* | -0.235 (0.031) | 1.76E-14 | 40814 |
| | 8 | 145732114 | G | C | rs141505249 | GPT | missense | p.Glu430Gln | -0.224 (0.013) | 8.84E-64 | 40795 |
| | 8 | 145732151 | G | A | rs1434362595 | GPT | missense | p.Arg442His | -0.077 (0.013) | 1.18E-09 | 40826 |
| | 8 | 145732180 | G | C | rs147998249 | GPT | missense | p.Val452Leu | -0.225 (0.013) | 8.19E-65 | 40833 |
| | 8 | 145733305 | G | GC | | GPT | frameshift | p.Glu475fs | -0.271 (0.031) | 1.00E-18 | 40834 |
| | 8 | 145748532 | A | G | rs567402720 | LRRC24 | missense | p.Leu290Ser | -0.185 (0.028) | 3.42E-11 | 40813 |
| | 9 | 117122202 | C | T | rs3748177 | AKNA | synonymous | p.Glu755Glu | -0.007 (0.001) | 9.51E-09 | 40834 |
| | 9 | 117124731 | G | A | rs3748176 | AKNA | missense | p.Pro624Leu | -0.007 (0.001) | 4.31E-09 | 40832 |
| | 10 | 101595996 | T | A | rs17222723 | ABCC2 | missense | p.Val1188Glu | -0.015 (0.003) | 2.97E-08 | 40834 |

Gray shading indicates P-values meeting the Bonferroni significance threshold of P < 1.43x10-3

* Replication meta-analysis includes the three replication cohorts: GHS Bariatric Surgery Cohort, Dallas Heart Study, and Penn Medicine Biobank

* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3

| Trait | Chr | BP | Ref | Alt | RSID | Gene | Annotation | AA Substitution | GHS Discovery Cohort Beta (SE) | P discovery | N |
|---|---|---|---|---|---|---|---|---|---|---|---|
| | 10 | 101606861 | G | T | rs113796 | ABCC2 | synonymous | p.Val1430Val | -0.015 (0.003) | 2.71E-08 | 40834 |
| | 10 | 101610533 | C | T | rs818770 | ABCC2 | synonymous | p.His1496His | -0.015 (0.003) | 2.77E-08 | 40834 |
| | 10 | 101611294 | G | A | rs818771 | ABCC2 | missense | p.Cys1515Tyr | -0.015 (0.003) | 2.15E-08 | 40834 |
| | 10 | 101912064 | T | C | rs286293 | ERLIN1 | missense | p.Ile291Val | -0.012 (0.001) | 2.43E-21 | 40834 |
| | 10 | 101977883 | C | T | rs223080 | CHUK | missense | p.Val268Ile | -0.009 (0.001) | 1.93E-13 | 40834 |
| | 10 | 113917085 | T | A | rs2254453 | GPAM | synonymous | p.Pro681Pro | -0.008 (0.001) | 4.61E-10 | 40834 |
| | 10 | 113940329 | T | C | rs2792751 | GPAM | missense | p.Ile43Val | -0.008 (0.001) | 2.54E-10 | 40832 |
| | 14 | 94844947 | C | T | rs28929474 | SERPINA1 | missense | p.Glu366Lys | 0.042 (0.005) | 9.28E-21 | 40834 |
| | 19 | 19379549 | C | T | rs58542926 | TM6SF2 | missense | p.Glu167Lys | 0.014 (0.002) | 4.76E-09 | 40833 |
| | 22 | 44324727 | C | G | rs738409 | PNPLA3 | missense | p.Ile148Met | 0.023 (0.002) | 1.34E-50 | 40834 |
| | 22 | 44324730 | C | T | rs738408 | PNPLA3 | synonymous | p.Pro149Pro | 0.023 (0.002) | 1.11E-50 | 40834 |
| | 22 | 44342116 | A | G | rs2294915 | PNPLA3 | missense | p.Lys434Glu | 0.007 (0.001) | 8.26E-08 | 40832 |
| | 22 | 44368122 | A | G | rs376147 | SAMM50 | missense | p.Asp110Gly | 0.019 (0.002) | 8.85E-30 | 40833 |
| | 22 | 44395451 | T | C | rs100786 | PARVB | missense | p.Trp37Arg | 0.011 (0.001) | 7.98E-16 | 40834 |

Grey shading indicates P-values meeting the Bonferroni significance threshold of $P < 1.43 \times 10^{-3}$
* Replication meta-analysis includes the three replication cohorts: GHS Bariatric Surgery Cohort, Dallas Heart Study, and Penn Medicine Biobank
* Joint meta-analysis includes the discovery cohort and the three replication cohorts: GHS Discovery Cohort, GHS Bariatric Surgery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | BP | Ref | Alt | RSID | Gene | Annotation | AA Substitution | GHS Discovery Cohort | | |
|---|---|---|---|---|---|---|---|---|---|---|---|
| | | | | | | | | | Beta (SE) | P discovery | N |
| AST | 4 | 98231392 | T | TA | rs72613567 | HSD17B13 | splice donor | | -0.005 (0.001) | 6.24E-10 | 40193 |
| | 10 | 18242311 | A | G | rs10764176 | SLC39A12 | missense | p.Ser36Gly | -0.006 (0.001) | 1.09E-10 | 40193 |
| | 10 | 101157378 | CGTT | C | | GOT1 | inframe indel | p.Asn389del | -0.221 (0.024) | 1.96E-20 | 40193 |
| | 10 | 101165533 | G | C | rs374966349 | GOT1 | missense | p.Gln208Glu | 0.271 (0.027) | 2.43E-24 | 40193 |
| | 10 | 101912064 | T | C | rs2286954 | ERLIN1 | missense | p.Ile291Val | -0.005 (0.001) | 4.82E-09 | 40193 |
| | 11 | 22271870 | A | T | rs7481951 | ANO5 | missense | p.Leu322Phe | 0.004 (0.001) | 9.61E-08 | 40162 |
| | 14 | 94844947 | C | T | rs28929474 | SERPINA1 | missense | p.Glu366Lys | 0.027 (0.003) | 2.44E-20 | 40193 |
| | 19 | 19379549 | C | T | rs58542926 | TM6SF2 | missense | p.Glu167Lys | 0.008 (0.002) | 6.54E-08 | 40192 |
| | 22 | 44324727 | C | G | rs738409 | PNPLA3 | missense | p.Ile148Met | 0.014 (0.001) | 8.31E-46 | 40193 |
| | 22 | 44324730 | C | T | rs738408 | PNPLA3 | synonymous | p.Pro149Pro | 0.014 (0.001) | 8.93E-46 | 40193 |
| | 22 | 44368122 | A | G | rs3761472 | SAMM50 | missense | p.Asp110Gly | 0.011 (0.001) | 1.22E-22 | 40192 |
| | 22 | 44395451 | T | C | rs1807863 | PARVB | missense | p.Trp37Arg | 0.006 (0.001) | 1.31E-13 | 40193 |

Gray shading indicates P-values meeting the Bonferroni significance threshold of P < 1.43x10-3
* Replication meta-analysis includes the three replication cohorts: GHS Bariatric Sugery Cohort, Dallas Heart Study, and Penn Medicine Biobank
* Joint meta-analysis includes the discovery cohort and the three replication cohorts: GHS Discovery Cohort, GHS Bariatric Surgery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Cohorts | | | | | | | | |
|---|---|---|---|---|---|---|---|---|---|---|
| | | GHS Bariatric Surgery Cohort | | | Dallas Heart Study | | | Penn Medicine Biobank | | |
| | | Beta (SE) | P | N | Beta (SE) | P | N | Beta (SE) | P | N |
| ALT | 1 | 0.005 (0.005) | 3.10E-01 | 2475 | 0.009 (0.008) | 2.58E-01 | 1356 | 0.006 (0.004) | 1.81E-01 | 6158 |
| | 4 | -0.010 (0.005) | 5.57E-02 | 2475 | -0.014 (0.008) | 9.68E-02 | 1356 | -0.012 (0.004) | 4.85E-03 | 6158 |
| | 8 | -0.492 (0.165) | 2.84E-03 | 2475 | NA (NA) | NA | NA | -0.054 (0.071) | 4.46E-01 | 6158 |
| | 8 | -0.161 (0.165) | 3.29E-01 | 2475 | NA (NA) | NA | NA | -0.259 (0.143) | 6.90E-02 | 6158 |
| | 8 | -0.089 (0.02) | 6.48E-01 | 2475 | 0.027 (0.035) | 4.48E-01 | 1355 | -0.051 (0.019) | 7.52E-03 | 6158 |
| | 8 | -0.189 (0.165) | 2.50E-01 | 2475 | NA (NA) | NA | NA | -0.305 (0.101) | 2.54E-03 | 6158 |
| | 8 | -0.341 (0.074) | 3.64E-06 | 2475 | NA (NA) | NA | NA | -0.144 (0.054) | 7.67E-03 | 6158 |
| | 8 | -0.089 (0.02) | 6.45E-01 | 2475 | 0.024 (0.035) | 5.01E-01 | 1356 | -0.059 (0.018) | 1.13E-03 | 6158 |
| | 8 | -0.314 (0.165) | 5.71E-02 | 2475 | -0.334 (0.137) | 1.49E-02 | 1355 | -0.151 (0.143) | 2.90E-01 | 6157 |
| | 8 | -0.273 (0.048) | 9.83E-09 | 2474 | -0.244 (0.073) | 8.91E-04 | 1356 | -0.188 (0.041) | 5.52E-06 | 6157 |
| | 8 | -0.115 (0.058) | 4.82E-02 | 2475 | -0.092 (0.097) | 3.43E-01 | 1355 | -0.042 (0.043) | 3.36E-01 | 6157 |
| | 8 | -0.273 (0.050) | 4.26E-08 | 2475 | -0.198 (0.068) | 3.90E-03 | 1356 | -0.188 (0.041) | 5.52E-06 | 6158 |
| | 8 | -0.161 (0.165) | 3.29E-01 | 2475 | NA (NA) | NA | NA | -0.506 (0.202) | 1.22E-02 | NA |
| | 8 | -0.161 (0.165) | 3.29E-01 | 2475 | NA (NA) | NA | NA | -0.303 (0.143) | 3.37E-02 | NA |
| | 9 | -0.004 (0.005) | 4.09E-01 | 2475 | 0.003 (0.008) | 6.46E-01 | 1356 | -0.007 (0.004) | 6.38E-02 | 6158 |

Gray shading indicates P-values meeting the Bonferroni significance threshold of $P < 1.43 \times 10^{-3}$.

* Replication meta-analysis includes the three replication cohorts: GHS Bariatric Surgery Cohort, Dallas Heart Study, and Penn Medicine Biobank

* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Dallas Heart Study | | | Penn Medicine Biobank | | |
|---|---|---|---|---|---|---|---|---|---|---|
| | | Beta (SE) | P | N | Beta (SE) | P | N | Beta (SE) | P | N |
| | 9 | -0.004 (0.005) | 3.90E-01 | 2475 | 0.002 (0.008) | 7.69E-01 | 1355 | -0.007 (0.004) | 5.29E-02 | 6158 |
| | 10 | -0.002 (0.010) | 8.01E-01 | 2475 | -0.003 (0.017) | 8.37E-01 | 1356 | -0.015 (0.007) | 4.49E-02 | 6158 |
| | 10 | -0.003 (0.010) | 7.74E-01 | 2475 | -0.005 (0.017) | 7.49E-01 | 1356 | -0.014 (0.007) | 4.86E-02 | 6158 |
| | 10 | -0.003 (0.010) | 7.93E-01 | 2475 | -0.005 (0.017) | 7.49E-01 | 1356 | -0.014 (0.007) | 5.02E-02 | 6158 |
| | 10 | -0.001 (0.010) | 9.11E-01 | 2475 | -0.008 (0.016) | 6.41E-01 | 1356 | -0.013 (0.007) | 7.46E-02 | 6158 |
| | 10 | -0.01 (0.005) | 2.91E-02 | 2475 | -0.006 (0.007) | 4.02E-01 | 1356 | -0.009 (0.004) | 2.06E-02 | 6158 |
| | 10 | -0.006 (0.005) | 2.05E-01 | 2475 | -0.001 (0.007) | 9.07E-01 | 1356 | -0.011 (0.004) | 5.26E-03 | 6158 |
| | 10 | -0.003 (0.005) | 5.80E-01 | 2475 | -0.014 (0.008) | 8.25E-02 | 1356 | -0.007 (0.004) | 7.45E-02 | 6158 |
| | 10 | -0.003 (0.005) | 5.61E-01 | 2475 | -0.014 (0.008) | 9.08E-02 | 1356 | -0.008 (0.004) | 6.34E-02 | 6158 |
| | 14 | 0.035 (0.020) | 7.97E-02 | 2475 | 0.044 (0.032) | 1.63E-01 | 1356 | 0.056 (0.013) | 1.38E-05 | 6158 |
| | 19 | 0.040 (0.010) | 2.40E-05 | 2475 | 0.025 (0.014) | 7.24E-02 | 1356 | 0.013 (0.008) | 1.07E-01 | 6158 |
| | 22 | 0.019 (0.006) | 5.54E-04 | 2475 | 0.005 (0.009) | 5.75E-01 | 1356 | 0.018 (0.005) | 5.51E-05 | 6158 |
| | 22 | 0.019 (0.006) | 5.51E-04 | 2475 | 0.005 (0.009) | 5.75E-01 | 1356 | 0.018 (0.005) | 5.78E-05 | 6158 |
| | 22 | 0.001 (0.005) | 7.77E-01 | 2475 | 0.004 (0.008) | 6.26E-01 | 1356 | 0.005 (0.004) | 2.00E-01 | 6158 |
| | 22 | 0.009 (0.006) | 1.66E-01 | 2475 | -0.002 (0.01) | 8.80E-01 | 1356 | 0.021 (0.005) | 5.29E-05 | 6158 |
| | 22 | 0.003 (0.005) | 5.22E-01 | 2475 | 0.007 (0.008) | 3.31E-01 | 1356 | 0.008 (0.004) | 3.82E-02 | 6158 |

Gray shading indicates P-values meeting the Bonferroni significance threshold of $P < 1.43 \times 10^{-3}$

* Replication meta-analysis includes the three replication cohorts: GHS Bariatric Surgery Cohort, Dallas Heart Study, and Penn Medicine Biobank † Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| ALT | 1 | 0.006 (0.003) | 4.77E-02 | 0.007 (0.001) | 6.91E-09 |
| | 4 | -0.012 (0.003) | 1.67E-04 | -0.010 (0.001) | 3.85E-15 |
| | 8 | -0.124 (0.066) | 5.92E-02 | -0.155 (0.024) | 2.41E-10 |
| | 8 | -0.259 (0.143) | 6.90E-02 | -0.264 (0.03) | 4.65E-18 |
| | 8 | -0.024 (0.013) | 6.89E-02 | -0.032 (0.005) | 3.36E-12 |
| | 8 | -0.305 (0.101) | 2.54E-03 | -0.308 (0.033) | 2.21E-20 |
| | 8 | -0.213 (0.044) | 1.01E-06 | -0.223 (0.013) | 4.00E-64 |
| | 8 | -0.029 (0.013) | 2.09E-02 | -0.032 (0.005) | 2.89E-12 |
| | 8 | -0.264 (0.085) | 1.84E-03 | -0.238 (0.029) | 1.35E-16 |
| | 8 | -0.227 (0.029) | 2.39E-15 | -0.224 (0.012) | 1.94E-77 |
| | 8 | -0.070 (0.033) | 3.12E-02 | -0.076 (0.012) | 1.12E-10 |
| | 8 | -0.218 (0.029) | 3.94E-14 | -0.224 (0.012) | 2.92E-77 |
| | 8 | -0.506 (0.202) | 1.22E-02 | -0.272 (0.030) | 6.42E-20 |
| | 8 | -0.303 (0.143) | 3.37E-02 | -0.189 (0.027) | 2.99E-12 |
| | 9 | -0.005 (0.003) | 9.79E-02 | -0.007 (0.001) | 3.57E-09 |

Gray shading indicates P-values meeting the Bonferroni significance threshold of P < 1.43x10-3
* Replication meta-analysis includes the three replication cohorts: GHS Bariatric Sugery Cohort, Dallas Heart Study, and Penn Medicine Biobank
* Joint meta-analysis includes the discovery cohort and the three replication cohorts: GHS Discovery Cohort, GHS Bariatric Sugery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| | 9 | -0.005 (0.003) | 7.27E-02 | -0.007 (0.001) | 1.19E-09 |
| | 10 | -0.01 (0.006) | 8.55E-02 | -0.014 (0.002) | 9.49E-09 |
| | 10 | -0.01 (0.006) | 7.96E-02 | -0.014 (0.002) | 8.03E-09 |
| | 10 | -0.01 (0.006) | 8.38E-02 | -0.014 (0.002) | 8.70E-09 |
| | 10 | -0.009 (0.006) | 1.19E-01 | -0.014 (0.002) | 1.07E-08 |
| | 10 | -0.009 (0.003) | 1.14E-03 | -0.011 (0.001) | 1.76E-23 |
| | 10 | -0.008 (0.003) | 5.11E-03 | -0.009 (0.001) | 4.17E-15 |
| | 10 | -0.007 (0.003) | 2.44E-02 | -0.008 (0.001) | 3.82E-11 |
| | 10 | -0.007 (0.003) | 2.13E-02 | -0.008 (0.001) | 1.85E-11 |
| | 14 | 0.049 (0.010) | 1.51E-06 | 0.044 (0.004) | 9.55E-26 |
| | 19 | 0.024 (0.006) | 1.58E-05 | 0.016 (0.002) | 1.35E-12 |
| | 22 | 0.017 (0.003) | 2.60E-07 | 0.022 (0.001) | 7.75E-56 |
| | 22 | 0.017 (0.003) | 2.71E-07 | 0.022 (0.001) | 6.77E-56 |
| | 22 | 0.004 (0.003) | 2.03E-01 | 0.006 (0.001) | 6.49E-08 |
| | 22 | 0.014 (0.004) | 2.57E-04 | 0.018 (0.002) | 2.36E-32 |
| | 22 | 0.006 (0.003) | 2.63E-02 | 0.01 (0.001) | 1.83E-16 |

Gray shading indicates P-values meeting the Bonferroni significance threshold of $P < 1.43 \times 10^{-3}$

* Replication meta-analysis includes the three replication cohorts: GHS Bariatric Sugery Cohort, Dallas Heart Study, and Penn Medicine Biobank

** Joint meta-analysis includes the discovery cohort and the three replication cohorts: GHS Discovery Cohort, GHS Bariatric Sugery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Replication Cohorts Dallas Heart Study | | | Penn Medicine Biobank | | |
|---|---|---|---|---|---|---|---|---|---|---|
| | | Beta (SE) | P | N | Beta (SE) | P | N | Beta (SE) | P | N |
| AST | 4 | -0.010 (0.003) | 3.12E-03 | 2469 | -0.012 (0.006) | 5.87E-02 | 1356 | -0.006 (0.004) | 1.02E-01 | 6166 |
| | 10 | -0.010 (0.003) | 2.91E-03 | 2469 | -0.003 (0.006) | 6.25E-01 | 1356 | -0.010 (0.004) | 6.75E-03 | 6166 |
| | 10 | -0.205 (0.062) | 8.57E-04 | 2469 | NA (NA) | NA | NA | -0.244 (0.089) | 5.90E-03 | 6165 |
| | 10 | NA (NA) | NA | 2469 | NA (NA) | NA | NA | 0.339 (0.079) | 1.85E-05 | 6166 |
| | 10 | -0.004 (0.003) | 1.54E-01 | 2469 | -0.007 (0.006) | 2.18E-01 | 1356 | -0.003 (0.003) | 3.13E-01 | 6166 |
| | 11 | -0.001 (0.003) | 7.85E-01 | 2466 | 0.006 (0.006) | 2.80E-01 | 1356 | -0.003 (0.003) | 3.54E-01 | 6165 |
| | 14 | 0.023 (0.013) | 7.79E-02 | 2469 | 0.046 (0.024) | 6.09E-02 | 1356 | 0.052 (0.011) | 4.75E-06 | 6166 |
| | 19 | 0.023 (0.006) | 1.99E-04 | 2469 | 0.010 (0.011) | 3.42E-01 | 1356 | 0.004 (0.007) | 5.94E-01 | 6166 |
| | 22 | 0.014 (0.004) | 1.27E-04 | 2469 | 0.004 (0.007) | 5.53E-01 | 1356 | 0.017 (0.004) | 1.16E-05 | 6166 |
| | 22 | 0.014 (0.004) | 1.32E-04 | 2469 | 0.004 (0.007) | 5.53E-01 | 1356 | 0.017 (0.004) | 1.17E-05 | 6166 |
| | 22 | 0.008 (0.004) | 6.03E-02 | 2469 | -0.001 (0.008) | 9.33E-01 | 1356 | 0.018 (0.005) | 6.47E-05 | 6166 |
| | 22 | 0.003 (0.003) | 4.12E-01 | 2469 | 0.006 (0.006) | 3.03E-01 | 1356 | 0.009 (0.003) | 1.37E-02 | 6166 |

Gray shading indicates P-values meeting the Bonferroni significance threshold of $P < 1.43 \times 10^{-3}$

* Replication meta-analysis includes the three replication cohorts: GHS Bariatric Sugery Cohort, Dallas Heart Study, and Penn Medicine Biobank

* Joint meta-analysis includes the discovery cohort and the three replication cohorts: GHS Discovery Cohort, GHS Bariatric Sugery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| AST | 4 | -0.009 (0.002) | 1.69E-04 | -0.006 (0.001) | 1.13E-12 |
| | 10 | -0.009 (0.002) | 8.86E-05 | -0.006 (0.001) | 9.66E-14 |
| | 10 | -0.205 (0.062) | 8.57E-04 | -0.220 (0.022) | 1.66E-24 |
| | 10 | 0.339 (0.079) | 1.85E-05 | 0.271 (0.027) | 2.43E-24 |
| | 10 | -0.004 (0.002) | 3.92E-02 | -0.005 (0.001) | 5.52E-10 |
| | 11 | -0.001 (0.002) | 7.03E-01 | 0.004 (0.001) | 1.48E-06 |
| | 14 | 0.040 (0.008) | 6.56E-07 | 0.029 (0.003) | 2.78E-25 |
| | 19 | 0.014 (0.004) | 1.20E-03 | 0.009 (0.002) | 5.92E-10 |
| | 22 | 0.014 (0.002) | 2.00E-08 | 0.014 (0.001) | 1.12E-52 |
| | 22 | 0.014 (0.002) | 2.10E-08 | 0.014 (0.001) | 1.26E-52 |
| | 22 | 0.011 (0.003) | 1.77E-04 | 0.011 (0.001) | 1.01E-25 |
| | 22 | 0.005 (0.002) | 1.34E-02 | 0.006 (0.001) | 6.61E-15 |

Gray shading indicates P-values meeting the Bonferroni significance threshold of $P < 1.43 \times 10^{-3}$.
* Replication meta-analysis includes the three replication cohorts: GHS Bariatric Surgery Cohort, Dallas Heart Study, and Penn Medicine Biobank
* Joint meta-analysis includes the discovery cohort and the three replication cohorts: GHS Discovery Cohort, GHS Bariatric Surgery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| CHR:BP:Ref:Alt | Gene | rsID | Alcoholic liver disease | | Alcoholic cirrhosis | |
|---|---|---|---|---|---|---|
| | | | OR (95% CI) | P | OR (95% CI) | P |
| 4:88231392:TT:A | HSD17B13 | rs72613567 | 0.62 (0.48-0.81) | 1.82E-04 | 0.56 (0.41-0.78) | 3.35E-04 |
| 8:145730161:C:T | GPT | rs201815297 | 3.83 (1.05-13.94) | 8.88E-02 | 6.33 (1.71-23.43) | 2.88E-02 |
| 8:145732114:G:C | GPT | rs141505249 | 0.77 (0.06-10.73) | 8.43E-01 | 1.13 (0.08-15.39) | 9.30E-01 |
| 8:145732180:G:C | GPT | rs147998249 | 0.73 (0.05-11.76) | 8.17E-01 | 1.07 (0.07-17.16) | 9.60E-01 |
| 10:18242311:A:G | SLC39A12 | rs10764176 | 0.85 (0.68-1.07) | 1.64E-01 | 0.92 (0.70-1.22) | 5.80E-01 |
| 10:101157378:CGTT:C | GOT1 | | 4.60 (0.25-86.41) | 3.93E-01 | 7.11 (0.38-133.19) | 3.00E-01 |
| 10:101165533:G:C | GOT1 | rs374966349 | 2.20 (0.13-37.68) | 6.24E-01 | 3.47 (0.20 - 59.04) | 4.70E-01 |
| 10:101912064:T:C | ERLIN1 | rs2862954 | 0.92 (0.75-1.12) | 4.05E-01 | 1.05 (0.82-1.34) | 7.13E-01 |
| 14:94844947:C:T | SERPINA1 | rs28929474 | 2.49 (1.49-4.17) | 2.30E-03 | 3.35 (1.93-5.83) | 3.01E-04 |
| 19:19379549:C:T | TM6SF2 | rs58542926 | 1.47 (1.06-2.04) | 2.76E-02 | 1.35 (0.89-2.04) | 1.80E-01 |
| 22:44324727:C:G | PNPLA3 | rs738409 | 1.76 (1.43-2.18) | 4.98E-07 | 2.07 (1.60-2.67) | 1.08E-07 |
| 22:44324730:C:T | PNPLA3 | rs738408 | 1.77 (1.43-2.18) | 4.70E-07 | 2.07 (1.61-2.67) | 1.03E-07 |
| 22:44368122:A:G | SAMM50 | rs3761472 | 1.90 (1.52-2.38) | 1.36E-07 | 2.28 (1.75-2.98) | 1.83E-08 |

Gray shading indicates P-values meeting the Bonferroni significance threshold of $P < 1.92 \times 10^{-3}$

Figure 4

| CHR:BP:Ref:Alt | Gene | rsID | Nonalcoholic liver disease | | Nonalcoholic cirrhosis | | Hepatocellular carcinoma | |
|---|---|---|---|---|---|---|---|---|
| | | | OR (95% CI) | P | OR (95% CI) | P | OR (95% CI) | P |
| 4:88231392:T:A | HSD17B13 | rs72613567 | 0.84 (0.78-0.91) | 1.31E-05 | 0.74 (0.62-0.88) | 4.48E-04 | 0.67 (0.45-1.00) | 4.66E-02 |
| 8:145730161:C:T | GPT | rs201815297 | 0.23 (0.04-1.14) | 1.86E-02 | 1.25 (0.24-6.38) | 7.98E-01 | 3.66 (0.70-19.01) | 2.01E-01 |
| 8:145732114:G:C | GPT | rs141505249 | 1.02 (0.49-2.11) | 9.70E-01 | 0.36 (0.02-5.37) | 3.82E-01 | 1.84 (0.15-23.25) | 6.88E-01 |
| 8:145732180:G:C | GPT | rs147998249 | 1.03 (0.49-2.17) | 9.30E-01 | 0.34 (0.02-5.59) | 3.67E-01 | 1.74 (0.11-27.05) | 7.21E-01 |
| 10:18242311:A:G | SLC39A12 | rs10764176 | 0.92 (0.86-0.99) | 3.43E-02 | 1.03 (0.88-1.21) | 7.15E-01 | 1.29 (0.93-1.79) | 1.37E-01 |
| 10:101157378:CGTT:C | GOT1 | | 2.37 (0.61-9.27) | 2.50E-01 | 8.27 (1.44-47.49) | 5.92E-02 | 9.81 (0.52-183.54) | 2.43E-01 |
| 10:101165533:G:C | GOT1 | rs374966349 | 1.63 (0.53-4.96) | 4.20E-01 | 1.17 (0.07-20.09) | 9.13E-01 | 5.37 (0.32-91.12) | 3.55E-01 |
| 10:101912064:T:C | ERLIN1 | rs2862954 | 0.98 (0.91-1.04) | 4.61E-01 | 1.13 (0.98-1.31) | 9.90E-02 | 0.94 (0.69-1.28) | 6.94E-01 |
| 14:94844947:C:T | SERPINA1 | rs28929474 | 1.50 (1.21-1.87) | 5.29E-04 | 2.99 (2.11-4.24) | 9.08E-08 | 1.86 (0.74-4.67) | 2.40E-01 |
| 19:19379549:C:T | TM6SF2 | rs58542926 | 1.36 (1.21-1.52) | 2.42E-07 | 1.64 (1.31-2.05) | 6.04E-05 | 1.93 (1.22-3.04) | 1.08E-02 |
| 22:44324727:C:G | PNPLA3 | rs738409 | 1.65 (1.54-1.78) | 1.31E-41 | 2.05 (1.76-2.38) | 1.70E-19 | 2.20 (1.60-3.02) | 5.59E-06 |
| 22:44324730:C:T | PNPLA3 | rs738408 | 1.65 (1.54-1.78) | 1.42E-41 | 2.05 (1.77-2.38) | 1.45E-19 | 2.20 (1.60-3.03) | 5.41E-06 |
| 22:44368122:A:G | SAMM50 | rs3761472 | 1.52 (1.41-1.65) | 7.33E-24 | 1.86 (1.58-2.19) | 1.81E-12 | 1.66 (1.16-2.39) | 1.05E-02 |

Gray shading indicates P-values meeting the Bonferroni significance threshold of $P < 1.92 \times 10^{-3}$

Figure 4 (cont.)

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Age (years) – median (IQR) | 55 (48 - 60) | 44 (36 - 53) | 12 (10 - 15) | 12 (11 - 14) |
| Female sex – number (%) | 277 (54) | 2,494 (58) | 65 (32) | 126 (52) |
| Body mass index – median (IQR) | 30 (27 - 35) | 30 (26 - 35) | 30 (27 - 34) | 31 (28 - 35) |
| Self-reported ethnicity | | | | |
| African American | 33 (6) | 2,291 (54) | - | - |
| European American | 158 (31) | 1,266 (30) | - | - |
| Hispanic American | 326 (63) | 722 (17) | 203 (100) | 244 (100) |
| Presence of liver disease – N (%) | | | | |
| Alcoholic liver disease | 223 (43) | - | - | - |
| Alcoholic cirrhosis | 215 (42) | - | - | - |
| Nonalcoholic (non-viral) liver disease | 212 (20) | - | - | - |
| Nonalcoholic cirrhosis | 100 (19) | - | - | - |
| Hepatocellular carcinoma | 44 (9) | - | - | - |
| No liver disease | - | 4,279 (100) | - | 244 (100) |

Figure 5

| Phenotype/Subset | | | HSD17B13 rs72613567 [Interaction effect] | | | HSD17B13 rs72613567 [Main effect] | | | PNPLA3 rs738409 [Main effect] | | |
|---|---|---|---|---|---|---|---|---|---|---|---|
| | | | Effect (95% CI) | p | AAF | Effect (95% CI) | p | AAF | Effect (95% CI) | p |
| log₁₀(ALT) | | | | | | | | | | | |
| Subset | N | | Effect (95% CI) | p | AAF | Effect (95% CI) | p | AAF | Effect (95% CI) | p |
| All | 43,309 | | -0.007 (-0.011,-0.002) | 1.80E-03 | 26.36% | -0.006 (-0.009,-0.003) | 1.88E-04 | 23.54% | 0.026 (0.022,0.029) | 1.97E-50 |
| Obese | 23,051 | | -0.01 (-0.015,-0.004) | 1.01E-03 | 26.48% | -0.009 (-0.013,-0.005) | 6.53E-05 | 23.57% | 0.037 (0.032,0.042) | 3.13E-55 |
| Non-obese | 20,258 | | -0.004 (-0.01,0.002) | 1.49E-01 | 26.22% | -0.002 (-0.007,0.002) | 3.53E-01 | 23.51% | 0.013 (0.008,0.018) | 1.56E-07 |
| log₁₀(AST) | | | | | | | | | | | |
| Subset | N | | Effect (95% CI) | p | AAF | Effect (95% CI) | p | AAF | Effect (95% CI) | p |
| All | 42,662 | | -0.004 (-0.007,-0.001) | 4.53E-03 | 26.40% | -0.004 (-0.006,-0.002) | 4.78E-04 | 23.47% | 0.016 (0.014,0.018) | 9.69E-46 |
| Obese | 22,719 | | -0.006 (-0.01,-0.003) | 1.04E-03 | 26.51% | -0.006 (-0.009,-0.003) | 1.42E-04 | 23.53% | 0.023 (0.02,0.027) | 7.65E-49 |
| Non-obese | 19,943 | | -0.001 (-0.005,0.003) | 4.97E-01 | 26.26% | -0.001 (-0.004,0.002) | 3.42E-01 | 23.41% | 0.008 (0.005,0.011) | 1.56E-06 |
| Nonalcoholic liver disease | | | | | | | | | | | |
| Subset | N Controls | N Cases | OR (95% CI) | p | AAF | OR (95% CI) | p | AAF | OR (95% CI) | p |
| All | 29,928 | 1,857 | 0.919 (0.812,1.039) | 1.78E-01 | 26.43% | 0.88 (0.787,0.983) | 2.40E-02 | 23.51% | 1.764 (1.606,1.938) | 1.76E-32 |
| Obese | 14,243 | 1,445 | 0.906 (0.786,1.044) | 1.74E-01 | 26.36% | 0.894 (0.788,1.012) | 7.81E-02 | 23.65% | 1.714 (1.537,1.91) | 2.06E-22 |
| Non-obese | 15,685 | 412 | 0.964 (0.75,1.239) | 7.71E-01 | 26.50% | 0.845 (0.662,1.069) | 1.67E-01 | 23.38% | 1.887 (1.566,2.269) | 1.96E-11 |
| Alcoholic liver disease | | | | | | | | | | | |
| Subset | N Controls | N Cases | OR (95% CI) | p | AAF | OR (95% CI) | p | AAF | OR (95% CI) | p |
| All | 29,928 | 190 | 1.112 (0.749,1.637) | 5.94E-01 | 26.57% | 0.578 (0.391,0.834) | 4.56E-03 | 22.99% | 1.689 (1.298,2.185) | 7.80E-05 |
| Obese | 14,243 | 97 | 1.295 (0.741,2.224) | 3.56E-01 | 26.53% | 0.501 (0.283,0.839) | 1.22E-02 | 22.83% | 1.533 (1.052,2.201) | 2.30E-02 |
| Non-obese | 15,685 | 93 | 0.956 (0.544,1.65) | 8.72E-01 | 26.55% | 0.666 (0.382,1.105) | 1.33E-01 | 23.13% | 1.853 (1.275,2.664) | 1.00E-03 |

Figure 9

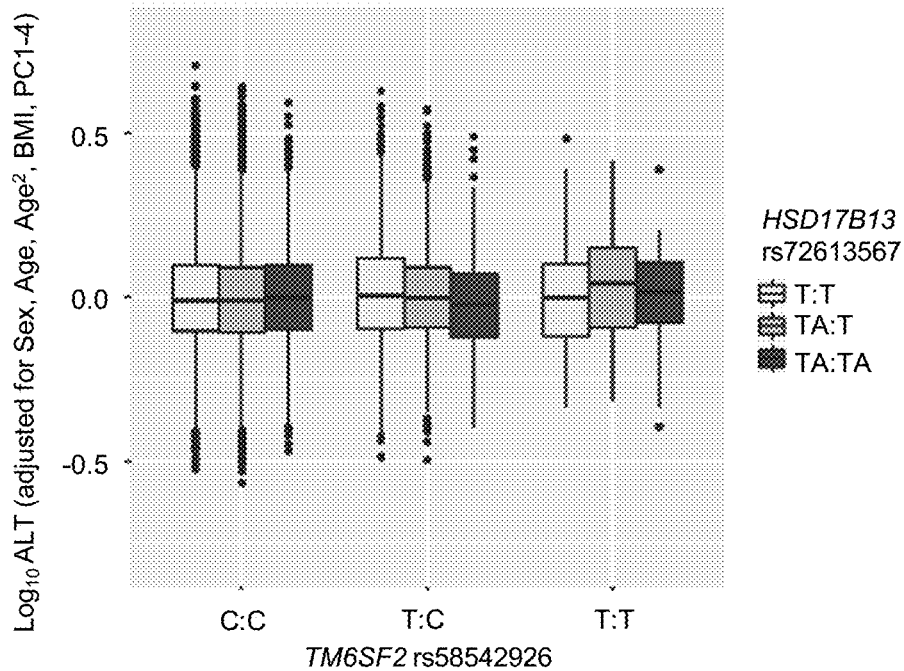
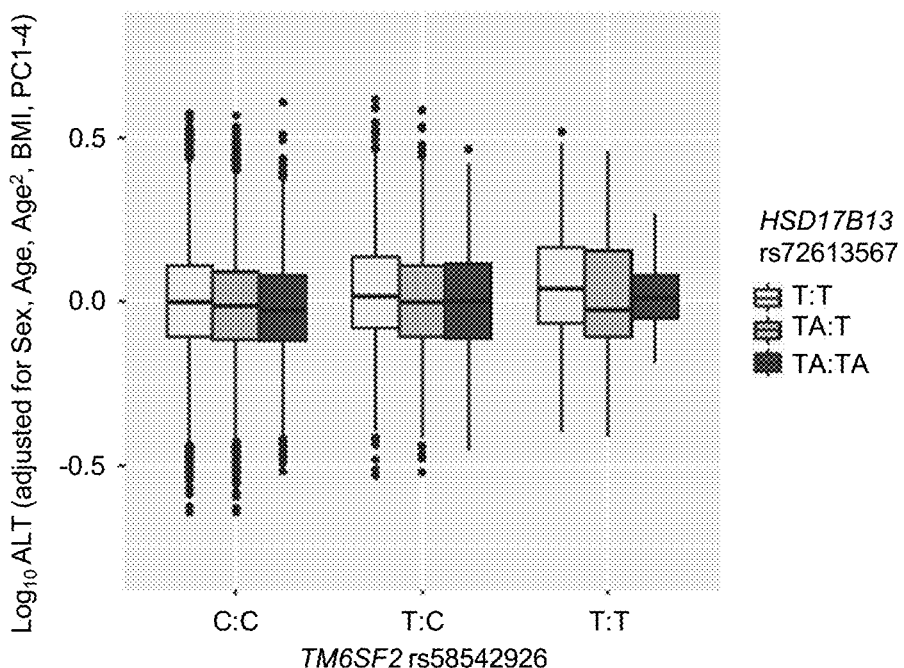
Figure 11 (cont.)

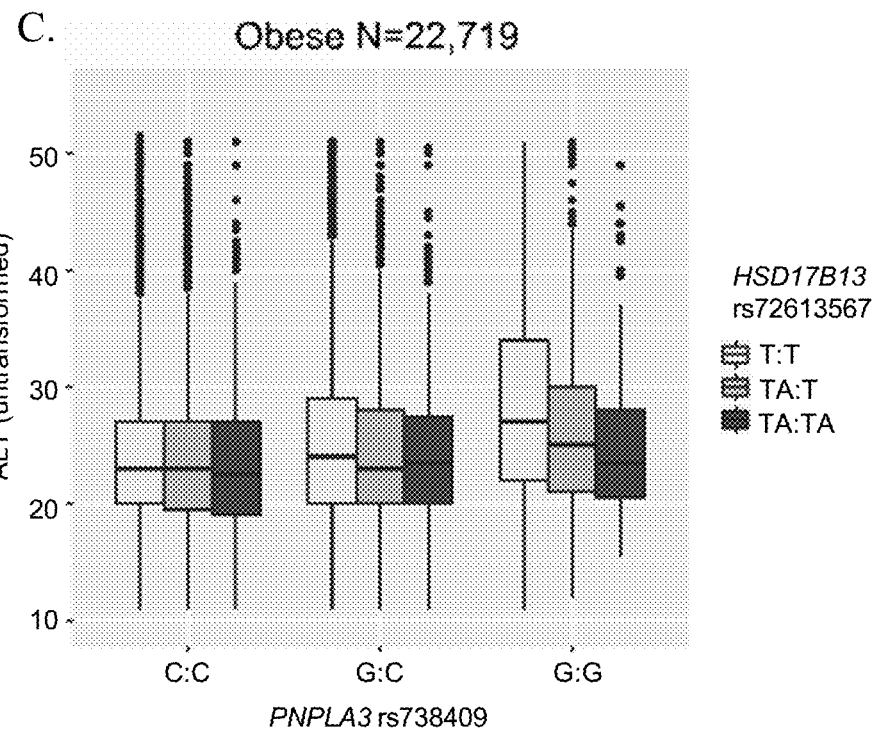
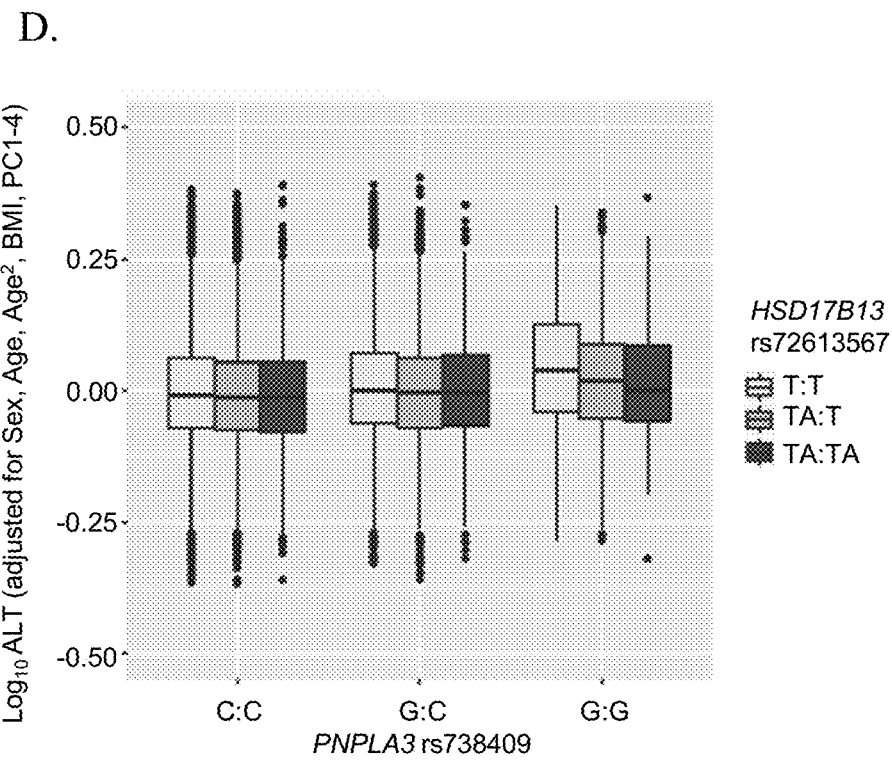
Figure 12 (cont.)

E.
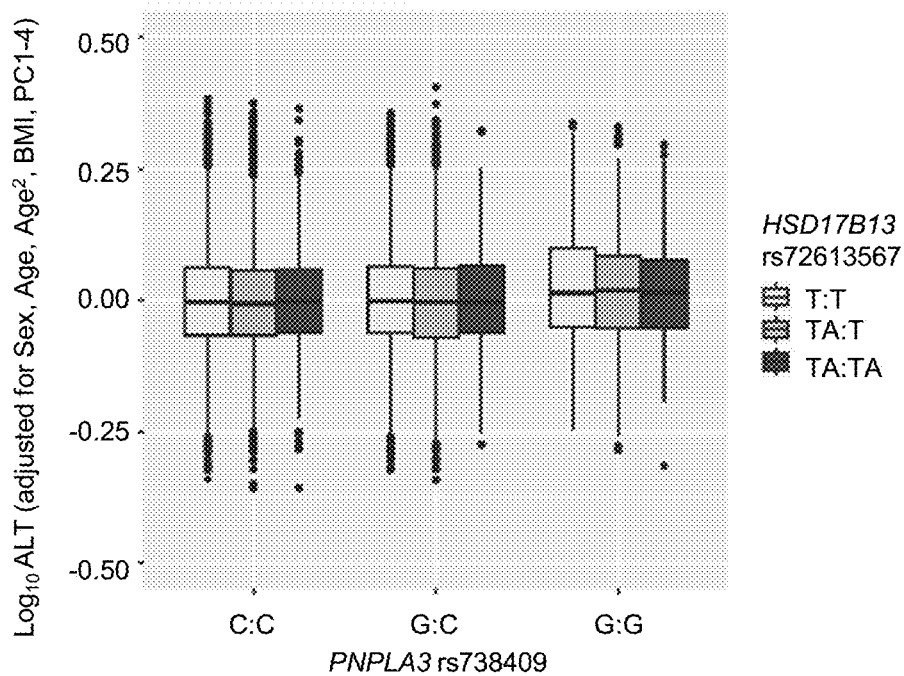
F.
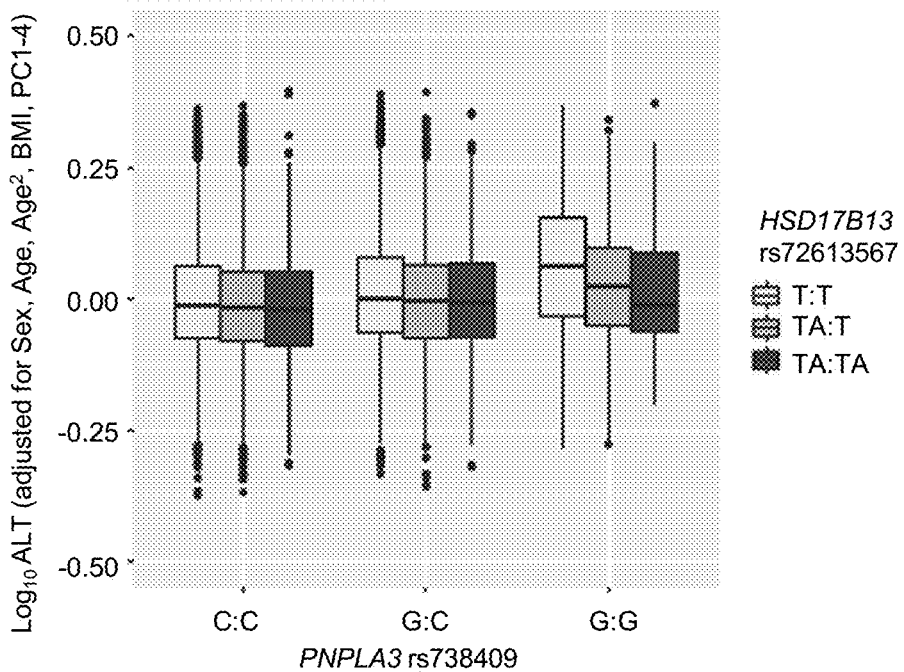
Figure 12 (cont.)

C.
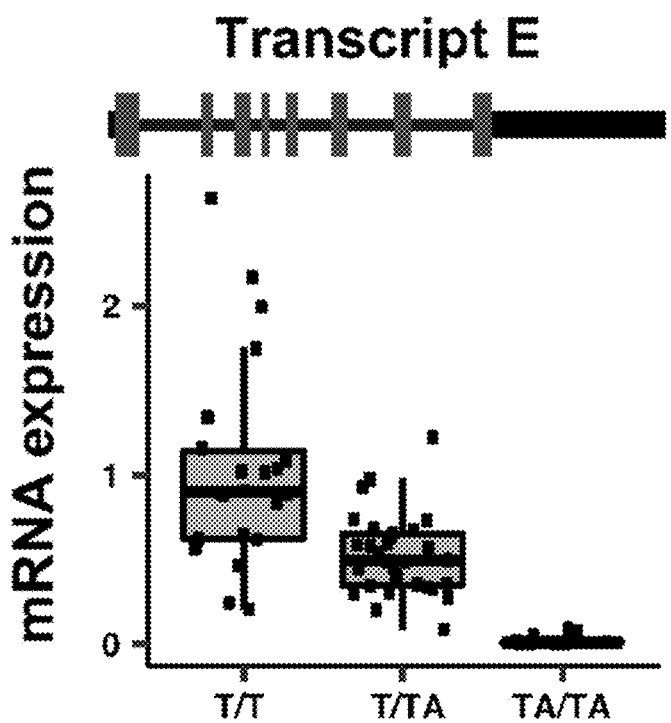
D.
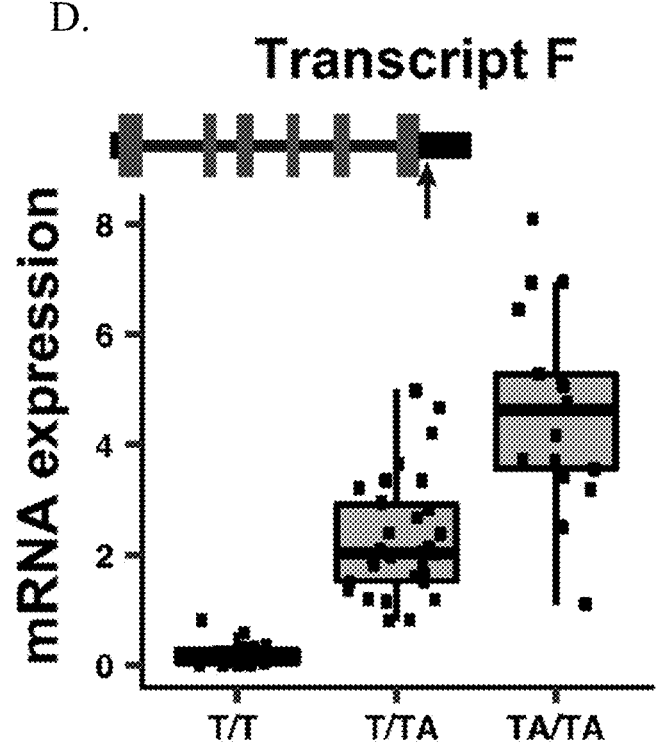
Figure 13 (cont.)

E.
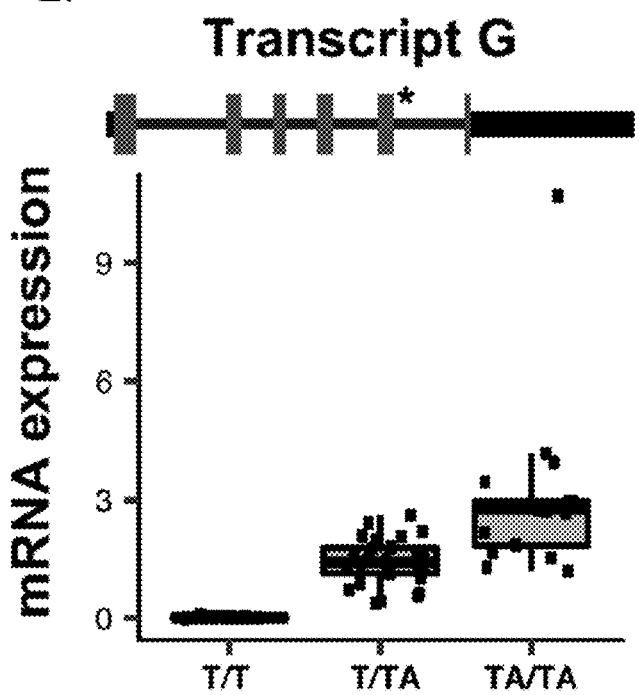
F.
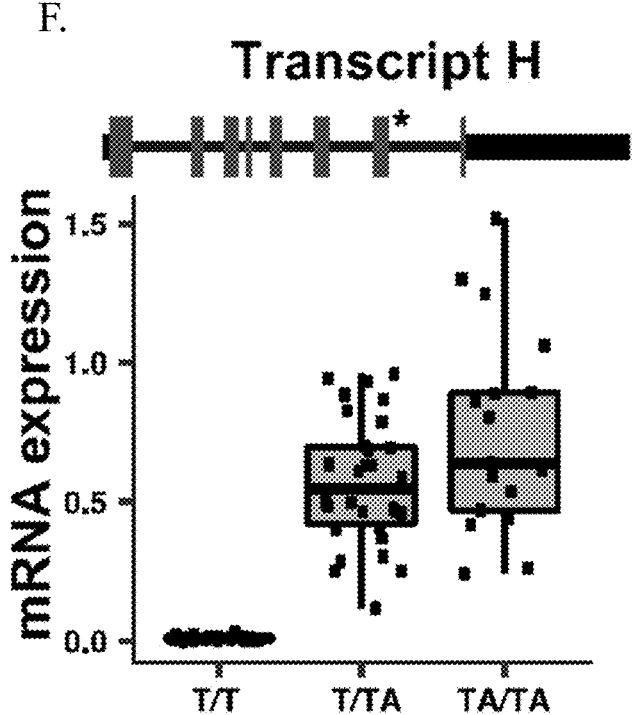
Figure 13 (cont.)

A.
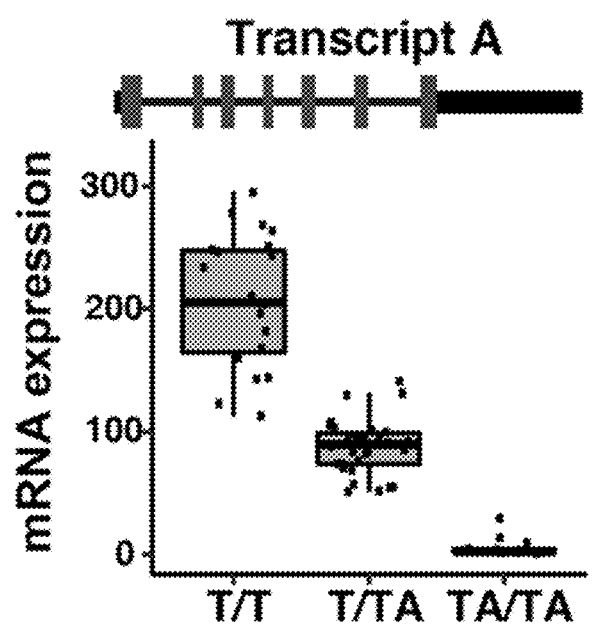
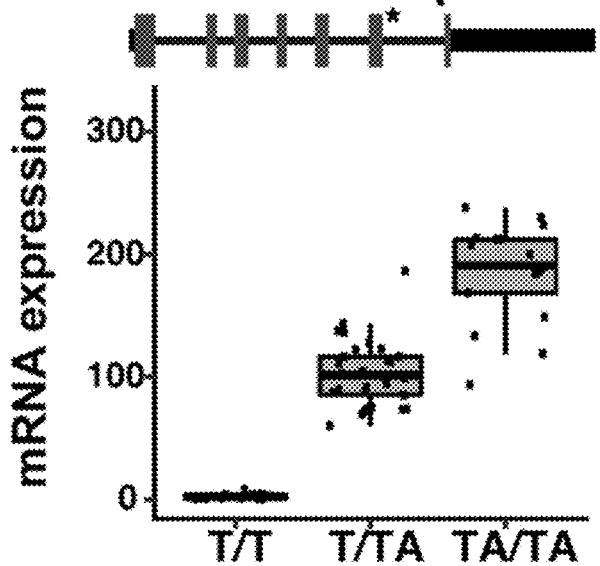
Figure 18

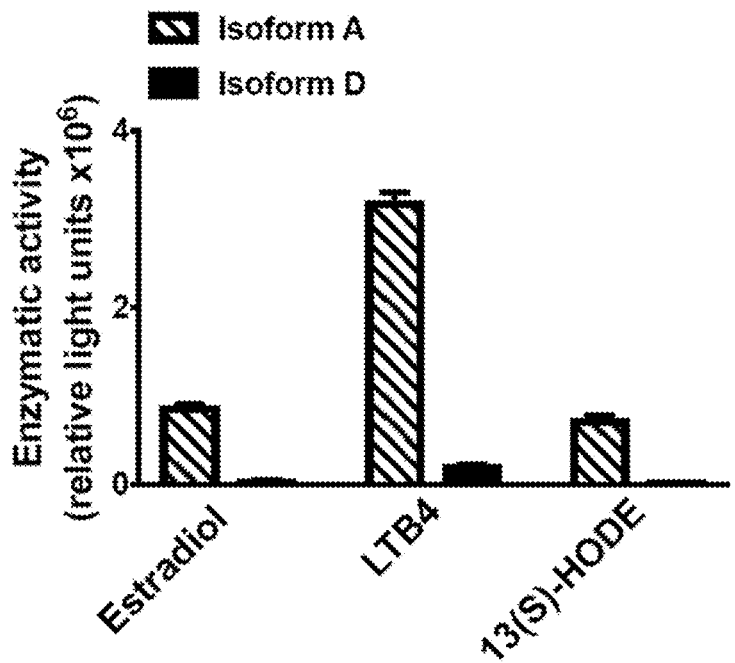
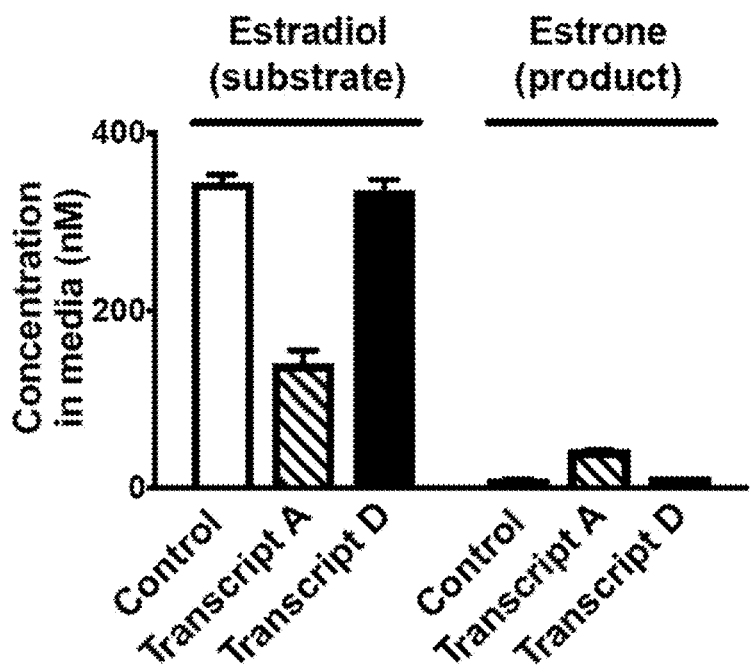
Figure 18 (cont.)

SEQUENCE LISTING

<160> NUMBER OF SEQ ID NOS: 66

<210> SEQ ID NO 1
<211> LENGTH: 19118
<212> TYPE: DNA
<213> ORGANISM: Homo sapien

<400> SEQUENCE: 1

```
agacagtacc tcctccctag gactacacaa ggactgaacc agaaggaaga ggacagagca        60
aagccatgaa catcatccta gaaatccttc tgcttctgat caccatcatc tactcctact       120
```

```
tggagtcgtt ggtgaagttt ttcattcctc agaggagaaa atctgtggct ggggagattg      180
ttctcattac tggagctggg catggaatag gcaggcagac tacttatgaa tttgcaaaac      240
gacagagcat attggttctg tgggatatta ataaggtaat gtatacatct tccaactttt      300
taaagtcaca gagtaagata tgtattttaa gaattatttg acttaccatc tacttatctt      360
tgtatttttg tttttcaaag tttgataaat tccctggtcc cttagtctgt atatgtgtca      420
ggttagttag atgaagggaa tgtaattaag aactaagcag cgattttat gacatggtgt        480 gcaggttgat agaaagactc aggagccagt ctccttccaa gctgctaaat gaggcaagtc      540
acatattatc tctcagcctg ttttcttggc tctgaagtgg ggataataac ttaggggatg      600
ggcaagaacg ggatctgaaa attacagcta caaacaaaag tcaaacgaag aacttgcaac      660
agaaaccttt agtgcctccc ctcatgcaca agcaacacag ttctaaaata tttactgtct      720 gacccttac agaaaatgtt tgccagtccg tagtcaaaag gattaaataa gtaatatttt        780
cagcacttag catatgataa acgatacgtg gcacatgata aacaataact gtgttaaata      840
aaatatgtgc gcagtgagtc aggcttttcc ttggacatta gtatttttcc tgtgttctta      900
cttgtaaaca ctacattaac aaccccaaat aaaactgaag gaactgaaat cttgtatcat      960
tttctctaaa cttgtaaatt ctggtaaggc catgaaaata tatgcagaga agtgtttaca      1020 ggatttagg attggaaaaa ttgtgaagta ctccttgaga atcacatttt ctgcaaatta       1080
cagtggtttt aattaccatt atattattac tttctcatgt tctttgctgt catgtttagt      1140
tgaaacctaa aatgtctctt acacttagag aactaattct tttctgtttt ttttctgaat      1200
agtgaagaat actatacaaa aaagctacta cattttatt taacagatat gagcatttat        1260
ataatagagg agttgatgta tataaaaatg atttgccatc tttttggtct ttgaagaaat      1320
tcgaatgaac tttctggaag atagcaagaa tttacaaata gagaaaattg ttgcctgctg      1380
ttctcaggca tttgtccaaa aatataaata agtataaatc tatgaaaagg gcttgatgaa      1440 atctaaccttt caaatctctt tccagatgtg tattttggg gaaagggcta tatttattaa       1500 gttttttta aattttaaaa tttccagaga caagagaaaa gtaaattaga aggaagtcgt       1560
attaaaaatg acttaagggc gggtgcagtg gctcacacct gtaatcccag cactttggga      1620
gacggaggtg ggcagattgc tggagcccag gagttcaaga ccagcctggg cagcacagca      1680 aaaccccccaa ctctacaaaa aatacaaaaa ttagctgggt gcggggtgc acacccgtag       1740 tcccagctac tcgggaggct gaggtgggag gatcgtttca gttcaggaag ccaaggctgc      1800
aatgagctat gatggcatca ttgcactcca agctgggcaa tagagccagg ctctgtctca      1860
aaaaaaataa aaaagactt aagaaaaata ggtaacccaa cctcaaaaat tctctttgaa        1920
tcattaaatt tcatggttaa acatttaagc tactgaatga ttcactctaa ggctgtaatg      1980
taactcagat ctcctttagg cgaggaagat gctggctgag ttttcatcat aactggctcc      2040
ttttgccctg tgagatgaga gacacagtag cagtttggct cttatgcaat ctaaactgtt      2100
gcgttgggaa tacggttcaa aaaacacatt ggagtttaag ctaaagcaag tgttttgcta      2160
acaaaaagac aaggcatcac atttgcaat tgtctagctc agttataaaa cagaagaata       2220
ggccggacgc ggtggctcac gcctgtaatc ccagcacttt gggaggccga gacgggcgga      2280
tcacgaggtc aggagatcga gaccatcctg gataacacag tgaaaccccg tctctactaa      2340
aaatacaaaa aaattagcca ggcgtagtgg cgggcgcctg tagtcccagc tactcgggag      2400
gctgaggcag gagaatggtg tgaacccggg aggcggagct tgcagtgagc cgagatgacg      2460
ccactgcact ccagcctggg cgacagagcg agactccgtc tcaaaaaaaa aaaaaaaaaa      2520
```

```
aaaactgaag aataattaat tcttcaatca aaacatctga tgaatgctct ggtaacttat    2580
gctctctact gacctagaaa caaatgagag agtatggtgt ggtttgtgca atctggcagt    2640
gagcaagcta ccaactaaat cagtgaaaga ctctcctatt cttttttac tcttctgcaa     2700 tcccacaaaa ggctatttga ggggatactg actttgagac tgggtcctaa catccatgtt    2760
tggggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000
tgaaaacttg aaaagaatta taattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
agaatcatca agaaaaatat gatgggcaga ggcatacagt ttaccattac cactagttta    3360
gaattactac ttagcacttt actgcctatt acatagttgg tgctcaacaa atgtatgata    3420
aattaatggt tgagttttc tttcttctcc atattcatct tccatgacac cacgaagagc    3480 aatgttttc aagaatgttc ttcaaggttt gaaagtagcc tgctttagag aaactgccta    3540
ctgtacagcc tccaaccaag aggaaaaagct gaaaaaagca tgaagggatt ttgttttgtt    3600
ttgtttgttt tggttttaat atgagcattc cctggcagaa aagccagggg taatctcatt    3660
gcaactaggc aatcactctc aagaaatttt ctaacaaata aggaggccaa tttttatttt    3720
attttgagac gaagtcccac tctgtcaccc aggttggagt gcaatggaat gatttcagct    3780
cactgcaacc tccgcctccc gggttcaagt gattctcctg tctaaacttc ccgagtagct    3840
gggattacag gctcccacca ccacgcccag ctaatttttt gtatttttag tagagatggg    3900
gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aaatgaatgt taattgttca ttttggacat    4080
gaatgttaat tttttttttt ttttttttg agacagagtc tcactctgtt gcccaggctg    4140
gagtccagtg gcactatctc cactcactgc aacttcctcc tcccaggttc aagcaattat    4200
cctgcctcag cctcccaagt agctgggatt acagcccac accatcaggc ctggctaatt    4260 tttgtattttt tagtagagac ggggtttcac catgttggcc aggctggtct gaactcctg    4320 acctcgtgat ccgcctcct cggccaacca aagtgctggg attacaggcg tgagccaccg    4380
cgcctagccg aatgttaatt gtctaaaaat ttttcttctc caatgtcttc tcctccactt    4440
ttttcggaat tgtttcttc ctaattacag cgcggtgtgg aggaaactgc agctgagtgc    4500
cgaaaactag gcgtcactgc gcatgcgtat gtggtagact gcagcaacag agaagagatc    4560
tatcgctctc taaatcaggt gagactgcag gttcacaaat tcttcagat tattttgttt    4620 cctaggacgc tgacgtggaa aatgagaaag gtctttatga ctgcctgatt taaattggat    4680
tttagctgct aactgaagta gttatgtcac caaggaagga tatatacttt ttttcttgta    4740
tgtaatccac tcagctctgc ccattattat tgttcatatt attaatcaat tcattctga    4800 tcagaagtgt gagcagtggc acagagtgac tgacaaaaga tttatcatca gggaatatgg    4860
```

```
atcacttcct agttttgttt tagtcctatt aactttgcag taattccagc ttctctttaa    4920
ttatttccct tgtgagattt tattttggtg ttaatgtagt cttctgtaga aaatgtaata    4980
ttaataatta ttatcacaat tattttaaaa gagtaaatac caaataatca caatgaacta    5040
agcactctaa caaactttac atttttaat tcaatcccta caataactct gtaaacttca     5100
ttttacagat aagcaaatta tgactcagag aggttaagcc agacccaggt catgtagtta    5160
ttaggttatg aaaccaggat ttctcaacca gcactttaga ccaggtgcgg tggttcacac    5220
atgtaatccc agcactttgt gaggccaagg tggaaggatc acatgagacc aagagttcaa    5280
gaccagccca ggcaacatag tgagacccta tctctaaaaa aaaaaaaaaa aaaaaaaaa     5340
aaagtttaaa gaaaaacaca ttttaaaaa atgaacactt taaaaatatt tggtcagaat     5400
ttatatagga atttatcaac ataaatgtta atttcacttt actgataaac ttgcaaaaca    5460
tgatgtgctg ggtactgaaa tttagatgtt aaaagaacag tttatcccac ctttatgaca    5520
gtgttccctt ggcctccacg atttgagctc aacagtctgt cttgcctgaa ctctgagaga    5580
cctcatacaa tagaagaaag actctcatct ttggattata ttggtcccaa aactttgagt    5640
ttgaataata cacccagtga aagtgttctt tcaatttcaa aaggtgaaga aagaagtggg    5700
tgatgtaaca atcgtggtga ataatgctgg gacagtatat ccagccgatc ttctcagcac    5760
caaggatgaa gagattacca agacatttga ggtcaacatc ctaggacatt tttgggtgag    5820
tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
acacaacaca ccagaatgta agctacttgg tctgtcttgt ccaccagtat ctgacacaaa    6060
gcttggcatg taccaggagc tcaacaaatg tttgtggagg tttgttaagg gttgtcagtg    6120
tacatctttt caatgctgtc acttgtgact tcattttttt ccctccacac catgattttg    6180
taatgtgtcc tcattttgtg gaattttaga atggaaagga catcagaagt aattacttgg    6240
atgtatatag gatcgaggac acttttggac gagactctga ggcaagtgtt ctagatccat    6300
ggggtgctgg aactgagaaa tgcagctata cagacctcat ataattggtt agttttgtgg    6360
gagatggaaa tatcaacttc aactgccttt gtatagaaat ttttatgatt aatcttccag    6420
tgcctcaata ttagtgtaga atctagggca gatctggatt ctagaagaaa gaagaaaaaa    6480
aagagatgtg tccccttac ctttaccagc tcttcacata tgtgaattgg ctcccatgcc     6540
caccaaacta cacggagacc tcatacatta gctacctata gctgcataac aaattataca    6600
aaacttagtg gtttaaagca acaatgtatg ttcactatcc tctcacagtt tctatgggtt    6660
gggaatttgg aggtagcttg ggtttgggagt tctagttcta tgaatttgca taggatttat   6720
taaattctta taaaattta ttgatgtttc tcacaaaaga ggttttgga aaaaagaaa       6780
gacttgtttt ctgtaacatc aacatataat atacaatatt acaaataggg agatagtgaa    6840
ttcaatcatg attcattagt gtggtgtaga actctcagct tacactactc aactgtctta    6900
atacagttac acaagatttc actctttaa ttagaatgat aaagccccaa accaaaaaat     6960
tatatgacac caaattatca taaggaataa ttttagttct gaaaactctg aattttttccc   7020
ttaatattgt ttagatgaca tatccaaaaa aggatctatt tgattccttc tgaagggaag    7080
gaggggagt actgagatta gtgttggcat ggggcttacc ataccaataa atttgtatct     7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
```

```
ctaacgtcta tgtcattgtc tttcttcttt ctgcaatgat ccttaagatc acaaaagcac   7320
ttcttccatc gatgatggag agaaatcatg gccacatcgt cacagtggct tcagtgtgcg   7380
gccacgaagg gattccttac ctcatcccat attggtaagt atcacatgcc agccatgtta   7440
tatattttta tactttgaag ggagcattac acttcaaatt gttaccactg gagagtcctg   7500
gttcttggca tcttgaacaa agaattggac aaaactcacc aacaaagcca ggaaagaatg   7560
aagcaacaaa agcagagatt tattgaaaat gaaagtacgc tttacagggt gggagtgggc   7620
ccaagcacag gggctcaaga gccaattaca gaattttctg gggtttaaat accccctaga   7680
ggtttccact ggttacttgg tgtacgccct atgtaaatga agaggatgaa ttaaagttac   7740
agagtcgttt actcagtgta caccatatgt aaatggagag gatatttcct gtcatagctg   7800
gagtgtttcc atttgattta gttctaggaa gtcagcatga atcggcctta tgttccctgc   7860
ctccagaccc tgttctcctg cctcaagatt acaatgctga gagcagagtg atttggattt   7920
acagaattta aatttatagt agtttagaat gattttttaa atgactttt ctaaaacaat    7980 gaaaccaggt tgtaattata tttaagatat ttttagattt ctgcaaactc ctctgtagaa   8040
caatgagaga aaacagtaat gccaagcatg tttccattgt ttcctggaat aagaaacaga   8100
aaccccacag actgagaagc aaaacctaca gaagctaaaa tgaacacatg tctatgtcat   8160
ggccttggtg cccaagataa gacaatcaga gtggtccctg gatcaaaaca ttttacagtg   8220
tgcttgtgcc atgaaagtgt gtgtgtgtgt gtgtgtgtgt gtgtgagaga gagagagaga   8280
gagaaaacga ctctacctga ctaaaagttg cagataccac actccatgca ccaccaaaga   8340
cataaaggga aggaggtgag aggcgttaag gatgtactgc tgtatttgcc aaatatcctt   8400
tcctgtaaac tcttctccag atcctcataa taaaattaag aggccaaagt ggcaaccatt   8460
gtcaagagaa aaactatcaa ccattgtcaa gagaataact cagttattga gagagagagg   8520
agaaatgagc agagtcctac agaagtctgt caacacagat accagtttg tagaatttct    8580 aaatgtattt ttcctgattc atatttttca aaataaaagc agcaataaaa actgattaga   8640
aaacagtttg aagattcaat ggaaaaacct tacatgtagg atggaaaact gaacattaag   8700
ccaatcaata gagttatttt tgttctttg ttatcattgt tgtttaagaa atgagatacg    8760
ttcacaattc tgcttaatca tgtaagaaaa tgaaaatgaa ttgccattta tactctcaga   8820
aaaatcacaa gtggctgatt tttggcttcc acttgttctt aagccaaatg ataccgcctt   8880
ctcacagaaa gctgaggatt ggtttcactc tcccttagct aacaatgctt ataattctc    8940 ttacagttcc agcaaatttg ccgctgttgg ctttcacaga ggtctgacat cagaacttca   9000
ggccttggga aaaactggta tcaaaacctc atgtctctgc ccagttttg tgaatactgg    9060 gttcaccaaa aatccaagca caggtaaggt caaaatcaa gttagaatgg gtatgtgta    9120 tgataaattg atatgaaaac taatgagaaa tgtttaggca ggccaactaa tagaagaaaa   9180
tgaagaagga aaaataattt ttcttattat tattattatc ttgaaattaa aggaataaag   9240
ggggaaaaca cattagggac tagcaggaat gatcagccac cgatgaactg ggatatttat   9300
ttgtgtccgg gagaaagcac atacatttga tcaccgttac caccctgtct ttaaaatgca   9360
aatgttccaa ggaccagcaa ataaattgag tatctagctc cttagtcaag gtgaatttct   9420
gcaagaactc ttgtctctgg tgagacagga tttgagacca caagagaaga aaaattagtc   9480
ctgaaaggag aagaaaaaag caggaaggtg tggataagaa cccgaaaatt aagccatctg   9540
cttaacaaat ttttctaatc ctagtatata ttctgctgca ggttaacaaa atatactaag   9600
```

```
cttaatgatt cgaaaccaat tttttactgg aagggaatta atcctaaata tattcattca    9660
aaagaactaa acaattctct gttgagtgcc gcctcatttg aggatactga ctcttacagc    9720
ctgagttagc tatgtggtct ctgcagctgg aatcactccc tgccactgga gtccttcatg    9780
gtgttagacc ataggtactg ttgactaaag aaaaaaaaaa gttttttgttt ttattttttgt   9840
ttttttttgag acagagtctc actctgtcac ccaggctgga gtacagtggc gcgatctcag   9900
ctcaccgcaa cctccgcctt tctgggttca agcaattctc cttcctcagc ctcctgagta    9960
tttggattac aggcgcccac caccacgcct ggctaatttt tgtattttta gtagagacgg   10020
ggtttcacca tgttggccag gctggtctca aactcctgac ctcaggtgtc ctacctgcct   10080
tggcctccta aaatgctggg attacaggag tgagccacca tgcccggcca aaaaaataag   10140
ttttaaaga attaaggtc atcctggcta acacagtgaa accccgtctc tactaaaaaa   10200
cacaaaaaaa ttagccgggc gtggtggcgg gcgcctgtag tcccagctgc gcggaggct   10260
gaggcaggag aatggcgtga acccgggagg cggagcttgc agtgagccga gatcgcgcca   10320
ctgcactcca gcctgggcga cagagcgaga ctccgtctca aaaaaaaaa aaaaaaaaa   10380
aaaaaaaga attaaggtg ttaattttat ttagaagcct tactgaagac tacagtcgga   10440
ggcctatagc ctgagagcag ccctttagag aggttcagtt gaactgttct gatagtgggg   10500
gccatgtgct ctatcctgta ttgtcttcaa agcatctttc cagagagctg cacattgtca   10560
cagagtcagg gactttgtga aattatgctg acaaccagaa gtgagtaaac gtggcttctt   10620
acatttgcta cgttgtctca cagtacttaa taagtatgca atatgtaagt aaatactata   10680
gtactattgc aactcctgat tgttttctta gacaaggaat tgggcccaat aaaaaccctc   10740
ttggtaggca ttcaggcttc gtgtaccatg agctttccta agggtatcct gccactcttg   10800
gggaaggcat gatagatgag gggagtaagg ataatgaac tctgggtaca gggttcctgg   10860
gggctaactt agaggtagac acaggcaatg ctaaatattt gggattgatt ttatagaggt   10920
tgctagattg tgaatttcct tagtaagggc taaggcattg atatgtaatg tcacacttgg   10980
ctccgaggct gggttgttgg atccatgtag atgaaatcag ggagagaaag gcagaacgg   11040
agtaatttag aaatgtattg atttgtatta ctctctgttg gcttgctatt caaggcagtg   11100
gagaactcaa tcacataata atctgcagca aaccacagat catcccaggg aatgaagttt   11160
taacattcgc tggctcccta actcctcacc cagcctttac attcactggc tgttcagtcc   11220
atgcctggac atcttaattt gaatacaaca ttttaaatcc attttctgt catcatcttg   11280
cactaacaga caattctaca ctaagcctat gtttatgaat atttctcaag agtacatgta   11340
cacagccttc agtataagga aaactggaag tatgacatac ctccagttgt catactcctt   11400
gggcccctct taaattctca ttaaactgca ggataggcaa gtcagaggtg aatctcaaat   11460
acgaaattct taccggaaag gggttccaat ccagacccca agagagggtt cttagatttc   11520
tcgcaagaaa taattcgggg caaggccaca gtgcaaagca aaagcaagtt tattaggaaa   11580
gtaaaggagt agagaacagc tactccatgg agaagaatgg cttgagctgc tccaccaagg   11640
gtatttagag ttacttcttg attatatgct aaacaagggg tggattattc atgagttttc   11700
cgggaaaagg gtgagcaatt cccagaactg agatttcctc ccctttttag gccatatagg   11760
gtaacttcct gccattgcca tggtatttgt aaactgtcat agtgctggtg gaagtgtctc   11820
ttagcttgct aatgtattat agttagctta taatgagcag tgaggacaac cagaggtcac   11880
tttcatcacc atcttggttt tggtgggttt tggccggctt ctttactgca ccctattta   11940
tcaacaaggt ctttatgacc tgaatcttgt gccaacctcc tatctcatcc tgtgacaaag   12000
```

```
aatgccttaa cttcctggga atgcagccca gtaggtgtca gccttatttt acccagaccc    12060
tattcaagat ggagttgctc tgatttaaac gcctctgaca aaatgacgac ctcaaaacaa    12120
tccagcttta tggaatacct ccacaagaaa gaaagtatac ttagctatag aattttctcc    12180
ttgcatccaa caggctttga gatgtcagat gtttccttcc tgtcccatga ttaatcctag    12240
ccattcctct ttcttgtctg gctccactac tccttaccat ctaatgcctc gccaccattt    12300
tgatattttg actaagtgag ctatgaaaca cacctactgg atatgaaagt ataagtttct    12360
gataacaaaa catcaacatg ggatgtggag gaagtgggta gggtggcatt aatgcagcaa    12420
atcctggaat atttaaatc ttcattctaa atttagtaaa aatataggat aattttcctg    12480
ccatcattta cttataaaat taaaatttta gaaaataaaa ataatatttt cctcttttta    12540
atcacagatt atggcctgta ttggagacag atgaagtcgt aagaagtctg atagatggaa    12600
tacttaccaa taagaaaatg attttttgttc catcgtatat caatatcttt ctgagactac    12660
agaagtaagt acagcacaga acacccaaat actaaaacac caatagagct tttttttttg    12720
cttttttttt ttttagacag agtctcactc tgtcaccctg gctggattgc ggtggttgca    12780
gtggcatgat cttggctcac tgcaacctcc gcctcctggg ttcaagcaat tctcatgcct    12840
cagaccccca agtaactggg attataggtg tgtgctgcca cactcacccc agctaatttt    12900 tgtattttt gatagagaca ggtttcccca tgttggccag gctggactcg aactcctgac    12960
ctcaagttat cctcctgtct cggcctccca agtgctggg attacagtca tgagccacca    13020
tgcctggccc aatagagcta ttattatgga gcatctttca gttgtgaaaa ttggcatgga    13080
aactctccat ccctggggag aacagttatt tcctctgtta ttttcctacc cagtctataa    13140
aaagagagtg attcattttc tctaccaaat ctactgtctc tgcccaaact ttgctgaaga    13200
ctattctaac taaaggaaac acagtttaaa aagaatgcaa tatagtgaag tagttaataa    13260
taaagactcc attttaaaa gtctgctgga agtttggttg ggattgcact gaatctatag    13320
agcaattggg gagtattgac atatcaacaa tattgagttt tctaatccaa gaacataata    13380 tctatttta aaatcttctt caaaatcttt aaatctttaa attgtatttt gtagtttttg    13440
gtgtttaagt cttgcacata ttttgtcaga tttattccaa agtatttcac gggttctttt    13500
tttttttttt tttttttttt ttgagacaga gtttcaccct tgttgccag gctggagtgc    13560 agtggcgtga tcttggctca ctgcagcttc tgcctcctgg cttcaagtga ttctcctgcc    13620
tcagcctccc aagtagctgg gattacaggc acctgccccc tcgcccaact aacttttgt    13680 gtttgtagta gagacagggt ttcaccatgt tggccaggct ggtctcgaac tcctgacctc    13740
atgtgatcca cctgcctcag cctcccaaag tgctgggatt acaggcatga gccatcatgc    13800
ccagccctat ttgacggttt ttgacgctaa tgcaagtggc attttaaaaa atttatatt    13860 tcccattgtt tgttgtcagt atatattgga ttttttgtaat ttgatctcat attttgcagt    13920
cttgctaaat tgctaaacct cttttttgcta aactcgataa gctttttttt tttggtaga    13980 ttcctgggcc tctaattttc tttatgggaa agttttaat tacaaattta atttctttaa    14040
tagctacatg gctattcaat ttacttatta attcttggta atgtgtgtct ttcaaggaat    14100
ttgtccattt catctaagtt gtagaatttc tttggcataa atttgtacat aacattccct    14160
tattatcctt ttaatgtctt tagaatgtct tatttattta tttatttatt tttattatat    14220 tttttgaga cagagtctcg ctctgttgcc caggctggag tgcagtggca caatcttggc    14280
tcactgcaag ctccgccttc tgggttcatg ccattctcct gcctcagcct ccctagttgc    14340
```

```
tgggactaca ggcgcctgca accatgccca gcttattttt tttttttttt tttttttttt   14400
tttttttttt tttttttttt tagtagagac ggggtttcac cctgttagcc aggatggtct   14460
cgatctcctg acctggtgat ccgcccgcct cagcctccca aagtgctggg attacaggcg   14520
tgagccacca agcccagcct atttatttat ttagtagaga cagtctcact ttgctgccca   14580
ggcaacaaag gttttgaatg cctggcctca agcagtcctc ctgccttggc ctcccaaagt   14640
gctgggatta caggcatgag ccactgcacc tggccaaatg aatatgctga taatatcttc   14700
tttataagga tgacataaga ataaaataat gtaatacaaa caaagcccct gtcactgaaa   14760
atgtatagac ttcaaatgtt aaagtcttag agaacagaat ttatatgaaa tagcaacagc   14820
aacaatttcc cagaggaaat actctctcag ctttcttctg aggagcagtt tctaaattga   14880
aattgtatca gtgagaagat aactatacta acttcataag ccttgggcct ttttgaaaca   14940
aatccatata aactatgaac aaacttgaaa tagaacaatt tgagaacagg gtacaaactg   15000
cattggtgta tcaatttcag tatttggttt tagcttaaat agactgactt gagataacat   15060
aaggagaacc ttgaccccca agcaacatca tctcgcgagt tgactaggcc gggtgtggtg   15120
tctcacgcct gtaattccag cactttggga ggccacagca ggcagatcac ttgaggtcag   15180
gcattcgaga ccagcctggc caacatggtg aaacctcagc tctactaaag atacgaaaat   15240
tagcaggcat agtggcctgc acctgtaata ccaggcactc gcaggagaat cccttgaacc   15300
cggaaggcgg agattgcagt aaaccatgat tgtgccactg cactccagcc tgggcaacag   15360
gagactctgt ctcggaaaaa taaattttt aaaaaaatga aaaaaaataa aagttgacta   15420
aattagtgtc ttggtactaa gcactgtagg aagtgagttt catggaaccc caactctctt   15480
ggggcccaaa gcaagtcata ttaatattga aaattacatg catatacatg catatgacca   15540
aggtgataaa aacaattatt ctgcctgagt tggagaatag tatcccagta aaataaacaa   15600
gagtctcaaa gtcttttgta tcctttgaag ctgtcatggt ggtttgtaac taggcaacag   15660
gtatatattg ttaatcttct ttgcatttaa ttcctttat agagagacac aattttacga   15720
gcagatgcaa ttactagcat gaaggtttct ttgtgagggt agttaaaagg cccacatgag   15780
ctctcttctt atccttgtcc ttcttcagc cagatcttcc ctgcccctt gctcattcca   15840
tctttcaccc acctaccccc aaaacaagga agtaaatctt gcattagtca acaataccaa   15900
agtgattttc aatatgactt tctctgcaga atgttattat ttctgcctct ttacattcac   15960
atactgtctt cctttttttt tttttttttt tttttttttt tagattgggt ctcactctgt   16020
tgcccaggct ggagtgcagt ggcttgatct cagctcactg taacctccac ctcctgagtt   16080
caagcaattc tcctgcctca gcctcctgag tagctgggat tacaggcatg tgccaccaca   16140
cctggctagt tttttgtat ttttagtaga cagggtttt caccatgttg gtcaagctgg   16200
tctcgaactc ctgacctcat gatctgacca cctgtgcctc tcaaagtgct gggattacag   16260
gcgtgagcca ccgggccagc cactctcttc ctttcagttg cctactcatc tcttatgcat   16320
tcctggacat cagttgtcct tttgaagctt cctccacta tcccagccca tgtgaatcct   16380
ccttccagtt atagccctta attctagatg gctgatattt tcaataatt gttttaagat   16440
gaccatttta gcctatcagc taaacaatat caaagacaat agctatttt caagtacttt   16500
agtttacctt attatagagt gcataataga tattcagtaa atagtaaagg agaggtgaag   16560
gcttgcatag aatggattct ggtggtgtct cttggtgagc ttttagcatc aagattaatc   16620
agcagtttca gcaatgagct cagaccttca gtttagatc tttactcata tcagataaga   16680
gagtgagaag agtggtatgt atcagtgctt tatttatatt tgcatccaat ttgaactatg   16740
```

```
aatattacaa aggtgcacac ataggttcag acagattgat ttaaaatgac caaagatgac    16800
ctgtcgtaag caacctgggt atcttaagat gcactccttg gagagggaat gttcctaaaa    16860
acattttcag agggacgaac tgtatgaaat tcagtaaaac ataaatcatg aggaaaactg    16920
attactctct ttttgacatg aaatgagagt tttaatgcat ggttacgatt attaacgtac    16980
tccgctgcaa gacgttaata aagttactgt tttgcaggct agaatgtctt gatgctgtaa    17040
tcagaacaca cttttccccc tttcttccag cttcaaatgc agattcataa ttgggctgac    17100
ttctaataac tgcaatgttt tctgccttgg gcttgcagca gaagcctgac aaaatagtgt    17160
ttgtttaggc aataatttat ttatttattt attgagatgg agtttcattc ttgtcgccca    17220
ggctggagtg caatggcgtg atctcggctc actgcaacct ctgtgttcag caataatttt    17280
agactttacc ttacttgtga ttactatagc aattactata gccacaaggc ataattttac    17340
tgtctcattt caattttatg aatttgaatg ttttttacact tttcctaatg aagtccacta    17400
tgaagttatg tcaaaaaaaa aaagaaaaa gaaagatgca cacgtaaaag agaggtggtt    17460
gcaagagaag aaaagaacgg aggaaagtta aacgcaaacc agataactct cagcgtattc    17520
taaatgacca aaaacagaac tctgttgtca aagattttaa atggaaaatt tttcaatttt    17580
tttttctttt ttgtacaggt ttcttcctga acgcgcctca gcgattttaa atcgtatgca    17640
gaatattcaa tttgaagcag tggttggcca caaaatcaaa atgaaatgaa taaataagct    17700
ccagccagag atgtatgcat gataatgata tgaatagttt cgaatcaatg ctgcaaagct    17760
ttatttcaca tttttttcagt cctgataata ttaaaaacat tggtttggca ctagcagcag    17820
tcaaacgaac aagattaatt acctgtcttc ctgtttctca agaatattta cgtagttttt    17880
cataggtctg tttttccttt catgcctctt aaaaacttct gtgcttacat aaacatactt    17940
aaaaggtttt ctttaagata ttttattttt ccatttaaag gtggacaaaa gctacctccc    18000
taaaagtaaa tacaaagaga acttattac acagggaagg tttaagactg ttcaagtagc    18060
attccaatct gtagccatgc cacagaatat caacaagaac acagaatgag tgcacagcta    18120
agagatcaag tttcagcagg cagcttttatc tcaacctgga catattttaa gattcagcat    18180
ttgaaagatt tccctagcct cttccttttt cattagccca aaacggtgca actctattct    18240
ggactttatt acttgattct gtcttctgta taactctgaa gtccaccaaa agtggaccct    18300
ctatatttcc tcccttttta tagtcttata agatacatta tgaaaggtga ccgactctat    18360
tttaaatctc agaattttaa gttctagccc catgataacc ttttttctttg taatttatgc    18420 tttcatatat ccttggtccc agagatgttt agacaatttt aggctcaaaa attaaagcta    18480
acacaggaaa aggaactgta ctggctatta cataagaaac aatggaccca agagaagaaa    18540
aggaagaaag aaaggttttt tggttttgt tttgttttgt tttgtttttt gttttttga    18600 gatggagtct cactctttcg cccaggctgg agtgcagtgg tatgatctca gctcactgca    18660
agctccacct cccgggttca cgccattctc ctgcctcagc ctcctgagta gctgggacta    18720
caggcgcccg ccaccacacc cggctaattt tttgtatttt ttgtagagac ggggtttcac    18780
catgttagcc aagatggtct cgatctcctg acctcgtgat ccacctgcct cggcctccca    18840
aagtgctggg attacgggtg tgagccaccg tgcccagcct tttttttttt aatagaaaaa    18900
ataatccgac tcccactaca tcaagactaa tcttgttttg tgtgttttc acatgtatta    18960 tagaatgctt ttgcatggac tatcctcttg ttttttattaa aaacaaatga ttttttttaaa    19020 agtcacaaaa acaattcact aaaaataaat atgtcattgt gctttaaaaa aataacctct    19080
```

| | |
|---|---|
| tgtagttata aaataaaacg tttgacttct aaactctg | 19118 |

<210> SEQ ID NO 2
<211> LENGTH: 19119
<212> TYPE: DNA
<213> ORGANISM: Homo sapien

<400> SEQUENCE: 2

| | |
|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta ataaggtaat gtatacatct tccaactttt | 300 |
| taaagtcaca gagtaagata tgtattttaa gaattatttg acttaccatc tacttatctt | 360 |
| tgtattttg tttttcaaag tttgataaat tccctggtcc cttagtctgt atatgtgtca | 420 |
| ggttagttag atgaagggaa tgtaattaag aactaagcag cgattttat gacatggtgt | 480 |
| gcaggttgat agaaagactc aggagccagt ctccttccaa gctgctaaat gaggcaagtc | 540 |
| acatattatc tctcagcctg ttttcttggc tctgaagtgg ggataataac ttaggggatg | 600 |
| ggcaagaacg ggatctgaaa attacagcta caaacaaaag tcaaacgaag aacttgcaac | 660 |
| agaaaccttt agtgcctccc ctcatgcaca agcaacacag ttctaaaata tttactgtct | 720 |
| gaccctttac agaaaatgtt tgccagtccg tagtcaaaag gattaaataa gtaatatttt | 780 |
| cagcacttag catatgataa acgatacgtg gcacatgata aacaataact gtgttaaata | 840 |
| aaatatgtgc gcagtgagtc aggcttttcc ttggacatta gtattttcc tgtgttctta | 900 |
| cttgtaaaca ctacattaac aaccccaaat aaaactgaag gaactgaaat cttgtatcat | 960 |
| tttctctaaa cttgtaaatt ctggtaaggc catgaaaata tatgcagaga agtgtttaca | 1020 |
| ggatttttagg attggaaaaa ttgtgaagta ctccttgaga atcacatttt ctgcaaatta | 1080 |
| cagtggtttt aattaccatt atattattac tttctcatgt tctttgctgt catgtttagt | 1140 |
| tgaaacctaa aatgtctctt acacttagag aactaattct tttctgtttt ttttctgaat | 1200 |
| agtgaagaat actatacaaa aaagctacta catttttatt taacagatat gagcatttat | 1260 |
| ataatagagg agttgatgta tataaaaatg atttgccatc ttttggtct ttgaagaaat | 1320 |
| tcgaatgaac tttctggaag atagcaagaa tttacaaata gagaaaattg ttgcctgctg | 1380 |
| ttctcaggca tttgtccaaa aatataaata agtataaatc tatgaaaagg gcttgatgaa | 1440 |
| atctaacctt caaatctctt tccagatgtg tattttggg gaaagggcta tatttattaa | 1500 |
| gttttttta aattttaaaa tttccagaga caagagaaaa gtaaattaga aggaagtcgt | 1560 |
| attaaaaatg acttaagggc gggtgcagtg gctcacacct gtaatcccag cactttggga | 1620 |
| gacggaggtg ggcagattgc tggagcccag gagttcaaga ccagcctggg cagcacagca | 1680 |
| aaaccccaa ctctacaaaa aatacaaaaa ttagctgggt gcggggtgc acccgtag | 1740 |
| tcccagctac tcgggaggct gaggtgggag gatcgtttca gttcaggaag ccaaggctgc | 1800 |
| aatgagctat gatggcatca ttgcactcca agctgggcaa tagagccagg ctctgtctca | 1860 |
| aaaaaataa aaaagagactt aagaaaaata ggtaacccaa cctcaaaaat tctctttgaa | 1920 |
| tcattaaatt tcatggttaa acatttaagc tactgaatga ttcactctaa ggctgtaatg | 1980 |
| taactcagat ctcccttagg cgaggaagat gctggctgag ttttcatcat aactggctcc | 2040 |
| ttttgccctg tgagatgaga gacacagtag cagtttggct cttatgcaat ctaaactgtt | 2100 |

-continued

```
gcgttgggaa tacggttcaa aaaacacatt ggagtttaag ctaaagcaag tgttttgcta    2160
acaaaaagac aaggcatcac attttgcaat tgtctagctc agttataaaa cagaagaata    2220
ggccggacgc ggtggctcac gcctgtaatc ccagcacttt gggaggccga cgggcgga     2280 tcacgaggtc aggagatcga gaccatcctg gataacacag tgaaacccg tctctactaa    2340 aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaaa aaaaaaaaa    2520 aaaactgaag aataattaat tcttcaatca aacatctga tgaatgctct ggtaacttat     2580
gctctctact gacctagaaa caaatgagag agtatggtgt ggtttgtgca atctggcagt    2640
gagcaagcta ccaactaaat cagtgaaaga ctctcctatt cttttttac tcttctgcaa     2700 tcccacaaaa ggctatttga ggggatactg actttgagac tgggtcctaa catccatgtt    2760
tggggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000 tgaaacttg aaaagaatta taattttcca gaatgtgagt caagaaacat tagagcaatt     3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
agaatcatca agaaaaatat gatgggcaga ggcatacagt ttaccattac cactagtta    3360 gaattactac ttagcacttt actgccatt acatagttgg tgctcaacaa atgtatgata     3420
aattaatggt tgagtttttc tttcttctcc atattcatct tccatgacac cacgaagagc    3480 aatgttttc aagaatgttc ttcaaggttt gaaagtagcc tgcttagag aaactgccta     3540 ctgtacagcc tccaaccaag aggaaaagct gaaaaaagca tgaagggatt ttgttttgtt    3600
ttgtttgttt tggttttaat atgagcattc cctggcagaa aagccagggg taatctcatt    3660
gcaactaggc aatcactctc aagaaatttt ctaacaaata aggaggccaa ttttatttt     3720 attttgagac gaagtcccac tctgtcaccc aggttggagt gcaatggaat gatttcagct    3780
cactgcaacc tccgcctccc gggttcaagt gattctcctg tctaaacttc ccgagtagct    3840
gggattacag gctcccacca ccacgcccag ctaatttttt gtatttttag tagagatggg    3900
gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aaatgaatgt taattgttca ttttggacat    4080
gaatgttaat ttttttttt tttttttttg agacagagtc tcactctgtt gcccaggctg     4140
gagtccagtg gcactatctc cactcactgc aacttcctcc tcccaggttc aagcaattat    4200
cctgcctcag cctcccaagt agctgggatt acaggcccac accatcaggc ctggctaatt    4260
tttgtatttt tagtagagac ggggtttcac catgttggcc aggctggtct tgaactcctg    4320
acctcgtgat ccgccctcct cggccaacca agtgctggg attacaggcg tgagccaccg     4380
cgcctagccg aatgttaatt gtctaaaaat ttttcttctc caatgtcttc tcctccactt    4440
```

```
ttttcggaat tgtttcttc ctaattacag cgcggtgtgg aggaaactgc agctgagtgc     4500
cgaaaactag gcgtcactgc gcatgcgtat gtggtagact gcagcaacag agaagagatc     4560
tatcgctctc taaatcaggt gagactgcag gttcacaaat ttcttcagat tattttgttt     4620
cctaggacgc tgacgtggaa aatgagaaag gtctttatga ctgcctgatt taaattggat     4680
tttagctgct aactgaagta gttatgtcac caaggaagga tatatacttt ttttcttgta     4740
tgtaatccac tcagctctgc ccattattat tgttcatatt attaatcaat ttcattctga     4800
tcagaagtgt gagcagtggc acagagtgac tgacaaaaga tttatcatca gggaatatgg     4860
atcacttcct agttttgttt tagtcctatt aactttgcag taattccagc ttctctttaa     4920
ttatttccct tgtgagattt tattttggtg ttaatgtagt cttctgtaga aaatgtaata     4980
ttaataatta ttatcacaat tattttaaaa gagtaaatac caaataatca caatgaacta     5040
agcactctaa caaactttac attttttaat tcaatcccta caataactct gtaaacttca     5100
ttttacagat aagcaaatta tgactcagag aggttaagcc agacccaggt catgtagtta     5160
ttaggttatg aaaccaggat ttctcaacca gcactttaga ccaggtgcgg tggttcacac     5220
atgtaatccc agcactttgt gaggccaagg tggaaggatc acatgagacc aagagttcaa     5280
gaccagccca ggcaacatag tgagacccta tctctaaaaa aaaaaaaaaa aaaaaaaaa     5340 aaagtttaaa gaaaaacaca tttttaaaaa atgaacactt taaaaatatt tggtcagaat     5400
ttatatagga atttatcaac ataaatgtta atttcacttt actgataaac ttgcaaaaca     5460
tgatgtgctg ggtactgaaa tttagatgtt aaaagaacag tttatcccac ctttatgaca     5520
gtgttccctt ggcctccacg atttgagctc aacagtctgt cttgcctgaa ctctgagaga     5580
cctcatacaa tagaagaaag actctcatct ttggattata ttggtcccaa aactttgagt     5640
ttgaataata cacccagtga agtgttctt tcaatttcaa aaggtgaaga agaagtgggg     5700
tgatgtaaca atcgtggtga ataatgctgg gacagtatat ccagccgatc ttctcagcac     5760
caaggatgaa gagattacca agacatttga ggtcaacatc ctaggacatt tttgggtgag     5820
tgtgagtcag aaacatttct gatttgtgca ccttctctta agatacatga aacttataac     5880
ggagttcaca tacttctgga caggaaactg gccagatctt tgccttaatc aagaatcatt     5940
aaatttgttt gagtagaaga gccacagagt ctctgacaca aggacacaga attcaagtgg     6000
acacaacaca ccagaatgta agctacttgg tctgtcttgt ccaccagtat ctgcacaaaa     6060
gcttggcatg taccaggagc tcaacaaatg tttgtggagg tttgttaagg gttgtcagtg     6120
tacatctttt caatgctgtc acttgtgact tcattttttt ccctccacac catgattttg     6180
taatgtgtcc tcattttgtg gaattttaga atggaaagga catcagaagt aattacttgg     6240
atgtatatag gatcgaggac acttttggac gagactctga ggcaagtgtt ctagatccat     6300
ggggtgctgg aactgagaaa tgcagctata cagacctcat ataattggtt agttttgtgg     6360
gagatggaaa tatcaacttc aactgccttt gtatagaaat ttttatgatt aatcttccag     6420
tgcctcaata ttagtgtaga atctagggca gatctggatt ctagaagaaa gaagaaaaaa     6480
aagagatgtg tcccccttac ctttaccagc tcttcacata tgtgaattgg ctcccatgcc     6540
caccaaacta cacggagacc tcatacatta gctacctata gctgcataac aaattataca     6600
aaacttagtg gtttaaagca acaatgtatg ttcactatcc tctcacagtt tctatgggtt     6660
gggaatttgg aggtagcttg ggttgggagt tctagttcta tgaatttgca taggatttat     6720
taaattctta taaaattttta ttgatgtttc tcacaaaaga ggttttttgga aaaaagaaa     6780 gacttgtttt ctgtaacatc aacatataat atacaatatt acaaataggg agatagtgaa     6840
```

```
ttcaatcatg attcattagt gtggtgtaga actctcagct tacactactc aactgtctta    6900
atacagttac acaagatttc actcttttaa ttagaatgat aaagccccaa accaaaaaat    6960
tatatgacac caaattatca taaggaataa ttttagttct gaaaactctg aatttttccc    7020
ttaatattgt ttagatgaca tatccaaaaa aggatctatt tgattccttc tgaagggaag    7080
gaggggagt actgagatta gtgttggcat ggggcttacc ataccaataa atttgtatct     7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
ctaacgtcta tgtcattgtc tttcttcttt ctgcaatgat ccttaagatc acaaaagcac    7320
ttcttccatc gatgatggag agaaatcatg ccacatcgt cacagtggct tcagtgtgcg     7380
gccacgaagg gattccttac ctcatcccat attggtaagt atcacatgcc agccatgtta    7440
tatatttta  tactttgaag ggagcattac acttcaaatt gttaccactg gagagtcctg    7500
gttcttggca tcttgaacaa agaattggac aaaactcacc aacaaagcca ggaaagaatg    7560
aagcaacaaa agcagagatt tattgaaaat gaaagtacgc tttacagggt gggagtgggc    7620
ccaagcacag gggctcaaga gccaattaca gaattttctg gggtttaaat accccctaga    7680
ggtttccact ggttacttgg tgtacgccct atgtaaatga agaggatgaa ttaaagttac    7740
agagtcgttt actcagtgta caccatatgt aaatggagag gatatttcct gtcatagctg    7800
gagtgtttcc atttgattta gttctaggaa gtcagcatga atcggcctta tgttccctgc    7860
ctccagaccc tgttctcctg cctcaagatt acaatgctga gagcagagtg atttggatt     7920
acagaattta aatttatagt agtttagaat gatttttaa  atgactttt  ctaaaacaat    7980
gaaaccaggt tgtaattata tttaagatat ttttagattt ctgcaaactc ctctgtagaa    8040
caatgagaga aaacagtaat gccaagcatg tttccattgt ttcctggaat aagaaacaga    8100
aacccccacag actgagaagc aaaacctaca gaagctaaaa tgaacacatg tctatgtcat   8160
ggccttggtg cccaagataa gacaatcaga gtggtccctg gatcaaaaca ttttacagtg    8220
tgcttgtgcc atgaaagtgt gtgtgtgtgt gtgtgtgtgt gtgtgagaga gagagagaga    8280
gagaaaacga ctctacctga ctaaaagttg cagataccac actccatgca ccaccaaaga    8340
cataaaggga aggaggtgag aggcgttaag gatgtactgc tgtatttgcc aaatatcctt    8400
tcctgtaaac tcttctccag atcctcataa taaaattaag aggccaaagt ggcaaccatt    8460
gtcaagagaa aaactatcaa ccattgtcaa gagaataact cagttattga gagagagg     8520
agaaatgagc agagtcctac agaagtctgt caacacagat accagttttg tagaatttct    8580
aaatgtattt ttcctgattc atattttca  aaataaaagc agcaataaaa actgattaga    8640
aaacagtttg aagattcaat ggaaaaacct tacatgtagg atggaaaact gaacattaag    8700
ccaatcaata gagttatttt tgttcttttg ttatcattgt tgtttaagaa atgagatacg    8760
ttcacaattc tgcttaatca tgtaagaaaa tgaaaatgaa ttgccattta tactctcaga    8820
aaaatcacaa gtggctgatt tttggcttcc acttgttctt aagccaaatg ataccgcctt    8880
ctcacagaaa gctgaggatt ggtttcactc tcccttagct aacaatgctt ataattctc     8940
ttacagttcc agcaaatttg ccgctgttgg ctttcacaga ggtctgacat cagaacttca    9000
ggccttggga aaaactggta tcaaaacctc atgtctctgc ccagtttttg tgaatactgg    9060
gttcaccaaa aatccaagca caaggtaagg tcaaaatcaa gttagaatgg gtatgtggta    9120
tgataaattg atatgaaaac taatgagaaa tgtttaggca ggccaactaa tagaagaaaa    9180
```

```
tgaagaagga aaaataattt ttcttattat tattattatc ttgaaattaa aggaataaag      9240 gggaaaaca cattagggac tagcaggaat gatcagccac cgatgaactg ggatatttat       9300
ttgtgtccgg gagaaagcac atacatttga tcaccgttac caccctgtct ttaaaatgca     9360
aatgttccaa ggaccagcaa ataaattgag tatctagctc cttagtcaag gtgaatttct     9420
gcaagaactc ttgtctctgg tgagacagga tttgagacca caagagaaga aaaattagtc     9480
ctgaaaggag aagaaaaaag caggaaggtg tggataagaa cccgaaaatt aagccatctg     9540
cttaacaaat ttttctaatc ctagtatata ttctgctgca ggttaacaaa atatactaag     9600
cttaatgatt cgaaaccaat tttttactgg aagggaatta atcctaaata tattcattca     9660
aaagaactaa acaattctct gttgagtgcc gcctcatttg aggatactga ctcttacagc     9720
ctgagttagc tatgtggtct ctgcagctgg aatcactccc tgccactgga gtccttcatg     9780
gtgttagacc ataggtactg ttgactaaag aaaaaaaaaa gttttttgttt ttatttttgt    9840 tttttttgag acagagtctc actctgtcac ccaggctgga gtacagtggc gcgatctcag     9900
ctcaccgcaa cctccgcctt tctgggttca agcaattctc cttcctcagc ctcctgagta    9960
tttggattac aggcgcccac caccacgcct ggctaatttt tgtattttta gtagagacgg     10020
ggtttcacca tgttggccag gctggtctca aactcctgac ctcaggtgtc ctacctgcct    10080
tggcctccta aaatgctggg attacaggag tgagccacca tgcccggcca aaaaaataag    10140
tttttaaaga attaaaggtc atcctggcta acacagtgaa accccgtctc tactaaaaaa    10200
cacaaaaaaa ttagccgggc gtggtggcgg gcgcctgtag tcccagctgc gcgggaggct    10260
gaggcaggag aatggcgtga acccgggagg cggagcttgc agtgagccga tcgcgccaa    10320 ctgcactcca gcctgggcga cagagcgaga ctccgtctca aaaaaaaaa aaaaaaaaa     10380 aaaaaaaga attaaaggtg ttaattttat ttagaagcct tactgaagac tacagtcgga    10440
ggcctatagc ctgagagcag cccttagag aggttcagtt gaactgttct gatagtgggg    10500
gccatgtgct ctatcctgta ttgtcttcaa agcatctttc cagagagctg cacattgtca   10560
cagagtcagg gactttgtga aattatgctg acaaccagaa gtgagtaaac gtggcttctt    10620
acatttgcta cgttgtctca cagtacttaa taagtatgca atatgtaagt aaatactata    10680
gtactattgc aactcctgat tgttttctta gacaaggaat tgggcccaat aaaaaccctc    10740
ttggtaggca ttcaggcttc gtgtaccatg agctttccta agggtatcct gccactcttg    10800
gggaaggcat gatagatgag gggagtaagg ataatggaac tctgggtaca gggttcctgg    10860
gggctaactt agaggtagac acaggcaatg ctaaatattt gggattgatt ttatagaggt    10920
tgctagattg tgaatttcct tagtaagggc taaggcattg atatgtaatg tcacacttgg    10980
ctccgaggct gggttgttgg atccatgtag atgaaatcag ggagagaaag ggcagaacgg    11040
agtaatttag aaatgtattg atttgtatta ctctctgttg gcttgctatt caaggcagtg    11100
gagaactcaa tcacataata atctgcagca aaccacagat catcccaggg aatgaagttt    11160
taacattcgc tggctcccta actcctcacc cagcctttac attcactggc tgttcagtcc    11220
atgcctggac atcttaattt gaatacaaca ttttaaatcc attttctgt catcatcttg     11280 cactaacaga caattctaca ctaagcctat gtttatgaat atttctcaag gtacatgta     11340 cacagccttc agtataagga aaactggaag tatgacatac ctccagttgt catactcctt    11400
gggcccctct taaattctca ttaaactgca ggataggcaa gtcagaggtg aatctcaaat    11460
acgaaattct taccggaaag gggttccaat ccagacccca agagagggtt cttagatttc    11520
tcgcaagaaa taattcgggg caaggccaca gtgcaaagca aaagcaagtt tattaggaaa   11580
```

```
gtaaaggagt agagaacagc tactccatgg agaagaatgg cttgagctgc tccaccaagg    11640
gtatttagag ttacttcttg attatatgct aaacaagggg tggattattc atgagttttc    11700
cgggaaaagg gtgagcaatt cccagaactg agatttcctc ccctttttag gccatatagg    11760
gtaacttcct gccattgcca tggtatttgt aaactgtcat agtgctggtg gaagtgtctc    11820
ttagcttgct aatgtattat agttagctta taatgagcag tgaggacaac cagaggtcac    11880
tttcatcacc atcttggttt tggtgggttt tggccggctt cttttactgca ccctatttta   11940 tcaacaaggt ctttatgacc tgaatcttgt gccaacctcc tatctcatcc tgtgacaaag    12000
aatgccttaa cttcctggga atgcagccca gtaggtgtca gccttatttt acccagaccc    12060
tattcaagat ggagttgctc tgatttaaac gcctctgaca aaatgacgac ctcaaaacaa    12120
tccagcttta tggaatacct ccacaagaaa gaaagtatac ttagctatag aattttctcc    12180
ttgcatccaa caggctttga gatgtcagat gtttccttcc tgtcccatga ttaatcctag    12240
ccattcctct ttcttgtctg gctccactac tccttaccat ctaatgcctc gccaccattt    12300
tgatattttg actaagtgag ctatgaaaca cacctactgg atatgaaagt ataagtttct    12360
gataacaaaa catcaacatg ggatgtggag gaagtgggta gggtggcatt aatgcagcaa    12420
atcctggaat attttaaatc ttcattctaa atttagtaaa aatataggat aattttcctg    12480
ccatcattta cttataaaat taaaatttta gaaaataaaa ataatatttt cctctttta    12540 atcacagatt atggcctgta ttggagacag atgaagtcgt aagaagtctg atagatggaa    12600
tacttaccaa taagaaaatg attttttgttc catcgtatat caatatcttt ctgagactac    12660
agaagttaag tacagcacag aacacccaaa tactaaaaca ccaatagagc tttttttttt    12720 gcttttttttt tttttagaca gagtctcact ctgtcaccct ggctggattg cggtggttgc    12780
agtggcatga tcttggctca ctgcaacctc cgcctcctgg gttcaagcaa ttctcatgcc    12840
tcagaccccc aagtaactgg gattataggt gtgtgctgcc acactacacc cagctaattt    12900
ttgtattttt tgatagagac aggtttcccc atgttggcca ggctggactc gaactcctga    12960
cctcaagtta tcctcctgtc tcggcctccc aaagtgctgg gattacagtc atgagccacc    13020
atgcctggcc caatagagct attattatgg agcatctttc agttgtgaaa attggcatgg    13080
aaactctcca tccctgggga gaacagttat ttcctctgtt attttcctac ccagtctata    13140
aaaagagagt gattcatttt ctctaccaaa tctactgtct ctgcccaaac tttgctgaag    13200
actattctaa ctaaaggaaa cacagtttaa aaagaatgca atatagtgaa gtagttaata    13260
ataaagactc cattttttaaa agtctgctgg aagtttggtt gggattgcac tgaatctata    13320
gagcaattgg ggagtattga catatcaaca atattgagtt ttctaatcca agaacataat    13380
atctattttt aaaatcttct tcaaaatctt taaatcttta aattgtattt tgtagttttt    13440
ggtgtttaag tcttgcacat attttgtcag atttattcca aagtatttca cgggttcttt    13500
tttttttttt tttttttttt tttgagacag agtttcaccc ttgttcccca ggctggagtg    13560
cagtggcgtg atcttggctc actgcagctt ctgcctcctg gcttcaagtg attctcctgc    13620
ctcagcctcc caagtagctg ggattacagg cacctgcccc ctcgcccaac taacttttttg   13680 tgtttgtagt agagacaggg tttcaccatg ttggccaggc tggtctcgaa ctcctgacct    13740
catgtgatcc acctgcctca gcctcccaaa gtgctgggat tacaggcatg agccatcatg    13800
cccagcccta tttgacggtt tttgacgcta atgcaagtgg catttaaaaa aattttatat    13860
ttcccattgt ttgttgtcag tatatattgg attttttgtaa tttgatctca tattttgcag    13920
```

```
tcttgctaaa ttgctaaacc tcttttttgct aaactcgata agcttttttt ttttttggtag    13980 attcctgggc ctctaatttt ctttatggga aagttttttaa ttacaaattt aatttcttta    14040
atagctacat ggctattcaa tttacttatt aattcttggt aatgtgtgtc tttcaaggaa    14100
tttgtccatt tcatctaagt tgtagaattt ctttggcata aatttgtaca taacattccc    14160
ttattatcct tttaatgtct ttagaatgtc ttatttattt atttatttat tttattata    14220 ttttttttgag acagagtctc gctctgttgc ccaggctgga gtgcagtggc acaatcttgg    14280
ctcactgcaa gctccgcctt ctgggttcat gccattctcc tgcctcagcc tccctagttg    14340
ctgggactac aggcgcctgc aaccatgccc agcttatttt tttttttttt ttttttttt    14400 tttttttttt tttttttttt ttagtagaga cggggtttca ccctgttagc caggatggtc    14460
tcgatctcct gacctggtga tccgcccgcc tcagcctccc aaagtgctgg gattacaggc    14520
gtgagccacc aagcccagcc tatttattta tttagtagag acagtctcac tttgctgccc    14580
aggcaacaaa ggttttgaat gcctggcctc aagcagtcct cctgccttgg cctcccaaag    14640
tgctgggatt acaggcatga gccactgcac ctggccaaat gaatatgctg ataatatctt    14700
ctttataagg atgacataag aataaaataa tgtaatacaa acaaagcccc tgtcactgaa    14760
aatgtataga cttcaaatgt taaagtctta gagaacagaa tttatatgaa atagcaacag    14820
caacaatttc ccagaggaaa tactctctca gctttcttct gaggagcagt ttctaaattg    14880
aaattgtatc agtgagaaga taactatact aacttcataa gccttgggcc tttttgaaac    14940
aaatccatat aaactatgaa caaacttgaa atagaacaat ttgagaacag ggtacaaact    15000
gcattggtgt atcaatttca gtatttggtt ttagcttaaa tagactgact tgagataaca    15060
taaggagaac cttgaccccc aagcaacatc atctcgcgag ttgactaggc cgggtgtggt    15120
gtctcacgcc tgtaattcca gcactttggg aggccacagc aggcagatca cttgaggtca    15180
ggcattcgag accagcctgg ccaacatggt gaaacctcag ctctactaaa gatacgaaaa    15240
ttagcaggca tagtggcctg cacctgtaat accaggcact cgcaggagaa tcccttgaac    15300
ccggaaggcg gagattgcag taaaccatga ttgtgccact gcactccagc ctgggcaaca    15360
ggagactctg tctcggaaaa ataaatttt taaaaaaatg aaaaaaaata aaagttgact    15420
aaattagtgt cttggtacta agcactgtag gaagtgagtt tcatggaacc ccaactctct    15480
tggggcccaa agcaagtcat attaatattg aaaattacat gcatatacat gcatatgacc    15540
aaggtgataa aaacaattat tctgcctgag ttggagaata gtatcccagt aaaataaaca    15600
agagtctcaa agtcttttgt atcctttgaa gctgtcatgg tggtttgtaa ctaggcaaca    15660
ggtatatatt gttaatcttc tttgcattta attccttta tagagagaca caattttacg    15720
agcagatgca attactagca tgaaggtttc tttgtgaggg tagttaaaag gcccacatga    15780
gctctcttct tatccttgtc cttctttcag ccagatcttc cctgcccctt tgctcattcc    15840
atctttcacc cacctacccc caaaacaagg aagtaaatct tgcattagtc aacaatacca    15900
aagtgatttt caatatgact ttctctgcag aatgttatta tttctgcctc tttacattca    15960
catactgtct tcctttttt tttttttttt tttttttttt ttagattggg tctcactctg    16020
ttgcccaggc tggagtgcag tggcttgatc tcagctcact gtaacctcca cctcctgagt    16080
tcaagcaatt ctcctgcctc agcctcctga gtagctggga ttacaggcat gtgccaccac    16140
acctggctag tttttttgta ttttagtag agacagggtt tcaccatgtt ggtcaagctg    16200
gtctcgaact cctgacctca tgatctgacc acctgtgcct ctcaaagtgc tgggattaca    16260
ggcgtgagcc accgggccag ccactctctt cctttcagtt gcctactcat ctcttatgca    16320
```

```
ttcctggaca tcagttgtcc ttttgaagct ttcctccact atcccagccc atgtgaatcc    16380
tccttccagt tatagccctt aattctagat ggctgatatt tttcaataat tgttttaaga    16440
tgaccatttt agcctatcag ctaaacaata tcaaagacaa tagctatttt tcaagtactt    16500
tagtttacct tattatagag tgcataatag atattcagta aatagtaaag gagaggtgaa    16560
ggcttgcata gaatggattc tggtggtgtc tcttggtgag cttttagcat caagattaat    16620
cagcagtttc agcaatgagc tcagaccttc agttttagat ctttactcat atcagataag    16680
agagtgagaa gagtggtatg tatcagtgct ttatttatat ttgcatccaa tttgaactat    16740
gaatattaca aaggtgcaca cataggttca gacagattga tttaaaatga ccaaagatga    16800
cctgtcgtaa gcaacctggg tatcttaaga tgcactcctt ggagagggaa tgttcctaaa    16860
aacattttca gagggacgaa ctgtatgaaa ttcagtaaaa cataaatcat gaggaaaact    16920
gattactctc tttttgacat gaaatgagag ttttaatgca tggttacgat tattaacgta    16980
ctccgctgca agacgttaat aaagttactg ttttgcaggc tagaatgtct tgatgctgta    17040
atcagaacac acttttttccc ctttcttcca gcttcaaatg cagattcata attgggctga    17100
cttctaataa ctgcaatgtt ttctgccttg ggcttgcagc agaagcctga caaaatagtg    17160
tttgtttagg caataattta tttatttatt tattgagatg gagtttcatt cttgtcgccc    17220
aggctggagt gcaatggcgt gatctcggct cactgcaacc tctgtgttca ggcaataatt    17280
tagactttac cttacttgtg attactatag caattactat agccacaagg cataatttta    17340
ctgtctcatt tcaattttat gaatttgaat gtttttacac ttttcctaat gaagtccact    17400
atgaagttat gtcaaaaaaa aaaagaaaa agaaagatgc acacgtaaaa gagaggtggt    17460
tgcaagagaa gaaagaacg gaggaaagtt aaacgcaaac cagataactc tcagcgtatt    17520
ctaaatgacc aaaaacagaa ctctgttgtc aaagatttta aatggaaaat ttttcaattt    17580 tttttttcttt tttgtacagg tttcttcctg aacgcgcctc agcgatttta aatcgtatgc    17640
agaatattca atttgaagca gtggttggcc acaaaatcaa aatgaaatga ataaataagc    17700
tccagccaga gatgtatgca tgataatgat atgaatagtt tcgaatcaat gctgcaaagc    17760
tttatttcac attttttcag tcctgataat attaaaaaca ttggtttggc actagcagca    17820
gtcaaacgaa caagattaat tacctgtctt cctgtttctc aagaatattt acgtagtttt    17880
tcataggtct gttttttcctt tcatgcctct taaaaacttc tgtgcttaca taaacatact    17940
taaaaggttt tctttaagat attttatttt tccatttaaa ggtggacaaa agctacctcc    18000
ctaaaagtaa atacaaagag aacttattta cacagggaag gtttaagact gttcaagtag    18060
cattccaatc tgtagccatg ccacagaata tcaacaagaa cacagaatga gtgcacagct    18120
aagagatcaa gttcagcag gcagctttat ctcaacctgg acatatttta agattcagca    18180
tttgaaagat ttccctagcc tcttcctttt tcattagccc aaaacggtgc aactctattc    18240
tggactttat tacttgattc tgtcttctgt ataactctga agtccaccaa aagtggaccc    18300
tctatatttc ctcccttttt atagtcttat aagatacatt atgaaaggtg accgactcta    18360
ttttaaatct cagaatttta agttctagcc ccatgataac cttttttcttt gtaatttatg    18420 ctttcatata tccttggtcc cagagatgtt tagacaattt taggctcaaa aattaaagct    18480
aacacaggaa aaggaactgt actggctatt acataagaaa caatggaccc aagagaagaa    18540
aaggaagaaa gaaaggtttt ttggttttttg ttttgttttg ttttgttttt tgttttttg    18600 agatggagtc tcactctttc gcccaggctg gagtgcagtg gtatgatctc agctcactgc    18660
```

| | |
|---|---|
| aagctccacc tcccgggttc acgccattct cctgcctcag cctcctgagt agctgggact | 18720 |
| acaggcgccc gccaccacac ccggctaatt ttttgtattt tttgtagaga cggggtttca | 18780 |
| ccatgttagc caagatggtc tcgatctcct gacctcgtga tccacctgcc tcggcctccc | 18840 |
| aaagtgctgg gattacgggt gtgagccacc gtgcccagcc tttttttttt taatagaaaa | 18900 |
| aataatccga ctcccactac atcaagacta atcttgtttt gtgtgttttt cacatgtatt | 18960 |
| atagaatgct tttgcatgga ctatcctctt gttttttatta aaacaaatg atttttttaa | 19020 |
| aagtcacaaa aacaattcac taaaaataaa tatgtcattg tgctttaaaa aaataacctc | 19080 |
| ttgtagttat aaaataaaac gtttgacttc taaactctg | 19119 |

```
<210> SEQ ID NO 3
<211> LENGTH: 900
<212> TYPE: DNA
<213> ORGANISM: Homo sapien

<400> SEQUENCE: 3
```

| | |
|---|---|
| augaacauca uccuagaaau ccuucugcuu cugaucacca ucaucuacuc cuacuuggag | 60 |
| ucguuggug aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag cgcggugugg aggaaacugc agcugagugc | 240 |
| cgaaaacuag gcgucacugc gcaugcguau guguagacu gcagcaacag agaagagauc | 300 |
| uaucgcucuc uaaaucaggu gaagaaagaa gugggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aucacaaaag cacuucuucc aucgaugaug | 480 |
| gagagaaauc auggccacau cgucacagug gcuucagugu gcggccacga agggauuccu | 540 |
| uaccucaucc cauauuguuc cagcaaauuu gccgcuguug cuuucacag aggucugaca | 600 |
| ucagaacuuc aggccuuggg aaaaacuggu aucaaaaccu caugucucug cccaguuuuu | 660 |
| gugaauacug gguucaccaa aaauccaagc acaagauuau ggccuguauu ggagacagau | 720 |
| gaagucguaa gaagucugau agauggaaua cuuaccaaua agaaaaugau uuuuguucca | 780 |
| ucguauauca auaucuuucu gagacuacag aaguucuuc cugaacgcgc cucagcgauu | 840 |
| uuaaaucgua ugcagaauau ucaauuugaa gcaguggaug gccacaaauu caaaaugaaa | 900 |

```
<210> SEQ ID NO 4
<211> LENGTH: 792
<212> TYPE: DNA
<213> ORGANISM: Homo sapien

<400> SEQUENCE: 4
```

| | |
|---|---|
| augaacauca uccuagaaau ccuucugcuu cugaucacca ucaucuacuc cuacuuggag | 60 |
| ucguuggug aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag gugaagaaag agugggugaa uguaacaauc | 240 |
| guggugaauaa augcugggac aguauauccca gccgaucuuc ucagcaccaa ggaugaagag | 300 |
| auuaccaaga cauuugaggu caacauccua ggacauuuuu ggaucacaaa agcacuucuu | 360 |
| ccaucgauga uggagagaaa ucauggccac aucgucacag uggcuucagu gugcggccac | 420 |
| gaagggauuc cuuaccucau cccauauugu uccagcaaau uugccgcugu ugcuuucac | 480 |
| agaggucuga caucagaacu ucaggccuug ggaaaaacug guaucaaaac cucaugucuc | 540 |

```
ugcccaguuu uugugaauac ugggUUcacc aaaaauccaa gcacaagauu auggccugua    600
uuggagacag augaagucgu aagaagucug auagauggaa uacuuaccaa uaagaaaaug    660
auuuuuguuc caucguauau caauaucuuu cugagacuac agaaguuucu uccugaacgc    720
gccucagcga uuuuaaaucg uaugcagaau uucaauuug aagcaguggu uggccacaaa     780
aucaaaauga aa                                                        792

<210> SEQ ID NO 5
<211> LENGTH: 783
<212> TYPE: DNA
<213> ORGANISM: Homo sapien

<400> SEQUENCE: 5
augaacauca uccuagaaau ccuucugcuu cugaucacca ucaucuacuc cuacuuggag     60
ucguuggUga aguuuucau uccucagagg agaaaaucug uggcuggga gauuguucuc     120 auuacuggag cugggcaugg aauaggcagg cagacuacuu augaauuugc aaaacgacag    180
agcauauugg uucguggga uauuaauaag cgcggugugg aggaaacugc agcugagugc    240
cgaaaacuag gcgucacugc gcaugcguau guggUagacu gcagcaacag agaagagauc    300
uaucgcucuc uaaaucaggu gaagaaagaa guggguggaug uaacaaucgu ggugaauaau    360
gcugggacag uauauccagc cgaucuucuc agcaccaagg augaagagau uaccaagaca    420
uuugagguca acauccuagg acauuuuugg aucacaaaag cacuucuucc aucgaugaug    480
gagagaaauc auggccacau cgucacagug gcuucagugu gcggccacga agggauuccu    540
uaccucaucc cauauuguuc cagcaaauuu gccgcuguug gcuuucacag aggucugaca    600
ucagaacuuc aggccuuggg aaaaacuggu aucaaaaccu caugucucug cccaguuuuu    660
gugaauacug gguucaccaa aaauccaagc acaagguuuc uuccgaacg cgccucagcg    720 auuuuaaauc guaugcagaa uauucaauuu gaagcagugg uuggccacaa aaucaaaaug    780
aaa                                                                  783

<210> SEQ ID NO 6
<211> LENGTH: 822
<212> TYPE: DNA
<213> ORGANISM: Homo sapien

<400> SEQUENCE: 6
augaacauca uccuagaaau ccuucugcuu cugaucacca ucaucuacuc cuacuuggag     60
ucguuggUga aguuuucau uccucagagg agaaaaucug uggcuggga gauuguucuc     120 auuacuggag cugggcaugg aauaggcagg cagacuacuu augaauuugc aaaacgacag    180
agcauauugg uucguggga uauuaauaag cgcggugugg aggaaacugc agcugagugc    240
cgaaaacuag gcgucacugc gcaugcguau guggUagacu gcagcaacag agaagagauc    300
uaucgcucuc uaaaucaggu gaagaaagaa guggguggaug uaacaaucgu ggugaauaau    360
gcugggacag uauauccagc cgaucuucuc agcaccaagg augaagagau uaccaagaca    420
uuugagguca acauccuagg acauuuuugg aucacaaaag cacuucuucc aucgaugaug    480
gagagaaauc auggccacau cgucacagug gcuucagugu gcggccacga agggauuccu    540
uaccucaucc cauauuguuc cagcaaauuu gccgcuguug gcuuucacag aggucugaca    600
ucagaacuuc aggccuuggg aaaaacuggu aucaaaaccu caugucucug cccaguuuuu    660
gugaauacug gguucaccaa aaauccaagc acaagauuau ggccuguauu ggagacagau    720
```

| | |
|---|---|
| gaagucguaa gaagucugau agauggaaua cuuaccaaua agaaaaugau uuuuguucca | 780 |
| ucguauauca auaucuuucu gagacuacag aagguuucuu cc | 822 |

<210> SEQ ID NO 7
<211> LENGTH: 972
<212> TYPE: DNA
<213> ORGANISM: Homo sapien

<400> SEQUENCE: 7

| | |
|---|---|
| augaacauca uccuagaaau ccuucugcuu cugaucacca ucaucuacuc cuacuuggag | 60 |
| ucguugguga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag cgcggugugg aggaaacugc agcugagugc | 240 |
| cgaaaacuag gcgucacugc gcaugcguau gugguagacu gcagcaacag agaagagauc | 300 |
| uaucgcucuc uaaaucaggu gaagaaagaa gugggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aauggaaagg acaucagaag uaauuacuug | 480 |
| gauguauaua ggaucgagga cacuuuugga cgagacucug agaucacaaa agcacuucuu | 540 |
| ccaucgauga uggagagaaa ucauggccac aucgucacag uggcuucagu gucggccac | 600 |
| gaagggauuc cuuaccucau cccauauugu ccagcaaauu ugccgcugu ggcuuucac | 660 |
| agaggucuga caucagaacu ucaggccuug ggaaaaacug uaucaaaac cucaugucuc | 720 |
| ugcccaguuu uugugaauac ugggucacc aaaaauccaa gcacaagauu auggccugua | 780 |
| uuggagacag augaagucgu aagaagucug auagauggaa uacuuaccaa uaagaaaaug | 840 |
| auuuuuguuc caucguauau caauaucuuu cugagacuac agaaguuucu uccugaacgc | 900 |
| gcccucagcga uuuuaaaucg uaugcagaau auucaauuug aagcagguggu uggccacaaa | 960 |
| aucaaaauga aa | 972 |

<210> SEQ ID NO 8
<211> LENGTH: 852
<212> TYPE: DNA
<213> ORGANISM: Homo sapien

<400> SEQUENCE: 8

| | |
|---|---|
| augaacauca uccuagaaau ccuucugcuu cugaucacca ucaucuacuc cuacuuggag | 60 |
| ucguugguga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag cgcggugugg aggaaacugc agcugagugc | 240 |
| cgaaaacuag gcgucacugc gcaugcguau gugguagacu gcagcaacag agaagagauc | 300 |
| uaucgcucuc uaaaucaggu gaagaaagaa gugggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aucacaaaag cacuucuucc aucgaugaug | 480 |
| gagagaaauc auggccacau cgucacagug gcuucagugu cggcacga agggauuccu | 540 |
| uaccucaucc cauauuguuc cagcaaauuu gccgcguuug cuuucacag aggucugaca | 600 |
| ucagaacuuc aggccuuggg aaaaacuggu aucaaaaccu caugucucug cccaguuuuu | 660 |
| gugaauacug ggucaccaa aaauccaagc acaagauuau ggccuguauu ggagacagau | 720 |
| gaagucguaa gaagucugau agauggaaua cuuaccaaua agaaaaugau uuuuguucca | 780 |

```
ucguauauca auaucuuucu gagacuacag aaguuaagua cagcacagaa cacccaaaua     840
cuaaaacacc aa                                                         852
```

<210> SEQ ID NO 9
<211> LENGTH: 714
<212> TYPE: DNA
<213> ORGANISM: Homo sapien

<400> SEQUENCE: 9

```
augaacauca uccuagaaau ccuucugcuu cugaucacca ucaucuacuc cuacuuggag      60
ucguuggugu aguuuuucau uccucagagg agaaaaucug uggcugggga gauuguucuc     120
auuacuggag cugggcaugg aauaggcagg cagacuacuu augaauuugc aaaacgacag     180
agcauauugg uucuguggga uauuaauaag gugaagaaag aagugggugu aguaacaauc     240
guggugaaua augcugggac aguauaucca gccgaucuuc ucagcaccaa ggaugaagag     300
auuaccaaga cauuugaggu caacauccua ggacauuuuu ggaucacaaa agcacuucuu     360
ccaucgauga uggagagaaa ucauggccac aucgucacag uggcuucagu gugcggccac     420
gaagggauuc cuaccucau cccauauugu ccagcaaau uugccgcugu ggcuuucac       480 agagucuga caucagaacu ucaggccuug ggaaaaacug guaucaaaac cucaugucuc     540
ugcccaguuu uugugaauac uggguucacc aaaaauccaa gcacaagauu auggccugua    600
uuggagacag augaagucgu aagaagucug auagauggaa uacuuaccaa uaagaaaaug    660
auuuuuguuc caucguauau caauaucuuu cugagacuac agaagguuuc uucc          714
```

<210> SEQ ID NO 10
<211> LENGTH: 894
<212> TYPE: DNA
<213> ORGANISM: Homo sapien

<400> SEQUENCE: 10

```
augaacauca uccuagaaau ccuucugcuu cugaucacca ucaucuacuc cuacuuggag      60
ucguuggugu aguuuuucau uccucagagg agaaaaucug uggcugggga gauuguucuc     120
auuacuggag cugggcaugg aauaggcagg cagacuacuu augaauuugc aaaacgacag     180
agcauauugg uucuguggga uauuaauaag cgcggugugg aggaaacugc agcugagugc     240
cgaaaacuag gcgucacugc gcaugcguau guguagacu gcagcaacag agaagagauc     300
uaucgcucuc uaaaucaggu gaagaaagaa gugggugaug uaacaaucgu ggugaauaau    360
gcugggacag uauauccagc cgaucuucuc agcaccaagg augaagagau uaccaagaca    420
uuugagguca caucuagg acauuuuugg aauggaaagg acaucagaag uaauuacuug      480
gauguauaua ggaucgagga cacuuuugga cgagacucug aucacaaa agcacuucuu      540 ccaucgauga uggagagaaa ucauggccac aucgucacag uggcuucagu gugcggccac    600
gaagggauuc cuaccucau cccauauugu ccagcaaau uugccgcugu ggcuuucac       660 agagucuga caucagaacu ucaggccuug ggaaaaacug guaucaaaac cucaugucuc     720
ugcccaguuu uugugaauac uggguucacc aaaaauccaa gcacaagauu auggccugua    780
uuggagacag augaagucgu aagaagucug auagauggaa uacuuaccaa uaagaaaaug    840
auuuuuguuc caucguauau caauaucuuu cugagacuac agaagguuuc uucc          894
```

<210> SEQ ID NO 11
<211> LENGTH: 813
<212> TYPE: DNA

<213> ORGANISM: Homo sapien

<400> SEQUENCE: 11

| | | | | | |
|---|---|---|---|---|---|
| augaacauca | uccuagaaau | ccuucugcuu | cugaucacca | ucaucuacuc | cuacuuggag | 60 |
| ucguuggnga | aguuuuucau | uccucagagg | agaaaaucug | uggcugggga | gauuguucuc | 120 |
| auuacuggag | cugggcaugg | aauaggcagg | cagacuacuu | augaauuugc | aaaacgacag | 180 |
| agcauauugg | uucugnggga | uauuaauaag | cgcggngugg | aggaaacugc | agcugagugc | 240 |
| cgaaaacuag | gcgucacugc | gcaugcguau | guggnagacu | gcagcaacag | agaagagauc | 300 |
| uaucgcucuc | uaaaucaggu | gaagaaagaa | gugggugaug | uaacaaucgu | ggngaauaau | 360 |
| gcugggacag | uauauccagc | cgaucuucuc | agcaccaagg | augaagagau | uaccaagaca | 420 |
| uuugagguca | acauccuagg | acauuuuugg | aucacaaaag | cacuucuucc | aucgaugaug | 480 |
| gagagaaauc | auggccacau | cgucacagug | gcuucagugu | gcggccacga | agggauuccu | 540 |
| uaccucaucc | cauauuguuc | cagcaaauuu | gccgcuguug | gcuuuacag | aggucugaca | 600 |
| ucagaacuuc | aggccuuggg | aaaaacuggu | aucaaaaccu | caugucucug | cccaguuuuu | 660 |
| gugaauacug | gguucaccaa | aaauccaagc | acaagauuau | ggccuguauu | ggagacagau | 720 |
| gaagucguaa | gaagucugau | agauggaaua | cuuaccaaua | agaaaaugau | uuuuguucca | 780 |
| ucguauauca | auaucuuucu | gagacuacag | aag | | | 813 |

<210> SEQ ID NO 12
<211> LENGTH: 900
<212> TYPE: DNA
<213> ORGANISM: Homo sapien

<400> SEQUENCE: 12

| | | | | | |
|---|---|---|---|---|---|
| atgaacatca | tcctagaaat | ccttctgctt | ctgatcacca | tcatctactc | ctacttggag | 60 |
| tcgttggtga | agttttcat | tcctcagagg | agaaaatctg | tggctgggga | gattgttctc | 120 |
| attactggag | ctgggcatgg | aataggcagg | cagactactt | atgaatttgc | aaaacgacag | 180 |
| agcatattgg | ttctgtggga | tattaataag | cgcggtgtgg | aggaaactgc | agctgagtgc | 240 |
| cgaaaactag | gcgtcactgc | gcatgcgtat | gtggtagact | gcagcaacag | agaagagatc | 300 |
| tatcgctctc | taaatcaggt | gaagaaagaa | gtgggtgatg | taacaatcgt | ggtgaataat | 360 |
| gctgggacag | tatatccagc | cgatcttctc | agcaccaagg | atgaagagat | taccaagaca | 420 |
| tttgaggtca | acatcctagg | acattttgg | atcacaaaag | cacttcttcc | atcgatgatg | 480 |
| gagagaaatc | atggccacat | cgtcacagtg | gcttcagtgt | gcggccacga | agggattcct | 540 |
| tacctcatcc | catattgttc | cagcaaattt | gccgctgttg | gctttacag | aggtctgaca | 600 |
| tcagaacttc | aggccttggg | aaaaactggt | atcaaaacct | catgtctctg | cccagttttt | 660 |
| gtgaatactg | ggttcaccaa | aaatccaagc | acaagattat | ggcctgtatt | ggagacagat | 720 |
| gaagtcgtaa | gaagtctgat | agatggaata | cttaccaata | agaaaatgat | ttttgttcca | 780 |
| tcgtatatca | atatctttct | gagactacag | aagtttcttc | tgaacgcgc | ctcagcgatt | 840 |
| ttaaatcgta | tgcagaatat | tcaatttgaa | gcagtggttg | ccacaaaat | caaatgaaa | 900 |

<210> SEQ ID NO 13
<211> LENGTH: 792
<212> TYPE: DNA
<213> ORGANISM: Homo sapien

<400> SEQUENCE: 13

| | | | | | |
|---|---|---|---|---|---|
| atgaacatca | tcctagaaat | ccttctgctt | ctgatcacca | tcatctactc | ctacttggag | 60 |

```
tcgttggtga agttttcat tcctcagagg agaaaatctg tggctgggga gattgttctc        120
attactggag ctgggcatgg aataggcagg cagactactt atgaatttgc aaaacgacag       180
agcatattgg ttctgtggga tattaataag gtgaagaaag aagtgggtga tgtaacaatc       240
gtggtgaata atgctgggac agtatatcca gccgatcttc tcagcaccaa ggatgaagag       300
attaccaaga catttgaggt caacatccta ggacattttt ggatcacaaa agcacttctt      360
ccatcgatga tggagagaaa tcatggccac atcgtcacag tggcttcagt gtgcggccac       420
gaagggattc cttacctcat cccatattgt ccagcaaat tgccgctgt tggctttcac        480 agaggtctga catcagaact tcaggccttg gaaaaactg gtatcaaaac ctcatgtctc        540
tgcccagttt ttgtgaatac tgggttcacc aaaaatccaa gcacaagatt atggcctgta     600
ttggagacag atgaagtcgt aagaagtctg atagatggaa tacttaccaa taagaaaatg    660 attttttgttc catcgtatat caatatcttt ctgagactac agaagtttct tcctgaacgc   720
gcctcagcga ttttaaatcg tatgcagaat attcaatttg aagcagtggt tggccacaaa  780
atcaaaatga aa                                                         792

<210> SEQ ID NO 14
<211> LENGTH: 783
<212> TYPE: DNA
<213> ORGANISM: Homo sapien

<400> SEQUENCE: 14
atgaacatca tcctagaaat ccttctgctt ctgatcacca tcatctactc ctacttggag       60
tcgttggtga agttttcat tcctcagagg agaaaatctg tggctgggga gattgttctc       120
attactggag ctgggcatgg aataggcagg cagactactt atgaatttgc aaaacgacag       180
agcatattgg ttctgtggga tattaataag cgcggtgtgg aggaaactgc agctgagtgc       240
cgaaaactag gcgtcactgc gcatgcgtat gtggtagact gcagcaacag agaagagatc       300
tatcgctctc taaatcaggt gaagaaagaa gtgggtgatg taacaatcgt ggtgaataat       360
gctgggacag tatatccagc cgatcttctc agcaccaagg atgaagagat taccaagaca      420
tttgaggtca catcctagg acatttttgg atcacaaaag cacttcttcc atcgatgatg      480
gagagaaatc atggccacat cgtcacagtg gcttcagtgt gcggccacga agggattcct     540
tacctcatcc catattgttc agcaaattt gccgctgttg ctttcacag aggtctgaca       600 tcagaacttc aggccttggg aaaaactggt atcaaaacct catgtctctg cccagttttt     660
gtgaatactg ggttcaccaa aaatccaagc acaaggtttc ttcctgaacg cgcctcagcg     720
attttaaatc gtatgcagaa tattcaattt gaagcagtgg ttggccacaa aatcaaaatg     780
aaa                                                                   783

<210> SEQ ID NO 15
<211> LENGTH: 822
<212> TYPE: DNA
<213> ORGANISM: Homo sapien

<400> SEQUENCE: 15
atgaacatca tcctagaaat ccttctgctt ctgatcacca tcatctactc ctacttggag       60
tcgttggtga agttttcat tcctcagagg agaaaatctg tggctgggga gattgttctc       120
attactggag ctgggcatgg aataggcagg cagactactt atgaatttgc aaaacgacag       180
agcatattgg ttctgtggga tattaataag cgcggtgtgg aggaaactgc agctgagtgc       240
```

| | |
|---|---|
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |
| gctgggacag tatatccagc cgatcttctc agcaccaagg atgaagagat taccaagaca | 420 |
| tttgaggtca acatcctagg acattttggg atcacaaaag cacttcttcc atcgatgatg | 480 |
| gagagaaatc atggccacat cgtcacagtg gcttcagtgt gcggccacga agggattcct | 540 |
| tacctcatcc catattgttc cagcaaattt gccgctgttg gctttcacag aggtctgaca | 600 |
| tcagaacttc aggccttggg aaaaactggt atcaaaacct catgtctctg cccagttttt | 660 |
| gtgaatactg ggttcaccaa aaatccaagc acaagattat ggcctgtatt ggagacagat | 720 |
| gaagtcgtaa gaagtctgat agatggaata cttaccaata agaaaatgat ttttgttcca | 780 |
| tcgtatatca atatctttct gagactacag aaggtttctt cc | 822 |

<210> SEQ ID NO 16
<211> LENGTH: 972
<212> TYPE: DNA
<213> ORGANISM: Homo sapien

<400> SEQUENCE: 16

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |
| gctgggacag tatatccagc cgatcttctc agcaccaagg atgaagagat taccaagaca | 420 |
| tttgaggtca acatcctagg acattttggg aatggaaagg acatcagaag taattacttg | 480 |
| gatgtatata ggatcgagga cacttttgga cgagactctg agatcacaaa agcacttctt | 540 |
| ccatcgatga tggagagaaa tcatggccac atcgtcacag tggcttcagt gtgcggccac | 600 |
| gaagggattc cttacctcat cccatattgt tccagcaaat ttgccgctgt tggctttcac | 660 |
| agaggtctga catcagaact tcaggccttg ggaaaaactg gtatcaaaac ctcatgtctc | 720 |
| tgcccagttt ttgtgaatac tgggttcacc aaaaatccaa gcacaagatt atggcctgta | 780 |
| ttggagacag atgaagtcgt aagaagtctg atagatggaa tacttaccaa taagaaaatg | 840 |
| attttttgttc catcgtatat caatatcttt ctgagactac agaagtttct tcctgaacgc | 900 |
| gcctcagcga ttttaaatcg tatgcagaat attcaatttg aagcagtggt tggccacaaa | 960 |
| atcaaaatga aa | 972 |

<210> SEQ ID NO 17
<211> LENGTH: 852
<212> TYPE: DNA
<213> ORGANISM: Homo sapien

<400> SEQUENCE: 17

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |

```
tatcgctctc taaatcaggt gaagaaagaa gtgggtgatg taacaatcgt ggtgaataat      360
gctgggacag tatatccagc cgatcttctc agcaccaagg atgaagagat taccaagaca      420
tttgaggtca acatcctagg acattttggg atcacaaaag cacttcttcc atcgatgatg      480
gagagaaatc atggccacat cgtcacagtg gcttcagtgt gcggccacga agggattcct      540
tacctcatcc catattgttc cagcaaattt gccgctgttg gctttcacag aggtctgaca      600
tcagaacttc aggccttggg aaaaactggt atcaaaacct catgtctctg cccagttttt      660
gtgaatactg ggttcaccaa aaatccaagc acaagattat ggcctgtatt ggagacagat      720
gaagtcgtaa gaagtctgat agatggaata cttaccaata agaaaatgat ttttgttcca      780
tcgtatatca atatctttct gagactacag aagttaagta cagcacagaa cacccaaata      840
ctaaaacacc aa                                                          852
```

<210> SEQ ID NO 18
<211> LENGTH: 714
<212> TYPE: DNA
<213> ORGANISM: Homo sapien

<400> SEQUENCE: 18

```
atgaacatca tcctagaaat ccttctgctt ctgatcacca tcatctactc ctacttggag       60
tcgttggtga agttttttcat tcctcagagg agaaaatctg tggctgggga gattgttctc     120
attactggag ctgggcatgg aataggcagg cagactactt atgaatttgc aaaacgacag     180
agcatattgg ttctgtggga tattaataag gtgaagaaag aagtgggtga tgtaacaatc     240
gtggtgaata atgctgggac agtatatcca gccgatcttc tcagcaccaa ggatgaagag     300
attaccaaga catttgaggt caacatccta ggacattttt ggatcacaaa agcacttctt     360
ccatcgatga tggagagaaa tcatggccac atcgtcacag tggcttcagt gtgcggccac     420
gaagggattc cttacctcat cccatattgt tccagcaaat ttgccgctgt tggctttcac     480
agaggtctga catcagaact tcaggccttg gaaaaactg gtatcaaaac ctcatgtctc     540
tgcccagttt ttgtgaatac tgggttcacc aaaaatccaa gcacaagatt atggcctgta     600
ttggagacag atgaagtcgt aagaagtctg atagatggaa tacttaccaa taagaaaatg     660 attttttgttc catcgtatat caatatcttt ctgagactac agaaggtttc ttcc           714
```

<210> SEQ ID NO 19
<211> LENGTH: 894
<212> TYPE: DNA
<213> ORGANISM: Homo sapien

<400> SEQUENCE: 19

```
atgaacatca tcctagaaat ccttctgctt ctgatcacca tcatctactc ctacttggag       60
tcgttggtga agttttttcat tcctcagagg agaaaatctg tggctgggga gattgttctc     120
attactggag ctgggcatgg aataggcagg cagactactt atgaatttgc aaaacgacag     180
agcatattgg ttctgtggga tattaataag cgcggtgtgg aggaaactgc agctgagtgc     240
cgaaaactag cgtcactgc gcatgcgtat gtggtagact gcagcaacag agaagagatc     300
tatcgctctc taaatcaggt gaagaaagaa gtgggtgatg taacaatcgt ggtgaataat     360
gctgggacag tatatccagc cgatcttctc agcaccaagg atgaagagat taccaagaca     420
tttgaggtca acatcctagg acattttggg aatggaaagg acatcagaag taattacttg     480
gatgtatata ggatcgagga cacttttgga cgagactctg agatcacaaa agcacttctt     540
```

```
ccatcgatga tggagagaaa tcatggccac atcgtcacag tggcttcagt gtgcggccac      600
gaagggattc cttacctcat cccatattgt tccagcaaat tgccgctgtg tggctttcac      660
agaggtctga catcagaact tcaggccttg gaaaaactg gtatcaaaac ctcatgtctc      720
tgcccagttt ttgtgaatac tgggttcacc aaaaatccaa gcacaagatt atggcctgta      780
ttggagacag atgaagtcgt aagaagtctg atagatggaa tacttaccaa taagaaaatg      840 attttgttc catcgtatat caatatcttt ctgagactac agaaggtttc ttcc             894

<210> SEQ ID NO 20
<211> LENGTH: 813
<212> TYPE: DNA
<213> ORGANISM: Homo sapien

<400> SEQUENCE: 20
atgaacatca tcctagaaat ccttctgctt ctgatcacca tcatctactc ctacttggag       60
tcgttggtga agttttcat tcctcagagg agaaaatctg tggctgggga gattgttctc      120
attactggag ctgggcatgg aataggcagg cagactactt atgaatttgc aaaacgacag      180
agcatattgg ttctgtggga tattaataag cgcggtgtgg aggaaactgc agctgagtgc      240
cgaaaactag gcgtcactgc gcatgcgtat gtggtagact gcagcaacag agaagagatc      300
tatcgctctc taaatcaggt gaagaaagaa gtgggtgatg taacaatcgt ggtgaataat      360
gctgggacag tatatccagc cgatcttctc agcaccaagg atgaagagat taccaagaca      420
tttgaggtca acatcctagg acattttgg atcacaaaag cacttcttcc atcgatgatg      480
gagagaaatc atggccacat cgtcacagtg gcttcagtgt gcggccacga agggattcct      540
tacctcatcc catattgttc cagcaaattt gccgctgttg ctttcacag aggtctgaca      600 tcagaacttc aggccttggg aaaaactggt atcaaaaccct catgtctctg cccagttttt      660
gtgaatactg ggttcaccaa aaatccaagc acaagattat ggcctgtatt ggagacagat      720
gaagtcgtaa aagtctgat agatggaata cttaccaata gaaaatgat ttttgttcca       780 tcgtatatca atatctttct gagactacag aag                                  813

<210> SEQ ID NO 21
<211> LENGTH: 300
<212> TYPE: PRT
<213> ORGANISM: Homo sapien

<400> SEQUENCE: 21

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125
```

-continued

```
Leu Leu Ser Thr Lys Asp Glu Glu Ile Thr Lys Thr Phe Glu Val Asn
        130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
        275                 280                 285

Phe Glu Ala Val Val Gly His Lys Ile Lys Met Lys
    290                 295                 300

<210> SEQ ID NO 22
<211> LENGTH: 264
<212> TYPE: PRT
<213> ORGANISM: Homo sapien

<400> SEQUENCE: 22

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
        115                 120                 125

Gly His Ile Val Thr Val Ala Ser Val Cys Gly His Glu Gly Ile Pro
    130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
            180                 185                 190

Pro Ser Thr Arg Leu Trp Pro Val Leu Glu Thr Asp Glu Val Val Arg
```

```
                195                 200                 205

Ser Leu Ile Asp Gly Ile Leu Thr Asn Lys Met Ile Phe Val Pro
    210                 215                 220

Ser Tyr Ile Asn Ile Phe Leu Arg Leu Gln Lys Phe Leu Pro Glu Arg
225                 230                 235                 240

Ala Ser Ala Ile Leu Asn Arg Met Gln Asn Ile Gln Phe Glu Ala Val
                245                 250                 255

Val Gly His Lys Ile Lys Met Lys
            260

<210> SEQ ID NO 23
<211> LENGTH: 261
<212> TYPE: PRT
<213> ORGANISM: Homo sapien

<400> SEQUENCE: 23

Met Asn Ile Ile Leu Glu Ile Leu Leu Leu Ile Thr Ile Ile Tyr
1               5                   10                  15

Ser Tyr Leu Glu Ser Leu Val Lys Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
                100                 105                 110

Asp Val Thr Ile Val Val Asn Asn Ala Gly Thr Val Tyr Pro Ala Asp
                115                 120                 125

Leu Leu Ser Thr Lys Asp Glu Glu Ile Thr Lys Thr Phe Glu Val Asn
            130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
                180                 185                 190

Val Gly Phe His Arg Gly Leu Thr Ser Glu Leu Gln Ala Leu Gly Lys
            195                 200                 205

Thr Gly Ile Lys Thr Ser Cys Leu Cys Pro Val Phe Val Asn Thr Gly
        210                 215                 220

Phe Thr Lys Asn Pro Ser Thr Arg Phe Leu Pro Glu Arg Ala Ser Ala
225                 230                 235                 240

Ile Leu Asn Arg Met Gln Asn Ile Gln Phe Glu Ala Val Val Gly His
                245                 250                 255

Lys Ile Lys Met Lys
            260

<210> SEQ ID NO 24
<211> LENGTH: 274
<212> TYPE: PRT
<213> ORGANISM: Homo sapien
```

-continued

```
<400> SEQUENCE: 24

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Val
            260                 265                 270

Ser Ser

<210> SEQ ID NO 25
<211> LENGTH: 324
<212> TYPE: PRT
<213> ORGANISM: Homo sapien

<400> SEQUENCE: 25

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
```

```
                    85                  90                  95
Arg Glu Glu Ile Tyr Arg Ser Leu Asn Gln Val Lys Lys Glu Val Gly
                100                 105                 110

Asp Val Thr Ile Val Val Asn Asn Ala Gly Thr Val Tyr Pro Ala Asp
            115                 120                 125

Leu Leu Ser Thr Lys Asp Glu Glu Ile Thr Lys Thr Phe Glu Val Asn
        130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205

Tyr Cys Ser Ser Lys Phe Ala Ala Val Gly Phe His Arg Gly Leu Thr
210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
            260                 265                 270

Gly Ile Leu Thr Asn Lys Lys Met Ile Phe Val Pro Ser Tyr Ile Asn
        275                 280                 285

Ile Phe Leu Arg Leu Gln Lys Phe Leu Pro Glu Arg Ala Ser Ala Ile
290                 295                 300

Leu Asn Arg Met Gln Asn Ile Gln Phe Glu Ala Val Val Gly His Lys
305                 310                 315                 320

Ile Lys Met Lys

<210> SEQ ID NO 26
<211> LENGTH: 284
<212> TYPE: PRT
<213> ORGANISM: Homo sapien

<400> SEQUENCE: 26

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
```

```
                130               135                140
Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
                180                 185                 190

Val Gly Phe His Arg Gly Leu Thr Ser Glu Leu Gln Ala Leu Gly Lys
                195                 200                 205

Thr Gly Ile Lys Thr Ser Cys Leu Cys Pro Val Phe Val Asn Thr Gly
                210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Leu
                260                 265                 270

Ser Thr Ala Gln Asn Thr Gln Ile Leu Lys His Gln
                275                 280

<210> SEQ ID NO 27
<211> LENGTH: 238
<212> TYPE: PRT
<213> ORGANISM: Homo sapien

<400> SEQUENCE: 27

Met Asn Ile Ile Leu Glu Ile Leu Leu Leu Ile Thr Ile Ile Tyr
1                 5                  10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
                35                  40                  45

Gly Arg Gln Thr Thr Tyr Glu Phe Ala Lys Arg Gln Ser Ile Leu Val
                50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
                100                 105                 110

Phe Trp Ile Thr Lys Ala Leu Leu Pro Ser Met Met Glu Arg Asn His
                115                 120                 125

Gly His Ile Val Thr Val Ala Ser Val Cys Gly His Glu Gly Ile Pro
                130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
                180                 185                 190

Pro Ser Thr Arg Leu Trp Pro Val Leu Glu Thr Asp Glu Val Val Arg
                195                 200                 205

Ser Leu Ile Asp Gly Ile Leu Thr Asn Lys Lys Met Ile Phe Val Pro
                210                 215                 220
```

-continued

```
Ser Tyr Ile Asn Ile Phe Leu Arg Leu Gln Lys Val Ser Ser
225                 230                 235

<210> SEQ ID NO 28
<211> LENGTH: 298
<212> TYPE: PRT
<213> ORGANISM: Homo sapien

<400> SEQUENCE: 28

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205

Tyr Cys Ser Ser Lys Phe Ala Ala Val Gly Phe His Arg Gly Leu Thr
    210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
            260                 265                 270

Gly Ile Leu Thr Asn Lys Lys Met Ile Phe Val Pro Ser Tyr Ile Asn
        275                 280                 285

Ile Phe Leu Arg Leu Gln Lys Val Ser Ser
    290                 295

<210> SEQ ID NO 29
<211> LENGTH: 271
<212> TYPE: PRT
<213> ORGANISM: Homo sapien

<400> SEQUENCE: 29

Met Asn Ile Ile Leu Glu Ile Leu Leu Leu Ile Thr Ile Ile Tyr
1               5                   10                  15
```

```
Ser Tyr Leu Glu Ser Leu Val Lys Phe Phe Ile Pro Gln Arg Arg Lys
         20                  25                  30

Ser Val Ala Gly Glu Ile Val Leu Ile Thr Gly Ala Gly His Gly Ile
             35                  40                  45

Gly Arg Gln Thr Thr Tyr Glu Phe Ala Lys Arg Gln Ser Ile Leu Val
     50                  55                  60

Leu Trp Asp Ile Asn Lys Arg Val Glu Glu Thr Ala Ala Glu Cys
65                  70                  75                  80

Arg Lys Leu Gly Val Thr Ala His Ala Tyr Val Asp Cys Ser Asn
             85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
            115                 120                 125

Leu Leu Ser Thr Lys Asp Glu Glu Ile Thr Lys Thr Phe Glu Val Asn
        130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys
            260                 265                 270

<210> SEQ ID NO 30
<211> LENGTH: 23830
<212> TYPE: DNA
<213> ORGANISM: Homo sapien

<400> SEQUENCE: 30
atggtccgag ggggcgggg ctgacgtcgc gctgggaatg ccctggccga gacactgagg      60
cagggtagag agcgcttgcg ggcgccgggc ggagctgctg cggatcagga cccgagccga    120
ttcccgatcc cgacccagat cctaacccgc gccccgccc cgccgccgcc gccatgtacg    180
acgcagagcg cggctggagc ttgtccttcg cgggctgcgg cttcctgggc ttctaccacg    240
tcggggcgac ccgctgcctg agcgagcacg ccccgcacct cctccgcgac gcgcgcatgt    300
tgttcggcgc ttcggccggg gcgttgcact cgtcggcgt cctctccggt atcccgctgg    360
gtgcgtctgg ggacgctgcc cgggctccac gtgcggagtg ggtgccccct aggccgggga    420 gcggggatc cccaggggtc gcgggcccct ggaggagcgg gcatcggacg cggacacggc    480
ggggtgcatc ccgagggccc cctccgaggc agatgcttcc tgcgggggcg ctgttcctgg    540
gcccgggaag ggggcgttgg aaccccgagc ggtccgggcc gaagcctggg actctcgtgc    600
gtccccaccc ctaccccat cagggcgccg tgcatgaagg agaccctca cctccggact    660 gagagtcgga gcgtctcgga gcgacgggga gtagggagcg ggacccgggg cggagggtag    720
```

```
tgctggcccc tgcggactcc gggtcccctg tgtcctctcg ggaggggctg acgggctga      780 gctgccgagg ggccgatttg ccctgggccg gacaaagagt ggggctttgg ccggtccccc     840
acggtgggct ccttccctct ggggattgag ggactcaaga caccccgcgc ctgcgctttt     900
cttttctttt tttcttttt tttttttgag acggagtttc gctcagtcgc ccaggctgga     960
gtgcagtggc gtgatctcaa ctcactgcaa gctccacctc ccaggttcac gccattctcc    1020
tgcctcagcc tcccgagtag ctgggactac aggcgccagc caccaagccc ggctaatttt    1080
ttgtattttt tagtagagac ggggtttcac cgtgttagcc aggatggtct cgatctcctg    1140
acctcgtgat ctgcccacct cggcctccca gaatgctggg ttacaggcg tgagccactg     1200 ctccctgctg cctacgctct ctgggtcgca gcccagcctt ctggggctg gtagcctcc     1260 cagaagggca accctgggca tcctccaggg caggctaact ggagtctagt ggggaggggt    1320
accttgaaag aggaaagttg tttcctcctc ctcctcctcc tccagtgttt gggacccttc    1380
ctgggggctg gagtgcatcc ctggacaccc cccaatccca tcctcttctc tagtttccac    1440
tgacctaggc ccaccctccc ctctccggct cagtactcct ggaaatgaga ttccgtacat    1500
ttgaatcttg tcctaatgaa atatttgtcc atgtgggtac ctgtgtgtgt gtggtggggg    1560
tgcagacgga gggtttgttt ctcactagct ggaactactg gggtgtggta tgcttcctgg    1620
gaatttgtgt gccacagtcc tggaggcgag gaggggttg tgagccagta ggcagggct     1680 ggggcaagta gcattgtgaa gctattgaca cccagacgtc cccaggcagg agattatgcc    1740
cccattagcc ccctttatc tgggcttcct taacaatgga ctctttgccc tgcctgccag    1800
agccagcagg gagtgactgt tcagtggtga ggaagcgggc agaggaagcc ctgccattgg    1860
gtaggagcag tgggcagccc ctgggctgac tgggaggtgg ggattaggga ttagacagtc    1920
ctggctgtct gccttcccct aagccagggg gagaggagca aagggcacga aatgtggcct    1980
ccaggaggat tagaccgcca catgatcatt tgcacaccct ggggtttagc aacaataaaa    2040
gtcagctttt ttgtatccca aggtggcctg tggacaccca catggacaaa tgtttacact    2100
gggacagaat tcaaatgcag aggtcccagg agcctaaagt acactcactc tggtatagaa    2160
aggattcctt actgggcaga ggacaggtgc agcctggggc tttcccaggc aggacacagg    2220
gaggctcagg aaccaccaag tccctggaag gtggatctgg aggcgttggc aggagccact    2280
ccctgggttc cagggctcca ggttcctgct ttaaccccct gtctcacaga gggctgtgca    2340
cttgggggct gctgagcatg tcccagaggc tgcatcctgg acacagcacc tcagtgcatc    2400
tgagctgagg ctaacttggc aggagggaca ggcagaacct gccagccacg tgcaattcca    2460
cccctctggc cactcaggga aggagagctg tgagtcaaga tcagatttgg gtcaggacag    2520 gctgggcct gcctgtccct gtgcatccca agatttatgg ctggccaggg gttgggctgg    2580
gaggggtggt cttgcatgcc aggagagtgc agatcagcct gagaggccag gccagtaagt    2640
gaggtcagat ctcctgcacc tgatagcatt aaggccatct acaccaaagc tctaatgctg    2700
atatgttcct ggcctctatg tggggcatgg aggtggggca tggaggtgag gcctgctcgc    2760
ctgggcttct ggaagtggga gactcattcc tgtggctgag gcctacagca gtgctgtgtg    2820
gtaggaatac actggaagcc atgatgtcat tgtgcatttt ctagaagcca cattgaataa    2880
agtaaaagac acaggtagaa ttaatttcat tgagcccaat atatccaaaa taatatcatt    2940
ttcacatcta ttcaatataa aaatttacta atgagatatt tcatactaag ccactgaaat    3000
ccagtttgta tcttacacat ctcagttttg acgagccaca tttcaagggc gtgatagcca    3060
```

```
catgtggctc ccatagtaga cagtactggt ctagagaaat gttggtggca tccttgctgt   3120
ctggtttctg gccttgccaa aagtattacc atcccagtgt ggtacattct ttcatgtatt   3180
tgtctcctgt ccccagagca gactctgcag gtcctctcag atcttgtgcg aaggccagg    3240 agtcggaaca ttggcatctt ccatccatcc ttcaacttaa gcaagttcct ccgacagggt   3300
ctctgcaaat gcctcccggc caatgtccac cagctcatct ccggcaaaat aggcatctct   3360
cttaccagag tgtctgatgg ggaaaacgtt ctggtgtctg actttcggtc caaagacgaa   3420
gtcgtggatg taagcagttt gcttatctgg acgttgtcaa gttagaaaag ctgttttggg   3480
atgggtgtgg tggctcatgc ctgtcatccc ggcactttgg gaggccgaag cgggtgggtt   3540
gcttgagccc aggagctcga gaccaacatg atgaaaccca gtctctacaa aaattacaga   3600
aaaattagct aggcatggtg ttgtgggccc atagtcccag ctactaggga ggctgaggca   3660
ggagaattgc ttgagcctgg gaggtggagg ttgcagtaag tcatgatcat gccactgtac   3720
tccagcccgg gtgacagtga gatgctgtct ggaaaaaaaa aaaaagaaa gactgttttg    3780 ttttggaagc aacacaggca gttgtaggcc ccctgtgcca gagtgacata aactctgtac   3840
acctccagtg atttggtcca tgtttgtaaa ccctgaatgt tccagggcag tttcttttct   3900 tcactttta tctcttttt ttgggtgggg gggcggggta cagagtcttg ctctgtctcc      3960
caggctggag tgcagtggcg caatctcaac ctcccgagga gctgggacta caggcacagg   4020
ccatcacacc ttgctaatgt ttgtactttt tgtagacgag ggttttgcc ctgttgccca    4080 ggctggtccc aaactcctgc acccaagtaa tctgcccacc tctgcctggc agttacaatt   4140
tcaaataatt cctccctttc cttcaacact tggctcatga ccgtccagtc caaggaacct   4200
gtcctgcagg tgtgcctctc ccgagcttcc tctatgcatc ttccataatg aagatgcctt   4260
ctcactggaa accctacaag ggtgggaacg tgccttattt gcctgtatcc tcagggtcta   4320
gcagagagaa gataatttgt aataccaaaa caccattaaa ttcagctgat gctttcataa   4380
gcgctccttg gaggaaggac tccatttact tgacagatct gtgcaagaca gcagcctggc   4440
gcgtctaacc tgcagccagt tgcatcctct gtttaacctt gtttgcggaa gctttctcta   4500
aacagccagc acttgtctgt tcccacatgg gtccgttctc ccagtgaatc accgtggtgc   4560
ctgctgactg ctctgtagca cagtgcttcg caaagtgtga tcctgggacc agcagagcag   4620
cagctccttt gagcttattg gaatggcaga ccctcaggtc ccacctctga cctgctgcat   4680
gggaattctg gggagggacg cagaatctct ggttccacag gctctccggt gatgctaatg   4740
aataccggca tttgaacagc accgatctag ccccttttcag tccatgagcc aacaacccttt 4800 ggtcctgtct gtggtgaccc agtgtgactc tcatggggag caaggagagg aagttgaagt   4860
tcactgacag ggttgttaag gggattatgc aatagatgag acccatgggc ctgaagtccg   4920
agggtgtatg ttagttcccc gttcttttga cccatggatt aacctactct gtgcaaaggg   4980
cattttcaag tttgttgccc tgctcacttg gagaaagctt atgaaggatc aggaaaatta   5040
aaagggtgct ctcgcctata acttctctct cctttgcttt cacaggcctt ggtatgttcc   5100
tgcttcatcc ccttctacag tggccttatc cctccttcct tcagaggcgt ggtaagtcgg   5160
ctttctctgc tagcgctgag tcctgggggc ctctgaagtg tgctcacaca tctcctgcct   5220
gcagggcact ggtgtcgggc acctcagggt ctgtcccatg gtggagcccc atgcctcact   5280
gcctttcaga cagagtagcc acagctggcc ctatttccag gctacccggg cagcaaaact   5340
tactgcatgt gtaattaatt atttggctat ctgtaaggta aactggctgg ttcacttaat   5400
ctgcacctta agcatcagat agcttctcag tgatctagtt aaactatatg atgttggcca   5460
```

```
ggcgcggtgg ctcatgtctg taatcccagc actttgggag cctgaagcag gcagatcact   5520
tgaggtcagg agttcgagac cagcctggcc aacagtgtga aactctgtct ctcctaaaaa   5580
tacaaaaatt agctgggcat ggtggtgtgc acctgtaatc ccagctgctc gggaggctga   5640
ggcaggagaa ttgcttgaac ttgggaggcg gaagttgcag tgagccaaga tcgcaccact   5700
gcactccatc ctgggtgaca gagcgagact ctatctcaaa agaaaaaaa aaaaaaaggt    5760 aaataaagta tatgacactg aagaatctgt taccccctgga aggtggagct ttactcttag  5820
ggggaactat aacagtcata tatatatatt tttttctttt cttttttttt tttttgaga    5880 tggagtctgg ctctgtcgcc caggctggag tgcagtggtg caatctcggc tcactgcaac   5940
ctccacctca caggttcagg caattctcct gcctcaacct cccgagtagc tgggattaca   6000
ggtgcctgcc gtcacgccaa gctaattttt gtattttag tagagacagg gtttcatcat    6060
attggccagg ctggtctcca actcctgacc tcaggtgatc cgcccgcctt ggcctcccaa   6120
agtgctgaga ttacaggcgt gagccatggt gcccggccaa caatcacatg tgttgtaaac   6180
aacaacaaaa atctgtcagc ctggtctaac ctagatttgt gctttgtttt gttttgccac   6240
tttgtgatgc acaggaggaa gtttaggctg taaaatacta gccttttagg gtaattttg    6300 aactcacaag agcagcagcg gaacctttga tgcaatcctg tatgtagcac cagcagagcc   6360
acgtggcaga gggactcgca ttaggagcct cccattacag actacgtgct cctgtgcgtt   6420
atcttatagg gtccccacaa ccaaggggag atgtgattat tcatcctgtg tggctgtggg   6480
gaacttgaga gtcatacttg cccaaagagc acggccagcg agcttgcacc caggtcactc   6540
tctgctcctc tgtcagaaca gggcatgtct tggttcactg cagggcggct cttctcattc   6600
tctgtagttt ggggtccagg atagtggtcc acggagccac tggagtgccc agctactgag   6660
tgaccaaagc atattttgga tttccgacat tgccacagca tggttgggca tcagcaggac   6720
cccaacccct tgttatgctg gtggctttat gtggttattt gatcttcccc agaactcagc   6780
aggagtgcac ccagcagcac cgtagtgatg ctctctggct ccccagtgca cggttctggc   6840
tttccttcct ggtcgagagt ttcaagcccc ctgggtccta ctctgtcctt ttcagcccat   6900
agctttgttc aaaagctgct ggcagtgttc agatttggct gagttcagtg aatatgtgca   6960
ttggctgatt tctgagccat gccagggga tggagaagcc gaagcaggag tgtttgttct    7020
gcaggctctg gagtaggcat tgggtctgtg ccggctcact tgctagtctt gcatccttcc   7080
ccaaccccct ctggggatgt ctggccacat cagaagacag tttggggttgt cagaactggg  7140 ggagtaccag gccgaggtgg gtggatcatg aggtcaggag atcgagacca tcctggctaa   7200
cacagtgaaa cctcatctct actaaacata cgaaaaaaat tagctgggcg tggtggcggg  7260
cgcctgtagt cccagctact cgggaggctg aggcaggaga atggtgtgaa ccgggggggc   7320
ggagcttgca gtgagctgag atcctgccac tgcactccag cctgggcaac aaagcgagac   7380
tccgtctcac aaacaaaaca aaacaaaaca aacaaaatc tggggagtg ccactggcat     7440 ctgatgtata gaggcccgag atgctgtgtc atcacccgtt gagtgcgctc ataggcatct   7500
tcctgacaat tagaacccat tattcttcaa attcaatgca agcaaattca aagcattact   7560
gtgtacatac cgcatgctaa tcaattgcac cactggagct cctaaattca aaacattact   7620
ataaaaaagt tcaaaatgca tggaaaagtt gtacatggca ggagaatatt tgggcttctg   7680 actaccccctt gaatgaagat gatccaccag ccgccttcct ccttggtctt cactccagat  7740
tcctagcatt tcattctgtg tctctttatg cagtgaggtt tttgtttgtt ttttgagaca   7800
```

```
gagtctcact gtatcaccta ggcctggagt gcagtggcgc gatctcagct cactgcaacc    7860
ctcggctcct gggtttaagc gattctcctg cctcagcctc ccgagcagct gagattacaa    7920
gcacacatcc ccatgcccag ctaattttg tatttttagc agagacaggg tttcaccatg    7980
ttgcccaggc tggtctcgaa ctcctggcct caagtgatcc atgtgcctca gccttccaaa    8040
gtgctgggat tacaggcgtg agccaccatg cccagctcct agtgaggttt ttgatgcctt    8100
gctacatctg ccctagaaat tgtgtgacta cgatttgga aatgttgctg tgtaaacttg    8160
tgatcatttc tggactccag gcaagaatct tgatggctaa ggtgtggctg aacatgtctg    8220
attctctcct ggacctgttt taggccaaac tctgctctga aattcctccg tgtggaaggg    8280
cgggctgggg agagcctccc agctggaatc ttttggatgc ctttctctgt gggtatctga    8340
tggctggctc tgatgctgg ctgtgatggc tgtggctgga aatcattgtt gacatgagtt    8400
tcacagatgc aggctctgtc caaattgtag caaaagctgc ctgccccagc cgagctatgg    8460
gcaataaggt ggtttaagga tatagatgaa ggaaaactca cccttagaat aatttatcca    8520
aaatgctgct gtgttgtggg ttagaggaca ttttctgagg tcccaggttc attgtttcat    8580
ttaagtctca aaagtccctc caggtgttgg ttctaattgt caaagcatgg ggggagatgg    8640
gctcatgggt taaggtcttt atcccagatt tctgtatcct ccttgcaagc agcaaagggg    8700 tctggattg aatccatgac catgtttctc ctttgggttt ccatcacact ctgtccccgt    8760
gcactgagca cccttagtt catatgaccc ccttaggcat gttacatggg cactcctata    8820 ggtgccatc tggccctagg acttggccaa cacaacatgg actccagttt ccatctgcct    8880 cttgccagg cacttttgtg cagtgcacac actgtacaac agtagacggc aaccctgaga    8940
gccagagtag agcctgtcct agcaccggaa tgctcggtaa ggatttgtcg caggagtgat    9000
tccaaagcca atgtcctccc tccatatcag cctgtttgtg gctctgagaa gctctgccca    9060
catgtgaaag cttgttaagc acttaagcac taacccagag cttcagacag tgccagtcct    9120
ttttcccctt ctttaaagc gatatgtgga tggaggagtg agtgacaacg tacccttcat    9180
tgatgccaaa acaaccatca ccgtgtcccc cttctatggg gagtacgaca tctgccctaa    9240
agtcaagtcc acgaactttc ttcatgtgga catcaccaag ctcagtctac gcctctgcac    9300
agggaacctc taccttctct cgagagcttt tgtcccccg gatctcaagg tgagttggtg    9360
gtgagggggc aggtgttctg gggtgcagct cttctttgcc tccctgattg ccaggagcta    9420
ccagttactg tctgcacaat caaacagaaa tagacctgtc cttgatggtt aacggaaata    9480
aaaggcgctt gtcccagaag ctcaggtgag gcaccaccct gattatggga atcacctggg    9540
aacatatacc cagacctaaa actcagatcc acttcccagg ctgtggttat atagtcaggg    9600
gggtgcagta tgggtattag gatttttat tttttagtta taaagatttt ttttggttt    9660 gttttttgaga cagggtcttg ctctgccgct taggctggag tgcagtggtg caatcatagc    9720
tcactgaagc ctcagactcc tgggttcaag cagtcctccc acctcagcct cctaaggagc    9780
tgggacccac aggcatgcag caccacacct ggctaatttt taaaaatttt gtggagtgtt    9840
gcccaggctg gtctcacact cctggcctca agcgatcctc ccaccccagc ctcccaatgt    9900
gttgggatta caggcatgag ccattgtacc cagccactaa gatgattctt atttggaaac    9960
acggtcaaga acaactgcgt tcggtagttt aacctttttt gattgtggtg gttttagtat    10020
gccttaccac tctaccatag taagaaattt gcagaccatg tacccaacc tttggtgctc    10080 ctggggagaa agaaagaagg ctatgcaatg caatgcatgc tcacagtcca agggagaggg    10140
aaagctgtct aacaggattg gttttcccgt gtgctttata agcagatgag tagaggagac    10200
```

```
agctcttatt gtcctagtgg caattgggat aggctgcaaa gtttgttagg gtggaggctt   10260
attccgggac caagggagcc caaagaaaca agctcctgcc aggcgcggtg gctcacgcct   10320
gtaatcccag cactttggga ggctgaggca ggtggatcac ctgaggtcag gagtttgaga   10380
ccagcctggc caacatggtg aaaccccgtc tccatgaaaa atacaaaaat tacccgggca   10440
tggtggcggg cacctgtaat cccagctact agggaggctg aggcaggaaa atggcttgaa   10500
cctcggaagt ggaggtggcc gttagccgag atcacgccac tgcactccag cctgggcaac   10560
agagcaagac tctgccttaa aaaaaaaaaa aaaaaaaaga aaagtaaaag gaaaaaaaag   10620
aggctctggc ctgctgggt gcctgcaaag tctccgtgga agggtgacat tcaagccgag   10680
acctccaggg aactgtctcc tgggagcaca gagcccttg ctcagccccc aggtggctca   10740
gtgcccccag ccagcagact cagagcttgc atgattcttt ggtgctctct gcggtcttcc   10800
aatgatgctg aaataaatgg tgcttggtgt ctccctgctg tagtcccctt gcttgctttg   10860
ctcacaggtg ctgggagaga tatgccttcg aggatatttg gatgcattca ggttcttgga   10920
agagaagggt atgtatgggc tgggaggatc agccatgccc ttttgacaag catttactag   10980
cggtcttggt aaagacttga gatttgcctt agttctaaca cttagtgccc aacgccttcc   11040
ttgtgttgct caacctactc atgagcccag gagataggaa atctccgtcc cattgtacag   11100
atggggaaac agaattttgg aaaggagagc caagcagcac acacccctcc ctgaggggca   11160
gagccgagat ttgaactggg atgtcatgac tccagggccc tctccctccc cagggtcccc   11220
ttatctgaag gcggttttc tttccagctc gacctcttgt gacccttagt ttaacaaggg   11280
ccgaagttaa agagtttctg cgcctggacc ccaaatgaag caatcagatt tctcatctcc   11340
agtcaggtgt gggtccaagc ccactagaca agtttgctct tcccagagca catttctgcc   11400
ttcaagtcat cctggcttgt cagggctggg ggagttctgc tgtagaaata ttagagtgga   11460
aggaaaaaga tgtgttggga gctatttttc tttaatacta aaagttggtt gatgaatttg   11520
tcgttggcca agaccaagga gactgcattt ttaaggacat atgtgtattt atctgctcag   11580
aaaatgttca ttgctgtgtg ctagggatac tgcagtgaac acagaggtgt gacccttgcc   11640
agccttgtga gagaagtgag cagataagta agcagaaggg tgatgctgtg tcgatgggaa   11700
agtacaggtg ccaatgagaa ggcacaggtg tcaaggagaa gacacaggat gctggaggct   11760
catgcaggat ggatctccaa ggcccagggg aagaagggcc tctcggagga cgtgaatcca   11820
cattaagact ttggggataa gtaggagcgc cttaggcatg ggacccatg gatgcgaggc   11880 ctgtaggaca cagacaggat ggcatgaagg cctgtgcaac tggaggggtg gggatgggaa   11940
cactaagaga tggctggaag tgtggggtg gggacactaa gagatgactg gagaagaggg   12000
ggtcaggagt ggtgaaaaat gggagaggag ggcaggctgg gccttttgga tacagggga   12060 ttgcatcctg cagtggtagg gagccactga gggctgctgc agtaggagtg aggggatcag   12120
aggagagctt tggaagcccc ctggatgcgg gacaggaagc gagataccag tgtctaggag   12180
gccagtgagg cagccacagg ctccaccagg atcagggctg cgagggtcat gaggaggaaa   12240
ccaatttgaa ggagtccagg ggaataggac ttggaaatga ccgatgggac atttgggaag   12300
aggaagacag aagagcgcag tcccggcttc tggctttagc agttgggcaa ggggagatgg   12360
ggagatgtgc ccatgggttg agggttgagg acattaggag ggagccggta tggcaggaag   12420
agctggtgtg ccagagatgc tggaagcagc atctgcctga gaacagatac ctggcaatat   12480
tcctaaggga aagtgacatc tcggagggtg aggagggcat ctgatagggc ctggaaagag   12540
```

```
ccggggcaag catgaatgtg aggttatctt gggggggcaag gctcaggcgt tgaggagcag    12600
cccctggtct cttcagcctg aagttggaag ccagagttgg gccaggtgca gctgtggttg    12660
tctgaagtcc ccctcccccca gcccagtgtg ccaatgctgt aagagcaagg gccgctcact    12720
ggtgctggtg gctgagtccc agcacccagg acagggcctg gcacatactg gtgcccaatc    12780
ctcccttctg ggtgcttctt ccaaggcctt gtgatggaag tgagtaccct cttcgacatc    12840
agacccagct tcaaatcctg gctctgctat gtattggctg cgtggcttta gacaagtctt    12900
ttaaccttgc tgtgcttctg atttctcagc tgaaaaatgg agatgatgat agtggtttct    12960
gtaaggcctt atggtgaagc acctagctca gggcctggaa ggcaggtgta accagtggtt    13020
cagttgttat aaaccaacac taaccctcgc ctttgcacct catgaaacca gatatgtaga    13080
tggagcccac aaagctagca ggagccaagc tcacgtgtgt cctgctttaa agccccatac    13140 cccttctcc gggtgacaaa cacctgtgct cgttctcttc ccttccctc ttccccttgc    13200 atttggctaa taacaggcca gctgcctgcc tccctgcagt ttggtagatg ggtgggtaac    13260
gaccaccact cccacgttcg cctgatgggc ttgttttccg tgcccttcac aggcatctgc    13320
aacaggcccc agccaggcct gaagtcatcc tcagaaggga tggatcctga ggtcgccatg    13380
cccagctggg caaacatgag tctggattct tccccgagt cggctgcctt ggctgtgagg    13440
ctggagggag atgagctgct agaccacctg cgtctcagca tcctgccctg ggatgagagc    13500
atcctggaca ccctctcgcc caggctcgct acaggtaccc actcctcggg gtgagcacgg    13560
gcagcacctt gttttctttc ttgtgcatta tggaggaaga tggtactgcc acatgggagc    13620
gatagggtga ggcaaccatg acaggtggtt gggaacatct ccttccatgt gtacagcctg    13680
ggctgctgcc atcactccca gcacagcccc caacccccc aatcctggaa ccttgccaag    13740
tctcccttcc catggggtca tgaccaggag gaaaacaaac tccagctgag ccccttgggg    13800
ttccccatat aggctcctgc ctgtggcagc tgggccctct gtaccccttt ccaactctgt    13860
ctccctaaca tggcacctga gctcctgcca tcctggattt catggacccc aaggatgggg    13920
gtcctgcatc tgggacttgg cctattactc ggagctcctt ttcagccgcc tccctccacc    13980
tgtccaccca cctcaaggct cctttcttga gacctctcct aatttctccc ttcccctaaa    14040
cccacaattt tgaacctcca tcgaatggtg ctgtatttta taatgtcatc aaatatcaaa    14100
tggagacagt gctatggtcc aaatgattgt gtacccccca gaatttgtct tttgaaatcc    14160
taacccccaa catgatggtc ttaggaggtg gggcctttgg gaggagatta ggtcatgagg    14220
aaagggctgt catgaatggg attggtgccc ttattaaaca gacccaagag aggtcccttg    14280
tcccttctac tgtgtgagga ctcagaaggt ggtgtctatg aagaagcagg ccctcaccag    14340
acaccaacat gtctgctgcc ccttgatctg ggaccttgca gcctctagaa ctctgaaaaa    14400
tcgatgtttg ttgtttata agccactcag ttggtggcat tttgttagag tagcctgaac    14460
acggactaag tcaaacagaa gaacccacaa accagctaca gagttgggca tttgagaaa    14520 ttcaaaaatg agtcagacat aactccttat tcttgaggtg ccctaagaga tgggacacag    14580
cagctgccca ggtgcattag tttgttctca cattgctata aagaaatacc tgagactggg    14640
taactcataa agaaagaggt tgaattggct cacagttgca caggctggac aggaagcatg    14700
gtgctggcat ctgctcagct tctggggagg cctcaggaaa cttacaatca tggcagaagg    14760
tgaacgggaa gcatgcacat cccatgactg gagcaggagt gagagagaga gggaaataga    14820
gggaaggtgc catacacttt taaacaacca gatctcatga gaacacattc actatcaaga    14880
gaacagcacc agtgggggaaa tccgccccca tgatccaatc acctcccatc aggctccgcc    14940
```

```
tccaacactg ggaattacaa tttgacatga gatgtgggca gggacacaga tccaaaccat   15000
atgaccagat taatacgatt tgaggcatca cgaggtcatt aaagagaggg aataaaagac   15060
tggggctcca ggaagaaggc tctggaatcc agcagagggt caaggaccag cttgtaaagc   15120
tggtggtgcc tgagaagtac ctaggagaac atagatgctg tgacgtttga tgtagctgtt   15180
ttttgttttg tgttttggtt tttgagacag agtctcactc tgttgcccag gctggagtgt   15240
gcagtggcgt gatcttggct cactggagcc tccatctccc aggttcaaat gatcctcatg   15300
cctcagcctc ctgagttgct gggattacag gtgcacacca ccacgcctgg ctaattttg   15360 tgttttcagt agagacaggg tttcaccatg ttggccaggc tggtcttgaa ctcctgacct   15420
caagtgatcc aacaacttca gcctcccaaa gtgctgggat gacaggcatg agccaccatg   15480
cccagcctga tgtagctgtt tctgtgcaca ttatttgctg tggggtatat tcagatttct   15540
taatacaaga tgattctttg cctcatgact tacacaccat tttctattta atttcagcta   15600
tgatattgga aatggacatg tcttttcaag gaaaataaaa gcaggctttc tggaatggcg   15660
acttccaaac atatttgtca atttaaagga gctgggagtg gggaccctat gctccgtaag   15720
cactctctta gctgttcttg gctgtgctcc ccgcttcagc ttcacactgc ccttgctgtg   15780
aagggagcag cctgggccgg gcgcggtggc ttacacctgt aatcctagca ctttgggagg   15840
ccgaggtggg tggatcacct gaggtcagga gttcaagacc agcctggcca acatggtgaa   15900
actccatctc tactaaaaat acaaaaaatt agctgggcat ggtggcaggt gcctgtaatc   15960
ccagctactt gggaggctga ggcagaagaa tcgcttgaac ccaggaggcg gaggttgcag   16020
tgagccgaga ttgcgccatt gcactccagc ctgggggcaa caagagcaaa actctgtctg   16080
gaaaaaaaag aaaggagcag cttggcaaac cccaccttgt cgcttttgtg agtgcctctg   16140 acccctttggc tgccaggacg ggcgtatttt atggaaatgc taagcaccaa cagagtaaag   16200
tggtttggtt tttcacagtg gtgggagata atagctccaa attgtctttt tcagcactga   16260
gtgaagaaat gaaagacaaa ggtggataca tgagcaagat ttgcaacttg ctacccatta   16320
ggataatgtc ttatgtaatg ctgccctgta ccctgcctgt ggaatctgcc attgcgattg   16380
tccagaggtg agcattttag gtggctccgt gtcttcctca cagggttgat atgaggatga   16440
aacaagatga tagatcatgg tggcatgtag tctgggacct ggattgtcgt gccacagatc   16500
acagctcaca gtctatgtgc aatgcccctg aatgttgccc acctgtcctc aagccacaca   16560
tgcacctgta actcagtgca agcccagaaa ctccccgtgg ggactcctag agctgtcagt   16620
ggcctcacat agcagctggt ccagtctctt gtgattgccc aaggaaactg aggcctggag   16680
agcttggggt cactgctctg aggccataga gatgcctagt agaagggcca ggcctagaag   16740
caggatcctt gctgccctc tgagctgttt ccatttaaaa tcacatgaag gccggcgccg   16800
tggctcacgg ctgtaatccc agcattttgg gaggccaagg tgggtggatc atgtgaggtc   16860
aggagtttga gaccagcttg gccaacatgg tgaaatgcca tctgtactaa aaatacaaaa   16920
attagtggag catggtggca cgtgcctgta ctcccagcta cttggaaggc tggggcagaa   16980
gaatcgcttg agcctgggag gcagaggttg tagtgagcca agattgtacc actgcactcc   17040
agcctgggtg acaggagaga aaccctatct caaaataaaa tgaaaggtaa tgaaatgaat   17100
aaaataataa atcaagtcac ggccgggcac ggtggctcac acctgtaatc ccagcgcttt   17160
gggaggccga ggtgggtgga taatgaggtc aggagttcaa gaccagcctg gccaacatgg   17220
tgaaaccatg tctctactaa aaatacaaaa attagctggg catggtggtg catgcctgta   17280
```

```
atcccagcta ctccggaggc taaggcagga gaattgcttg aagcaggacc taggaggcgg   17340
aggttggttg cagtgagccg agatcatgcc actgcactct agcctgggct acagagcgaa   17400
actccgactc aaaaaaaaaa aaaaaaaaa atcaaatcac atgaaagtag aacataggga    17460
attccatctt tcgttctagg catagtttgt taatatgatt cagagccagc agttaggaga   17520
acacagtgtg actctcctag aacttcttga ttgggcttcc tctgattggg tttcctctga   17580
ttgggcttcc tctgaaagtg gggggatgg ggggtgggga gcagaatggt cagagcttgg    17640
ctcagcagtc agactgctct tcttcaaatc ctggctgcat tgcttactac agctgtgtga   17700
ctccagatga ctgaatccac ctctctgtgc tgcagcttcc cgtctagaga gatcacctgg   17760
agcagagggt ggtcaggaga ctcaatctgg ttactgactc acagtgcagg agtactcatc   17820
ccatagtaag catccagcta gagatgttga tttctatttt caggtaataa tgatgatcgt   17880
aaaattagag acagataaaa ggtatgggca ttaggccagg gcactgcaat ttctaagctg   17940
tgtgacctca ggcaagttac tcgacttctc tgagcctcag cggtttcatc cgcaatatat   18000
ggataggaaa accgacctca gtgggttgtc tgacagtgga gggcacttga ttaaaaaaaa   18060
aaaaattacc ctggtctgaa tattaccctg gactgaaaga aaaatattga gctaatacag   18120
gcatcaggaa tggggctgca gggagtccag ggaagggaga acgaagagcc tgaaggtgtg   18180
aggaggtgcg agtgctgatc tgtctgctac aaagaggctg ctgagcctcc tgtggatgtg   18240
gccctggact tggcagttta atacctgagc tgttaaaata acctcagatg ctgtgttctt   18300
taaggggtag gattcagatt cctgctgaaa tgcttctgaa agggagggaa tgagccagcc   18360 catcccagt tgcttttttaa gatcattggg aagttctggt cttgccattt gtccctggac    18420
cactcttagg tcctcctgcc ccacttccat ctgggtgtgt gccctgggct gtccaccaca   18480
cagctacatc ctgccatctt ccctcctgga gccactgtgc catgcatgga tctgtagctt   18540
cattttcttt ggcttttccc tggttttttct ggagcagagt ctctagtaaa ctcccaagga   18600
agaaaacgtt tgactttatg tgtgttggga aacgtgcttt ttttctatta catctcagtg   18660
ataggttggc catgtctaga attgcaggtt gaaaatcatt tcctctcagt atattggtta   18720
gtgagaagcc tgggactgag acagtcacat tctcacttct ttgcaggtga gtgctcttag   18780
gactgtcttt ttatcccctta tactctgaaa tgtcatatgt cttggtgtaa gtccttattt   18840
cagttattga gctggacaag tactggagac cccttcagtc aaagccttct gtcattctcc   18900
agctctagga aattatcttc tattgttatt tctgttattc cttcccttcc attttctttt   18960 ttctttttt tttttttttt ttgagacagg gtcttactct ggtgcccagg ctggaatgca    19020
gtgacctgat catggtacac tgcagcctga acctcccaga ctcaagtgat cctcccacct   19080
caacctccta agtagctggg actgcaagca cacatcacca cacccaacaa atatttttta   19140
aaaattttgt aagatgggat cttactatgt tgcccagact ttttcttcct cttcctgggg   19200
ctcttattag gaagatgttt gacttcctgg gttggattcc tgtctccgtg tctgactttc   19260
tctctttgtc atatttttca tcactcgttg tcttttttgcg tctgctctga cagatttcct   19320
caaattttgt cttctagtcc tatcctacag ttttttacttt cagcaaatat aatttaatct   19380
ccaagagtac tctcttgttc ttttttctta gcattctgtt cttgttttat ggatgtaaca   19440
ttctcttgga atatttgctg tcctctagat catcccttct ccatttcttc ttgggctagt   19500
ttttctgttt cttcatcttt ctcttttatg ctacttattc tgggcgtgtt cttggtgggt   19560
tttttcccat atagcaacag aggacttgga gctcagggag aaaagggtag gtgcatcacc   19620
tggcagagct cccagacagt gacaggcagg ctgcgggaag gatgtctact tggcggtgct   19680
```

| | | | | |
|---|---|---|---|---|
| accgctttcc | tagaaaccct | ttccctggag | ctggttgaac | tgttgggttt | tgccctggtg | 19740 |
| gtgaacgctg | gctccccgtg | ctctgcctgt | ttcatcacca | gcccctccc | cttctgcctg | 19800 |
| gggtccagta | atctgttgaa | atatatatct | tgctcattgg | tgagctcctg | ctccttcctc | 19860 |
| gttgctcttg | cagatttatc | acttctcgta | aggctgcgct | tgtacttcgg | gattttctct | 19920 |
| gtgccacact | gggaaacata | gggtggttgc | atgctgcagt | cctgagcact | tatttcactc | 19980 |
| acatctttac | acgaagattt | ggtgggtgtt | tactttgttt | ttagtaagtt | agtctgtcat | 20040 |
| gtcctttgat | ccttttttt | tgttttttga | gatggagtct | ctctgtgtcc | tccaggctgg | 20100 |
| agtgcaatgt | cgcgatctca | gctcactgca | acctccacct | cctgggctca | agagattctc | 20160 |
| ctgcttcagt | ctcctgagta | gctgggatta | caggcatgtg | ccaccacacc | tggctaattt | 20220 |
| ttgtattttt | agtagaggtg | gggttttgca | tgttggccag | cctggtctca | aactcctgac | 20280 |
| ctcctgacct | gcctgccttg | gcctcccaaa | gtgctgggat | tacaggtgtg | agccaccaca | 20340 |
| cctggccctg | attaatcttt | taatgcccag | tctctccttc | aaaagccggc | tcctttctct | 20400 |
| ccctcgcctt | cctagattcc | ttctccactc | cccaggatca | gcctcctcct | ccccacccca | 20460 |
| ccactgccgg | ggggatgtct | gtggtcaggc | atttatcaga | gaccctgagg | tgggggtcct | 20520 |
| ttatgtgtct | gggggatgga | gagtctagag | gaggtagcgt | tcagacctct | ccatggtgcc | 20580 |
| tctgctgggc | tcacatgtga | ccaagcacag | caaaccatga | ggcaggggat | ggtcttgacc | 20640 |
| atgagagccc | ttgcagcagc | tgccatgggc | ctcagctcct | ctccaagctg | ggaagagccc | 20700 |
| tgaaaagcca | aggtgttttt | ttttccctct | ttatttcagt | gtaagtccct | tgagcttct | 20760 |
| tgaaccagaa | gtgggctcat | tttgctttag | agatttcagg | tgggcttgtc | cttgtcctag | 20820 |
| catcccagat | ccaccttctg | ggaagtcatc | agattggagg | tgatgttggc | agcttttgta | 20880 |
| aacaaagggt | agtgttgtaa | gctgttgtgt | ctgcctatgt | gtgtgtttgt | gtacttggtc | 20940 |
| tcatctctgc | agactggtga | catggcttcc | agatatgccc | gacgatgtcc | tgtggttgca | 21000 |
| gtgggtgacc | tcacaggtgt | tcactcgagt | gctgatgtgt | ctgctccccg | cctccaggta | 21060 |
| aatactttgg | ctgtgggtgt | gtgggccgga | cgggcacctc | tctcatctga | tgaggcctca | 21120 |
| cacgacattc | tagaaacagc | tggctgaaca | ccaagcaagg | agcttgccct | tgggtgtggg | 21180 |
| gaccctgtct | catgggaggc | agctgagtca | gtcagaggtc | ctggcacacc | tgctgagagc | 21240 |
| tgccacccag | gccaacctga | accggagcct | gggaagactt | cccgtcggat | gagtctcttt | 21300 |
| gagtgcagca | ttgatggtgg | aagagcagag | aggccccaga | taagcaggga | aaggtgcttc | 21360 |
| agacagagtg | gctgggatga | ggactgggga | gtgtcagata | gcgctggcgt | gtctgagcga | 21420 |
| aggagctctg | gcacccatgg | cacaggaagg | aggtgggacc | ctggagggggc | agggctagca | 21480 |
| gagctcctcg | gagcgtgtgg | ctaggtgcct | ggtaatgcaa | gccccctgtc | ctccaccctc | 21540 |
| tgttgtactg | agtcacagtc | tccggggtga | agcctagcag | tctgcgttga | caggccccag | 21600 |
| gggatgccgc | tacttcctga | attctgaatt | ctggaaactg | agccggagtt | cagggcctgg | 21660 |
| ctcccattac | cagggttggg | cgttatcctg | aaaatcatag | gccttggttt | cctcacttgg | 21720 |
| ctaacagggg | tgatccccat | cccctcaatg | ggtttccgtg | agctcctgag | agcccgtagc | 21780 |
| atggtacttg | gcacatgctg | ggcatcagga | ggtatggcct | ctcttgctat | tgttgttatt | 21840 |
| ggtagacaca | gaaggattta | aaagtagggg | aatgcaaaga | tccgatttgc | tagggaagag | 21900 |
| ggcagtagtg | gccaagtaga | gggtggatcc | tgggccctgg | ctggcagcag | gcagcaaggg | 21960 |
| gggctgccag | ggcccaggca | gggacgatct | gtagaccgag | aggcttccta | aggctcttgg | 22020 |

```
acaggaggag gtgtcggttc caagcctaag gagtggggca gccctggtga ctggtggtca    22080
gtggtgccag gcggtgggtg gtaggacacc ctggcaggca agtaggtttg tgtgggggaa    22140
actgataggc ccctccaggg attcgttggt ggacaacacc tgtgatgtcc agtgggaggt    22200
gtccaggtag ctgggagggc cacaggcttg aagacctag gtggtgacat cagcccagca     22260
ctgagggcta aagaagctg tgtctctggc tgtgacggca ccctagagtg tgtgtggtgc     22320
cctctactgg ccggcaatgt gggtccaccg tagctcagac tgcacactgc agcagcggga    22380
acggcctcta agccaacttc ctccatgtgt ttcaggtccc aaatgccagt gagcagccaa    22440
caggcctccc catgcacacc tgagcaggac tggccctgct ggactccctg ctcccccaag    22500
ggctgtccag cagagaccaa agcagaggcc accccgcggt ccatcctcag gtccagcctg    22560
aacttcttct tgggcaataa agtacctgct ggtgctgagg ggctctccac ctttcccagt    22620
ttttcactag agaagagtct gtgagtcact tgaggaggcg agtctagcag attctttcag    22680
aggtgctaaa gtttcccatc tttgtgcagc tacctccgca ttgctgtgta gtgaccctg    22740
cctgtgacgt ggaggatccc agcctctgag ctgagttggt ttttatgaaaa gctaggaagc   22800
aacctttcgc ctgtgcagcg gtccagcact taactctaat acatcagcat gcgttaattc    22860
agctggttgg gaaatgacac caggaagccc agtgcagagg gtcccttact gactgtttcg    22920
tggccctatt aatggtcaga ctgttccagc atgaggttct tagaatgaca ggtgtttgga    22980
tgggtggggg ccttgtgatg gggggtaggc tggcccatgt gtgatcttgt ggggtggagg    23040
gaagagaata gcatgatccc acttcccccat gctgtgggaa ggggtgcagt tcgtccccaa   23100
gaacgacact gcctgtcagg tggtctgcaa agatgataac cttgactact aaaaacgtct    23160
ccatggcggg ggtaacaaga tgataatcta cttaatttta gaacaccttt ttcacctaac    23220
taaaataatg tttaaagagt tttgtataaa aatgtaagga agcgttgtta cctgttgaat    23280
tttgtattat gtgaatcagt gagatgttag tagaataagc cttaaaaaaa aaaaaatcgg    23340
ttgggtgcag tggcacacgg ctgtaatccc agcactttgg gaggccaagg ttggcagatc    23400
acctgaggtc aggagttcaa gaccagtctg gccaacatag caaaaccctg tctctactaa    23460
aaatacaaaa attatctggg catggtggtg catgcctgta atcccagcta ttcggaaggc    23520
tgaggcagga gaatcacttg aacccaggag gcggaggttg cggtgagctg agattgcacc    23580
atttcattcc agcctgggca acatgagtga aagtctgact caaaaaaaaa aaatttaaaa    23640
aacaaaataa tctagtgtgc agggcattca cctcagcccc ccaggcagga gccaagcaca    23700
gcaggagctt ccgcctcctc tccactggag cacacaactt gaacctggct tattttctgc    23760
agggaccagc cccacatggt cagtgagttt ctccccatgt gtggcgatga gagagtgtag    23820
aaataaagac                                                          23830
```

<210> SEQ ID NO 31
<211> LENGTH: 23830
<212> TYPE: DNA
<213> ORGANISM: Homo sapien

<400> SEQUENCE: 31

```
atggtccgag gggggcgggg ctgacgtcgc gctgggaatg ccctggccga gacactgagg      60
cagggtagag agcgcttgcg ggcgccgggc ggagctgctg cggatcagga cccgagccga    120
ttcccgatcc cgacccagat cctaacccgc gccccgccc cgccgccgcc gccatgtacg     180
acgcagagcg cggctggagc ttgtccttcg cgggctgcgg cttcctgggc ttctaccacg    240
tcggggcgac ccgctgcctg agcgagcacg ccccgcacct cctccgcgac gcgcgcatgt    300
```

```
tgttcggcgc ttcggccggg gcgttgcact gcgtcggcgt cctctccggt atcccgctgg   360
gtgcgtctgg ggacgctgcc cgggctccac gtgcggagtg ggtgcccect aggccgggga   420 gcggggggatc cccagggggtc gcgggggccect ggaggagcgg gcatcggacg cggacacggc   480
ggggtgcatc ccgagggccc cctccgaggc agatgcttcc tgcggggcg ctgttcctgg   540 gcccgggaag gggcgttgg aaccccgagc ggtccgggcc gaagcctggg actctcgtgc   600
gtccccaccc ctaccccat caggcgcccg tgcatgaagg gagaccctca cctccggact   660
gagagtcgga gcgtctcgga gcgacgggga gtagggagcg ggacccgggg cggagggtag   720
tgctggcccc tgcggactcc gggtcccctg tgtcctctcg ggaggggctg gacgggctga   780
gctgccgagg ggccgattttg ccctgggccg gacaaagagt ggggctttgg ccggtcccccc   840 acggtgggct ccttccctct ggggattgag ggactcaaga cacccccgcgc ctgcgcttt   900 cttttcttt tttctttttt ttttttttgag acggagtttc gctcagtcgc ccaggctgga   960
gtgcagtggc gtgatctcaa ctcactgcaa gctccacctc ccaggttcac gccattctcc  1020
tgcctcagcc tcccgagtag ctgggactac aggcgccagc caccaagccc ggctaatttt  1080
ttgtattttt tagtagagac ggggtttcac cgtgttagcc aggatggtct cgatctcctg  1140
acctcgtgat ctgcccacct cggcctccca gaatgctggg gttacaggcg tgagccactg  1200
ctccctgctg cctacgctct ctgggtcgca gcccagcctt ctggggggctg ggtagcctcc  1260 cagaagggca accctgggca tcctccaggg caggctaact ggagtctagt ggggaggggt  1320
accttgaaag aggaaagttg tttcctcctc ctcctcctcc tccagtgttt gggacccttc  1380
ctgggggctg gagtgcatcc ctggacaccc cccaatccca tcctcttctc tagtttccac  1440
tgacctaggc ccaccctccc ctctccggct cagtactcct ggaaatgaga ttccgtacat  1500
ttgaatcttg tcctaatgaa atatttgtcc atgtgggtac ctgtgtgtgt gtggtggggg  1560
tgcagacgga gggtttgttt ctcactagct ggaactactg gggtgtggta tgcttcctgg  1620
gaatttgtgt gccacagtcc tggaggcgag gaggggttg tgagccagta ggcagggggct  1680 ggggcaagta gcattgtgaa gctattgaca cccagacgtc cccaggcagg agattatgcc  1740
cccattagcc cccttttatc tgggcttcct taacaatgga ctctttgccc tgcctgccag  1800
agccagcagg gagtgactgt tcagtggtga ggaagcgggc agaggaagcc ctgccattgg  1860
gtaggagcag tgggcagccc ctgggctgac tgggaggtgg ggattaggga ttagacagtc  1920
ctggctgtct gccttcccct aagccagggg gagaggagca aagggcacga aatgtggcct  1980
ccaggaggat tagaccgcca catgatcatt tgcacaccct ggggtttagc aacaataaaa  2040
gtcagctttt ttgtatccca aggtggcctg tggacaccca catggacaaa tgtttacact  2100
gggacagaat tcaaatgcag aggtcccagg agcctaaagt acactcactc tggtatagaa  2160
aggattcctt actgggcaga ggacaggtgc agcctgggggc tttcccaggc aggacacagg  2220
gaggctcagg aaccaccaag tccctggaag gtggatctgg aggcgttggc aggagccact  2280
ccctgggttc cagggctcca ggttcctgct ttaacccccct gtctcacaga gggctgtgca  2340 cttggggggct gctgagcatg tcccagaggc tgcatcctgg acacagcacc tcagtgcatc  2400
tgagctgagg ctaacttggc aggagggaca ggcagaacct gccagccacg tgcaattcca  2460
cccctctggc cactcaggga aggagagctg tgagtcaaga tcagatttgg gtcaggacag  2520 gctgggggcct gcctgtccct gtgcatccca agatttatgg ctggccaggg gttgggctgg  2580
gaggggtggt cttgcatgcc aggagagtgc agatcagcct gagaggccag gccagtaagt  2640
```

```
gaggtcagat ctcctgcacc tgatagcatt aaggccatct acaccaaagc tctaatgctg    2700
atatgttcct ggcctctatg tggggcatgg aggtggggca tggaggtgag gcctgctcgc    2760
ctgggcttct ggaagtggga gactcattcc tgtggctgag gcctacagca gtgctgtgtg    2820
gtaggaatac actggaagcc atgatgtcat tgtgcatttt ctagaagcca cattgaataa    2880
agtaaaagac acaggtagaa ttaatttcat tgagcccaat atatccaaaa taatatcatt    2940
ttcacatcta ttcaatataa aaatttacta atgagatatt tcatactaag ccactgaaat    3000
ccagtttgta tcttacacat ctcagttttg acgagccaca tttcaagggc gtgatagcca    3060
catgtggctc ccatagtaga cagtactggt ctagagaaat gttggtggca tccttgctgt    3120
ctggtttctg gccttgccaa aagtattacc atcccagtgt ggtacattct ttcatgtatt    3180
tgtctcctgt ccccagagca gactctgcag gtcctctcag atcttgtgcg gaaggccagg    3240
agtcggaaca ttggcatctt ccatccatcc ttcaacttaa gcaagttcct ccgacagggt    3300
ctctgcaaat gcctcccggc caatgtccac cagctcatct ccggcaaaat aggcatctct    3360
cttaccagag tgtctgatgg ggaaaacgtt ctggtgtctg actttcggtc caaagacgaa    3420
gtcgtggatg taagcagttt gcttatctgg acgttgtcaa gttagaaaag ctgttttggg    3480
atgggtgtgg tggctcatgc ctgtcatccc ggcactttgg gaggccgaag cgggtgggtt    3540
gcttgagccc aggagctcga gaccaacatg atgaaaccca gtctctacaa aaattacaga    3600
aaaattagct aggcatggtg ttgtgggccc atagtcccag ctactaggga ggctgaggca    3660
ggagaattgc ttgagcctgg gaggtggagg ttgcagtaag tcatgatcat gccactgtac    3720
tccagcccgg gtgacagtga gatgctgtct ggaaaaaaaa aaaaaagaaa gactgttttg    3780
ttttggaagc aacacaggca gttgtaggcc ccctgtgcca gagtgacata aactctgtac    3840
acctccagtg atttggtcca tgtttgtaaa ccctgaatgt tccagggcag tttcttttct    3900
tcacttttta tctctttttt ttgggtgggg gggcgggta cagagtcttg ctctgtctcc    3960
caggctggag tgcagtggcg caatctcaac ctcccgagga gctgggacta caggcacagg    4020
ccatcacacc ttgctaatgt ttgtactttt tgtagagacg gggttttgcc ctgttgccca    4080
ggctggtccc aaactcctgc acccaagtaa tctgcccacc tctgcctggc agttacaatt    4140
tcaaataatt cctcccttc cttcaacact tggctcatga ccgtccagtc caaggaacct    4200
gtcctgcagg tgtgcctctc ccgagcttcc tctatgcatc ttccataatg aagatgcctt    4260
ctcactggaa accctacaag ggtgggaacg tgccttattt gcctgtatcc tcagggtcta    4320
gcagagagaa gataaatttgt aataccaaaa caccattaaa ttcagctgat gctttcataa    4380
gcgctccttg gaggaaggac tccatttact tgacagatct gtgcaagaca gcagcctggc    4440
gcgtctaacc tgcagccagt tgcatcctct gtttaacctt gtttgcggaa gctttctcta    4500
aacagccagc acttgtctgt tcccacatgg gtccgttctc ccagtgaatc accgtggtgc    4560
ctgctgactg ctctgtagca cagtgcttcg caaagtgtga tcctgggacc agcagagcag    4620
cagctccttt gagcttattg gaatggcaga ccctcaggtc ccacctctga cctgctgcat    4680
gggaattctg ggagggacg cagaatctct ggttccacag gctctccggt gatgctaatg    4740
aataccggca tttgaacagc accgatctag cccctttcag tccatgagcc aacaacccctt   4800 ggtcctgtct gtggtgaccc agtgtgactc tcatggggag caaggagagg aagttgaagt    4860
tcactgacag ggttgttaag gggattatgc aatagatgag acccatgggc ctgaagtccg    4920
agggtgtatg ttagttcccc gttcttttga cccatggatt aacctactct gtgcaaaggg    4980
cattttcaag tttgttgccc tgctcacttg gagaaagctt atgaaggatc aggaaaatta    5040
```

```
aaagggtgct ctcgcctata acttctctct cctttgcttt cacaggcctt ggtatgttcc    5100
tgcttcatgc ccttctacag tggccttatc cctccttcct tcagaggcgt ggtaagtcgg    5160
ctttctctgc tagcgctgag tcctgggggc ctctgaagtg tgctcacaca tctcctgcct    5220
gcagggcact ggtgtcgggc acctcagggt ctgtcccatg gtggagcccc atgcctcact    5280
gcctttcaga cagagtagcc acagctggcc ctatttccag gctacccggg cagcaaaact    5340
tactgcatgt gtaattaatt atttggctat ctgtaaggta aactggctgg ttcacttaat    5400
ctgcacctta agcatcagat agcttctcag tgatctagtt aaactatatg atgttggcca    5460
ggcgcggtgg ctcatgtctg taatcccagc actttgggag cctgaagcag gcagatcact    5520
tgaggtcagg agttcgagac cagcctggcc aacagtgtga aactctgtct ctcctaaaaa    5580
tacaaaaatt agctgggcat ggtggtgtgc acctgtaatc ccagctgctc gggaggctga    5640
ggcaggagaa ttgcttgaac ttgggaggcg gaagttgcag tgagccaaga tcgcaccact    5700
gcactccatc ctgggtgaca gagcgagact ctatctcaaa aagaaaaaaa aaaaaaggt    5760 aaataaagta tatgacactg aagaatctgt tacccctgga aggtggagct ttactcttag    5820
ggggaactat aacagtcata tatatatatt tttttctttt cttttttttt tttttgaga    5880 tggagtctgg ctctgtcgcc caggctggag tgcagtggtg caatctcggc tcactgcaac    5940
ctccacctca caggttcagg caattctcct gcctcaacct cccgagtagc tgggattaca    6000
ggtgcctgcc gtcacgccaa gctaattttt gtattttag tagagacagg gtttcatcat    6060
attggccagg ctggtctcca actcctgacc tcaggtgatc cgcccgcctt ggcctcccaa    6120
agtgctgaga ttacaggcgt gagccatggt gcccggccaa caatcacatg tgttgtaaac    6180
aacaacaaaa atctgtcagc ctggtctaac ctagatttgt gctttgtttt gttttgccac    6240
tttgtgatgc acaggaggaa gtttaggctg taaaatacta gccttttagg gtaattttg    6300 aactcacaag agcagcagcg gaacctttga tgcaatcctg tatgtagcac cagcagagcc    6360
acgtggcaga gggactcgca ttaggagcct cccattacag actacgtgct cctgtgcgtt    6420
atcttatagg gtccccacaa ccaaggggag atgtgattat tcatcctgtg tggctgtggg    6480
gaacttgaga gtcatacttg cccaaagagc acggccagcg agcttgcacc caggtcactc    6540
tctgctcctc tgtcagaaca gggcatgtct tggttcactg cagggcggct cttctcattc    6600
tctgtagttt ggggtccagg atagtggtcc acggagccac tggagtgccc agctactgag    6660
tgaccaaagc atattttgga tttccgacat tgccacagca tggttgggca tcagcaggac    6720
cccaacccct tgttatgctg gtggctttat gtggttattt gatcttcccc agaactcagc    6780
aggagtgcac ccagcagcac cgtagtgatg ctctctggct ccccagtgca cggttctggc    6840
tttccttcct ggtcgagagt ttcaagccct ctgggtccta ctctgtcctt ttcagcccat    6900
agctttgttc aaaagctgct ggcagtgttc agatttggct gagttcagtg aatatgtgca    6960
ttggctgatt tctgagccat gccaggggga tggagaagcc gaagcaggag tgtttgttct    7020
gcaggctctg gagtaggcat tgggtctgtg ccggctcact tgctagtctt gcatccttcc    7080
ccaaccccct ctggggatgt ctggccacat cagaagacag tttggttgt cagaactggg    7140 ggagtaccag gccgaggtgg gtggatcatg aggtcaggag atcgagacca tcctggctaa    7200
cacagtgaaa cctcatctct actaaacata cgaaaaaaat tagctgggcg tggtggcggg    7260
cgcctgtagt cccagctact cgggaggctg aggcaggaga atggtgtgaa cccggggggc    7320
ggagcttgca gtgagctgag atcctgccac tgcactccag cctgggcaac aaagcgagac    7380
```

```
tccgtctcac aaacaaaaca aaacaaaaca aaacaaaatc tgggggagtg ccactggcat    7440
ctgatgtata gaggcccgag atgctgtgtc atcacccgtt gagtgcgctc ataggcatct    7500
tcctgacaat tagaacccat tattcttcaa attcaatgca agcaaattca aagcattact    7560
gtgtacatac cgcatgctaa tcaattgcac cactggagct cctaaattca aaacattact    7620 ataaaaagt tcaaaatgca tggaaaagtt gtacatggca ggagaatatt tgggcttctg     7680 actaccctt gaatgaagat gatccaccag ccgccttcct ccttggtctt cactccagat      7740
tcctagcatt tcattctgtg tctctttatg cagtgaggtt tttgtttgtt ttttgagaca    7800
gagtctcact gtatcaccta ggcctggagt gcagtggcgc gatctcagct cactgcaacc    7860
ctcggctcct gggtttaagc gattctcctg cctcagcctc ccgagcagct gagattacaa    7920
gcacacatcc ccatgcccag ctaatttttg tattttagc agagacaggg tttcaccatg     7980
ttgcccaggc tggtctcgaa ctcctggcct caagtgatcc atgtgcctca gccttccaaa    8040
gtgctgggat tacaggcgtg agccaccatg cccagctcct agtgaggttt ttgatgcctt    8100
gctacatctg ccctagaaat tgtgtgacta cgattttgga aatgttgctg tgtaaacttg    8160
tgatcatttc tggactccag gcaagaatct tgatggctaa ggtgtggctg aacatgtctg    8220
attctctcct ggacctgttt taggccaaac tctgctctga aattcctccg tgtggaaggg    8280
cgggctgggg agagcctccc agctggaatc ttttggatgc cttctctgt gggtatctga     8340 tggctggctc tgatgctgg ctgtgatggc tgtggctgga aatcattgtt gacatgagtt      8400
tcacagatgc aggctctgtc caaattgtag caaaagctgc ctgccccagc cgagctatgg    8460
gcaataaggt ggtttaagga tatagatgaa ggaaaactca cccttagaat aatttatcca    8520
aaatgctgct gtgttgtggg ttagaggaca ttttctgagg tcccaggttc attgtttcat    8580
ttaagtctca aaagtccctc caggtgttgg ttctaattgt caaagcatgg ggggagatgg    8640
gctcatgggt taaaggtctt atcccagatt tctgtatcct ccttgcaagc agcaaagggg    8700
tctggatttg aatccatgac catgtttctc ctttgggttt ccatcacact ctgtccccgt    8760
gcactgagca ccctttagtt catatgaccc ccttaggcat gttacatggg cactcctata    8820
ggtgcccatc tggccctagg acttggccaa cacaacatgg actccagttt ccatctgcct    8880 cttttgccagg cacttttgtg cagtgcacac actgtacaac agtagacggc aaccctgaga   8940
gccagagtag agcctgtcct agcaccggaa tgctcggtaa ggattgtcg caggagtgat     9000 tccaaagcca atgtcctccc tccatatcag cctgtttgtg gctctgagaa gctctgccca    9060
catgtgaaag cttgttaagc acttaagcac taacccagag cttcagacag tgccagtcct    9120 ttttccccatt cttttaaaagc gatatgtgga tggaggagtg agtgacaacg tacccttcat   9180
tgatgccaaa acaaccatca ccgtgtcccc cttctatggg gagtacgaca tctgccctaa    9240
agtcaagtcc acgaactttc ttcatgtgga catcaccaag ctcagtctac gcctctgcac    9300
agggaacctc taccttctct cgagagcttt tgtccccccg gatctcaagg tgagttggtg    9360 gtgaggggggc aggtgttctg gggtgcagct cttctttgcc tccctgattg ccaggagcta   9420
ccagttactg tctgcacaat caaacagaaa tagacctgtc cttgatggtt aacggaaata    9480
aaaggcgctt gtcccagaag ctcaggtgag gcaccaccct gattatggga atcacctggg    9540
aacatatacc cagacctaaa actcagatcc acttcccagg ctgtggttat atagtcaggg    9600
gggtgcagta tgggtattag gattttttat ttttttagtta taaagatttt tttttggttt   9660 gttttttgaga cagggtcttg ctctgccgct taggctggag tgcagtggtg caatcatagc   9720
tcactgaagc ctcagactcc tgggttcaag cagtcctccc acctcagcct cctaaggagc    9780
```

```
tgggacccac aggcatgcag caccacacct ggctaatttt taaaaatttt gtggagtgtt   9840
gcccaggctg gtctcacact cctggcctca agcgatcctc ccaccccagc ctcccaatgt   9900
gttgggatta caggcatgag ccattgtacc cagccactaa gatgattctt atttggaaac   9960
acggtcaaga acaactgcgt tcggtagttt aaccttttt gattgtggtg gttttagtat    10020
gccttaccac tctaccatag taagaaattt gcagaccatg tacaccaacc tttggtgctc   10080
ctggggagaa agaagaaagg ctatgcaatg caatgcatgc tcacagtcca agggagaggg   10140
aaagctgtct aacaggattg gttttcccgt gtgctttata agcagatgag tagaggagac   10200
agctcttatt gtcctagtgg caattgggat aggctgcaaa gtttgttagg gtggaggctt   10260
attccgggac caagggagcc caaagaaaca agctcctgcc aggcgcggtg gctcacgcct   10320
gtaatcccag cactttggga ggctgaggca ggtggatcac ctgaggtcag gagtttgaga   10380
ccagcctggc caacatggtg aaaccccgtc tccatgaaaa atacaaaaat tacccgggca   10440
tggtggcggg cacctgtaat cccagctact agggaggctg aggcaggaaa atggcttgaa   10500
cctcggaagt ggaggtggcc gttagccgag atcacgccac tgcactccag cctgggcaac   10560
agagcaagac tctgccttaa aaaaaaaaaa aaaaaaaaga aaagtaaaag gaaaaaaaag   10620
aggctctggc ctgctggggt gcctgcaaag tctccgtgga agggtgacat tcaagccgag   10680
acctccaggg aactgtctcc tgggagcaca gagcccttg ctcagccccc aggtggctca    10740
gtgcccccag ccagcagact cagagcttgc atgattcttt ggtgctctct gcggtcttcc   10800
aatgatgctg aaataaatgg tgcttggtgt ctccctgctg tagtcccctt gcttgctttg   10860
ctcacaggtg ctgggagaga tatgccttcg aggatatttg gatgcattca ggttcttgga   10920
agagaagggt atgtatgggc tgggaggatc agccatgccc ttttgacaag catttactag   10980
cggtcttggt aaagacttga gatttgcctt agttctaaca cttagtgccc aacgccttcc   11040
ttgtgttgct caacctactc atgagcccag gagataggaa atctccgtcc cattgtacag   11100
atggggaaac agaattttgg aaaggagagc caagcagcac acacccctcc ctgaggggca   11160
gagccgagat ttgaactggg atgtcatgac tccagggccc tctccctccc cagggtcccc   11220
ttatctgaag gcggttttc tttccagctc gacctcttgt gacccttagt ttaacaaggg    11280
ccgaagttaa agagtttctg cgcctggacc ccaaatgaag caatcagatt tctcatctcc   11340
agtcaggtgt gggtccaagc ccactagaca agtttgctct tcccagagca catttctgcc   11400
ttcaagtcat cctggcttgt cagggctggg ggagttctgc tgtagaaata ttagagtgga   11460
aggaaaaaga tgtgttggga gctattttc tttaatacta aaagttggtt gatgaatttg    11520
tcgttggcca agaccaagga gactgcattt ttaaggacat atgtgtattt atctgctcag   11580
aaaatgttca ttgctgtgtg ctagggatac tgcagtgaac acagaggtgt gacccttgcc   11640
agccttgtga gagaagtgag cagataagta agcagaaggg tgatgctgtg tcgatgggaa   11700
agtacaggtg ccaatgagaa ggcacaggtg tcaaggagaa gacacaggat gctgaggct    11760 catgcaggat ggatctccaa ggcccagggg aagaagggcc tctcggagga cgtgaatcca   11820
cattaagact ttgggggataa gtaggagcgc cttaggcatg gggacccatg gatgcgaggc   11880
ctgtaggaca cagacaggat ggcatgaagg cctgtgcaac tggaggggtg gggatgggaa   11940
cactaagaga tggctggaag tgtgggggtg gggacactaa gagatgactg gagaagaggg   12000
ggtcaggagt ggtgaaaaat gggagaggag ggcaggctgg gccttttgga tacagggga    12060 ttgcatcctg cagtggtagg gagccactga gggctgctgc agtaggagtg aggggatcag   12120
```

```
aggagagctt tggaagcccc ctggatgcgg gacaggaagc gagataccag tgtctaggag    12180
gccagtgagg cagccacagg ctccaccagg atcagggctg cgagggtcat gaggaggaaa    12240
ccaatttgaa ggagtccagg ggaataggac ttggaaatga ccgatgggac atttgggaag    12300
aggaagacag aagagcgcag tcccggcttc tggctttagc agttgggcaa ggggagatgg    12360
ggagatgtgc ccatgggttg agggttgagg acattaggag ggagccggta tggcaggaag    12420
agctggtgtg ccagagatgc tggaagcagc atctgcctga gaacagatac ctggcaatat    12480
tcctaaggga aagtgacatc tcggagggtg aggagggcat ctgatagggc ctggaaagag    12540
ccggggcaag catgaatgtg aggttatctt gggggcaag gctcaggcgt tgaggagcag     12600
cccctggtct cttcagcctg aagttggaag ccagagttgg gccaggtgca gctgtggttg    12660
tctgaagtcc ccctccccca gcccagtgtg ccaatgctgt aagagcaagg gccgctcact    12720
ggtgctggtg gctgagtccc agcacccagg acagggcctg gcacatactg gtgcccaatc    12780
ctcccttctg ggtgcttctt ccaaggcctt gtgatggaag tgagtaccct cttcgacatc    12840
agacccagct tcaaatcctg gctctgctat gtattggctg cgtggcttta gacaagtctt    12900
ttaaccttgc tgtgcttctg atttctcagc tgaaaaatgg agatgatgat agtggtttct    12960
gtaaggcctt atggtgaagc acctagctca gggcctggaa ggcaggtgta accagtggtt    13020
cagttgttat aaaccaacac taaccctcgc ctttgcacct catgaaacca gatatgtaga    13080
tggagcccac aaagctagca ggagccaagc tcacgtgtgt cctgctttaa agccccatac    13140 cccttctcc gggtgacaaa cacctgtgct cgttctcttc ccttcccctc ttccccttgc     13200
atttggctaa taacaggcca gctgcctgcc tccctgcagt ttggtagatg ggtgggtaac    13260
gaccaccact cccacgttcg cctgatgggc ttgttttccg tgcccttcac aggcatctgc    13320
aacaggcccc agccaggcct gaagtcatcc tcagaaggga tggatcctga ggtcgccatg    13380
cccagctggg caaacatgag tctggattct tccccggagt cggctgcctt ggctgtgagg    13440
ctggagggag atgagctgct agaccacctg cgtctcagca tcctgccctg ggatgagagc    13500
atcctggaca ccctctcgcc caggctcgct acaggtaccc actcctcggg gtgagcacgg    13560
gcagcacctt gttttctttc ttgtgcatta tggaggaaga tggtactgcc acatgggagc    13620
gatagggtga ggcaaccatg acaggtggtt gggaacatct ccttccatgt gtacagcctg    13680
ggctgctgcc atcactccca gcacagcccc caaccccccc aatcctggaa ccttgccaag    13740 tctccctcc catggggtca tgaccaggag gaaaacaaac tccagctgag ccccttgggg    13800
ttccccatat aggctcctgc ctgtggcagc tgggccctct gtaccccttt ccaactctgt    13860
ctccctaaca tggcacctga gctcctgcca tcctggattt catggacccc aaggatgggg    13920
gtcctgcatc tgggacttgg cctattactc ggagctcctt ttcagccgcc tcctccacc    13980 tgtccaccca cctcaaggct ccttttcttga dacctctcct aatttctccc ttcccctaaa    14040
cccacaattt tgaacctcca tcgaatggtg ctgtatttta taatgtcatc aaatatcaaa    14100
tggagacagt gctatggtcc aaatgattgt gtaccccca gaatttgtct tttgaaatcc     14160
taacccccaa catgatggtc ttaggaggtg gggcctttgg gaggagatta ggtcatgagg    14220
aaagggctgt catgaatggg attggtgccc ttattaaaca gacccaagag aggtcccttg    14280
tcccttctac tgtgtgagga ctcagaaggt ggtgtctatg aagaagcagg ccctcaccag    14340
acaccaacat gtctgctgcc ccttgatctg ggaccttgca gcctctagaa ctctgaaaaa    14400
tcgatgtttg ttgttttata agccactcag ttggtggcat tttgttagag tagcctgaac    14460
acggactaag tcaaacagaa gaacccacaa accagctaca gagttgggca tttggagaaa    14520
```

```
ttcaaaaatg agtcagacat aactccttat tcttgaggtg ccctaagaga tgggacacag   14580
cagctgccca ggtgcattag tttgttctca cattgctata aagaaatacc tgagactggg   14640
taactcataa agaaagaggt tgaattggct cacagttgca caggctggac aggaagcatg   14700
gtgctggcat ctgctcagct tctggggagg cctcaggaaa cttacaatca tggcagaagg   14760
tgaacgggaa gcatgcacat cccatgactg gagcaggagt gagagagaga gggaaataga   14820
gggaaggtgc catacacttt taaacaacca gatctcatga gaacacattc actatcaaga   14880
gaacagcacc agtggggaaa tccgccccca tgatccaatc acctcccatc aggctccgcc   14940
tccaacactg ggaattacaa tttgacatga gatgtgggca gggacacaga tccaaaccat   15000
atgaccagat taatacgatt tgaggcatca cgaggtcatt aaagagaggg aataaaagac   15060
tggggctcca ggaagaaggc tctggaatcc agcagagggt caaggaccag cttgtaaagc   15120
tggtggtgcc tgagaagtac ctaggagaac atagatgctg tgacgtttga tgtagctgtt   15180
ttttgttttg tgttttggtt tttgagacag agtctcactc tgttcccag gctggagtgt   15240
gcagtggcgt gatcttggct cactggagcc tccatctccc aggttcaaat gatcctcatg   15300
cctcagcctc ctgagttgct gggattacag gtgcacacca ccacgcctgg ctaatttttg   15360
tgttttcagt agagacaggg tttcaccatg ttggccaggc tggtcttgaa ctcctgacct   15420
caagtgatcc aacaacttca gcctcccaaa gtgctgggat gacaggcatg agccaccatg   15480
cccagcctga tgtagctgtt tctgtgcaca ttatttgctg tggggtatat tcagatttct   15540
taatacaaga tgattctttg cctcatgact tacacaccat tttctattta atttcagcta   15600
tgatattgga aatggacatg tcttttcaag gaaaataaaa gcaggctttc tggaatggcg   15660
acttccaaac atatttgtca atttaaagga gctgggagtg gggaccctat gctccgtaag   15720
cactctctta gctgttcttg gctgtgctcc ccgcttcagc ttcacactgc ccttgctgtg   15780
aagggagcag cctgggccgg gcgcggtggc ttacacctgt aatcctagca ctttgggagg   15840
ccgaggtggg tggatcacct gaggtcagga gttcaagacc agcctggcca acatggtgaa   15900
actccatctc tactaaaaat acaaaaaatt agctgggcat ggtggcaggt gcctgtaatc   15960
ccagctactt gggaggctga ggcagaagaa tcgcttgaac ccaggaggcg gaggttgcag   16020
tgagccgaga ttgcgccatt gcactccagc ctggggcaa caagagcaaa actctgtctg   16080
gaaaaaaaag aaaggagcag cttggcaaac cccaccttgt cgcttttgtg agtgcctctg   16140
acccttggc tgccaggacg ggcgtatttt atggaaatgc taagcaccaa cagagtaaag   16200
tggtttggtt tttcacagtg gtgggagata atagctccaa attgtctttt tcagcactga   16260
gtgaagaaat gaaagacaaa ggtggataca tgagcaagat ttgcaacttg ctacccatta   16320
ggataatgtc ttatgtaatg ctgccctgta ccctgcctgt ggaatctgcc attgcgattg   16380
tccagaggtg agcattttag gtggctccgt gtcttcctca cagggttgat atgaggatga   16440
aacaagatga tagatcatgg tggcatgtag tctgggacct ggattgtcgt gccacagatc   16500
acagctcaca gtctatgtgc aatgcccctg aatgttgccc acctgtcctc aagccacaca   16560
tgcacctgta actcagtgca agcccagaaa ctccccgtgg ggactcctag agctgtcagt   16620
ggcctcacat agcagctggt ccagtctctt gtgattgccc aaggaaactg aggcctggag   16680
agcttgggt cactgctctg aggccataga gatgcctagt agaagggcca ggcctagaag   16740
caggatcctt gctgccctc tgagctgttt ccatttaaaa tcacatgaag gccggcgccg   16800
tggctcacgg ctgtaatccc agcatttggg gaggccaagg tgggtggatc atgtgaggtc   16860
```

```
aggagtttga gaccagcttg gccaacatgg tgaaatgcca tctgtactaa aaatacaaaa    16920
attagtggag catggtggca cgtgcctgta ctcccagcta cttggaaggc tggggcagaa    16980
gaatcgcttg agcctgggag gcagaggttg tagtgagcca agattgtacc actgcactcc    17040
agcctgggtg acaggagaga aaccctatct caaaataaaa tgaaaggtaa tgaaatgaat    17100
aaaataataa atcaagtcac ggccgggcac ggtggctcac acctgtaatc ccagcgcttt    17160
gggaggccga ggtgggtgga taatgaggtc aggagttcaa gaccagcctg gccaacatgg    17220
tgaaaccatg tctctactaa aaatacaaaa attagctggg catggtggtg catgcctgta    17280
atcccagcta ctccggaggc taaggcagga gaattgcttg aagcaggacc taggaggcgg    17340
aggttggttg cagtgagccg agatcatgcc actgcactct agcctgggct acagagcgaa    17400
actccgactc aaaaaaaaaa aaaaaaaaaa atcaaatcac atgaaagtag aacataggga    17460
attccatctt tcgttctagg catagtttgt taatatgatt cagagccagc agttaggaga    17520
acacagtgtg actctcctag aacttcttga ttgggcttcc tctgattggg tttcctctga    17580
ttgggcttcc tctgaaagtg gggggatgg ggggtgggga gcagaatggt cagagcttgg    17640
ctcagcagtc agactgctct tcttcaaatc ctggctgcat tgcttactac agctgtgtga    17700
ctccagatga ctgaatccac ctctctgtgc tgcagcttcc cgtctagaga gatcacctgg    17760
agcagagggt ggtcaggaga ctcaatctgg ttactgactc acagtgcagg agtactcatc    17820
ccatagtaag catccagcta gagatgttga tttctatttt caggtaataa tgatgatcgt    17880
aaaattagag acagataaaa ggtatgggca ttaggccagg gcactgcaat ttctaagctg    17940
tgtgacctca ggcaagttac tcgacttctc tgagcctcag cggtttcatc cgcaatatat    18000
ggataggaaa accgacctca gtgggttgtc tgacagtgga gggcacttga ttaaaaaaaa    18060
aaaaattacc ctggtctgaa tattaccctg gactgaaaga aaaatattga gctaatacag    18120
gcatcaggaa tggggctgca gggagtccag ggaagggaga acgaagagcc tgaaggtgtg    18180
aggaggtgcg agtgctgatc tgtctgctac aaagaggctg ctgagcctcc tgtggatgtg    18240
gccctggact tggcagttta atacctgagc tgttaaaata acctcagatg ctgtgttctt    18300 taagggggtag gattcagatt cctgctgaaa tgcttctgaa agggagggaa tgagccagcc    18360
catccccagt tgcttttttaa gatcattggg aagttctggt cttgccattt gtccctggac    18420
cactcttagg tcctcctgcc ccacttccat ctgggtgtgt gccctgggct gtccaccaca    18480
cagctacatc ctgccatctt ccctcctgga gccactgtgc catgcatgga tctgtagctt    18540 cattttttctt ggcttttccc tggttttttct ggagcagagt ctctagtaaa ctcccaagga    18600
agaaaacgtt tgactttatg tgtgttggga aacgtgcttt ttttctatta catctcagtg    18660
ataggttggc catgtctaga attgcaggtt gaaaatcatt tcctctcagt atattggtta    18720
gtgagaagcc tgggactgag acagtcacat tctcacttct ttgcaggtga gtgctcttag    18780 gactgtctttt ttatcccctta tactctgaaa tgtcatatgt cttggtgtaa gtccttatttt    18840 cagttattga gctggacaag tactggagac cccttcagtc aaagccttct gtcattctcc    18900
agctctagga aattatcttc tattgttatt tctgttattc cttcccttcc attttctttt    18960 ttctttttttt tttttttttt ttgagacagg tcttactct ggtgcccagg ctggaatgca    19020
gtgacctgat catggtacac tgcagcctga acctcccaga ctcaagtgat cctcccacct    19080
caacctccta agtagctggg actgcaagca cacatcacca cacccaacaa atattttta    19140 aaaatttttgt aagatgggat cttactatgt tgcccagact ttttcttcct cttcctgggg    19200
ctcttattag gaagatgttt gacttcctgg gttggattcc tgtctccgtg tctgactttc    19260
```

```
tctctttgtc atattttca tcactcgttg ctttttgcg tctgctctga cagatttcct    19320
caaattttgt cttctagtcc tatcctacag tttttacttt cagcaaatat aatttaatct    19380
ccaagagtac tctcttgttc ttttttctta gcattctgtt cttgttttat ggatgtaaca    19440
ttctcttgga atatttgctg tcctctagat catcccttct ccatttcttc ttgggctagt    19500
ttttctgttt cttcatcttt ctcttttatg ctacttattc tgggcgtgtt cttggtgggt    19560
tttttcccat atagcaacag aggacttgga gctcagggag aaaagggtag gtgcatcacc    19620
tggcagagct cccagacagt gacaggcagg ctgcgggaag gatgtctact tggcggtgct    19680
accgctttcc tagaaaccct ttccctggag ctggttgaac tgttgggttt tgccctggtg    19740
gtgaacgctg gctccccgtg ctctgcctgt ttcatcacca gccccctccc cttctgcctg    19800
gggtccagta atctgttgaa atatatatct tgctcattgg tgagctcctg ctccttcctc    19860
gttgctcttg cagatttatc acttctcgta aggctgcgct tgtacttcgg gattttctct    19920
gtgccacact gggaaacata gggtggttgc atgctgcagt cctgagcact tatttcactc    19980
acatctttac acgaagattt ggtgggtgtt tactttgttt ttagtaagtt agtctgtcat    20040
gtccttgat cctttttttt tgttttttga gatggagtct ctctgtgtcc tccaggctgg    20100
agtgcaatgt cgcgatctca gctcactgca acctccacct cctgggctca agagattctc    20160
ctgcttcagt ctcctgagta gctgggatta caggcatgtg ccaccacacc tggctaattt    20220
ttgtatttt agtagaggtg gggtttggca tgttggccag cctggtctca aactcctgac    20280
ctcctgacct gcctgccttg gcctcccaaa gtgctgggat tacaggtgtg agccaccaca    20340
cctggccctg attaatcttt taatgcccag tctctccttc aaaagccggc tcctttctct    20400
ccctcgcctt cctagattcc ttctccactc cccaggatca gcctcctcct ccccacccca    20460
ccactgccgg ggggatgtct gtggtcaggc atttatcaga gaccctgagg tgggggtcct    20520
ttatgtgtct gggggatgga gagtctagag gaggtagcgt tcagacctct ccatggtgcc    20580
tctgctgggc tcacatgtga ccaagcacag caaaccatga ggcagggat ggtcttgacc    20640
atgagagccc ttgcagcagc tgccatgggc ctcagctcct ctccaagctg gaagagccc    20700
tgaaaagcca aggtgttttt ttttccctct ttatttcagt gtaagtccct tgagcttct    20760
tgaaccagaa gtgggctcat tttgctttag agatttcagg tgggcttgtc cttgtcctag    20820
catcccagat ccaccttctg ggaagtcatc agattggagg tgatgttggc agcttttgta    20880
aacaaagggt agtgttgtaa gctgttgtgt ctgcctatgt gtgtgtttgt gtacttggtc    20940
tcatctctgc agactggtga catggcttcc agatatgccc gacgatgtcc tgtggttgca    21000
gtgggtgacc tcacaggtgt tcactcgagt gctgatgtgt ctgctccccg cctccaggta    21060
aatactttgg ctgtgggtgt gtgggccgga cgggcacctc tctcatctga tgaggcctca    21120
cacgacattc tagaaacagc tggctgaaca ccaagcaagg agcttgccct tgggtgtggg    21180
gaccctgtct catgggaggc agctgagtca gtcagaggtc ctgcacacc tgctgagagc    21240
tgccacccag gccaacctga accggagcct gggaagactt cccgtcggat gagtctcttt    21300
gagtgcagca ttgatggtgg aagagcagag aggccccaga taagcaggga aaggtgcttc    21360
agacagagtg gctgggatga ggactgggga gtgtcagata cgctggcgt gtctgagcga    21420
aggagctctg gcacccatgg cacaggaagg aggtgggacc ctggaggggc agggctagca    21480
gagctcctcg gagcgtgtgg ctaggtgcct ggtaatgcaa gccccctgtc ctccacccte    21540
tgttgtactg agtcacagtc tccggggtga agcctagcag tctgcgttga caggccccag    21600
```

```
gggatgccgc tacttcctga attctgaatt ctggaaactg agccggagtt cagggcctgg    21660
ctcccattac cagggttggg cgttatcctg aaaatcatag gccttggttt cctcacttgg    21720
ctaacagggg tgatccccat cccctcaatg ggtttccgtg agctcctgag agcccgtagc    21780
atggtacttg gcacatgctg ggcatcagga ggtatggcct ctcttgctat tgttgttatt    21840
ggtagacaca gaaggattta aaagtagggg aatgcaaaga tccgatttgc tagggaagag    21900
ggcagtagtg gccaagtaga gggtggatcc tgggccctgg ctggcagcag gcagcaaggg    21960
gggctgccag ggcccaggca gggacgatct gtagaccgag aggcttccta aggctcttgg    22020
acaggaggag gtgtcggttc caagcctaag gagtggggca gccctggtga ctggtggtca    22080
gtggtgccag gcggtgggtg gtaggacacc ctggcaggca agtaggtttg tgtgggggaa    22140
actgataggc ccctccaggg attcgttggt ggacaacacc tgtgatgtcc agtgggaggt    22200
gtccaggtag ctgggagggc cacaggcttg gaagacctag gtggtgacat cagcccagca    22260
ctgagggcta aagaagctg tgtctctggc tgtgacggca ccctagagtg tgtgtggtgc    22320
cctctactgg ccggcaatgt gggtccaccg tagctcagac tgcacactgc agcagcggga    22380
acggcctcta agccaacttc ctccatgtgt ttcaggtccc aaatgccagt gagcagccaa    22440
caggcctccc catgcacacc tgagcaggac tggccctgct ggactccctg ctcccccaag    22500
ggctgtccag cagagaccaa agcagaggcc accccgcggt ccatcctcag gtccagcctg    22560
aacttcttct tgggcaataa agtacctgct ggtgctgagg ggctctccac ctttcccagt    22620
ttttcactag agaagagtct gtgagtcact tgaggaggcg agtctagcag attctttcag    22680
aggtgctaaa gtttcccatc tttgtgcagc tacctccgca ttgctgtgta gtgacccctg    22740
cctgtgacgt ggaggatccc agcctctgag ctgagttggt tttatgaaaa gctaggaagc    22800 aaccttcgc ctgtgcagcg gtccagcact taactctaat acatcagcat gcgttaattc    22860
agctggttgg gaaatgacac caggaagccc agtgcagagg gtcccttact gactgtttcg    22920
tggccctatt aatggtcaga ctgttccagc atgaggttct tagaatgaca ggtgtttgga    22980
tgggtggggg ccttgtgatg gggggtaggc tggcccatgt gtgatcttgt ggggtggagg    23040
gaagagaata gcatgatccc acttccccat gctgtgggaa ggggtgcagt tcgtccccaa    23100
gaacgacact gcctgtcagg tggtctgcaa agatgataac cttgactact aaaaacgtct    23160
ccatggcggg ggtaacaaga tgataatcta cttaatttta gaacaccttt ttcacctaac    23220
taaaataatg tttaaagagt tttgtataaa aatgtaagga agcgttgtta cctgttgaat    23280
tttgtattat gtgaatcagt gagatgttag tagaataagc cttaaaaaaa aaaaaatcgg    23340
ttgggtgcag tggcacacgg ctgtaatccc agcactttgg gaggccaagg ttggcagatc    23400
acctgaggtc aggagttcaa gaccagtctg gccaacatag caaaaccctg tctctactaa    23460
aaatacaaaa attatctggg catggtggtg catgcctgta atcccagcta ttcggaaggc    23520
tgaggcagga gaatcacttg aacccaggag gcggaggttg cggtgagctg agattgcacc    23580
atttcattcc agcctgggca acatgagtga aagtctgact caaaaaaaaa aaatttaaaa    23640
aacaaaataa tctagtgtgc agggcattca cctcagcccc ccaggcagga gccaagcaca    23700
gcaggagctt ccgcctcctc tccactggag cacacaactt gaacctggct tattttctgc    23760
agggaccagc cccacatggt cagtgagttt ctccccatgt gtggcgatga gagagtgtag    23820
aaataaagac                                                          23830

<210> SEQ ID NO 32
<211> LENGTH: 1443
```

<212> TYPE: DNA
<213> ORGANISM: Homo sapien

<400> SEQUENCE: 32

| | | | | | |
|---|---|---|---|---|---|
| auguacgacg | cagagcgcgg | cuggagcuug | uccuucgcgg | gcugcggcuu | ccugggcuuc | 60 |
| uaccacgucg | gggcgacccg | cugccugagc | gagcacgccc | cgcaccuccu | ccgcgacgcg | 120 |
| cgcauguugu | ucggcgcuuc | ggccggggcg | uugcacugcg | ucggcguccu | cuccgguauc | 180 |
| ccgcuggagc | agacucugca | gguccucuca | gaucuugucg | ggaaggccag | gagucggaac | 240 |
| auuggcaucu | ccauccauc | cuucaacuua | agcaaguucc | uccgacaggg | ucucugcaaa | 300 |
| ugccucccgg | ccaaugucca | ccagcucauc | uccggcaaaa | uaggcaucuc | ucuuaccaga | 360 |
| gugucugaug | gggaaaacgu | ucggugucu | gacuuucggu | ccaaagacga | agucguggau | 420 |
| gccuugguau | guuccugcuu | cauccccuuc | uacagugggcc | uuaucccucc | uuccuucaga | 480 |
| ggcgugcgau | augggauggg | aggagugagu | gacaacguac | ccuucauuga | ugccaaaaca | 540 |
| accaucaccg | uguccccuu | cuaugggag | uacgacaucu | gcccuaaagu | caaguccacg | 600 |
| aacuuucuuc | auguggacau | caccaagcuc | agucuacgcc | ucugcacagg | gaaccucuac | 660 |
| cuucucucga | gagcuuuugu | cccccccggau | cucaaggugc | uggagagau | augccuucga | 720 |
| ggauauuugg | augcauucag | guucuuggaa | gagaagggca | ucugcaacag | gccccagcca | 780 |
| ggccugaagu | cauccucaga | agggauggau | ccugaggucg | ccaugcccag | cugggcaaac | 840 |
| augagucugg | auucuucccc | ggagucggcu | gccuuggcug | ugaggcugga | gggagaugag | 900 |
| cugcuagacc | accugcgucu | cagcauccug | cccuggaug | agagcauccu | ggacacccuc | 960 |
| ucgcccaggc | ucgcuacagc | acugagugaa | gaaaugaaag | acaaaggugg | auacaugagc | 1020 |
| aagauuugca | acugcuacc | cauuaggaua | augucuuaug | uaaugcugcc | cuguacccug | 1080 |
| ccuguggaau | cugccauugc | gauuguccag | agacugguga | cauggcuucc | agauaugccc | 1140 |
| gacgaugucc | uguggugca | gugggugacc | ucacaggugu | ucacgagu | gcugaugugu | 1200 |
| cugcuccccg | ccuccaagguc | ccaaaugcca | gugagcagcc | aacaggccuc | cccaugcaca | 1260 |
| ccugagcagg | acuggcccug | cuggacuccc | ugcuccccca | agggcuguccc | agcagagacc | 1320 |
| aaagcagagg | ccaccccgcg | guccauccuc | aggccagccc | ugaacuucuu | cuugggcaau | 1380 |
| aaaguaccug | cuggugcuga | ggggcucucc | accuuuccca | guuuuucacu | agagaagagu | 1440 |
| cug | | | | | | 1443 |

<210> SEQ ID NO 33
<211> LENGTH: 1431
<212> TYPE: DNA
<213> ORGANISM: Homo sapien

<400> SEQUENCE: 33

| | | | | | |
|---|---|---|---|---|---|
| auguacgacg | cagagcgcgg | cuggagcuug | uccuucgcgg | gcugcggcuu | ccugggcuuc | 60 |
| uaccacgucg | gggcgacccg | cugccugagc | gagcacgccc | cgcaccuccu | ccgcgacgcg | 120 |
| cgcauguugu | ucggcgcuuc | ggccggggcg | uugcacugcg | ucggcguccu | cuccgagcag | 180 |
| acucugcagg | uccucucaga | ucuugugcgg | aaggccagga | gucggaacau | uggcaucuuc | 240 |
| cauccauccu | ucaacuuaag | caaguccuc | cgacagggu | cucugcaaau | gccucccggcc | 300 |
| aaugucacc | agcucaucuc | cggcaaaaua | ggcaucucuc | uuaccagagu | gucugauggg | 360 |
| gaaaacguuc | uggugucuga | cuuucgguc | aaagacgaag | ucguggaugc | cuugguaugu | 420 |
| uccugcuuca | uccccuucua | caguggccuu | auccccuccuu | ccuucagagg | cgugcgauau | 480 |

| | |
|---|---|
| guggauggag gagugaguga caacguaccc uucauugaug ccaaaacaac caucaccgug | 540 |
| uccccuucu augggagua cgacaucugc ccuaaaguca aguccacgaa cuuucuucau | 600 |
| guggacauca ccaagcucag ucuacgccuc ugcacaggga accucuaccu ucucucgaga | 660 |
| gcuuuugucc ccccggaucu caaggugcug ggagagauau gccuucgagg auauuuggau | 720 |
| gcauucaggu ucuuggaaga aagggcauc ugcaacaggc cccagccagg ccugaaguca | 780 |
| uccucagaag ggauggaucc ugaggucgcc augcccagcu gggcaaacau gagucuggau | 840 |
| ucuuccccgg agucggcugc cuuggcugug aggcuggagg gagaugagcu gcuagaccac | 900 |
| cugcgcucuca gcauccugcc cugggaugag agcauccugg acacccucuc gcccaggcuc | 960 |
| gcuacagcac ugagugaaga augaaagac aaagguggau acaugagcaa gauuugcaac | 1020 |
| uugcuaccca uuaggauaau gucuuaugua augcugcccu guacccugcc uguggaaucu | 1080 |
| gccauugcga uuguccagag acuggugaca uggcuuccag auaugcccga cgaugucucug | 1140 |
| ugguugcagu gggugaccuc acagguguuc acucgagugc ugaugugucu gcuccccgcc | 1200 |
| uccaggucccc aaaugccagu gagcagccaa caggccuccc caugcacacc ugagcaggac | 1260 |
| uggcccugcu ggacucccug ucccccaag ggcugcucag cagagaccaa agcagaggcc | 1320 |
| accccgcggu ccauccucag guccagccug aacuucuucu ugggcaauaa aguaccgcu | 1380 |
| ggugcugagg ggcucuccac cuuucccagu uuucacuag agaagaguccu g | 1431 |

<210> SEQ ID NO 34
<211> LENGTH: 1443
<212> TYPE: DNA
<213> ORGANISM: Homo sapien

<400> SEQUENCE: 34

| | |
|---|---|
| auguacgacg cagagcgcgg cuggagcuug uccuucgcgg gcugcggcuu ccugggcuuc | 60 |
| uaccacgucg gggcgacccg cugccugagc gagcacgccc cgcaccuccu ccgcgacgcg | 120 |
| cgcauguugu ucgcgcuuc ggccggggcg uugcacugcg ucggcguccu ucccgguauc | 180 |
| ccgcuggagc agacucugca gguccucuca gaucuugugc ggaaggccag gagucggaac | 240 |
| auuggcaucu uccauccauc cuucaacuua agcaaguucc uccgacaggg ucucugcaaa | 300 |
| ugccucccgg ccaaugucca ccagcucauc uccggcaaaa uaggcaucuc ucuuaccaga | 360 |
| gugucugaug gggaaaacgu ucggugucu gacuuucggu ccaaagacga agucguggau | 420 |
| gccuggguau guuccugcuu caugcccuuc uacagguggcc uuauccccucc uuccuucaga | 480 |
| ggcgugcgau auguggaugg aggagugagu gacaacguac ccuucauuga ugccaaaaca | 540 |
| accaucaccg ugucccccuu cuauggggag uacgacaucu gcccuaaagu caagucccacg | 600 |
| aacuuucuuc auguggacau caccaagcuc agucuacgcc ucugcacagg gaaccucuac | 660 |
| cuucucucga gagcuuuugu cccccggau cucaaggugc ugggagagau augccuucga | 720 |
| ggauauuugg augcauucag guucuuggaa gagaagggca ucugcaacag gccccagcca | 780 |
| ggccugaagu cauccucaga agggauggau ccugaggucg ccaugcccag cugggcaaac | 840 |
| augagucugg auucuucccc ggagucggcu gccuuggcug ugaggcugga gggagaugag | 900 |
| cugcuagacc accugcgucu cagcauccug cccugggaug agcauccug gacacccuc | 960 |
| ucgcccaggc ucgcuacagc acugagugaa gaaugaaag acaaagguggg auacaugagc | 1020 |
| aagauuugca acuugcuacc cauuaggaua augucuuaug uaaugcugcc cguacccug | 1080 |
| ccuguggaau cugccauugc gauuguccag agacuggga caugguccu agauaugccc | 1140 |
| gacgaugucc uguggucgca guggugaccc ucacagguguu cacucgagu gcugaugugu | 1200 | cugcucccg ccuccagguc ccaaaugcca gugagcagcc aacaggccuc cccaugcaca    1260 ccugagcagg acuggcccug cuggacuccc ugcuccccca agggcugucc agcagagacc    1320 aaagcagagg ccaccccgcg guccauccuc aguccagcc ugaacuucuu cuugggcaau     1380 aaaguaccug cuggugcuga ggggcucucc accuucca guuuucacu agagaagagu       1440 cug                                                                  1443

<210> SEQ ID NO 35
<211> LENGTH: 1431
<212> TYPE: DNA
<213> ORGANISM: Homo sapien

<400> SEQUENCE: 35
auguacgacg cagagcgcgg cuggagcuug uccuucgcgg gcugcggcuu ccugggcuuc    60
uaccacgucg gggcgacccg cugccugagc gagcacgccc cgcaccuccu ccgcgacgcg    120
cgcauguugu ucggcgcuuc ggccggggcg uugcacugcg ucggcguccu cuccgagcag    180
acucugcagg uccucucaga ucuugugcgg aaggccagga gucggaacau uggcaucuuc    240
cauccauccu ucaacuuaag caaguccuc cgacagggguc ucugcaaaug ccucccggcc    300 aaugccacc agcucaucuc cggcaaaaua ggcaucucuc uuaccagagu gucugauggg     360
gaaaacguuc uggugucuga cuuucggucc aaagacgaag ucguggaugc cuugguaugu    420
uccugcuuca ugcccuucua caguggccuu auccccuccuu ccuucagagg cgugcgauau    480
guggauggag gagugaguga caacguaccc uucauugaug ccaaaacaac caucaccgug    540 uccccccuucu auggggagua cgacaucugc ccuaaaguca aguccacgaa cuuucuucau    600
guggacauca ccaagcucag ucuacgcccuc ugcacaggga accucuaccu ucucucgaga    660
gcuuuuguuc cccccggaucu caaggugcug ggagagauau gccuucgagg auauuuggau    720
gcauucaggu ucuuggaaga aagggcauc ugcaacaggc cccagccagg ccugaaguca    780
uccucagaag ggauggaucc ugaggucgcc augcccagcu gggcaaacau gagucuggau    840
ucuuccccgg agucggcugc cuggcugug aggcuggagg gagaugagcu gcuagaccac    900
cugcgucuca gcauccugcc cugggaugag agcauccugg acacccucuc gcccaggcuc    960
gcuacagcac ugagugaaga aaugaaagac aaaggugggau acaugagcaa gauuugcaac   1020
uugcuaccca uuaggauaau gucuuaugua augcugcccu guaccccugcc uguggaaucu    1080 gccauugcga uuguccagag acugguagaca uggcuuccag auaugcccga cgauguccug   1140
ugguugcagu gggugaccuc acagguguuc acucgagugc ugaugugucu gcuccccgcc   1200 uccaggucc aaaugccagu gagcagccaa caggccuccc caugcacacc ugagcaggac    1260
uggcccugcu ggacccug cuccccaag gcuguccca cagagaccaa agcagaggc         1320 accccgcggu ccauccucag guccagccug aacucuucu ugggcaauaa aguaccugcu     1380
ggugcugagg ggcucuccac cuuuccagu uuuucacuag agaagagucu g              1431

<210> SEQ ID NO 36
<211> LENGTH: 1443
<212> TYPE: DNA
<213> ORGANISM: Homo sapien

<400> SEQUENCE: 36
atgtacgacg cagagcgcgg ctggagcttg tccttcgcgg gctgcggctt cctgggcttc    60
taccacgtcg gggcgacccg ctgcctgagc gagcacgccc cgcacctcct ccgcgacgcg    120

| | |
|---|---|
| cgcatgttgt tcggcgcttc ggccggggcg ttgcactgcg tcggcgtcct ctccggtatc | 180 |
| ccgctggagc agactctgca ggtcctctca gatcttgtgc ggaaggccag gagtcggaac | 240 |
| attggcatct tccatccatc cttcaactta agcaagttcc tccgacaggg tctctgcaaa | 300 |
| tgcctcccgg ccaatgtcca ccagctcatc tccggcaaaa taggcatctc tcttaccaga | 360 |
| gtgtctgatg gggaaaacgt tctggtgtct gactttcggt ccaaagacga agtcgtggat | 420 |
| gccttggtat gttcctgctt catcccttc tacagtggcc ttatccctcc ttccttcaga | 480 |
| ggcgtgcgat atgtggatgg aggagtgagt gacaacgtac ccttcattga tgccaaaaca | 540 |
| accatcaccg tgtcccccttt ctatggggag tacgacatct gccctaaagt caagtccacg | 600 |
| aactttcttc atgtggacat caccaagctc agtctacgcc tctgcacagg gaacctctac | 660 |
| cttctctcga gacttttgt cccccggat ctcaaggtgc tgggagagat atgccttcga | 720 |
| ggatatttgg atgcattcag gttcttggaa gagaagggca tctgcaacag gccccagcca | 780 |
| ggcctgaagt catcctcaga agggatggat cctgaggtcg ccatgccag ctgggcaaac | 840 |
| atgagtctgg attcttcccc ggagtcggct gccttggctg tgaggctgga gggagatgag | 900 |
| ctgctagacc acctgcgtct cagcatcctg ccctgggatg agagcatcct ggacaccctc | 960 |
| tcgcccaggc tcgctacagc actgagtgaa gaaatgaaag acaaaggtgg atacatgagc | 1020 |
| aagatttgca acttgctacc cattaggata atgtcttatg taatgctgcc ctgtaccctg | 1080 |
| cctgtggaat ctgccattgc gattgtccag agactggtga catggcttcc agatatgccc | 1140 |
| gacgatgtcc tgtggttgca gtgggtgacc tcacaggtgt tcactcgagt gctgatgtgt | 1200 |
| ctgctccccg cctccaggtc ccaaatgcca gtgagcagcc aacaggcctc cccatgcaca | 1260 |
| cctgagcagg actggccctg ctggactccc tgctccccca agggctgtcc agcagagacc | 1320 |
| aaagcagagg ccacccccgcg gtccatcctc aggtccagcc tgaacttctt cttgggcaat | 1380 |
| aaagtacctg ctggtgctga ggggctctcc acctttccca gttttttcact agagaagagt | 1440 |
| ctg | 1443 |

<210> SEQ ID NO 37
<211> LENGTH: 1431
<212> TYPE: DNA
<213> ORGANISM: Homo sapien

<400> SEQUENCE: 37

| | |
|---|---|
| atgtacgacg cagagcgcgg ctggagcttg tccttcgcgg gctgcggctt cctgggcttc | 60 |
| taccacgtcg gggcgacccg ctgcctgagc gagcacgccc cgcacctcct ccgcgacgcg | 120 |
| cgcatgttgt tcggcgcttc ggccggggcg ttgcactgcg tcggcgtcct ctccgagcag | 180 |
| actctgcagg tcctctcaga tcttgtgcgg aaggccagga gtcggaacat tggcatcttc | 240 |
| catccatcct tcaacttaag caagttcctc cgacagggtc tctgcaaatg cctcccggcc | 300 |
| aatgtccacc agctcatctc cggcaaaata ggcatctctc ttaccagagt gtctgatggg | 360 |
| gaaaacgttc tggtgtctga ctttcggtcc aaagacgaag tcgtggatgc cttggtatgt | 420 |
| tcctgcttca tcccccttcta cagtggcctt atccctcctt ccttcagagg cgtgcgatat | 480 |
| gtggatggag gagtgagtga caacgtaccc ttcattgatg ccaaaacaac catcaccgtg | 540 |
| tccccctttct atggggagta cgacatctgc cctaaagtca agtccacgaa ctttcttcat | 600 |
| gtggacatca ccaagctcag tctacgcctc tgcacaggga acctctacct tctctcgaga | 660 |
| gcttttgtcc cccggatct caaggtgctg ggagagatat gccttcgagg atatttggat | 720 |
| gcattcaggt tcttggaaga aagggcatc tgcaacaggc cccagccagg cctgaagtca | 780 |

```
tcctcagaag ggatggatcc tgaggtcgcc atgcccagct gggcaaacat gagtctggat    840
tcttccccgg agtcggctgc cttggctgtg aggctggagg gagatgagct gctagaccac    900
ctgcgtctca gcatcctgcc ctgggatgag agcatcctgg acaccctctc gcccaggctc    960
gctacagcac tgagtgaaga aatgaaagac aaaggtggat acatgagcaa gatttgcaac   1020
ttgctaccca ttaggataat gtcttatgta atgctgccct gtaccctgcc tgtggaatct   1080
gccattgcga ttgtccagag actggtgaca tggcttccag atatgcccga cgatgtcctg   1140
tggttgcagt gggtgacctc acaggtgttc actcgagtgc tgatgtgtct gctccccgcc   1200
tccaggtccc aaatgccagt gagcagccaa caggcctccc catgcacacc tgagcaggac   1260
tggccctgct ggactccctg ctcccccaag ggctgtccag cagagaccaa agcagaggcc   1320
accccgcggt ccatcctcag gtccagcctg aacttcttct tgggcaataa agtacctgct   1380
ggtgctgagg ggctctccac ctttcccagt ttttcactag agaagagtct g            1431

<210> SEQ ID NO 38
<211> LENGTH: 1443
<212> TYPE: DNA
<213> ORGANISM: Homo sapien

<400> SEQUENCE: 38
atgtacgacg cagagcgcgg ctggagcttg tccttcgcgg gctgcggctt cctgggcttc     60
taccacgtcg gggcgaccg ctgcctgagc gagcacgccc cgcacctcct ccgcgacgcg    120
cgcatgttgt tcggcgcttc ggccggggcg ttgcactgcg tcggcgtcct ctccggtatc    180
ccgctggagc agactctgca ggtcctctca gatcttgtgc ggaaggccag gagtcggaac    240
attggcatct tccatccatc cttcaactta agcaagttcc tccgacaggg tctctgcaaa    300
tgcctcccgg ccaatgtcca ccagctcatc tccggcaaaa taggcatctc tcttaccaga    360
gtgtctgatg gggaaaacgt tctggtgtct gactttcggt ccaaagacga agtcgtggat    420
gccttggtat gttcctgctt catgcccttc tacagtggcc ttatccctcc ttccttcaga    480
ggcgtgcgat atgtggatgg aggagtgagt gacaacgtac ccttcattga tgccaaaaca    540
accatcaccg tgtcccccct ctatggggag tacgacatct gccctaaagt caagtccacg    600
aactttcttc atgtggacat caccaagctc agtctacgcc tctgcacagg gaacctctac    660
cttctctcga gagcttttgt cccccgggat ctcaaggtgc tgggagagat atgccttcga    720
ggatatttgg atgcattcag gttcttggaa gagaagggca tctgcaacag gccccagcca    780
ggcctgaagt catcctcaga agggatggat cctgaggtcg ccatgcccag ctgggcaaac    840
atgagtctgg attcttcccc ggagtcggct gccttggctg tgaggctgga gggagatgag    900
ctgctagacc acctgcgtct cagcatcctg ccctgggatg agagcatcct ggacaccctc    960
tcgcccaggc tcgctacagc actgagtgaa gaaatgaaag acaaaggtgg atacatgagc   1020
aagatttgca acttgctacc cattaggata atgtcttatg taatgctgcc ctgtaccctg   1080
cctgtggaat ctgccattgc gattgtccag agactggtga catggcttcc agatatgccc   1140
gacgatgtcc tgtggttgca gtgggtgacc tcacaggtgt tcactcgagt gctgatgtgt   1200
ctgctccccg cctccaggtc ccaaatgcca gtgagcagca acaggcctc cccatgcaca   1260 cctgagcagg actggccctg ctggactccc tgctccccca gggctgtcca gcagagacc   1320 aaagcagagg ccaccccgcg gtccatcctc aggtccagcc tgaacttctt cttgggcaat   1380
aaagtacctg ctggtgctga ggggctctcc acctttccca gttttttcact agagaagagt   1440
``` ctg                                                                    1443

<210> SEQ ID NO 39
<211> LENGTH: 1431
<212> TYPE: DNA
<213> ORGANISM: Homo sapien

<400> SEQUENCE: 39
atgtacgacg cagagcgcgg ctggagcttg tccttcgcgg gctgcggctt cctgggcttc     60
taccacgtcg gggcgacccg ctgcctgagc gagcacgccc cgcacctcct ccgcgacgcg    120
cgcatgttgt tcggcgcttc ggccggggcg ttgcactgcg tcggcgtcct ctccgagcag    180
actctgcagg tcctctcaga tcttgtgcgg aaggccagga gtcggaacat ggcatcttc     240
catccatcct tcaacttaag caagttcctc cgacagggtc tctgcaaatg cctcccggcc    300
aatgtccacc agctcatctc cggcaaaata ggcatctctc ttaccagagt gtctgatggg    360
gaaaacgttc tggtgtctga ctttcggtcc aaagacgaag tcgtggatgc cttggtatgt    420
tcctgcttca tgcccttcta cagtggcctt atccctcctt ccttcagagg cgtgcgatat    480
gtggatggag gagtgagtga caacgtaccc ttcattgatg ccaaaacaac catcaccgtg    540
tccccttct atggggagta cgacatctgc cctaaagtca gtccacgaa cttttcttcat    600
gtggacatca ccaagctcag tctacgcctc tgcacaggga acctctacct tctctcgaga    660
gcttttgtcc ccccggatct caaggtgctg ggagagatat gccttcgagg atatttggat    720
gcattcaggt tcttggaaga aagggcatc tgcaacaggc cccagccagg cctgaagtca    780
tcctcagaag ggatggatcc tgaggtcgcc atgcccagct gggcaaacat gagtctggat    840
tcttccccgg agtcggctgc cttggctgtg aggctggagg gagatgagct gctagaccac    900
ctgcgtctca gcatcctgcc ctgggatgag agcatcctgg acaccctctc gcccaggctc    960
gctacagcac tgagtgaaga aatgaaagac aaaggtggat acatgagcaa gatttgcaac   1020
ttgctaccca ttaggataat gtcttatgta atgctgccct gtaccctgcc tgtggaatct   1080
gccattgcga ttgtccagag actggtgaca tggcttccag atatgcccga cgatgtcctg   1140
tggttgcagt gggtgacctc acaggtgttc actcgagtgc tgatgtgtct gctccccgcc   1200
tccaggtccc aaatgccagt gagcagccaa caggcctccc catgcacacc tgagcaggac   1260
tggccctgct ggactccctg ctcccccaag ggctgtccag cagagaccaa agcagaggcc   1320
accccgcggt ccatcctcag gtccagcctg aacttcttct tgggcaataa agtacctgct   1380
ggtgctgagg ggctctccac ctttcccagt ttttcactag agaagagtct g            1431

<210> SEQ ID NO 40
<211> LENGTH: 481
<212> TYPE: PRT
<213> ORGANISM: Homo sapien

<400> SEQUENCE: 40

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn

```
                65                  70                  75                  80
            Ile Gly Ile Phe His Pro Ser Phe Asn Leu Ser Lys Phe Leu Arg Gln
                            85                  90                  95
            Gly Leu Cys Lys Cys Leu Pro Ala Asn Val His Gln Leu Ile Ser Gly
                           100                 105                 110
            Lys Ile Gly Ile Ser Leu Thr Arg Val Ser Asp Gly Glu Asn Val Leu
                           115                 120                 125
            Val Ser Asp Phe Arg Ser Lys Asp Glu Val Val Asp Ala Leu Val Cys
            130                 135                 140
            Ser Cys Phe Ile Pro Phe Tyr Ser Gly Leu Ile Pro Ser Phe Arg
            145                 150                 155                 160
            Gly Val Arg Tyr Val Asp Gly Gly Val Ser Asp Asn Val Pro Phe Ile
                           165                 170                 175
            Asp Ala Lys Thr Thr Ile Thr Val Ser Pro Phe Tyr Gly Glu Tyr Asp
                           180                 185                 190
            Ile Cys Pro Lys Val Lys Ser Thr Asn Phe Leu His Val Asp Ile Thr
                           195                 200                 205
            Lys Leu Ser Leu Arg Leu Cys Thr Gly Asn Leu Tyr Leu Leu Ser Arg
            210                 215                 220
            Ala Phe Val Pro Pro Asp Leu Lys Val Leu Gly Glu Ile Cys Leu Arg
            225                 230                 235                 240
            Gly Tyr Leu Asp Ala Phe Arg Phe Leu Glu Glu Lys Gly Ile Cys Asn
                           245                 250                 255
            Arg Pro Gln Pro Gly Leu Lys Ser Ser Ser Glu Gly Met Asp Pro Glu
                           260                 265                 270
            Val Ala Met Pro Ser Trp Ala Asn Met Ser Leu Asp Ser Ser Pro Glu
                           275                 280                 285
            Ser Ala Ala Leu Ala Val Arg Leu Glu Gly Asp Glu Leu Leu Asp His
                           290                 295                 300
            Leu Arg Leu Ser Ile Leu Pro Trp Asp Glu Ser Ile Leu Asp Thr Leu
            305                 310                 315                 320
            Ser Pro Arg Leu Ala Thr Ala Leu Ser Glu Glu Met Lys Asp Lys Gly
                           325                 330                 335
            Gly Tyr Met Ser Lys Ile Cys Asn Leu Leu Pro Ile Arg Ile Met Ser
                           340                 345                 350
            Tyr Val Met Leu Pro Cys Thr Leu Pro Val Glu Ser Ala Ile Ala Ile
                           355                 360                 365
            Val Gln Arg Leu Val Thr Trp Leu Pro Asp Met Pro Asp Asp Val Leu
                           370                 375                 380
            Trp Leu Gln Trp Val Thr Ser Gln Val Phe Thr Arg Val Leu Met Cys
            385                 390                 395                 400
            Leu Leu Pro Ala Ser Arg Ser Gln Met Pro Val Ser Ser Gln Gln Ala
                           405                 410                 415
            Ser Pro Cys Thr Pro Glu Gln Asp Trp Pro Cys Trp Thr Pro Cys Ser
                           420                 425                 430
            Pro Lys Gly Cys Pro Ala Glu Thr Lys Ala Glu Ala Thr Pro Arg Ser
                           435                 440                 445
            Ile Leu Arg Ser Ser Leu Asn Phe Phe Leu Gly Asn Lys Val Pro Ala
                           450                 455                 460
            Gly Ala Glu Gly Leu Ser Thr Phe Pro Ser Phe Ser Leu Glu Lys Ser
            465                 470                 475                 480
            Leu
```

<210> SEQ ID NO 41
<211> LENGTH: 477
<212> TYPE: PRT
<213> ORGANISM: Homo sapien

<400> SEQUENCE: 41

```
Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Glu Gln Thr Leu Gln Val
    50                  55                  60

Leu Ser Asp Leu Val Arg Lys Ala Arg Ser Arg Asn Ile Gly Ile Phe
65                  70                  75                  80

His Pro Ser Phe Asn Leu Ser Lys Phe Leu Arg Gln Gly Leu Cys Lys
                85                  90                  95

Cys Leu Pro Ala Asn Val His Gln Leu Ile Ser Gly Lys Ile Gly Ile
            100                 105                 110

Ser Leu Thr Arg Val Ser Asp Gly Glu Asn Val Leu Val Ser Asp Phe
        115                 120                 125

Arg Ser Lys Asp Glu Val Val Asp Ala Leu Val Cys Ser Cys Phe Ile
    130                 135                 140

Pro Phe Tyr Ser Gly Leu Ile Pro Pro Ser Phe Arg Gly Val Arg Tyr
145                 150                 155                 160

Val Asp Gly Gly Val Ser Asp Asn Val Pro Phe Ile Asp Ala Lys Thr
                165                 170                 175

Thr Ile Thr Val Ser Pro Phe Tyr Gly Glu Tyr Asp Ile Cys Pro Lys
            180                 185                 190

Val Lys Ser Thr Asn Phe Leu His Val Asp Ile Thr Lys Leu Ser Leu
        195                 200                 205

Arg Leu Cys Thr Gly Asn Leu Tyr Leu Leu Ser Arg Ala Phe Val Pro
    210                 215                 220

Pro Asp Leu Lys Val Leu Gly Glu Ile Cys Leu Arg Gly Tyr Leu Asp
225                 230                 235                 240

Ala Phe Arg Phe Leu Glu Glu Lys Gly Ile Cys Asn Arg Pro Gln Pro
                245                 250                 255

Gly Leu Lys Ser Ser Ser Glu Gly Met Asp Pro Glu Val Ala Met Pro
            260                 265                 270

Ser Trp Ala Asn Met Ser Leu Asp Ser Ser Pro Glu Ser Ala Ala Leu
        275                 280                 285

Ala Val Arg Leu Glu Gly Asp Glu Leu Leu Asp His Leu Arg Leu Ser
    290                 295                 300

Ile Leu Pro Trp Asp Glu Ser Ile Leu Asp Thr Leu Ser Pro Arg Leu
305                 310                 315                 320

Ala Thr Ala Leu Ser Glu Glu Met Lys Asp Lys Gly Gly Tyr Met Ser
                325                 330                 335

Lys Ile Cys Asn Leu Leu Pro Ile Arg Ile Met Ser Tyr Val Met Leu
            340                 345                 350

Pro Cys Thr Leu Pro Val Glu Ser Ala Ile Ala Ile Val Gln Arg Leu
        355                 360                 365

Val Thr Trp Leu Pro Asp Met Pro Asp Asp Val Leu Trp Leu Gln Trp
    370                 375                 380
```

```
Val Thr Ser Gln Val Phe Thr Arg Val Leu Met Cys Leu Leu Pro Ala
385                 390                 395                 400

Ser Arg Ser Gln Met Pro Val Ser Ser Gln Gln Ala Ser Pro Cys Thr
            405                 410                 415

Pro Glu Gln Asp Trp Pro Cys Trp Thr Pro Cys Ser Pro Lys Gly Cys
        420                 425                 430

Pro Ala Glu Thr Lys Ala Glu Ala Thr Pro Arg Ser Ile Leu Arg Ser
        435                 440                 445

Ser Leu Asn Phe Phe Leu Gly Asn Lys Val Pro Ala Gly Ala Glu Gly
    450                 455                 460

Leu Ser Thr Phe Pro Ser Phe Ser Leu Glu Lys Ser Leu
465                 470                 475

<210> SEQ ID NO 42
<211> LENGTH: 481
<212> TYPE: PRT
<213> ORGANISM: Homo sapien

<400> SEQUENCE: 42

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
                20                  25                  30

Ala Pro His Leu Leu Arg Asp Ala Arg Met Leu Phe Gly Ala Ser Ala
            35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
    115                 120                 125

Val Ser Asp Phe Arg Ser Lys Asp Glu Val Val Asp Ala Leu Val Cys
130                 135                 140

Ser Cys Phe Met Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
    195                 200                 205

Lys Leu Ser Leu Arg Leu Cys Thr Gly Asn Leu Tyr Leu Leu Ser Arg
210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Glu Gly Met Asp Pro Glu
            260                 265                 270

Val Ala Met Pro Ser Trp Ala Asn Met Ser Leu Asp Ser Ser Pro Glu
```

```
            275                 280                 285
Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
                355                 360                 365

Val Gln Arg Leu Val Thr Trp Leu Pro Asp Met Pro Asp Asp Val Leu
    370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
                420                 425                 430

Pro Lys Gly Cys Pro Ala Glu Thr Lys Ala Glu Ala Thr Pro Arg Ser
            435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu

<210> SEQ ID NO 43
<211> LENGTH: 477
<212> TYPE: PRT
<213> ORGANISM: Homo sapien

<400> SEQUENCE: 43

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
                20                  25                  30

Ala Pro His Leu Leu Arg Asp Ala Arg Met Leu Phe Gly Ala Ser Ala
            35                  40                  45

Gly Ala Leu His Cys Val Gly Val Leu Ser Gln Thr Leu Gln Val
    50                  55                  60

Leu Ser Asp Leu Val Arg Lys Ala Arg Ser Arg Asn Ile Gly Ile Phe
65                  70                  75                  80

His Pro Ser Phe Asn Leu Ser Lys Phe Leu Arg Gln Gly Leu Cys Lys
                85                  90                  95

Cys Leu Pro Ala Asn Val His Gln Leu Ile Ser Gly Lys Ile Gly Ile
            100                 105                 110

Ser Leu Thr Arg Val Ser Asp Gly Glu Asn Val Leu Ser Asp Phe
    115                 120                 125

Arg Ser Lys Asp Glu Val Val Asp Ala Leu Val Cys Ser Cys Phe Met
    130                 135                 140

Pro Phe Tyr Ser Gly Leu Ile Pro Pro Ser Phe Arg Gly Val Arg Tyr
145                 150                 155                 160

Val Asp Gly Gly Val Ser Asp Asn Val Pro Phe Ile Asp Ala Lys Thr
```

```
                165                 170                 175
Thr Ile Thr Val Ser Pro Phe Tyr Gly Glu Tyr Asp Ile Cys Pro Lys
            180                 185                 190
Val Lys Ser Thr Asn Phe Leu His Val Asp Ile Thr Lys Leu Ser Leu
            195                 200                 205
Arg Leu Cys Thr Gly Asn Leu Tyr Leu Leu Ser Arg Ala Phe Val Pro
            210                 215                 220
Pro Asp Leu Lys Val Leu Gly Glu Ile Cys Leu Arg Gly Tyr Leu Asp
225                 230                 235                 240
Ala Phe Arg Phe Leu Glu Glu Lys Gly Ile Cys Asn Arg Pro Gln Pro
            245                 250                 255
Gly Leu Lys Ser Ser Glu Gly Met Asp Pro Glu Val Ala Met Pro
            260                 265                 270
Ser Trp Ala Asn Met Ser Leu Asp Ser Ser Pro Glu Ser Ala Ala Leu
            275                 280                 285
Ala Val Arg Leu Glu Gly Asp Glu Leu Leu Asp His Leu Arg Leu Ser
            290                 295                 300
Ile Leu Pro Trp Asp Glu Ser Ile Leu Asp Thr Leu Ser Pro Arg Leu
305                 310                 315                 320
Ala Thr Ala Leu Ser Glu Glu Met Lys Asp Lys Gly Gly Tyr Met Ser
            325                 330                 335
Lys Ile Cys Asn Leu Leu Pro Ile Arg Ile Met Ser Tyr Val Met Leu
            340                 345                 350
Pro Cys Thr Leu Pro Val Glu Ser Ala Ile Ala Ile Val Gln Arg Leu
            355                 360                 365
Val Thr Trp Leu Pro Asp Met Pro Asp Asp Val Leu Trp Leu Gln Trp
            370                 375                 380
Val Thr Ser Gln Val Phe Thr Arg Val Leu Met Cys Leu Leu Pro Ala
385                 390                 395                 400
Ser Arg Ser Gln Met Pro Val Ser Ser Gln Gln Ala Ser Pro Cys Thr
            405                 410                 415
Pro Glu Gln Asp Trp Pro Cys Trp Thr Pro Cys Ser Pro Lys Gly Cys
            420                 425                 430
Pro Ala Glu Thr Lys Ala Glu Ala Thr Pro Arg Ser Ile Leu Arg Ser
            435                 440                 445
Ser Leu Asn Phe Phe Leu Gly Asn Lys Val Pro Ala Gly Ala Glu Gly
            450                 455                 460
Leu Ser Thr Phe Pro Ser Phe Ser Leu Glu Lys Ser Leu
465                 470                 475

<210> SEQ ID NO 44
<211> LENGTH: 2397
<212> TYPE: DNA
<213> ORGANISM: Homo sapien

<400> SEQUENCE: 44
agacaguacc uccucccuag gacuacacaa ggacugaacc agaaggaaga ggacagagca      60
aagccaugaa caucauccua gaaauccuuc ugcuucugau caccaucauc uacuccuacu     120
uggagucguu ggugaaguuu ucauuccuc agaggagaaa aucuguggcu ggggagauug      180
uucucauuac uggagcuggg cauggaauag gcaggcagac uacuuaugaa uuugcaaaac     240
gacagagcau auugguucug uggauauua auaagcgcgg uggaggaa acugcagcug       300 agugccgaaa acuaggcguc acugcgcaug cguauggu agacugcagc aacagagaag      360
```

| | | | | |
|---|---|---|---|---|
| agaucuaucg | cucucuaaau | caggugaaga | agaaguggg | ugauguaaca aucgugguga | 420 |
| auaaugcugg | gacaguauau | ccagccgauc | uucucagcac | caaggaugaa gagauuacca | 480 |
| agacauuuga | ggucaacauc | cuaggacauu | uuuggaucac | aaaagcacuu cuuccaucga | 540 |
| ugauggagag | aaaucauggc | cacaucguca | caguggcuuc | agugugcggc cacgaaggga | 600 |
| uuccuuaccu | caucccauau | uguuccagca | auuugccgc | uguuggcuuu cacagagguc | 660 |
| ugacaucaga | acuucaggcc | uugggaaaaa | cugguaucaa | accucaugu cucugcccag | 720 |
| uuuuugugaa | uacuggguuc | accaaaaauc | caagcacaag | auuauggccu guauggaga | 780 |
| cagaugaagu | cguaagaagu | cugauagaug | gaauacuuac | caauaagaaa augauuuuug | 840 |
| uuccaucgua | uaucaauauc | uuucugagac | uacagaaguu | ucuuccugaa cgcgccucag | 900 |
| cgauuuaaaa | ucguaugcag | aauauucauu | ugaagcagu | gguuggccac aaaaucaaaa | 960 |
| ugaaaugaau | aaauaagcuc | cagccagaga | uguaugcaug | auaaugauau gaauaguuuc | 1020 |
| gaaucaaugc | ugcaaagcuu | uauucacau | uuuucaguc | cugauaauau uaaaaacauu | 1080 |
| gguuggcac | uagcagcagu | caaacgaaca | agauuaauua | ccugucuucc uguuucucaa | 1140 |
| gaauauuuac | guaguuuuuc | uaggucugu | uuuuccuuuc | augccucuua aaacuucug | 1200 |
| ugcuuacaua | aacauacuua | aaagguuuuc | uuuaagauau | uuuauuuuuc cauuuaaagg | 1260 |
| uggacaaaag | cuacccccu | aaaaguaaau | acaaagagaa | cuuauuuaca cagggaaggu | 1320 |
| uuaagacugu | ucaaguagca | uuccaaucug | uagccaugcc | acagauauc aacaagaaca | 1380 |
| cagaaugagu | gcacagcuaa | gagaucaagu | uucagcaggc | agcuuuaucu caaccuggac | 1440 |
| auauuuuaag | auucagcauu | ugaaagauuu | cccuagccuc | uuccuuuuuc auuagcccaa | 1500 |
| aacggugcaa | cucuauucug | gacuuuauua | cuugauucug | ucuucuguau aacucugaag | 1560 |
| uccaccaaaa | guggacccuc | uauauuuccu | cccuuuuuau | agcuauauaa gauacauuau | 1620 |
| gaaaggugac | cgacucuauu | uuaaaucuca | gaauuuuaag | uucuagccccc augauaaccu | 1680 |
| uuuucuuugu | aauuuaugcu | uucauauauc | cuuggucccca | gagauguuua gacaauuuua | 1740 |
| ggcucaaaaa | uuaaagcuaa | cacaggaaaa | ggaacuguac | uggcuauuac auaagaaaca | 1800 |
| auggacccaa | gagaagaaaa | ggaagaaaga | aagguuuuuu | gguuuugu uuguuuguu | 1860 |
| uuguuuuug | uuuuuugag | auggagucuc | acucuuucgc | ccaggcugga gugcaguggu | 1920 |
| augaucucag | cucacugcaa | gcuccaccuc | ccgggguucac | gccauucucc ugccucagcc | 1980 |
| uccugaguag | cugggacuac | aggcgcccgc | caccacaccc | ggcuaauuuu uuguauuuuu | 2040 |
| uguagagacg | ggguuucacc | auguuagcca | gauggucuc | gauccccuga ccucgugauc | 2100 |
| caccugccuc | ggccucccaa | agugcuggga | uuacggguguu | gagccaccgu gcccagccuu | 2160 |
| uuuuuuuua | auagaaaaaa | uaauccgacu | cccacuacau | caagacuaau cuuguuugu | 2220 |
| guguuuuuca | cauguauuau | agaaugcuuu | ugcauggacu | auccucuugu uuuuauuaaa | 2280 |
| aacaaaugau | uuuuuuaaaa | gucacaaaaa | caauucacua | aaauaaaua ugucauugug | 2340 |
| cuuuaaaaaa | auaaccucuu | guaguuauaa | aauaaaacgu | uugacuucua aacucug | 2397 |

<210> SEQ ID NO 45
<211> LENGTH: 2289
<212> TYPE: RNA
<213> ORGANISM: Homo sapien

<400> SEQUENCE: 45

| | | | | |
|---|---|---|---|---|
| agacaguacc | uccucccuag | gacuacacaa | ggacugaacc | agaaggaaga ggacagagca | 60 |
| aagccaugaa | caucauccua | gaaauccuuc | ugcuucugau | caccaucauc uacuccuacu | 120 |

-continued

```
uggagucguu ggugaaguuu uucauuccuc agaggagaaa aucuguggcu ggggagauug      180
uucucauuac uggagcuggg cauggaauag gcaggcagac uacuuaugaa uuugcaaaac      240
gacagagcau auugguucug ugggauauua auaaggugaa gaaagaagug ggugauguaa      300
caaucguggu gaauaaugcu gggacaguau auccagccga ucuucucagc accaaggaug      360
aagagauuac caagacauuu gaggucaaca uccaggacca uuuuggauc acaaaagcac       420 uucuuccauc gaugauggag agaaaucaug gccacaucgu cacaguggcu ucagugugcg      480
gccacgaagg gauuccuuac cucaucccau auuguuccag caaauuugcc gcuguuggcu     540
uucacagagg ucgacauca gaacuucagg ccuugggaaa aacugguauc aaaaccucau      600
gucucugccc aguuuugug aauacgggu ucaccaaaa uccaagcaca agauuauggc       660
cuguauugga gacagaugaa gucguaagaa gucugauaga uggaauacuu accaauaaga     720
aaaugauuuu uguccaucg uauaucaaua ucuuucugag acuacagaag uucuuccug       780 aacgcgccuc agcgauuuua aaucguaugc agaauauuca auugaagca guggcuggcc     840 acaaaaucaa aaugaaauga auaaauaagc uccagccaga gauguaugca ugauaaugau    900
augaauaguu ucgaaucaau gcugcaaagc uuuauuucac auuuuucag uccgauaau      960 auuaaaaaca uugguuuggc acuagcagca gucaaacgaa caagauuaau uaccugucuu   1020
ccuguuucuc aagaauauuu acguaguuuu ucauaggucu guuuuccuu ucaugccucu   1080 uaaaacuuc ugugcuuaca uaaacauacu uaaaagguuu ucuuuaagau auuuuauuuu    1140 uccauuaaa gguggacaaa agcuaccuc cuaaaaguaa auacaaagag aacuuauuua     1200
cacagggaag guuuaagacu guucaaguag cauuccaauc uguagccaug ccacagaaua    1260
ucaacaagaa cacagaauga gugcacagcu aagagaucaa guucagcag gcagcuuuau   1320 cucaaccugg acauauuuua agauucagca uugaaagau ucccuagcc ucuuccuuuu    1380 ucauuagccc aaaacgggugc aacucuauuc uggacuuuau acuugauuc ugucuucugu   1440 auaacucuga aguccaccaa aaguggaccc ucuauauuuc cucccuuuuu auagucuuau   1500
aagauacauu augaaaggug accgacucua uuuuuaaaucu cagaauuuua aguucuagcc    1560
ccaugauaac cuuuucuuu guaauuuaug cuuucauaua uccuuggucc cagagauguu    1620
uagacaauuu uaggcucaaa aauuaaagcu aacacaggaa aaggaacugu acuggcuauu    1680
acauaagaaa caauggaccc aagagaagaa aaggaagaaa gaaagguuuu uuggguuuug    1740
uuuuguuuug uuuuguuuuu uguuuuuuug agauggaguc ucacucuuuc gcccaggcug    1800
gagugcagug guaugaucuc agcucacugc aagcuccacc ucccggguuc acgccauucu    1860
ccugccucag ccuccugagu agcugggacu acaggcgccc gccaccacac ccggcuaauu    1920
uuuuguauuu uuuguagaga cggggguuuca ccauguuagc caagaugguc ucgaucccu    1980 gaccucguga uccaccugcc ucggccuccc aaagugcugg gauuacgggu gugagccacc    2040
gugcccagcc uuuuuuuuu uaauagaaaa aauaauccga cucccacuac aucaagacua    2100
aucuuguuuu guguguuuuu cacauguauu auagaaugcu uuugcaugga cuauccucuu    2160
guuuuuauua aaaacaaaug auuuuuuuaa aagucacaaa aacaauucac uaaaaauaaa    2220
uaugucauug ugcuuuaaaa aaauaaccuc uuguaguuau aaaauaaaac guuugacuuc    2280
uaaacucug                                                              2289
```

<210> SEQ ID NO 46
<211> LENGTH: 2280
<212> TYPE: RNA

<213> ORGANISM: Homo sapien

<400> SEQUENCE: 46

| | |
|---|---|
| agacaguacc uccucccuag dacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu uucauuccuc agaggagaaa aucguggcu ggggagauug | 180 |
| uucucauuac uggagcuggg cauggaauag gcaggcagac acuuaugaa uuugcaaaac | 240 |
| gacagagcau auugguucug ugggauauua auaagcgcgg uguggaggaa acugcagcug | 300 |
| agugccgaaa acuaggcguc acugcgcaug cguaugggu agacgcagc aacagagaag | 360 |
| agaucuaucg cucucuaaau caggugaaga aagaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuuggaucac aaaagcacuu cuuccaucga | 540 |
| ugauggagag aaaucauggc cacaucguca caguggcuuc agugugcggc cacgaaggga | 600 |
| uuccuuaccu caucccauau uguucagca aauuugccgc uguggcuuu cacagagguc | 660 |
| ugacaucaga acuucaggcc uugggaaaaa cugguaucaa aaccucaugu cucugcccag | 720 |
| uuuuugugaa uacugggguuc accaaaaauc caagcacaag guuucuuccu gaacgcgccu | 780 |
| cagcgauuuu aaaucguaug cagaauauuc aauuugaagc aguggcuggc cacaaaauca | 840 |
| aaaugaaaug aauaaauaag cuccagccag agaugauauc augauaauga uaugaauagu | 900 |
| uucgaaucaa ugcugcaaag cuuuauuuca cauuuuuca guccugauaa uauuaaaaac | 960 |
| auugguuugg cacuagcagc agucaaacga acaagauuaa uuaccugucu uccuguuucu | 1020 |
| caagaauauu uacguaguuu ucauaggguc uguuuuccu uucaugccuc uuaaaaacuu | 1080 |
| cugugcuuac auaaacauac uuaaaagguu ucuuuaaga uauuuauuu uuccauuuaa | 1140 |
| aggugacaa aagcuaccuc ccuaaaaguaa aauacaaaga gaacuuauuu acacagggaa | 1200 |
| gguuuaagc uguucaagua gcauuccaau cuguagccau gccacagaau ucaacaaga | 1260 |
| acacagaaug agugcacagc uaagagauca aguucagca ggcagcuuua ucucaaccug | 1320 |
| gacauauuuu aagauucagc auuugaagaa uuucccuagc cucuuccuuu uucauuagcc | 1380 |
| caaaacggug caacucuauu cuggacuuua uuacugauu cugucuucug uauaacucug | 1440 |
| aagucaccacca aaaguggacc cucuauauuu ccucccuuuu uauagcuuua uaagauacau | 1500 |
| uaugaaaggu gaccgacucu auuuuaaauc ucagaauuuu aaguucuagc cccaugauaa | 1560 |
| ccuuuucuu uguaauuuau gcuucauau auccuugguc ccagagaugu uuagacaauu | 1620 |
| uuaggcucaa aaauuaaagc uaacacagga aaggaacug uacuggcuau uacauaagaa | 1680 |
| acaauggacc caagagaaga aaggaagaa agaaagguuu uugguuuuu guuuuguuuu | 1740 |
| guuuuguuuu uuguuuuuuu gagauggagu cucacucuuu cgcccaggcu ggagugcagu | 1800 |
| gguaugaucu cagcucacug caagcuccac cucccggguu cacgccauuc uccugccuca | 1860 |
| gccuccugag uagcugggac uacaggcgcc cgccaccaca cccggcuaau uuuuuguauu | 1920 |
| uuuuguagag acggggguuuc accauguuag ccaagauggu cucgaucucc ugaccucgug | 1980 |
| auccaccugc cucggccucc caaagugcug gauuacggg ugagccac cgugcccagc | 2040 |
| cuuuuuuuu uuaauagaaa aaauaauccg acucccacua caucaagacu aaucuuguuu | 2100 |
| ugugugguuu ucacauguau uauagaaugc uuuugcaugg acauccucu uguuuuauu | 2160 |
| aaaaacaaau gauuuuuuua aagucacaa aaacaauuca cuaaaauaa auaugucauu | 2220 |
| gugcuuuaaa aaaauaaccu cuuguaguua uaaaauaaaa cguuugacuu cuaaacucug | 2280 |

<210> SEQ ID NO 47
<211> LENGTH: 2398
<212> TYPE: RNA
<213> ORGANISM: Homo sapien

<400> SEQUENCE: 47

| | | | | | |
|---|---|---|---|---|---|
| agacaguacc | uccucccuag | dacuacacaa | ggacugaacc | agaaggaaga | ggacagagca | 60 |
| aagccaugaa | caucauccua | gaaauccuuc | ugcuucugau | caccaucauc | uacuccuacu | 120 |
| uggagucguu | ggugaaguuu | ucauuccuc | agaggagaaa | aucguggcu | ggggagauug | 180 |
| uucucauuac | uggagcuggg | cauggaauag | gcaggcagca | uacuuaugaa | uugcaaaac | 240 |
| gacagagcau | auugguucug | ugggauauua | auaagcgcgg | uguggaggaa | acugcagcug | 300 |
| agugccgaaa | acuaggcguc | acugcgcaug | cguaugggu | agacgcagc | aacagagaag | 360 |
| agaucuaucg | cucucuaaau | caggugaaga | agaaguggg | ugauguaaca | aucgggguga | 420 |
| auaaugcugg | gacaguauau | ccagccgauc | uucucagcac | caaggaugaa | gagauuacca | 480 |
| agacauuuga | ggucaacauc | cuaggacauu | uuggaucac | aaaagcacuu | cuccaucga | 540 |
| ugauggagag | aaaucauggc | cacaucguca | caguggcuuc | agugcggc | cacgaaggga | 600 |
| uccuuaccu | caucccauau | uguccagca | aauugccgc | uguggcuuu | cacagagguc | 660 |
| ugacaucaga | acuucaggcc | uugggaaaaa | cugguacaa | aacccaugu | cucgcccag | 720 |
| uuuugugaa | uacuggguc | accaaaaauc | caagcacaag | auuauggccu | guauuggaga | 780 |
| cagaugaagu | cguaagaagu | cugauagaug | gaauacuuac | caauaagaaa | augauuuug | 840 |
| uuccaucgua | uaucaauauc | uuucugagac | uacagaaggu | uucuuccuga | acgcgccuca | 900 |
| gcgauuuuaa | aucguaugca | gaauauucaa | uuugaagcag | ugguuggcca | caaaucaaa | 960 |
| augaaaugaa | uaaauaagcu | ccagccagag | auguaugcau | gauaaugaua | ugaauaguuu | 1020 |
| cgaaucaaug | cugcaaagcu | uuauuucaca | uuuuucagu | ccugauaaua | uuaaaaacau | 1080 |
| ugguuuggca | cuagcagcag | ucaaacgaac | aagauuaauu | accgucuuc | cuguuucuca | 1140 |
| agaauauuua | cguaguuuuu | cauaggucug | uuuuuccuuu | caugcccucu | aaaaacuucu | 1200 |
| gugcuuacau | aaacauacuu | aaaagguuuu | cuuaagaua | uuuuauuuu | ccauuuaaag | 1260 |
| guggacaaaa | gcuaccuccc | uaaaaguaaa | uacaaagaga | acuuauuuac | acagggaagg | 1320 |
| uuuaagacug | uucaaguagc | auccaaaucu | guagccaugc | cacagaauau | caacaagaac | 1380 |
| acagaaugag | ugcacagcua | agagaucaag | uuucagcagg | cagcuuuauc | ucaaccugga | 1440 |
| cauauuuuaa | gauucagcau | uugaaagauu | ucccuagccu | cuuccuuuuu | cauuagccca | 1500 |
| aaacggugca | acucuauucu | ggacuuuauu | acuugauucu | gucuucugua | uaacucugaa | 1560 |
| guccaccaaa | aguggacccu | cuauauuccc | uccuuuuua | uagucuuaua | agauacauua | 1620 |
| ugaaagguga | ccgacucuau | uuuaaaucuc | agaauuuaa | guucuagccc | caugauaacc | 1680 |
| uuuuucuuug | uaauuuaugc | uuucauauau | ccuggucccc | agagauguuu | agacaauuu | 1740 |
| aggcucaaaa | auuaaagcua | acacaggaaa | aggaacugua | cuggcuauua | cauaagaaac | 1800 |
| aauggaccca | agagaagaaa | aggaagaaag | aaagguuuuu | ugguuuugu | uuuguuugu | 1860 |
| uuuguuuuu | guuuuuuga | gauggagucu | cacucuuucg | cccaggcugg | agucagugg | 1920 |
| uaugaucuca | gcucacugca | agcuccaccu | cccgggguuca | cgccauucuc | cugccucagc | 1980 |
| cuccugagua | gcugggacua | caggcgcccg | ccaccacacc | cggcuaauuu | uuuguauuuu | 2040 |
| uuguagagac | gggguuucac | cauguuagcc | aagauggucu | cgaucccug | accucgugau | 2100 |

| | |
|---|---|
| ccaccugccu cggccucccca aagugcuggg auuacggug ugagccaccg ugcccagccu | 2160 |
| uuuuuuuuu aauagaaaaa auaauccgac ucccacuaca ucaagacuaa ucuuguuuug | 2220 |
| uguguuuuuc acauguauua uagaaugcuu ugcauggac uauccucuug uuuuuauuaa | 2280 |
| aaacaaauga uuuuuuuaaa agucacaaaa acaauucacu aaaaauaaau augucauugu | 2340 |
| gcuuuaaaaa aauaaccucu uguaguuaua aaauaaaacg uuugacuucu aaacucug | 2398 |

<210> SEQ ID NO 48
<211> LENGTH: 2469
<212> TYPE: RNA
<213> ORGANISM: Homo sapien

<400> SEQUENCE: 48

| | |
|---|---|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauucccuc agaggagaaa aucuguggcu ggggagauug | 180 |
| uucucauuac uggagcuggg cauggaauag gcaggcagac uacuuaugaa uuugcaaaac | 240 |
| gacagagcau auugguucug ugggauauua auagcgcgg uguggaggaa acugcagcug | 300 |
| agugccgaaa acuaggcguc acugcgcaug cguauguggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuggaaugg aaaggacauc agaaguaauu | 540 |
| acuuggaugu auauaggauc gaggacacuu uggacgaga cucugagauc acaaaagcac | 600 |
| uucuuccauc gaugauggag agaaaucaug gccacaucgu cacaguggcu ucaguugcg | 660 |
| gccacgaagg gauccuuac cucaucccau auuguuccag caaauuugcc gcuguuggcu | 720 |
| uucacagagg ucugacauca gaacuucagg ccuugggaaa aacugguauc aaaaccucau | 780 |
| gucucugccc aguuuuugug aauacugggu ucaccaaaaa uccaagcaca agauuauggc | 840 |
| cuguauugga gacagaugaa gucguaagaa gucugauaga uggaauacuu accaauaaga | 900 |
| aaaugauuuu uguccaucg uauaucaaua ucuuucugag acuacagaag uuucuuccug | 960 |
| aacgcgccuc agcgauuuua aaucguaugc agaauauuca auuugaagca guggugcc | 1020 |
| acaaaaucaa aaugaauga auaaauaagc uccagccaga gauguaugca ugauaaugau | 1080 |
| augaauaguu ucgaaucaau gcugcaaagc uuuauuucac auuuuucag uccgauaau | 1140 |
| auuaaaaaca uugguuuggc acuagcagca gucaaacgaa caagauuaau uaccugucuu | 1200 |
| ccuguuucuc aagaauauuu acguaguuuu ucauaggucu guuuuccuu ucaugccucu | 1260 |
| uaaaacuuc ugugcuuaca uaaacauacu uaaaagguuu ucuuuaagau auuuuauuuu | 1320 |
| uccauuuaaa gguggacaaa agcuaccucc cuaaaaguaa auacaaagag aacuuauuua | 1380 |
| cacagggaag guuuaagacu guucaaguag cauuccaauc uguagccaug ccacagaaua | 1440 |
| ucaacaagaa cacagaauga gugcacagcu aagagaucaa guucagcag gcagcuuuau | 1500 |
| cucaaccugg acauauuuua agauucagca uuugaaagau ucccuagcc ucuuccuuuu | 1560 |
| ucauuagccc aaaacggugc aacucuauuc uggacuuuau acuugauuc ugucuucugu | 1620 |
| auaacucuga aguccaccaa aaguggaccc ucuauauuuc cucccuuuuu auagcuuau | 1680 |
| aagauacauu augaaggug accgacucua uuuuaaaucu cagaauuuua aguucuagcc | 1740 |
| ccaugauaac cuuuuucuuu guaauuuaug cuuucauaua uccuugucc cagagauguu | 1800 |
| uagacaauuu uaggcucaaa aauuaaagcu aacacaggaa aaggaacugu acuggcuauu | 1860 |

-continued

| | |
|---|---|
| acauaagaaa caauggaccc aagagaagaa aaggaagaaa gaaagguuuu uugguuuuug | 1920 |
| uuuuguuuug uuuuguuuuu uguuuuuuug agauggaguc ucacucuuuc gcccaggcug | 1980 |
| gagugcagug guaugaucuc agcucacugc aagcuccacc ucccggguuc acgccauucu | 2040 |
| ccugccucag ccuccugagu agcugggacu acaggcgccc gccaccacac ccggcuaauu | 2100 |
| uuuuguauuu uuuguagaga cggggauuuca ccauguuagc caagauggu ucgaucccu | 2160 |
| gaccucguga uccaccugcc ucggccuccc aaagugcugg gauuacgggu gugagccacc | 2220 |
| gugcccagcc uuuuuuuuuu aauagaaaaa aauaauccga cucccacuac aucaagacua | 2280 |
| aucuuguuuu gugugquuuuu cacauguauu auagaaugcu uuugcaugga cuauccucuu | 2340 |
| guuuuauua aaacaaaug auuuuuuaa aagucacaaa aacaauucac uaaaaauaaa | 2400 |
| uaugucauug ugcuuuaaaa aaauaaccuc uuguaguuau aaaauaaaac guuugacuuc | 2460 |
| uaaacucug | 2469 |

<210> SEQ ID NO 49
<211> LENGTH: 1715
<212> TYPE: RNA
<213> ORGANISM: Homo sapien

<400> SEQUENCE: 49

| | |
|---|---|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucuguggcu ggggagauug | 180 |
| uucucauuac uggagcuggg cauggaauag gcaggcagac uacuuaugaa uuugcaaaac | 240 |
| gacagagcau auugguucug ugggauauua auaagcgcgg uguggaggaa acugcagcug | 300 |
| agugccgaaa acuaggcguc acugcgcaug cguauguggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuuggaucac aaaagcacuu cuuccaucga | 540 |
| ugauggagag aaaucauggc cacaucguca caguggcuuc agugugcggc cacgaaggga | 600 |
| uccuuaccu cauccauuau uguuccagca aauugccgc uguuggcuuu cacagagguc | 660 |
| ugacaucaga acuucaggcc uugggaaaaa cugguaucaa aaccucaugu cucugcccag | 720 |
| uuuuugugaa uacuggguuc accaaaaauc caagcacaag auuauggccu guauuggaga | 780 |
| cagaugaagu cguaagaagu cugauagaug gaauacuuac caauaagaaa augauuuugu | 840 |
| uuccaucgua uaucaauauc uuucugagac uacagaaguu aagucagca cagaacaccc | 900 |
| aaauacuaaa acaccaauag agcuuuuuuu uugcuuuuu uuuuuuuuag acagagucuc | 960 |
| acucugucac ccuggcugga uugcgguggu ugcaguggca ugaucuuggc ucacugcaac | 1020 |
| cuccgccucc ugqguucaag caauucucau gccucagacc cccaaguaac ugggauuaua | 1080 |
| ggugugugcu gccacacuac acccagcuaa uuuuuguauu uuugauaga cagguuuc | 1140 |
| cccauguugg ccaggcugga cucgaacucc ugaccucaag uuauccccu gucucggccu | 1200 |
| cccaaagugc ugggauuaca gucaugagcc accaugccug gccaauaga gcauuauua | 1260 |
| uggagcaucu uucaguugug aaaauuggca uggaaacucu ccaucccugg ggagaacagu | 1320 |
| uauuccucu guuauuuccc uaccagucu auaaaagag agugauucau uucucuaccc | 1380 |
| aaaucuacug ucucugccca aacuuugcug aagacuauuc uaacuaaagg aaacacaguu | 1440 |

| | |
|---|---|
| uaaaaagaau gcauauagu gaaguaguua auaauaaaga cuccauuuuu aaaagucugc | 1500 |
| uggaaguuug guugggauug cacugaaucu auagagcaau uggggaguau ugacauauca | 1560 |
| acaauauuga guuucuaau ccaagaacau aauaucuauu uuuaaaaucu ucuucaaaau | 1620 |
| cuuuaaaucu uuaaauugua uuuguagu uuuggguguuu aagucuugca cauauuuugu | 1680 |
| cagauuuauu ccaaaguauu ucacggguuc uuuuu | 1715 |

```
<210> SEQ ID NO 50
<211> LENGTH: 2290
<212> TYPE: RNA
<213> ORGANISM: Homo sapien

<400> SEQUENCE: 50
```

| | |
|---|---|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucuguggcu ggggagauug | 180 |
| uucucauuac uggagcuggg cauggaauag gcaggcagac uacuuaugaa uuugcaaaac | 240 |
| gacagagcau auugguucug uggauauua auaaggugaa gaaagaagug ggugauguaa | 300 |
| caaucguggu gaauaaugcu gggacaguau accagccga ucuucucagc accaaggaug | 360 |
| aagagauuac caagacauuu gaggucaaca uccuaggaca uuuuuggauc acaaaagcac | 420 |
| uucuuccauc gaugauggag agaaaucaug gccacaucgu cacaguggcu ucagugugcg | 480 |
| gccacgaagg gauccuuac cucaucccau auuguuccag caaauuugcc gcuguuggcu | 540 |
| uucacagagg cucgacauca gaacuucagg ccuuggaaaa acugguauc aaaaccucau | 600 |
| gucucugccc aguuuuugug aauacggggu ucaccaaaaa uccaagcaca agauuauggc | 660 |
| cuguauugga gacagaugaa gucguaagaa gucugauaga uggaauacuu accaauaaga | 720 |
| aaaugauuuu uguuccaucg uauaucaaua ucuuucugag acuacagaag guuucuuccu | 780 |
| gaacgcgccu cagcgauuuu aaaucguaug cagaauauuc aauuugaagc aguggguugc | 840 |
| cacaaaauca aaaugaaaug aauaaauaag cuccagccag agaugauaugc augauaauga | 900 |
| uaugaauagu uucgaaucaa ugcugcaaag cuuuauuuca cauuuuuuca guccugauaa | 960 |
| uauuaaaac auugguuugg cacuagcagc agucaaacga acaagauuaa uuaccugucu | 1020 |
| uccuguuuucu caagaauauu uacguaguuu ucauaggguc uguuuuccu ucaugccuc | 1080 |
| uuaaaaacuu cugugcuuac auaaacauac uuaaaaggu ucuuaaga uauuuauuu | 1140 |
| uuccauuuaa aggugacaa aagcuacccc ccuaaagua aauacaaaga gaacuuauu | 1200 |
| acacagggaa gguuuaagac uguucaagua gcauccaau cuguagccau gccacagaau | 1260 |
| aucaacaaga acacagaaug agugcacagc uaagagauca aguucagca ggcagcuuua | 1320 |
| ucucaaccug gacauauuu aagauucagc auuugaaaga uuucccuagc cucuuccuuu | 1380 |
| uucauuagcc caaaacgguggc aacucuauu cuggacuuua uuacuugauu cugucuucg | 1440 |
| uauaacucug aaguccacca aaaguggacc cucuauauuu ccucccuuuu uauagucuua | 1500 |
| uaagauacau uaugaaaggu gaccgacucu auuuaaauc ucagaauuuu aaguucuagc | 1560 |
| cccaugauaa ccuuuuucuu uguaauuuau gcuuucauau auccuugguc ccagagaugu | 1620 |
| uuagacaauu uuaggcucaa aaauuaaagc uaacacagga aaaggaacug uacuggcuau | 1680 |
| uacauaagaa acaauggacc caagagaaga aaaggaagaa agaaagguuu uugguuuuu | 1740 |
| guuuguuuuu guuuuguuuu uuguuuuuuu gagauggagu cucacucuuu cgcccaggcu | 1800 |
| ggagugcagu gguaugaucu cagcucacug caagcuccac cucccggguu cacgccauuc | 1860 |

```
uccugccuca gccuccugag uagcugggac uacaggcgcc cgccaccaca cccggcuaau   1920
uuuuuguauu uuuuguagag acggggutuuc accauguuag ccaagauggu ucgaucucc    1980 ugaccucgug auccaccugc cucggccucc caaagugcug ggauuacggg ugugagccac   2040
cgugcccagc cuuuuuuuu uuaauagaaa aauaauccg acucccacua caucaagacu    2100
aaucuuguuu ugugguuuu ucacauguau uauagaaugc uuuugcaugg acuauccucu   2160
uguuuuuauu aaaacaaau gauuuuuuua aagucacaa aaacaauuca cuaaaaauaa    2220
auaugucauu gugcuuuaaa aaaauaaccu cuuguaguua uaaaauaaaa cguuugacuu   2280
cuaaacucug                                                          2290

<210> SEQ ID NO 51
<211> LENGTH: 2470
<212> TYPE: RNA
<213> ORGANISM: Homo sapien

<400> SEQUENCE: 51
agacaguacc uccucccuag gacuacacaa ggacugaacc agaaggaaga ggacagagca    60
aagccaugaa caucauccua gaaauccuuc ugcuucugau caccaucauc uacuccuacu   120
uggagucguu ggugaaguuu ucauuccuc agaggagaaa aucugugggcu ggggagauug   180 uucucauuac uggagcuggg cauggaauag gcaggcagac uacuuaugaa uuugcaaaac   240
gacagagcau auugguucug uggauauua auaagcgcgg uguggaggaa acugcagcug   300
agugccgaaa acuaggcguc acugcgcaug cguaugugu agacgcagc aacagagaag    360 agaucuaucg cucucuaaau caggugaaga agaaguggg ugauguaaca aucgugguga   420
auaaugcugg gacaguauau ccagccgauc uucucagcac caaggaugaa gagauuacca   480
agacauuuga ggucaacauc cuaggacauu uuggaaugg aaaggacauc agaaguaauu   540
acuuggaugu auauaggauc gaggacacuu uggacgaga cucugagauc acaaaagcac   600
uucuuccauc gaugauggag agaaaucaug gccacaucgu cacaguggcu ucagugugcg   660
gccacgaagg gauuccuuac cucaucccau auuguuccag caaauuugcc gcuguuggcu   720
uucacagagg ucugacauca gaacuucagg ccuuggaaa aacugguauc aaaaccucau   780
gucucugccc aguuuuugug aauacugggu ucaccaaaaa uccaagcaca agauuauggc   840
cuguauugga gacagaugaa gucguaagaa gucugauaga uggaauacuu accaauaaga   900
aaaugauuuu uguuccaucg uauaucaaua ucuuucugag acuacagaag guuucuuccu   960
gaacgcgccu cagcgauuuu aaaucguaug cagaauauuc aauuugaagc aguggguggc  1020
cacaaaauca aaaugaaaug aauaaauaag cuccagccag agauguaugc augauaauga  1080
uaugaauagu uucgaaucaa ugcugcaaag cuuuauuuca cauuuuuuca guccugauaa  1140
uauuaaaaac auugguuugg cacuagcagc agucaaacga caagauuaa uuaccugucu  1200 uccuguuucu caagaauauu acguaguuu ucauaggguc uguuuuuccu uucaugccuc   1260
uuaaaaacuu cugugcuuac auaaacauac uuaaaaggu ucuuuaaga uauuuauuu    1320 uuccauuuaa aggugggacaa agcuaccuc ccuaaaagua aauacaaaga gaacuuauuu   1380
acacagggaa gguuuaagac uguucaagua gcauuccaau cuguagccau gccacagaau   1440
aucaacaaga acacagaaug agugcacagc uaagagauca aguucagca ggcagcuuua    1500 ucucaaccug gacauauuuu aagauucagc auuugaaaga uucccuagc cucuuccuuu   1560 uucauuagcc caaacggug caacucuauu cuggacuuua uuacuugauu cugucuucug   1620
```

```
uauaacucug aaguccacca aaaguggacc cucuauauuu ccucccuuuu uauagucuua    1680
uaagauacau uaugaaaggu gaccgacucu auuuuaaauc ucagaauuuu aaguucuagc    1740
cccaugauaa ccuuuuucuu uguaauuuau gcuucauau auccuugguc ccagagaugu     1800
uuagacaauu uuaggcucaa aaauuaaagc uaacacagga aaaggaacug uacuggcuau    1860
uacauaagaa acaauggacc caagagaaga aaaggaagaa agaaagguuu uugguuuuu     1920
guuuuguuuu guuuuguuuu uuguuuuuuu gagauggagu cucacucuuu cgcccaggcu    1980
ggagugcagu gguaugaucu cagcucacug caagcuccac cucccggguu cacgccauuc    2040
uccugccuca gccuccugag uagcgggac uacaggcgcc cgccaccaca cccggcuaau     2100
uuuuguauu uuuguagag acggguuuc accauguuag ccaagauggu cucgaucucc       2160
ugaccucgug auccaccgc cucggccucc caaagugcug gguuacggg ugugagccac      2220
cgugcccagc cuuuuuuuu uuaauagaaa aaauaauccg acucccacua caucaagacu     2280
aaucuuguuu ugugguuuu ucacauguau uauagaaugc uuuugcaugg acuauccucu     2340
uguuuuuauu aaaacaaau gauuuuuua aagucacaa aaacaauuca cuaaaaauaa       2400
auaugucauu gugcuuuaaa aaauaaaccu cuuguaguua uaaaauaaaa cguuugacuu    2460
cuaaacucug                                                           2470

<210> SEQ ID NO 52
<211> LENGTH: 1714
<212> TYPE: RNA
<213> ORGANISM: Homo sapien

<400> SEQUENCE: 52
agacaguacc uccucccuag gacuacacaa ggacugaacc agaaggaaga ggacagagca      60
aagccaugaa caucauccua gaauccuuc ugcuucugau caccaucauc uacuccuacu     120
uggagucguu ggugaaguuu uucauuccuc agaggagaaa aucuguggcu ggggagauug    180
uucucauuac uggagcuggg cauggaauag gcaggcagca uacuuaugaa uuugcaaaac    240
gacagagcau auugguucug ugggauauua auaagcgcgg uggaggaa cugcagcug       300
agugccgaaa acuaggcguc acugcgcaug cguaugggu agacgcagc aacagagaag      360
agaucuaucg cucucuaaau caggugaaga agaagugggg ugauguaaca aucgugguga    420
auaaugcugg gacaguauau ccagccgauc uucuccagcac caaggaugaa gagauuacca   480
agacauuuga ggucaacauc cuaggacauu uuggaucac aaaagcacuu cuuccaucga    540
ugauggagag aaaucauggc cacaucguca cagugguuc agugugcggc cacgaaggga   600
uccuuaccu caucccauau uguuccagca aauuugccgc uguggcuuu cacagagguc    660
ugacaucaga acuucaggcc uugggaaaaa cugguaucaa aaccucaugu cucugcccag   720
uuuuugugaa uacgggguuc accaaaaauc caagcacaag auuauggccu guauggaga    780
cagaugaagu cguaagaagu cugauagaug gaauacuuac caauaagaaa augauuuuug   840
uuccaucgua uaucaauauc uuucugagac uacagaagua aguacagcac agaacacca    900
aauacuaaaa caccaauaga gcuuuuuuu uugcuuuuuu uuuuuuaga cagagucuca     960
cucugucacc cuggcuggau gcgguggu cagugcau gaucuggcu cacugcaacc        1020
uccgccuccu ggguucaagc aauucucaug ccucagaccc caaguaacu gggauuauag    1080
gugugugcug ccacacuaca cccagcuaau uuuuguauuu uuugauagag acagguuucc   1140
ccaugugugg caggcuggac ucgaacuccu gaccucaagu uauccucug ucucggccuc    1200
ccaaagugcu ggguuacag ucaugagcca ccaugccugg cccaauagag cuauuauuau    1260
```

```
ggagcaucuuu ucaguuguga aaauuggcau ggaaacucuc caucccuggg gagaacaguu    1320
auuuccucug uuauuuuccu acccagucua uaaaaagaga gugauucauu uucucuacca    1380
aaucuacugu cucugcccaa acuuugcuga agacuauucu aacuaaagga aacacaguuu    1440
aaaaagaaug caauauagug aaguaguuaa uaauaaagac uccauuuuua aaagucugcu    1500
ggaaguuugg uugggauugc acugaaucua uagagcaauu ggggaguauu gacauaucaa    1560
caauauugag uuuucuaauc caagaacaua auaucuauuu uuaaaaucuu cuucaaaauc    1620
uuuaaaucuu uaaauuguau uuuguaguuu uuggguguuua aagucuugcac auauuuuguc    1680 agauuuauuc caaaguauuu cacggguucu uuuu    1714

<210> SEQ ID NO 53
<211> LENGTH: 2397
<212> TYPE: DNA
<213> ORGANISM: Homo sapien

<400> SEQUENCE: 53
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt tcattcctc agaggagaaa atctgtggct ggggagattg      180
ttctcattac tggagctggg catggaatag caggcagac tacttatgaa tttgcaaaac      240
gacagagcat attggttctg tgggatatta ataagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtgggg tgatgtaaca atcgtggtga     420
ataatgctgg gacagtatat ccagccgatc ttctcagcac caaggatgaa gagattacca     480
agacatttga ggtcaacatc ctaggacatt tttggatcac aaaagcactt cttccatcga     540
tgatggagag aaatcatggc cacatcgtca cagtggcttc agtgtgcggc cacgaaggga     600
ttccttacct catcccatat tgttccagca aatttgccgc tgttggcttt cacagaggtc     660
tgacatcaga acttcaggcc ttgggaaaaa ctggtatcaa acctcatgt ctctgcccag      720 tttttgtgaa tactgggttc accaaaaatc caagcacaag attatggcct gtattggaga     780
cagatgaagt cgtaagaagt ctgatagatg gaatacttac caataagaaa atgattttg      840 ttccatcgta tatcaatatc tttctgagac tacagaagtt tcttcctgaa cgcgcctcag     900
cgattttaaa tcgtatgcag aatattcaat ttgaagcagt ggttggccac aaaatcaaaa     960
tgaaatgaat aaataagctc cagccagaga tgtatgcatg ataatgatat gaatagtttc    1020
gaatcaatgc tgcaaagctt tatttcacat tttttcagtc ctgataatat taaaaacatt    1080
ggtttggcac tagcagcagt caaacgaaca agattaatta cctgtcttcc tgtttctcaa    1140
gaatatttac gtagtttttc ataggtctgt ttttcctttc atgcctctta aaaacttctg    1200
tgcttacata aacatactta aaaggttttc tttaagatat tttatttttc catttaaagg    1260
tggacaaaag ctacctccct aaaagtaaat acaaagagaa cttatttaca cagggaaggt    1320
ttaagactgt tcaagtagca ttccaatctg tagccatgcc acagaatatc aacaagaaca    1380
cagaatgagt gcacagctaa gagatcaagt ttcagcagga agctttatct caacctggac    1440
atattttaag attcagcatt tgaaagattt ccctagcctc ttccttttc attagcccaa     1500 aacggtgcaa ctctattctg gacttttatta cttgattctg tcttctgtat aactctgaag    1560
tccaccaaaa gtggaccctc tatatttcct cccttttat agtcttataa gatacattat    1620
```

```
gaaaggtgac cgactctatt ttaaatctca gaattttaag ttctagcccc atgataacct    1680
ttttctttgt aatttatgct ttcatatatc cttggtccca gagatgttta gacaatttta    1740
ggctcaaaaa ttaaagctaa cacaggaaaa ggaactgtac tggctattac ataagaaaca    1800
atggacccaa gagaagaaaa ggaagaaaga aaggtttttt ggttttgtt ttgttttgtt     1860 ttgttttttg ttttttgag atggagtctc actctttcgc ccaggctgga gtgcagtggt     1920
atgatctcag ctcactgcaa gctccacctc ccgggttcac gccattctcc tgcctcagcc    1980
tcctgagtag ctgggactac aggcgcccgc caccacaccc ggctaatttt tgtattttt     2040 tgtagagacg gggtttcacc atgttagcca agatggtctc gatctcctga cctcgtgatc    2100
cacctgcctc ggcctcccaa agtgctggga ttacgggtgt gagccaccgt gcccagcctt    2160 tttttttta atagaaaaaa taatccgact cccactacat caagactaat cttgttttgt     2220 gtgttttca catgtattat agaatgcttt tgcatggact atcctcttgt ttttattaaa     2280
aacaaatgat ttttttaaaa gtcacaaaaa caattcacta aaaataaata tgtcattgtg    2340
ctttaaaaaa ataacctctt gtagttataa aataaaacgt ttgacttcta aactctg       2397
```

<210> SEQ ID NO 54
<211> LENGTH: 2289
<212> TYPE: DNA
<213> ORGANISM: Homo sapien
<400> SEQUENCE: 54

```
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt tcattcctc agaggagaaa atctgtggct ggggagattg    180
ttctcattac tggagctggg catggaatag gcaggcagac tacttatgaa tttgcaaaac    240
gacagagcat attggttctg tgggatatta ataaggtgaa gaagaagtg ggtgatgtaa     300 caatcgtggt gaataatgct gggacagtat atccagccga tcttctcagc accaaggatg    360
aagagattac caagacattt gaggtcaaca tcctaggaca ttttggatc acaaaagcac    420 ttcttccatc gatgatggag agaaatcatg gccacatcgt cacagtggct tcagtgtgcg    480
gccacgaagg gattccttac ctcatcccat attgttccag caaatttgcc gctgttggct    540
ttcacagagg tctgacatca gaacttcagg ccttgggaaa aactggtatc aaaacctcat    600
gtctctgccc agttttgtg aatactgggt tcaccaaaaa tccaagcaca agattatggc    660
ctgtattgga gacagatgaa gtcgtaagaa gtctgataga tggaatactt accaataaga    720
aaatgatttt tgttccatcg tatatcaata tctttctgag actacagaag tttcttcctg    780
aacgcgcctc agcgatttta aatcgtatgc agaatattca atttgaagca gtggttggcc    840
acaaaatcaa aatgaaatga ataaataagc tccagccaga gatgtatgca tgataatgat    900
atgaatagtt tcgaatcaat gctgcaaagc tttatttcac atttttcag tcctgataat     960 attaaaaaca ttggtttggc actagcagca gtcaaacgaa caagattaat tacctgtctt    1020
cctgtttctc aagaatattt acgtagtttt tcataggtct gtttttcctt tcatgcctct    1080
taaaaacttc tgtgcttaca taaacatact taaaaggttt tctttaagat attttatttt    1140
tccatttaaa ggtggacaaa agctacctcc ctaaaagtaa atacaaagag aacttattta    1200
cacagggaag gtttaagact gttcaagtag cattccaatc tgtagccatg ccacagaata    1260
tcaacaagaa cacagaatga gtgcacagct aagagatcaa gtttcagcag gcagctttat    1320
ctcaacctgg acatatttta agattcagca tttgaaagat ttccctagcc tcttcctttt    1380
```

```
tcattagccc aaaacggtgc aactctattc tggactttat tacttgattc tgtcttctgt    1440
ataactctga agtccaccaa aagtggaccc tctatatttc ctccctttt atagtcttat     1500 aagatacatt atgaaaggtg accgactcta ttttaaatct cagaattta agttctagcc    1560 ccatgataac ctttttcttt gtaatttatg ctttcatata tccttggtcc cagagatgtt   1620
tagacaattt taggctcaaa aattaaagct aacacaggaa aaggaactgt actggctatt   1680
acataagaaa caatggaccc aagagaagaa aaggaagaaa gaaaggtttt ttggtttttg   1740
ttttgttttg ttttgttttt tgtttttttg agatggagtc tcactctttc gcccaggctg   1800
gagtgcagtg gtatgatctc agctcactgc aagctccacc tcccgggttc acgccattct   1860
cctgcctcag cctcctgagt agctgggact acaggcgccc gccaccacac ccggctaatt   1920
ttttgtattt tttgtagaga cggggtttca ccatgttagc caagatggtc tcgatctcct   1980
gacctcgtga tccacctgcc tcggcctccc aaagtgctgg gattacgggt gtgagccacc   2040
gtgcccagcc ttttttttt taatagaaaa aataatccga ctcccactac atcaagacta    2100
atcttgtttt gtgtgttttt cacatgtatt atagaatgct tttgcatgga ctatcctctt   2160
gtttttatta aaacaaatg attttttaa aagtcacaaa aacaattcac taaaaataaa    2220
tatgtcattg tgctttaaaa aaataacctc ttgtagttat aaaataaaac gtttgacttc   2280
taaactctg                                                           2289

<210> SEQ ID NO 55
<211> LENGTH: 2280
<212> TYPE: DNA
<213> ORGANISM: Homo sapien

<400> SEQUENCE: 55
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catgaatag gcaggcagac tacttatgaa tttgcaaaac      240
gacagagcat attggttctg tgggatatta ataagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtgggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaagcactt cttccatcga   540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag gtttcttcct gaacgcgcct    780
cagcgatttt aaatcgtatg cagaatattc aatttgaagc agtggttggc cacaaaatca    840
aaatgaaatg aataaataag ctccagccag agatgtatgc atgataatga tatgaatagt    900
ttcgaatcaa tgctgcaaag cttttatttca cattttttca gtcctgataa tattaaaaac   960
attggtttgg cactagcagc agtcaaacga acaagattaa ttacctgtct tcctgtttct    1020
caagaatatt tacgtagttt ttcataggtc tgttttccct ttcatgcctc ttaaaaactt    1080
ctgtgcttac ataaacatac ttaaaaggtt ttctttaaga tatttatttt ttccatttaa    1140
```

```
aggtggacaa aagctaccto cctaaaagta aatacaaaga gaacttattt acacagggaa    1200
ggtttaagac tgttcaagta gcattccaat ctgtagccat gccacagaat atcaacaaga    1260
acacagaatg agtgcacagc taagagatca agtttcagca ggcagcttta tctcaacctg    1320
gacatatttt aagattcagc atttgaaaga tttccctagc ctcttccttt ttcattagcc    1380
caaaacggtg caactctatt ctggacttta ttacttgatt ctgtcttctg tataactctg    1440
aagtccacca aaagtggacc ctctatattt cctcccttttt tatagtctta taagatacat    1500
tatgaaaggt gaccgactct attttaaatc tcagaatttt aagttctagc cccatgataa    1560 ccttttttctt tgtaatttat gctttcatat atccttggtc ccagagatgt ttagacaatt    1620
ttaggctcaa aaattaaagc taacacagga aaggaactg tactggctat tacataagaa     1680
acaatggacc caagagaaga aaaggaagaa agaaaggttt tttggttttt gttttgtttt    1740
gttttgtttt ttgtttttttt gagatggagt ctcactcttt cgcccaggct ggagtgcagt    1800
ggtatgatct cagctcactg caagctccac ctcccgggtt cacgccattc tcctgcctca    1860
gcctcctgag tagctgggac tacaggcgcc cgccaccaca cccggctaat ttttttgtatt    1920 ttttgtagag acggggtttc accatgttag ccaagatggt ctcgatctcc tgacctcgtg    1980
atccacctgc ctcggcctcc caagtgctg ggattacggg tgtgagccac cgtgcccagc     2040
cttttttttt taatagaaa aataatccg actcccacta catcaagact aatcttgttt       2100
tgtgtgtttt tcacatgtat tatagaatgc ttttgcatgg actatcctct tgttttatt     2160 aaaaacaaat gatttttta aaagtcacaa aacaattca ctaaaaataa atatgtcatt       2220 gtgcttttaaa aaaataaccct cttgtagtta taaaataaaa cgtttgactt ctaaactctg    2280

<210> SEQ ID NO 56
<211> LENGTH: 2398
<212> TYPE: DNA
<213> ORGANISM: Homo sapien

<400> SEQUENCE: 56
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt tcattcctc agaggagaaa atctgtggct ggggagattg     180
ttctcattac tggagctggg catggaatag gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga agaagtgggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa acctcatgt ctctgcccag      720 tttttgtgaa tactgggttc accaaaaatc caagcacaag attatggcct gtattggaga    780
cagatgaagt cgtaagaagt ctgatagatg gaatacttac caataagaaa atgatttttg    840
ttccatcgta tatcaatatc tttctgagac tacagaaggt ttcttcctga acgcgcctca    900
gcgattttaa atcgtatgca gaatattcaa tttgaagcag tggttggcca caaatcaaa     960 atgaaatgaa taaataagct ccagccagag atgtatgcat gataatgata tgaatagttt    1020
```

```
cgaatcaatg ctgcaaagct ttatttcaca ttttttcagt cctgataata ttaaaaacat   1080
tggtttggca ctagcagcag tcaaacgaac aagattaatt acctgtcttc ctgtttctca   1140
agaatattta cgtagttttt cataggtctg ttttccttt catgcctctt aaaaacttct   1200
gtgcttacat aaacatactt aaaaggtttt ctttaagata ttttatttt ccatttaaag   1260 gtggacaaaa gctacctccc taaaagtaaa tacaaagaga acttatttac acagggaagg   1320
tttaagactg ttcaagtagc attccaatct gtagccatgc cacagaatat caacaagaac   1380
acagaatgag tgcacagcta agagatcaag tttcagcagg cagctttatc tcaacctgga   1440 catatttaa gattcagcat ttgaaagatt tccctagcct cttccttttt cattagccca   1500
aaacggtgca actctattct ggactttatt acttgattct gtcttctgta taactctgaa   1560
gtccaccaaa agtggaccct ctatatttcc tccttttta tagtcttata agatacatta   1620
tgaaaggtga ccgactctat tttaaatctc agaattttaa gttctagccc catgataacc   1680 ttttctttg taatttatgc tttcatatat ccttggtccc agagatgttt agacaatttt   1740
aggctcaaaa attaaagcta acacaggaaa aggaactgta ctggctatta cataagaaac   1800
aatggaccca agagaagaaa aggaagaaag aaaggtttt tggttttgt tttgttttgt   1860 tttgttttt gttttttga gatggagtct cactctttcg cccaggctgg agtgcagtgg   1920
tatgatctca gctcactgca agctccacct cccgggttca cgccattctc ctgcctcagc   1980
ctcctgagta gctgggacta caggcgcccg ccaccacacc cggctaattt tttgtatttt   2040
ttgtagagac ggggtttcac catgttagcc aagatggtct cgatctcctg acctcgtgat   2100
ccacctgcct cggcctccca agtgctggg attacgggtg tgagccaccg tgcccagcct   2160 tttttttt aatagaaaaa ataatccgac tcccactaca tcaagactaa tcttgttttg   2220 tgtgttttc acatgtatta tagaatgctt ttgcatggac tatcctcttg tttttattaa   2280
aaacaaatga ttttttaaa agtcacaaaa acaattcact aaaaataaat atgtcattgt   2340
gctttaaaaa aataacctct tgtagttata aaataaaacg tttgacttct aaactctg    2398
```

<210> SEQ ID NO 57
<211> LENGTH: 2469
<212> TYPE: DNA
<213> ORGANISM: Homo sapien

<400> SEQUENCE: 57

```
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt tcattcctc agaggagaaa atctgtggct ggggagattg    180
ttctcattac tggagctggg catggaatag gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga agaagtgggg tgatgtaaca atcgtggtga    420
ataatgctgg gacagtatat ccagccgatc ttctcagcac caaggatgaa gagattacca    480
agacatttga ggtcaacatc ctaggacatt tttggaatgg aaaggacatc agaagtaatt    540
acttggatgt atataggatc gaggacactt ttggacgaga ctctgagatc acaaaagcac    600
ttcttccatc gatgatggag agaaatcatg gccacatcgt cacagtggct tcagtgtgcg    660
gccacgaagg gattccttac ctcatcccat attgttccag caaatttgcc gctgttggct    720
```

```
ttcacagagg tctgacatca gaacttcagg ccttgggaaa aactggtatc aaaacctcat      780
gtctctgccc agttttttgtg aatactgggt tcaccaaaaa tccaagcaca agattatggc      840
ctgtattgga gacagatgaa gtcgtaagaa gtctgataga tggaatactt accaataaga      900
aaatgatttt tgttccatcg tatatcaata tctttctgag actacagaag tttcttcctg      960
aacgcgcctc agcgatttta aatcgtatgc agaatattca atttgaagca gtggttggcc     1020
acaaaatcaa aatgaaatga ataaataagc tccagccaga gatgtatgca tgataatgat     1080
atgaatagtt tcgaatcaat gctgcaaagc tttatttcac attttttcag tcctgataat     1140
attaaaaaca ttggtttggc actagcagca gtcaaacgaa caagattaat tacctgtctt     1200
cctgtttctc aagaatattt acgtagtttt tcataggtct gttttttcctt tcatgcctct     1260
taaaaacttc tgtgcttaca taaacatact taaaaggttt tctttaagat atttttatttt     1320
tccatttaaa ggtggacaaa agctacctcc ctaaaagtaa atacaaagag aacttattta     1380
cacagggaag gtttaagact gttcaagtag cattccaatc tgtagccatg ccacagaata     1440
tcaacaagaa cacagaatga gtgcacagct aagagatcaa gtttcagcag gcagctttat     1500
ctcaacctgg acatattttta agattcagca tttgaaagat ttccctagcc tcttccttttt     1560
tcattagccc aaaacggtgc aactctattc tggactttat tacttgattc tgtcttctgt     1620
ataactctga gtccaccaa aagtggaccc tctatatttc ctccctttttt atagtcttat     1680
aagatacatt atgaaaggtg accgactcta ttttaaatct cagaatttta agttctagcc     1740
ccatgataac cttttttcttt gtaatttatg ctttcatata tccttggtcc cagagatgtt     1800
tagacaattt taggctcaaa aattaaagct aacacaggaa aaggaactgt actggctatt     1860
acataagaaa caatggaccc aagagaagaa aaggaagaaa gaaaggtttt ttggtttttg     1920
ttttgttttg ttttgttttt tgttttttttg agatggagtc tcactctttc gcccaggctg     1980
gagtgcagtg gtatgatctc agctcactgc aagctccacc tcccgggttc acgccattct     2040
cctgcctcag cctcctgagt agctgggact acaggcgccc gccaccacac ccggctaatt     2100
ttttgtatttt tttgtagaga cggggtttca ccatgttagc caagatggtc tcgatctcct     2160
gacctcgtga tccacctgcc tcggcctccc aaagtgctgg gattacgggt gtgagccacc     2220
gtgcccagcc ttttttttttt taatagaaaa aataatccga ctcccactac atcaagacta     2280
atcttgtttt gtgtgttttt cacatgtatt atagaatgct tttgcatgga ctatcctctt     2340
gttttttatta aaaacaaatg atttttttaa aagtcacaaa aacaattcac taaaaataaa     2400
tatgtcattg tgctttaaaa aaataaccctc ttgtagttat aaaataaaac gtttgacttc     2460
taaactctg                                                              2469

<210> SEQ ID NO 58
<211> LENGTH: 1715
<212> TYPE: DNA
<213> ORGANISM: Homo sapien

<400> SEQUENCE: 58
agacagtacc tcctccctag gactacacaa ggactgaacc agaaggaaga ggacagagca       60
aagccatgaa catcatccta gaaatccttc tgcttctgat caccatcatc tactcctact      120
tggagtcgtt ggtgaagttt ttcattcctc agaggagaaa atctgtggct ggggagattg      180
ttctcattac tggagctggg catggaatag gcaggcagac tacttatgaa tttgcaaaac      240
gacagagcat attggttctg tgggatatta ataagcgcgg tgtggaggaa actgcagctg      300
agtgccgaaa actaggcgtc actgcgcatg cgtatgtggt agactgcagc aacagagaag      360
```

| | |
|---|---|
| agatctatcg ctctctaaat caggtgaaga aagaagtggg tgatgtaaca atcgtggtga | 420 |
| ataatgctgg gacagtatat ccagccgatc ttctcagcac caaggatgaa gagattacca | 480 |
| agacatttga ggtcaacatc ctaggacatt tttggatcac aaaagcactt cttccatcga | 540 |
| tgatggagag aaatcatggc cacatcgtca cagtggcttc agtgtgcggc cacgaaggga | 600 |
| ttccttacct catcccatat tgttccagca aatttgccgc tgttggcttt cacagaggtc | 660 |
| tgacatcaga acttcaggcc ttgggaaaaa ctggtatcaa acctcatgt ctctgcccag | 720 |
| ttttgtgaa tactgggttc accaaaaatc caagcacaag attatggcct gtattggaga | 780 |
| cagatgaagt cgtaagaagt ctgatagatg gaatacttac caataagaaa atgattttg | 840 |
| ttccatcgta tatcaatatc tttctgagac tacagaagtt aagtacagca cagaacaccc | 900 |
| aaatactaaa acaccaatag agcttttttt tttgcttttt tttttttag acagagtctc | 960 |
| actctgtcac cctggctgga ttgcggtggt tgcagtggca tgatcttggc tcactgcaac | 1020 |
| ctccgcctcc tgggttcaag caattctcat gcctcagacc cccaagtaac tgggattata | 1080 |
| ggtgtgtgct gccacactac acccagctaa ttttgtatt ttgataga gacaggtttc | 1140 |
| cccatgttgg ccaggctgga ctcgaactcc tgacctcaag ttatcctcct gtctcggcct | 1200 |
| cccaaagtgc tgggattaca gtcatgagcc accatgcctg gcccaataga gctattatta | 1260 |
| tggagcatct ttcagttgtg aaaattggca tggaaactct ccatccctgg ggagaacagt | 1320 |
| tatttcctct gttatttcc tacccagtct ataaaaagag agtgattcat tttctctacc | 1380 |
| aaatctactg tctctgccca aactttgctg aagactattc taactaaagg aaacacagtt | 1440 |
| taaaagaat gcaatatagt gaagtagtta ataataaga ctccattttt aaaagtctgc | 1500 |
| tggaagtttg gttgggattg cactgaatct atagagcaat ggggagtat tgacatatca | 1560 |
| acaatattga gttttctaat ccaagaacat aatatctatt tttaaaatct tcttcaaaat | 1620 |
| ctttaaatct ttaaattgta ttttgtagtt tttggtgttt aagtcttgca catattttgt | 1680 |
| cagatttatt ccaaagtatt tcacgggttc ttttt | 1715 |

<210> SEQ ID NO 59
<211> LENGTH: 2290
<212> TYPE: DNA
<213> ORGANISM: Homo sapien

<400> SEQUENCE: 59

| | |
|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta ataaggtgaa gaagaagtg ggtgatgtaa | 300 |
| caatcgtggt gaataatgct gggacagtat atccagccga tcttctcagc accaaggatg | 360 |
| aagagattac caagacattt gaggtcaaca tcctaggaca ttttggatc acaaaagcac | 420 |
| ttcttccatc gatgatggag agaaatcatg ccacatcgt cacagtggct tcagtgtgcg | 480 |
| gccacgaagg gattccttac ctcatcccat attgttccag caatttgcc gctgttggct | 540 |
| ttcacagagg tctgacatca gaacttcagg ccttgggaaa aactggtatc aaacctcat | 600 |
| gtctctgccc agttttgtg aatactgggt tcaccaaaaa tccaagcaca agattatggc | 660 |
| ctgtattgga gacagatgaa gtcgtaagaa gtctgataga tggaatactt accaataaga | 720 |

| | |
|---|---|
| aaatgattttt tgttccatcg tatatcaata tctttctgag actacagaag gtttcttcct | 780 |
| gaacgcgcct cagcgatttt aaatcgtatg cagaatattc aatttgaagc agtggttggc | 840 |
| cacaaaatca aaatgaaatg aataaataag ctccagccag agatgtatgc atgataatga | 900 |
| tatgaatagt ttcgaatcaa tgctgcaaag ctttatttca cattttttca gtcctgataa | 960 |
| tattaaaaac attggtttgg cactagcagc agtcaaacga acaagattaa ttacctgtct | 1020 |
| tcctgtttct caagaatatt tacgtagttt tcataggtc tgttttcct ttcatgcctc | 1080 |
| ttaaaaactt ctgtgcttac ataaacatac ttaaaaggtt ttctttaaga tatttatt | 1140 |
| ttccatttaa aggtggacaa aagctacctc cctaaaagta aatacaaaga gaacttattt | 1200 |
| acacagggaa ggtttaagac tgttcaagta gcattccaat ctgtagccat gccacagaat | 1260 |
| atcaacaaga acacagaatg agtgcacagc taagagatca agtttcagca ggcagcttta | 1320 |
| tctcaacctg gacatatttt aagattcagc atttgaaaga tttccctagc ctcttccttt | 1380 |
| ttcattagcc caaaacggtg caactctatt ctggacttta ttacttgatt ctgtcttctg | 1440 |
| tataactctg aagtccacca aaagtggacc ctctatattt cctcccttt tatagtctta | 1500 |
| taagatacat tatgaaaggt gaccgactct attttaaatc tcagaatttt aagttctagc | 1560 |
| cccatgataa ccttttcctt tgtaatttat gctttcatat atccttggtc ccagagatgt | 1620 |
| ttagacaatt ttaggctcaa aaattaaagc taacacagga aaggaactg tactggctat | 1680 |
| tacataagaa acaatggacc caagagaaga aaaggaagaa agaaaggttt tttggttttt | 1740 |
| gttttgtttt gtttgtttt ttgttttttt gagatggagt ctcactcttt cgcccaggct | 1800 |
| ggagtgcagt ggtatgatct cagctcactg caagctccac ctcccgggtt cacgccattc | 1860 |
| tcctgcctca gcctcctgag tagctgggac tacaggcgcc cgccaccaca cccggctaat | 1920 |
| tttttgtatt ttttgtagag acggggtttc accatgttag ccaagatggt ctcgatctcc | 1980 |
| tgacctcgtg atccacctgc ctcggcctcc caaagtgctg ggattacggg tgtgagccac | 2040 |
| cgtgcccagc ctttttttt taatagaaa aaataatccg actcccacta catcaagact | 2100 |
| aatcttgttt tgtgtgtttt tcacatgtat tatagaatgc ttttgcatgg actatcctct | 2160 |
| tgttttatt aaaaacaaat gattttttta aaagtcacaa aaacaattca ctaaaaataa | 2220 |
| atatgtcatt gtgctttaaa aaaataacct cttgtagtta taaaataaaa cgtttgactt | 2280 |
| ctaaactctg | 2290 |

<210> SEQ ID NO 60
<211> LENGTH: 2470
<212> TYPE: DNA
<213> ORGANISM: Homo sapien

<400> SEQUENCE: 60

| | |
|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta ataagcgcgg tgtggaggaa actgcagctg | 300 |
| agtgccgaaa actaggcgtc actgcgcatg cgtatgtggt agactgcagc aacagagaag | 360 |
| agatctatcg ctctctaaat caggtgaaga agaagtggg tgatgtaaca atcgtggtga | 420 |
| ataatgctgg gacagtatat ccagccgatc ttctcagcac caaggatgaa gagattacca | 480 |
| agacatttga ggtcaacatc ctaggacatt tttggaatgg aaaggacatc agaagtaatt | 540 |

```
acttggatgt atataggatc gaggacactt ttggacgaga ctctgagatc acaaaagcac      600
ttcttccatc gatgatggag agaaatcatg gccacatcgt cacagtggct tcagtgtgcg      660
gccacgaagg gattccttac ctcatcccat attgttccag caaatttgcc gctgttggct      720
ttcacagagg tctgacatca gaacttcagg ccttgggaaa aactggtatc aaaacctcat      780
gtctctgccc agttttttgtg aatactgggt tcaccaaaaa tccaagcaca agattatggc      840
ctgtattgga gacagatgaa gtcgtaagaa gtctgataga tggaatactt accaataaga      900
aaatgatttt tgttccatcg tatatcaata tctttctgag actacagaag gtttcttcct      960
gaacgcgcct cagcgatttt aaatcgtatg cagaatattc aatttgaagc agtggttggc     1020
cacaaaatca aatgaaatg aataaataag ctccagccag agatgtatgc atgataatga      1080
tatgaatagt ttcgaatcaa tgctgcaaag ctttatttca catttttttca gtcctgataa      1140 tattaaaaac attggtttgg cactagcagc agtcaaacga acaagattaa ttacctgtct      1200
tcctgtttct caagaatatt tacgtagttt tcataggtc tgttttttcct ttcatgcctc       1260 ttaaaaactt ctgtgcttac ataaacatac ttaaaaggtt ttctttaaga tattttatt      1320 ttccattta aggtggacaa aagctacctc cctaaaagta aatacaaaga gaacttattt      1380
acacagggaa ggtttaagac tgttcaagta gcattccaat ctgtagccat gccacagaat      1440
atcaacaaga acacagaatg agtgcacagc taagagatca agtttcagca ggcagcttta      1500
tctcaacctg gacatatttt aagattcagc atttgaaaga tttccctagc ctcttccttt      1560
ttcattagcc caaaacggtg caactctatt ctggacttta ttacttgatt ctgtcttctg      1620
tataactctg aagtccacca aagtggacc ctctatattt cctccctttt tatagtctta      1680
taagatacat tatgaaaggt gaccgactct attttaaatc tcagaatttt aagttctagc      1740
cccatgataa ccttttttctt tgtaatttat gctttcatat atccttggtc ccagagatgt      1800
ttagacaatt ttaggctcaa aaattaaagc taacacagga aaaggaactg tactggctat      1860
tacataagaa acaatggacc caagagaaga aaaggaagaa agaaaggttt tttggtttt       1920 gttttgtttt gttttgtttt ttgttttttt gagatggagt ctcactcttt cgcccaggct      1980
ggagtgcagt ggtatgatct cagctcactg caagctccac ctcccgggtt cacgccattc      2040
tcctgcctca gcctcctgag tagctgggac tacaggcgcc cgccaccaca cccggctaat      2100
tttttgtatt ttttgtagag acggggtttc accatgttag ccaagatggt ctcgatctcc      2160
tgacctcgtg atccacctgc ctcggcctcc caaagtgctg ggattacggg tgtgagccac      2220
cgtgcccagc cttttttttt taatagaaa aaataatccg actcccacta catcaagact      2280
aatcttgttt tgtgtgtttt tcacatgtat tatagaatgc ttttgcatgg actatcctct      2340 tgttttatt aaaacaaat gattttttta aagtcacaa aaacaattca ctaaaaataa        2400
atatgtcatt gtgctttaaa aaataaccct cttgtagtta taaaataaaa cgtttgactt      2460
ctaaactctg                                                             2470
```

<210> SEQ ID NO 61
<211> LENGTH: 1714
<212> TYPE: DNA
<213> ORGANISM: Homo sapien

<400> SEQUENCE: 61

```
agacagtacc tcctccctag gactacacaa ggactgaacc agaaggaaga ggacagagca       60
aagccatgaa catcatccta gaaatccttc tgcttctgat caccatcatc tactcctact      120
```

```
tggagtcgtt ggtgaagttt ttcattcctc agaggagaaa atctgtggct ggggagattg      180
ttctcattac tggagctggg catggaatag gcaggcagac tacttatgaa tttgcaaaac      240
gacagagcat attggttctg tgggatatta ataagcgcgg tgtggaggaa actgcagctg      300
agtgccgaaa actaggcgtc actgcgcatg cgtatgtggt agactgcagc aacagagaag      360
agatctatcg ctctctaaat caggtgaaga agaagtgggg tgatgtaaca atcgtggtga      420
ataatgctgg gacagtatat ccagccgatc ttctcagcac caaggatgaa gagattacca      480
agacatttga ggtcaacatc ctaggacatt tttggatcac aaaagcactt cttccatcga      540
tgatggagag aaatcatggc cacatcgtca cagtggcttc agtgtgcggc cacgaaggga      600
ttccttacct catcccatat tgttccagca aatttgccgc tgttggcttt cacagaggtc      660
tgacatcaga acttcaggcc ttgggaaaaa ctggtatcaa aacctcatgt ctctgcccag      720
tttttgtgaa tactgggttc accaaaaatc caagcacaag attatggcct gtattggaga      780
cagatgaagt cgtaagaagt ctgatagatg gaatacttac caataagaaa atgattttg      840 ttccatcgta tatcaatatc tttctgagac tacagaagta agtacagcac agaacaccca      900
aatactaaaa caccaataga gcttttttt ttgctttttt tttttttaga cagagtctca      960
ctctgtcacc ctggctggat tgcggtggtt gcagtggcat gatcttggct cactgcaacc      1020
tccgcctcct gggttcaagc aattctcatg cctcagaccc ccaagtaact gggattatag      1080
gtgtgtgctg ccacactaca cccagctaat ttttgtattt tttgatagag acaggtttcc      1140
ccatgttggc caggctggac tcgaactcct gacctcaagt tatcctcctg tctcggcctc      1200
ccaaagtgct gggattacag tcatgagcca ccatgcctgg cccaatagag ctattattat      1260
ggagcatctt tcagttgtga aaattggcat ggaaactctc catccctggg gagaacagtt      1320
atttcctctg ttattttcct acccagtcta taaaaagaga gtgattcatt ttctctacca      1380
aatctactgt ctctgcccaa actttgctga agactattct aactaaagga aacacagttt      1440
aaaaagaatg caatatagtg aagtagttaa taataaagac tccattttta aaagtctgct      1500
ggaagtttgg ttgggattgc actgaatcta tagagcaatt ggggagtatt gacatatcaa      1560
caatattgag ttttctaatc caagaacata atatctattt ttaaaatctt cttcaaaatc      1620
tttaaatctt taaattgtat tttgtagttt ttggtgttta agtcttgcac atattttgtc      1680
agatttattc caaagtattt cacgggttct tttt                                  1714

<210> SEQ ID NO 62
<211> LENGTH: 25
<212> TYPE: DNA
<213> ORGANISM: Artificial Sequence
<220> FEATURE:
<223> OTHER INFORMATION: forward primer

<400> SEQUENCE: 62
atgaacatca tcctagaaat ccttc                                            25

<210> SEQ ID NO 63
<211> LENGTH: 25
<212> TYPE: DNA
<213> ORGANISM: Artificial Sequence
<220> FEATURE:
<223> OTHER INFORMATION: reverse primer

<400> SEQUENCE: 63
atcatgcata catctctggc tggag                                            25
```

```
<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
atcagaactt caggccttgg                                                   20

<210> SEQ ID NO 65
<211> LENGTH: 21
<212> TYPE: DNA
<213> ORGANISM: Artificial Sequence
<220> FEATURE:
<223> OTHER INFORMATION: first exon

<400> SEQUENCE: 65
gcaaagccat gaacatcatc c                                                 21

<210> SEQ ID NO 66
<211> LENGTH: 24
<212> TYPE: DNA
<213> ORGANISM: Artificial Sequence
<220> FEATURE:
<223> OTHER INFORMATION: last exon

<400> SEQUENCE: 66
tcttgatgta gtgggagtcg gatt                                              24
```

INHIBITION OF HSD17B13 IN THE TREATMENT OF LIVER DISEASE IN PATIENTS EXPRESSING THE PNPLA3 I148M VARIATION

REFERENCE TO A SEQUENCE LISTING

This application includes a Sequence Listing submitted electronically as a text file named 18923801001SEQ, created on Oct. 9, 2018, with a size of 238 kilobytes. The Sequence Listing is incorporated by reference herein.

FIELD

The disclosure relates generally to the field of precision medicine. More particularly, the disclosure relates to methods of identifying subjects who are patatin like phospholipase domain containing 3 (PNPLA3) Ile148Met positive and have a liver disease or susceptibility to liver disease, and treating such subjects with an inhibitor of hydroxysteroid 17-beta dehydrogenase 13 (HSD17B13).

BACKGROUND

Various references, including patents, patent applications, accession numbers, technical articles, and scholarly articles are cited throughout the specification. Each reference is incorporated by reference herein, in its entirety and for all purposes.

Chronic liver disease and cirrhosis are leading causes of morbidity and mortality in the United States, accounting for 38,170 deaths (1.5% of total deaths) in 2014 (Kochanek et al., Nat'l. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of patients awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530), likely in conjunction with increased rates of obesity, its primary risk factor (Cohen et al., Science, 2011, 332, 1519-1523). While significant advances have been made in the treatment of hepatitis C, there are currently no evidence-based treatments for alcoholic or nonalcoholic liver disease and cirrhosis.

Previous genome wide association studies (GWAS) have identified sequence variations associated with increased risk of chronic liver disease. The most robustly validated association is with a common missense variant in patatin-like phospholipase domain-containing 3, encoded by the gene PNPLA3. This variant (rs738409, p.Ile148Met) was initially found to be associated with an increase in hepatic triglyceride levels (Romeo et al., Nat. Genet., 2008, 40, 1461-5), and subsequently associated with nonalcoholic steatohepatitis (NASH) (Batman et al., Hepatology, 2010, 52, 894-903; Sookoian et al., J. Lipid Res., 2009, 50, 2111-2116) and cirrhosis (Shen et al., J. Lipid Res., 2015, 56, 167-175). A missense variant in TM6SF2, encoding transmembrane 6 superfamily member 2, also confers increased risk of non-alcoholic fatty liver disease (NAFLD)(Kozlitina et al., Nat. Genet., 2014, 46, 352-6; Liu et al., Nat. Commun., 2014, 5, 4309; and Sookoian et al., Hepatology, 2015, 61, 515-25). Exactly how the variants in PNPLA3 and TM6SF2 contribute to liver disease has yet to be fully elucidated (Smagris et al., J. Biol. Chem., 2016, 291, 10659-76; Mahdessian et al., Proc. Natl. Acad. Sci. USA, 2014, 111, 8913-8; Huang et al., J. Biol. Chem., 2011, 286, 37085-93; and Pirazzi et al., J. Hepatol., 2012, 57, 1276-82). To date, no genetic variants that protect from chronic liver disease have been identified.

SUMMARY

The present disclosure provides methods for identifying a human subject as a candidate for treating or inhibiting a liver disease, the method comprising: determining whether or not a sample from the subject comprises: i) a first nucleic acid encoding a patatin like phospholipase domain containing 3 (PNPLA3) protein comprising an I148M variation and a second nucleic acid encoding a functional HSD17B13 protein; and/or ii) a PNPLA3 protein comprising an I148M variation and a functional HSD17B13 protein; and identifying the subject as a candidate for treating or inhibiting a liver disease by inhibiting HSD17B13 when both the first and second nucleic acids as defined in i) and/or both of the proteins as defined in ii) are detected.

In some embodiments, the first nucleic acid molecule comprises genomic DNA, mRNA, or a cDNA obtained from mRNA.

In some embodiments, the genomic DNA comprises an ATG codon at the positions corresponding to positions 5107 to 5109 according to SEQ ID NO:31; the mRNA comprises an AUG codon at the positions corresponding to positions 442 to 444 according to SEQ ID NO:34; the mRNA comprises an AUG codon at the positions corresponding to positions 430 to 432 according to SEQ ID NO:35; the cDNA comprises an ATG codon at the positions corresponding to positions 442 to 444 according to SEQ ID NO:38; or the cDNA comprises an ATG codon at the positions corresponding to positions 430 to 432 according to SEQ ID NO:39.

In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation; the mRNA comprises the nucleotide sequence according to SEQ ID NO:34, or a nucleotide sequence having at least 90% sequence identity to SEQ ID NO:34 and encoding a PNPLA3 protein which comprises the I148M variation; the mRNA comprises the nucleotide sequence according to SEQ ID NO:35, or a nucleotide sequence having at least 90% sequence identity to SEQ ID NO:35 and encoding a PNPLA3 protein which comprises the I148M variation; the cDNA comprises the nucleotide sequence according to SEQ ID NO:38, or a nucleotide sequence having at least 90% sequence identity to SEQ ID NO:38 and encoding a PNPLA3 protein which comprises the I148M variation; or the cDNA comprises the nucleotide sequence according to SEQ ID NO:39, or a nucleotide sequence having at least 90% sequence identity to SEQ ID NO:39 and encoding a PNPLA3 protein which comprises the I148M variation.

In some embodiments, detecting the first nucleic acid comprises: sequencing at least a portion of the first nucleic acid, wherein the portion comprises the codon which encodes the I148M variation; or hybridizing the first nucleic acid with a probe or primer that specifically hybridizes to a portion of the first nucleic acid, wherein the portion comprises the codon encoding the I148M variation.

In some embodiments, the probe or primer is an allele-specific probe or primer, and wherein the probe or primer optionally comprises a label.

In some embodiments, the methods further comprise determining whether the subject is homozygous or heterozygous for the I148M variation.

In some embodiments, the second nucleic acid comprises genomic DNA, mRNA, or a cDNA obtained from mRNA.

In some embodiments, the genomic DNA comprises an adenine at the position corresponding to position 12,667 according to SEQ ID NO:1; the genomic DNA comprises the nucleotide sequence according to SEQ ID NO:1, or a nucleotide sequence having at least 90% sequence identity to SEQ ID NO:1 and encoding a functional HSD17B13 protein; the mRNA comprises the nucleotide sequence according to SEQ ID NO:3, or a nucleotide sequence having at least 90% sequence identity to SEQ ID NO:3 and encoding a functional HSD17B13 protein; the mRNA comprises the nucleotide sequence according to SEQ ID NO:4 or a nucleotide sequence having at least 90% sequence identity to SEQ ID NO:4 and encoding a functional HSD17B13 protein; the mRNA comprises the nucleotide sequence according to SEQ ID NO:7 or a nucleotide sequence having at least 90% sequence identity to SEQ ID NO:7 and encoding a functional HSD17B13 protein; the mRNA comprises the nucleotide sequence according to SEQ ID NO:11 or a nucleotide sequence having at least 90% sequence identity to SEQ ID NO:11 and encoding a functional HSD17B13 protein; the cDNA comprises the nucleotide sequence according to SEQ ID NO:12 or a nucleotide sequence having at least 90% sequence identity to SEQ ID NO:12 and encoding a functional HSD17B13 protein; the cDNA comprises the nucleotide sequence according to SEQ ID NO:13 or a nucleotide sequence having at least 90% sequence identity to SEQ ID NO:13 and encoding a functional HSD17B13 protein; the cDNA comprises the nucleotide sequence according to SEQ ID NO:16 or a nucleotide sequence having at least 90% sequence identity to SEQ ID NO:16 and encoding a functional HSD17B13 protein; or the cDNA comprises the nucleotide sequence according to SEQ ID NO:20 or a nucleotide sequence having at least 90% sequence identity to SEQ ID NO:20 and encoding a functional HSD17B13 protein.

In some embodiments, detecting the second nucleic acid comprises: sequencing the second nucleic acid; or hybridizing the second nucleic acid with a probe or primer that specifically hybridizes to a portion of the second nucleic acid, wherein the portion comprises the adenine at the position corresponding to position 12,667 according to SEQ ID NO:1.

In some embodiments, the probe or primer is an allele-specific probe or primer, and wherein the probe or primer optionally comprises a label.

In some embodiments, the methods further comprise determining whether the subject is homozygous or heterozygous for the second nucleic acid encoding a functional HSD17B13 protein in the sample.

In some embodiments, the methods further comprise administering an inhibitor of HSD17B13 to the subject.

In some embodiments, the liver disease is an alcoholic liver disease. In some embodiments, the alcoholic liver disease comprises one or more of cirrhosis, steatosis, or hepatocellular carcinoma resulting from alcohol consumption.

In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

BRIEF DESCRIPTION OF THE FIGURES

The accompanying figures, which are incorporated in and constitute a part of this specification, illustrate several aspects and together with the description serve to explain the principles of the present disclosure.

FIG. 1 shows baseline characteristics of sequenced European-ancestry individuals from the discovery and replication cohorts.

FIG. 2 shows single nucleotide variants associated with serum transaminase levels at $P<1.0\times10^{-7}$ in the discovery cohort.

FIG. 3 shows replication and joint meta-analysis of 35 exome-wide significant single nucleotide variants from the discovery cohort in three separate European-ancestry cohorts.

FIG. 4 shows association of thirteen exome-wide significant and replicating single nucleotide variants with liver disease phenotypes in the discovery cohort.

FIG. 5 shows baseline characteristics of genotyped multi-ethnic cases and controls from the Dallas Liver and Pediatric Liver Studies.

FIG. 9 shows an analysis of the genetic interaction between PNPLA3 rs738409 (p.I148M) and HSD17B13 rs72613567.

Figure 6:
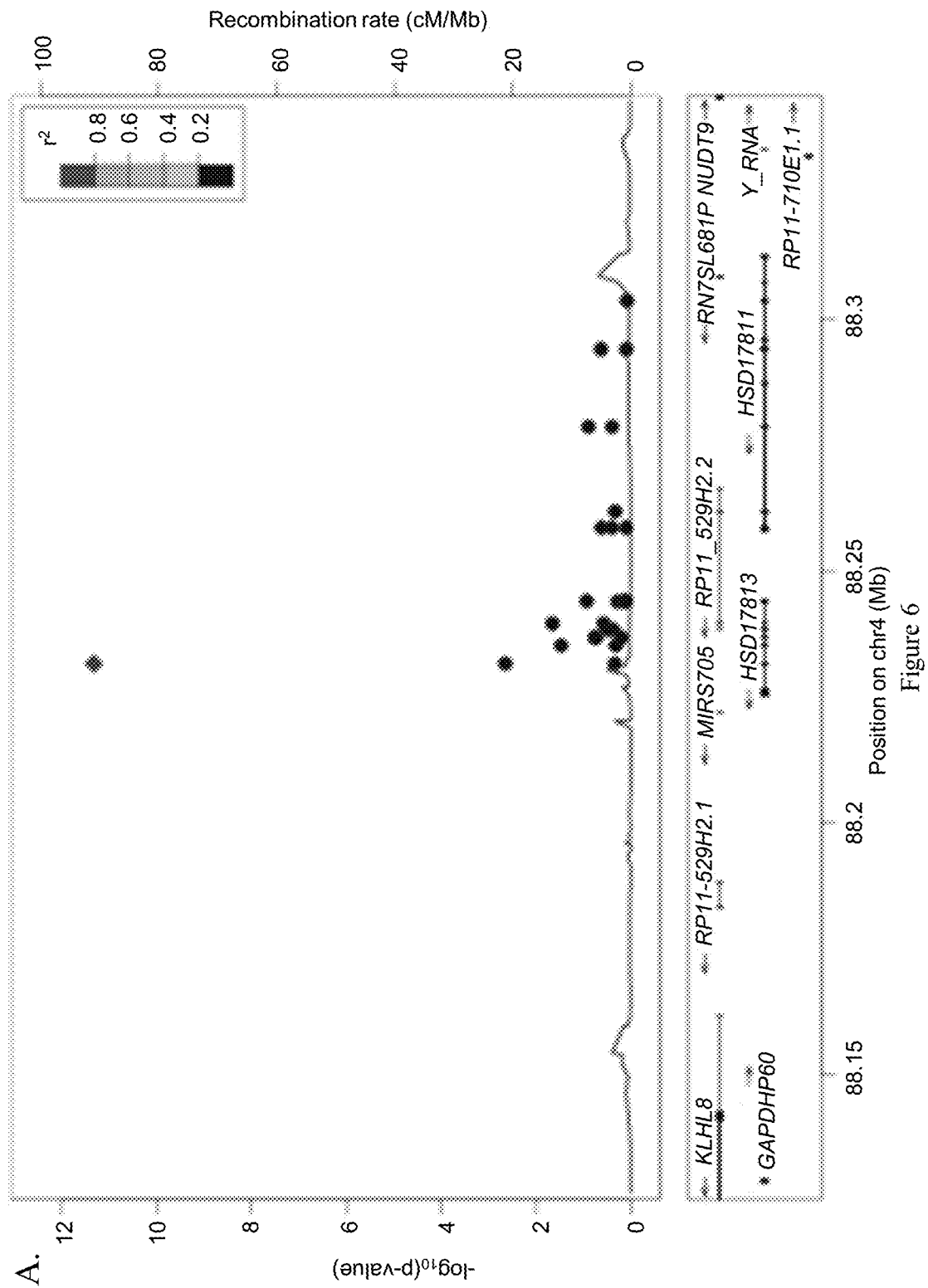
FIG. 6 (panels A and B) shows regional association plots for alanine aminotransferase (ALT; A) and aspartate aminotransferase (AST; B) levels in the GHS discovery cohort in the region around HSD17B13.
Figure 6:
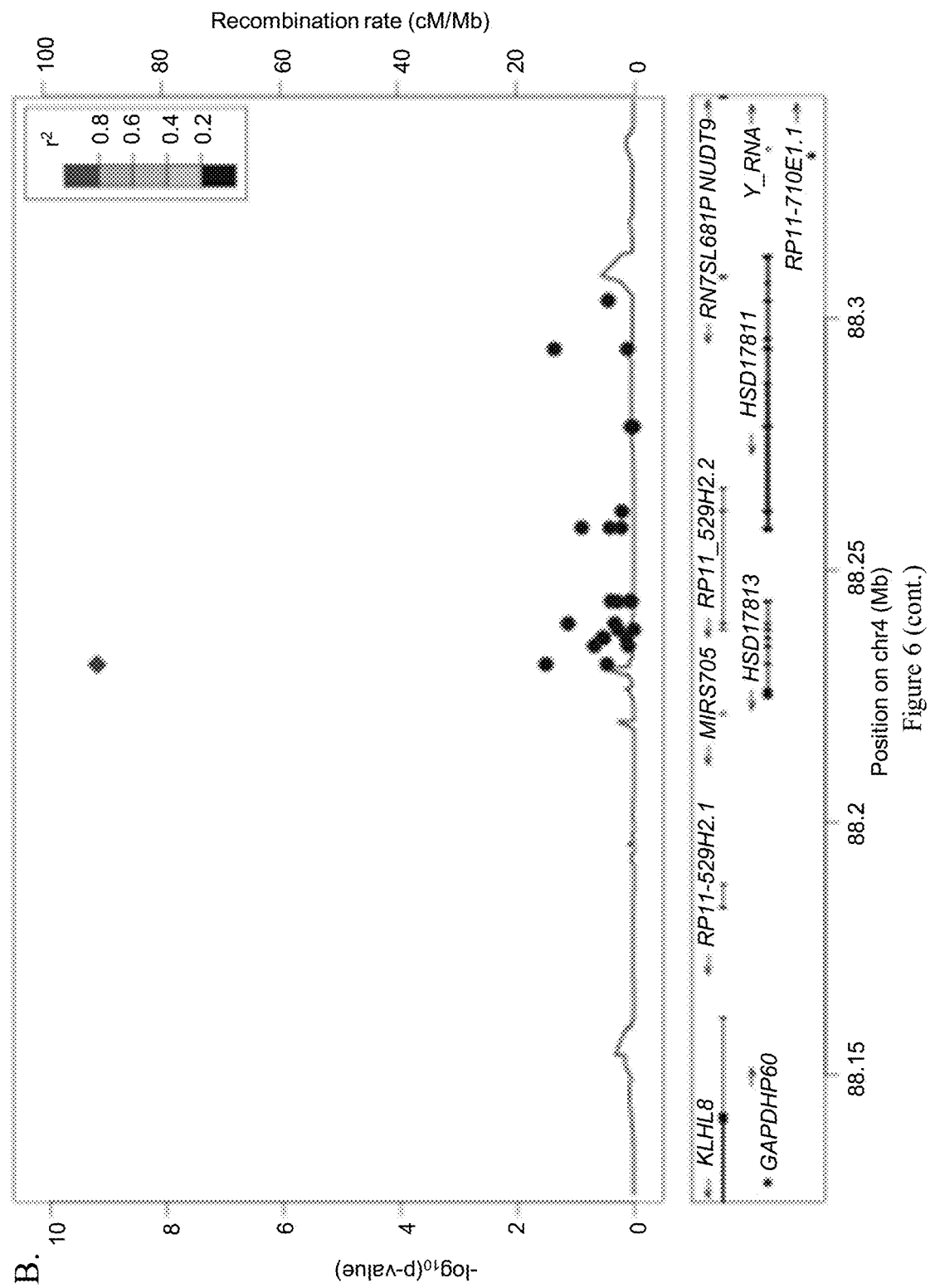

Additional advantages of the disclosure will be set forth in part in the description which follows, and in part will be apparent from the description, or can be learned by practice of the embodiments disclosed herein. The advantages of the disclosure will be realized and attained by means of the elements and combinations particularly pointed out in the appended claims. It is to be understood that both the foregoing general description and the following detailed description are exemplary and explanatory only and are not restrictive of the embodiments, as claimed.

DESCRIPTION

Various terms relating to aspects of disclosure are used throughout the specification and claims. Such terms are to be given their ordinary meaning in the art, unless otherwise indicated. Other specifically defined terms are to be construed in a manner consistent with the definition provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, without limitation, farm animals (e.g., horse, cow, pig), companion animals (e.g., dog, cat), laboratory animals (e.g., mouse, rat, rabbits), and non-human primates. In some embodiments, the subject is a human being.

As used herein, a "nucleic acid," a "nucleic acid molecule," a "nucleic acid sequence," "polynucleotide," or "oligonucleotide" can comprise a polymeric form of nucleotides of any length, may comprise DNA and/or RNA, and can be single-stranded, double-stranded, or multiple stranded. One strand of a nucleic acid also refers to its complement.

As used herein, the phrase "corresponding to" or grammatical variations thereof when used in the context of the numbering of a given amino acid or nucleic acid sequence or position refers to the numbering of a specified reference sequence when the given amino acid or nucleic acid sequence is compared to the reference sequence (e.g., with the reference sequence herein being the nucleic acid molecule or polypeptide of (functional or transcript behaving as a functional) HSD17B13, for example). In other words, the residue (e.g., amino acid or nucleotide) number or residue (e.g., amino acid or nucleotide) position of a given polymer is designated with respect to the reference sequence rather than by the actual numerical position of the residue within the given amino acid or nucleic acid sequence. For example, a given amino acid sequence can be aligned to a reference sequence by introducing gaps to optimize residue matches between the two sequences. In these cases, although the gaps are present, the numbering of the residue in the given amino acid or nucleic acid sequence is made with respect to the reference sequence to which it has been aligned.

For example, the phrase "nucleic acid molecule encoding an HSD17B13 loss-of-function variant protein which comprises a thymine at the position corresponding to position 12,667 according to SEQ ID NO:2" (and similar phrases) means that, if the nucleic acid sequence of the HSD17B13 genomic DNA being examined is aligned to the nucleotide sequence according to SEQ ID NO:2, the HSD17B13 genomic DNA being examined comprises a thymine at the position that corresponds to position 12,667 of SEQ ID NO:2.

A nucleic acid molecule encoding an HSD17B13 loss-of-function variant protein which comprises a thymine at the position corresponding to position 12,667 according to SEQ ID NO:2, for example, can easily be identified by performing a sequence alignment between the given HSD17B13 protein and the nucleic acid sequence of SEQ ID NO:2. Likewise, a PNPLA3 Ile148Met protein having a methionine at a position corresponding to position 148 according to SEQ ID NO:42, or at a position corresponding to position 144 according to SEQ ID NO:43 can easily be identified by performing a sequence alignment between the given PNPLA3 protein and the amino acid sequence of SEQ ID NO:42 or SEQ ID NO:43. A variety of computational algorithms exist that can be used for performing a sequence alignment in order to identify particular nucleic acid molecules and proteins having particular nucleotides or amino acids at the particular position that corresponds to a position of a particular SEQ ID NOs. For example, programs for identifying percent sequence identity can be used to perform a sequence alignment. Percent identity (or percent complementarity) between particular stretches of nucleic acid sequences within nucleic acids or amino acid sequences within polypeptides can be determined using BLAST programs (basic local alignment search tools) and Power-BLAST programs (Altschul et al., J. Mol. Biol., 1990, 215, 403-410; Zhang and Madden, Genome Res., 1997, 7, 649-656) or CLUSTALW software (Sievers et al., 2014, Methods Mol. Biol., 1079, 105-116) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). However, sequences can also be aligned manually. Herein, if reference is made to percent sequence identity, the higher percentages of sequence identity are preferred over the lower ones.

The present disclosure provides methods of identifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of identifying a subject having a protective effect against liver disease; and inhibitors of HSD17B13 for use in the treatment of a liver disease.

The present disclosure provides methods of classifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of classifying a subject having a protective effect against liver disease; and inhibitors of HSD17B13 for use in the treatment of a liver disease.

It has been observed in accordance with the disclosure that a splice variant (rs72613567:TA) in HSD17B13, which encodes 17-beta hydroxysteroid dehydrogenase 13, a hepatic lipid droplet protein, was reproducibly associated with reduced ALT (P=4.2×10$^{-12}$) and AST)(P=6.2×10$^{-10}$ levels. It was also observed that this variant was associated with reduced risk of alcoholic and nonalcoholic liver disease (by 38%, 95% confidence interval (CI) 19%-52%; and by 16%, 95% CI 9%-22%, respectively, for each rs72613567: TA allele) and cirrhosis (by 44%, 95% CI 22-59%; and by 26%, 95% CI 12%-38% for alcoholic and nonalcoholic cirrhosis, respectively, for each rs72613567:TA allele) in an allele dosage-dependent manner. The associations were confirmed in two independent cohorts. rs72613567:TA was associated with decreased severity of histological features of nonalcoholic steatohepatitis (NASH) (23% reduction, 95% CI 10%-34% in nonalcoholic steatohepatitis (NASH) for each rs72613567:TA allele among individuals with fatty liver disease), and mitigated liver injury associated with PNPLA3 p.I148M. rs72613567:TA results in a truncated isoform deficient in enzymatic activity against steroid substrates. Thus, a loss-of-function variant in HSD17B13 was associated with reduced risk of alcoholic and nonalcoholic liver disease, and progression from steatosis to NASH. U.S. Patent Application Publication No. US2018/0216084 (corresponding to PCT Publication No. WO 2018/136702) is incorporated herein by reference in its entirety.

The present disclosure provides methods for identifying a human subject as a candidate for treating or inhibiting a liver disease by inhibiting hydroxysteroid 17-beta dehydrogenase 13 (HSD17B13), the method comprising determining whether or not a sample from the subject comprises a first nucleic acid encoding a patatin like phospholipase domain containing 3 (PNPLA3) protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or both of the proteins are detected.

The present disclosure also provides methods of classifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of classifying a subject having a protective effect against liver disease; and inhibitors of HSD17B13 for use in the treatment of a liver disease.

The present disclosure also provides methods of treating or inhibiting liver disease, comprising administering an inhibitor of hydroxysteroid 17-beta dehydrogenase 13 (HSD17B13) to a human liver disease patient expressing a patatin like phospholipase domain containing 3 (PNPLA3) protein comprising an I148M variation such that liver disease is treated or inhibited in the patient.

In the methods described herein, various PNPLA3 and HSD17B13 proteins, and nucleic acid molecules (e.g., genomic DNA, mRNA, and cDNA derived from the mRNA) encoding the same are detected, expressed, or employed. These PNPLA3 and HSD17B13 proteins and nucleic acid molecules encoding the same are described in more detail.

The amino acid sequences for two wild type PNPLA3 proteins are set forth in SEQ ID NO:40 and SEQ ID NO:41. The wild type PNPLA3 protein having SEQ ID NO:40 is 481 amino acids in length, whereas the wild type PNPLA3 protein having SEQ ID NO:41 is 477 amino acids in length. The wild type PNPLA3 protein having SEQ ID NO:40 has an isoleucine at position 148. The wild type PNPLA3 protein having SEQ ID NO:41 has an isoleucine at position 144.

In some embodiments, a variant PNPLA3 Ile148Met protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:42, and comprises a methionine at a position corresponding to position 148 according to SEQ ID NO:42. In some embodiments, the variant PNPLA3 Ile148Met protein comprises an amino acid sequence that has at least about 95%, at least about 96%, at least about 97%, at least about 98%, or at least about 99% sequence identity to the amino acid sequence according to SEQ ID NO:42, and comprises a methionine at a position corresponding to position 148 according to SEQ ID NO:42. In some embodiments, the variant PNPLA3 Ile148Met protein comprises or consists of the amino acid sequence according to SEQ ID NO:42.

In some embodiments, a variant PNPLA3 Ile144Met protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:43, and comprises a methionine at a position corresponding to position 144 according to SEQ ID NO:43. In some embodiments, the variant PNPLA3 Ile144Met protein comprises an amino acid sequence that has at least about 95%, at least about 96%, at least about 97%, at least about 98%, or at least about 99% sequence identity to the amino acid sequence according to SEQ ID NO:43, and comprises a methionine at a position corresponding to position 144 according to SEQ ID NO:43. In some embodiments, the variant PNPLA3 Ile144Met protein comprises or consists of the amino acid sequence according to SEQ ID NO:43.

In some embodiments, the variant PNPLA3 Ile148Met and variant PNPLA3 Ile144Met proteins are fragments of the proteins described above, wherein the fragments comprise a methionine at a position corresponding to position 148 according to SEQ ID NO:42, or comprise a methionine at a position corresponding to position 144 according to SEQ ID NO:43. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, or at least about 200 contiguous amino acid residues of the encoded polypeptide (such as the polypeptide having the amino acid sequence of SEQ ID NO:42 or SEQ ID NO:43). In this regard, the longer fragments are preferred over the shorter ones. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous amino acid residues of the encoded polypeptide. In this regard, the longer fragments are preferred over the shorter ones.

The nucleic acid sequence for a genomic DNA molecule encoding wild type PNPLA3 protein is set forth in SEQ ID NO:30. The wild type PNPLA3 genomic DNA molecule having SEQ ID NO:30 comprises a cytosine at position 5109. The wild type PNPLA3 genomic DNA molecule having SEQ ID NO:30 comprises the codon ATC at the positions 5107 to 5109.

In some embodiments, the variant PNPLA3 genomic DNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 genomic DNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 genomic DNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 genomic DNA molecule encoding the variant PNPLA3 Ile148Met protein or the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:31, and comprises a guanine at a position corresponding to position 5109 according to SEQ ID NO:31, or comprises the codon ATG at the positions corresponding to positions 5107 to 5109 according to SEQ ID NO:31. In some embodiments, the variant PNPLA3 genomic DNA molecule encoding the variant PNPLA3 Ile148Met protein or the variant PNPLA3 Ile144Met protein comprises or consists of a nucleic acid sequence that has at least about 95%, at least about 96%, at least about 97%, at least about 98%, or at least about 99% sequence identity to SEQ ID NO:31, and comprises a guanine at a position corresponding to position 5109 according to SEQ ID NO:31, or comprises the codon ATG at the positions corresponding to positions 5107 to 5109 according to SEQ ID NO:31. In some embodiments, the variant PNPLA3 genomic DNA molecule encoding the variant PNPLA3 Ile148Met protein or the variant PNPLA3 Ile144Met protein comprises or consists of the nucleotide sequence according to SEQ ID NO:31.

In some embodiments, the variant PNPLA3 genomic DNA molecules comprise less than the entire genomic DNA sequence. In some embodiments, the variant PNPLA3 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500 contiguous nucleotides of SEQ ID NO:31. In some embodiments, the variant PNPLA3 genomic DNA molecules comprise or consist of at least about 1000 to at least about 2000 contiguous nucleotides of SEQ ID NO:31.

In some embodiments, the variant PNPLA3 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:31.

The nucleic acid sequences of two wild type PNPLA3 mRNA molecules are set forth in SEQ ID NO:32 and SEQ ID NO:33. The wild type PNPLA3 mRNA molecule having SEQ ID NO:32 comprises a cytosine at position 444. The wild type PNPLA3 mRNA molecule having SEQ ID NO:32 comprises the codon AUC at the positions 442 to 444. The wild type PNPLA3 mRNA molecule having SEQ ID NO:33 comprises a cytosine at position 432. The wild type PNPLA3 mRNA molecule having SEQ ID NO:33 comprises the codon AUC at the positions 430 to 432.

In some embodiments, the variant PNPLA3 mRNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 mRNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 mRNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 mRNA molecule encoding the variant PNPLA3 Ile148Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:34, and comprises a guanine at a position corresponding to position 444 according to SEQ ID NO:34, or comprises the codon AUG at the positions corresponding to positions 442 to 444 according to SEQ ID NO:34. In some embodiments, the variant PNPLA3 mRNA molecule encoding the variant PNPLA3 Ile148Met protein comprises or consists of a nucleic acid sequence that has at least about 95%, at least about 96%, at least about 97%, at least about 98%, or at least about 99% sequence identity to SEQ ID NO:34, and comprises a guanine at a position corresponding to position 444 according to SEQ ID NO:34, or comprises the codon AUG at the positions corresponding to positions 442 to 444 according to SEQ ID NO:34. In some embodiments, the variant PNPLA3 mRNA molecule encoding the variant PNPLA3 Ile148Met protein comprises or consists of the nucleotide sequence according to SEQ ID NO:34.

In some embodiments, the variant PNPLA3 mRNA molecule encoding the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:35, and comprises a guanine at a position corresponding to position 432 according to SEQ ID NO:35, or comprises the codon AUG at the positions corresponding to positions 430 to 432 according to SEQ ID NO:35. In some embodiments, the variant PNPLA3 mRNA molecule encoding the variant PNPLA3 Ile144Met protein comprises or consists of a nucleic acid sequence that has at least about 95%, at least about 96%, at least about 97%, at least about 98%, or at least about 99% sequence identity to SEQ ID NO:35, and comprises a guanine at a position corresponding to position 432 according to SEQ ID NO:35, or comprises the codon AUG at the positions corresponding to positions 430 to 432 according to SEQ ID NO:35. In some embodiments, the variant PNPLA3 mRNA molecule encoding the variant PNPLA3 Ile144Met protein comprises or consists of the nucleotide sequence according to SEQ ID NO:35.

In some embodiments, the variant PNPLA3 mRNA molecule comprises less nucleotides than the entire variant PNPLA3 mRNA sequence. In some embodiments, the variant PNPLA3 mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of SEQ ID NO:34 or SEQ ID NO:35. In some embodiments, the variant PNPLA3 mRNA molecules comprise or consist of at least about 200 to at least about 500 contiguous nucleotides of SEQ ID NO:34 or SEQ ID NO:35. In this regard, the longer mRNA molecules are preferred over the shorter ones. In some embodiments, the variant PNPLA3 mRNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:34 or SEQ ID NO:35. In this regard, the longer mRNA molecules are preferred over the shorter ones. In some embodiments, such variant PNPLA3 mRNA molecules include the codon that encodes the methionine at the position that corresponds to position 148 according to SEQ ID NO:42 or the codon that encodes the methionine at the position that corresponds to position 144 according to SEQ ID NO:43. In some embodiments, such variant PNPLA3 mRNA molecules include the guanine at the position corresponding to position 444 according to SEQ ID NO:34 or the guanine at the position corresponding to position 432 according to SEQ ID NO:35. In some embodiments, such variant PNPLA3 mRNA molecules include the codon AUG at the positions corresponding to positions 442 to 444 according to SEQ ID NO:34, or the codon AUG at the positions corresponding to positions 430 to 432 according to SEQ ID NO:35.

The nucleic acid sequences of two wild type PNPLA3 cDNA molecules are set forth in SEQ ID NO:36 and SEQ ID NO:37. The wild type PNPLA3 cDNA molecule having SEQ ID NO:36 comprises a cytosine at position 444. The wild type PNPLA3 cDNA molecule having SEQ ID NO:36 comprises the codon ATC at positions 442 to 444. The wild type PNPLA3 cDNA molecule having SEQ ID NO:37 comprises a cytosine at position 432. The wild type PNPLA3 cDNA molecule having SEQ ID NO:37 comprises the codon ATC at positions 430 to 432.

In some embodiments, the variant PNPLA3 cDNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 cDNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 cDNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 cDNA molecule encoding the variant PNPLA3 Ile148Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:38, and comprises a guanine at a position corresponding to position 444 according to SEQ ID NO:38, or comprises the codon ATG at the positions corresponding to positions 442 to 444 according to SEQ ID NO:38. In some embodiments, the variant PNPLA3 cDNA molecule encoding the variant PNPLA3 Ile148Met protein comprises or consists of a nucleic acid sequence that has at least about 95%, at least about 96%, at least about 97%, at least about 98%, or at least about 99% sequence identity to SEQ ID NO:38, and comprises a guanine at a position corresponding to position 444 according to SEQ ID NO:38, or comprises the codon ATG at the positions corresponding to positions 442 to 444 according to SEQ ID NO:38. In some embodiments, the variant PNPLA3 cDNA molecule encoding the variant PNPLA3 Ile148Met protein comprises or consists of the nucleotide sequence according to SEQ ID NO:38.

In some embodiments, the variant PNPLA3 cDNA molecule encoding the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:39, and comprises a guanine at a position corresponding to position 432 according to SEQ ID NO:39, or comprises the codon ATG at the positions corresponding to positions 430 to 432 according to SEQ ID NO:39. In some embodiments, the variant PNPLA3 cDNA molecule encoding the variant PNPLA3 Ile144Met protein comprises or consists of a nucleic acid sequence that has at least about 95%, at least about 96%, at least about 97%, at least about 98%, or at least about 99% sequence identity to SEQ ID NO:39, and comprises a guanine at a position corresponding to position 432 according to SEQ ID NO:39, or comprises the codon ATG at the positions corresponding to positions 430 to 432 according to SEQ ID NO:39. In some embodiments, the variant PNPLA3 cDNA molecule encoding the variant PNPLA3 Ile144Met protein comprises or consists of the nucleotide sequence according to SEQ ID NO:39.

In some embodiments, the variant PNPLA3 cDNA molecule comprises less nucleotides than the entire variant PNPLA3 cDNA sequence. In some embodiments, the variant PNPLA3 cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of SEQ ID NO:38 or SEQ ID NO:39. In some embodiments, the variant PNPLA3 cDNA molecules comprise or consist of at least about 200 to at least about 500 contiguous nucleotides of SEQ ID NO:38 or SEQ ID NO:39. In this regard, the longer cDNA molecules are preferred over the shorter ones. In some embodiments, the variant PNPLA3 cDNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:38 or SEQ ID NO:39. In this regard, the longer cDNA molecules are preferred over the shorter ones. In some embodiments, such variant PNPLA3 cDNA molecules include the codon that encodes the methionine at the position that corresponds to position 148 according to SEQ ID NO:42 or the codon that encodes the methionine at the position that corresponds to position 144 according to SEQ ID NO:43. In some embodiments, such variant PNPLA3 cDNA molecules include the guanine at the position corresponding to position 444 according to SEQ ID NO:38 or the guanine at the position corresponding to position 432 according to SEQ ID NO:39. In some embodiments, such variant PNPLA3 cDNA molecules include the codon ATG at the positions corresponding to positions 442 to 444 according to SEQ ID NO:38, or the codon ATG at the positions corresponding to positions 430 to 432 according to SEQ ID NO:39.

The amino acid sequences for four HSD17B13 isoform proteins associated with the functional HSD17B13 protein are set forth in SEQ ID NO:21 (Isoform A), SEQ ID NO:22 (Isoform B), SEQ ID NO:25 (Isoform E), and SEQ ID NO:29 (Isoform I). The HSD17B13 protein having SEQ ID NO:21 (Isoform A) is 300 amino acids in length. The HSD17B13 protein having SEQ ID NO:22 (Isoform B) is 264 amino acids in length. The HSD17B13 protein having SEQ ID NO:25 (Isoform E) is 324 amino acids in length. The HSD17B13 protein having SEQ ID NO:29 (Isoform I) is 271 amino acids in length.

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:21 (Isoform A). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:21 (Isoform A). In some embodiments, the HSD17B13 isoform protein associated with the functional HSD17B13 protein comprises or consists of the amino acid sequence according to SEQ ID NO:21 (Isoform A).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:22 (Isoform B). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:22 (Isoform B). In some embodiments, the HSD17B13 isoform protein associated with the functional HSD17B13 protein comprises or consists of the amino acid sequence according to SEQ ID NO:22 (Isoform B).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:25 (Isoform E). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:25 (Isoform E). In some embodiments, the HSD17B13 isoform protein associated with the functional HSD17B13 protein comprises or consists of the amino acid sequence according to SEQ ID NO:25 (Isoform E).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:29 (Isoform I). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:29 (Isoform I). In some embodiments, the HSD17B13 isoform protein associated with the functional HSD17B13 protein comprises or consists of the amino acid sequence according to SEQ ID NO:29 (Isoform I).

The amino acid sequences for five HSD17B13 isoform proteins associated with the loss-of-function rs72613567 HSD17B13 protein (SEQ ID NO:2) are set forth in SEQ ID NO:23 (Isoform C), SEQ ID NO:24 (Isoform D), SEQ ID NO:26 (Isoform F), SEQ ID NO:27 (Isoform G), and SEQ ID NO:28 (Isoform H). The HSD17B13 protein having SEQ ID NO:23 (Isoform C) is 261 amino acids in length. The HSD17B13 protein having SEQ ID NO:24 (Isoform D) is 274 amino acids in length. The HSD17B13 protein having SEQ ID NO:26 (Isoform F) is 284 amino acids in length. The HSD17B13 protein having SEQ ID NO:27 (Isoform G) is 238 amino acids in length. The HSD17B13 protein having SEQ ID NO:28 (Isoform H) is 298 amino acids in length.

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:23 (Isoform C). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:23 (Isoform C). In some embodiments, the HSD17B13 variant protein associated with a loss-of-function comprises or consists of the amino acid sequence according to SEQ ID NO:23 (Isoform C).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:24 (Isoform D). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:24 (Isoform D). In some embodiments, the HSD17B13 variant protein associated with a loss-of-function comprises an amino acid sequence that comprises or consists of the amino acid sequence according to SEQ ID NO:24 (Isoform D).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:26 (Isoform F). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:26 (Isoform F). In some embodiments, the HSD17B13 variant protein associated with a loss-of-function comprises or consists of the amino acid sequence according to SEQ ID NO:26 (Isoform F).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:27 (Isoform G). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:27 (Isoform G). In some embodiments, the HSD17B13 variant protein associated with a loss-of-function comprises or consists of the amino acid sequence according to SEQ ID NO:27 (Isoform G).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:28 (Isoform H). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:28 (Isoform H). In some embodiments, the HSD17B13 variant protein associated with a loss-of-function comprises or consists of the amino acid sequence according to SEQ ID NO:28 (Isoform H).

In some embodiments, the HSD17B13 isoform proteins associated with the functional HSD17B13 protein and the HSD17B13 variant proteins associated with a loss-of-function are fragments of the proteins described above. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, or at least about 200 contiguous amino acid residues of the encoded polypeptide (such as the polypeptides having the amino acid sequence of SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29). In this regard, the longer fragments are preferred over the shorter ones. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous amino acid residues of the encoded polypeptide. In this regard, the longer fragments are preferred over the shorter ones.

A nucleic acid sequence for the functional HSD17B13 genomic DNA molecule is set forth in SEQ ID NO:1. The functional HSD17B13 genomic DNA molecule having SEQ ID NO:1 comprises an adenine at position 12,667.

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the functional HSD17B13 genomic DNA molecule comprises or consists a nucleic acid sequence that encodes an HSD17B13 isoform protein that comprises or consists of an amino acid sequence according to SEQ ID NO:21 (Isoform A).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the functional HSD17B13 genomic DNA molecule comprises or consists a nucleic acid sequence that encodes an HSD17B13 isoform protein that comprises or consists of an amino acid sequence according to SEQ ID NO:22 (Isoform B).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the functional HSD17B13 genomic DNA molecule comprises or consists a nucleic acid sequence that encodes an HSD17B13 isoform protein that comprises or consists of an amino acid sequence according to SEQ ID NO:25 (Isoform E).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the functional HSD17B13 genomic DNA molecule comprises or consists a nucleic acid sequence that encodes an HSD17B13 isoform protein that comprises or consists of an amino acid sequence according to SEQ ID NO:29 (Isoform I).

In some embodiments, the functional HSD17B13 genomic DNA molecule comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:1. In some embodiments, the functional HSD17B13 genomic DNA molecule comprises or consists of a nucleic acid sequence that has at least about 95%, at least about 96%, at least about 97%, at least about 98%, or at least about 99% sequence identity to SEQ ID NO:1. In some embodiments, the functional HSD17B13 genomic DNA molecule comprises or consists a nucleic acid sequence according to SEQ ID NO:21.

A nucleic acid sequence for the variant HSD17B13 genomic DNA molecule encoding an HSD17B13 variant protein associated with a loss-of-function is set forth in SEQ ID NO:2. The variant HSD17B13 genomic DNA molecule having SEQ ID NO:2 comprises a thymine at position 12,667.

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the variant HSD17B13 genomic DNA molecule comprises or consists a nucleic acid sequence that encodes an HSD17B13 isoform protein that comprises or consists of an amino acid sequence according to SEQ ID NO:23 (Isoform C).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the variant HSD17B13 genomic DNA molecule comprises or consists a nucleic acid sequence that encodes an HSD17B13 isoform protein that comprises or consists of an amino acid sequence according to SEQ ID NO:24 (Isoform D).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the variant HSD17B13 genomic DNA molecule comprises or consists a nucleic acid sequence that encodes an HSD17B13 isoform protein that comprises or consists of an amino acid sequence according to SEQ ID NO:26 (Isoform F).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the variant HSD17B13 genomic DNA molecule comprises or consists a nucleic acid sequence that encodes an HSD17B13 isoform protein that comprises or consists of an amino acid sequence according to SEQ ID NO:27 (Isoform G).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the variant HSD17B13 genomic DNA molecule comprises or consists a nucleic acid sequence that encodes an HSD17B13 isoform protein that comprises or consists of an amino acid sequence according to SEQ ID NO:28 (Isoform H).

In some embodiments, the variant HSD17B13 genomic DNA molecule comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2. In some embodiments, the variant HSD17B13 genomic DNA molecule comprises or consists of a nucleic acid sequence that has at least about 95%, at least about 96%, at least about 97%, at least about 98%, or at least about 99% sequence identity to SEQ ID NO:2. In some embodiments, the variant HSD17B13 genomic DNA molecule comprises or consists a nucleic acid sequence according to SEQ ID NO:2.

In some embodiments, the functional HSD17B13 genomic DNA and variant HSD17B13 genomic DNA molecules comprise less than the entire genomic DNA sequence. In some embodiments, the functional HSD17B13 genomic DNA and variant HSD17B13 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500 contiguous nucleotides of SEQ ID NO:1 (functional HSD17B13 genomic DNA) or SEQ ID NO:2 (variant HSD17B13 genomic DNA). In some embodiments, the functional HSD17B13 genomic DNA and variant HSD17B13 genomic DNA molecules comprise or consist of at least about 1000 to at least about 2000 contiguous nucleotides of SEQ ID NO:1 (functional HSD17B13 genomic DNA) or SEQ ID NO:2 (variant HSD17B13 genomic DNA).

In some embodiments, the functional HSD17B13 genomic DNA and variant HSD17B13 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:1 (functional HSD17B13 genomic DNA) or SEQ ID NO:2 (variant HSD17B13 genomic DNA).

The nucleic acid sequences for four HSD17B13 RNA transcripts encoding isoform proteins associated with the functional HSD17B13 protein are set forth in SEQ ID NO:44 (Transcript A), SEQ ID NO:45 (Transcript B), SEQ ID NO:48 (Transcript E), and SEQ ID NO:52 (Transcript I).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:44 (Transcript A). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:44 (Transcript A). In some embodiments, the HSD17B13 RNA transcript encoding the isoform protein associated with the functional HSD17B13 protein comprises or consists of a nucleic acid sequence according to SEQ ID NO:44 (Transcript A).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:45 (Transcript B). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:45 (Transcript B). In some embodiments, the HSD17B13 RNA transcript encoding the isoform protein associated with the functional HSD17B13 protein comprises or consists of a nucleic acid sequence according to SEQ ID NO:45 (Transcript B).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:48 (Transcript E). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:48 (Transcript E). In some embodiments, the HSD17B13 RNA transcript encoding the isoform protein associated with the functional HSD17B13 protein comprises or consists of a nucleic acid sequence according to SEQ ID NO:48 (Transcript E).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:52 (Transcript I). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:52 (Transcript I). In some embodiments, the HSD17B13 RNA transcript encoding the isoform protein associated with the functional HSD17B13 protein comprises or consists of a nucleic acid sequence according to SEQ ID NO:52 (Transcript I).

The nucleic acid sequences for five HSD17B13 RNA transcripts encoding isoform proteins associated with a loss-of-function are set forth in SEQ ID NO:46 (Transcript C), SEQ ID NO:47 (Transcript D), SEQ ID NO:49 (Transcript F), SEQ ID NO:50 (Transcript G), and SEQ ID NO:51 (Transcript H).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:46 (Transcript C). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:46 (Transcript C). In some embodiments, the HSD17B13 RNA transcript encoding the isoform protein associated with a loss-of-function comprises or consists of a nucleic acid sequence according to SEQ ID NO:46 (Transcript C).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:47 (Transcript D). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:47 (Transcript D). In some embodiments, the HSD17B13 RNA transcript encoding the isoform protein associated with a loss-of-function comprises or consists of a nucleic acid sequence according to SEQ ID NO:47 (Transcript D).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:49 (Transcript F). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:49 (Transcript F). In some embodiments, the HSD17B13 RNA transcript encoding the isoform protein associated with a loss-of-function comprises or consists of a nucleic acid sequence according to SEQ ID NO:49 (Transcript F).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:50 (Transcript G). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:50 (Transcript G). In some embodiments, the HSD17B13 RNA transcript encoding the isoform protein associated with a loss-of-function comprises or consists of a nucleic acid sequence according to SEQ ID NO:50 (Transcript G).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:51 (Transcript H). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:51 (Transcript H). In some embodiments, the HSD17B13 RNA transcript encoding the isoform protein associated with a loss-of-function comprises or consists of a nucleic acid sequence according to SEQ ID NO:51 (Transcript H).

In some embodiments, the functional HSD17B13 RNA transcripts and variant HSD17B13 RNA transcripts comprise less than the RNA transcript sequence. In some embodiments, the functional HSD17B13 RNA transcripts and variant HSD17B13 RNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, or at least about 2500 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts). In some embodiments, the functional HSD17B13 RNA transcripts and variant HSD17B13 RNA transcripts comprise less than the RNA transcript sequence. In some embodiments, the functional HSD17B13 RNA transcripts and variant HSD17B13 RNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts). In some embodiments, the functional HSD17B13 RNA transcripts and variant HSD17B13 RNA transcripts comprise or consist of at least about 1000 to at least about 2000 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts).

The nucleic acid sequences for four HSD17B13 cDNA transcripts encoding isoform proteins associated with the functional HSD17B13 protein are set forth in SEQ ID NO:53 (Transcript A), SEQ ID NO:54 (Transcript B), SEQ ID NO:57 (Transcript E), and SEQ ID NO:61 (Transcript I).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:53 (Transcript A). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:53 (Transcript A). In some embodiments, the HSD17B13 cDNA transcript encoding the isoform protein associated with the functional HSD17B13 protein comprises or consists of a nucleic acid sequence according to SEQ ID NO:53 (Transcript A).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:54 (Transcript B). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:54 (Transcript B). In some embodiments, the HSD17B13 cDNA transcript encoding the isoform protein associated with the functional HSD17B13 protein comprises or consists of a nucleic acid sequence according to SEQ ID NO:54 (Transcript B).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:57 (Transcript E). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:57 (Transcript E). In some embodiments, the HSD17B13 cDNA transcript encoding the isoform protein associated with the functional HSD17B13 protein comprises or consists of a nucleic acid sequence according to SEQ ID NO:57 (Transcript E).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:61 (Transcript I). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:61 (Transcript I). In some embodiments, the HSD17B13 cDNA transcript encoding the isoform protein associated with the functional HSD17B13 protein comprises or consists of a nucleic acid sequence according to SEQ ID NO:61 (Transcript I).

The nucleic acid sequences for five HSD17B13 cDNA transcripts encoding isoform proteins associated with a loss-of-function are set forth in SEQ ID NO:55 (Transcript C), SEQ ID NO:56 (Transcript D), SEQ ID NO:58 (Transcript F), SEQ ID NO:59 (Transcript G), and SEQ ID NO:60 (Transcript H).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:55 (Transcript C). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:55 (Transcript C). In some embodiments, the HSD17B13 cDNA transcript encoding the isoform protein associated with a loss-of-function comprises or consists of a nucleic acid sequence according to SEQ ID NO:55 (Transcript C).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:56 (Transcript D). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:56 (Transcript D). In some embodiments, the HSD17B13 cDNA transcript encoding the isoform protein associated with a loss-of-function comprises or consists of a nucleic acid sequence according to SEQ ID NO:56 (Transcript D).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:58 (Transcript F). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:58 (Transcript F). In some embodiments, the HSD17B13 cDNA transcript encoding the isoform protein associated with a loss-of-function comprises or consists of a nucleic acid sequence according to SEQ ID NO:58 (Transcript F).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:59 (Transcript G). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:59 (Transcript G). In some embodiments, the HSD17B13 cDNA transcript encoding the isoform protein associated with a loss-of-function comprises or consists of a nucleic acid sequence according to SEQ ID NO:59 (Transcript G).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:60 (Transcript H). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:60 (Transcript H). In some embodiments, the HSD17B13 cDNA transcript encoding the isoform protein associated with a loss-of-function comprises or consists of a nucleic acid sequence according to SEQ ID NO:60 (Transcript H).

In some embodiments, the HSD17B13 cDNA transcripts comprise less than the cDNA transcript sequence. In some embodiments, the HSD17B13 cDNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, or at least about 2500 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60. In some embodiments, the HSD17B13 cDNA transcripts comprise less than the cDNA transcript sequence. In some embodiments, the HSD17B13 cDNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60. In some embodiments, the HSD17B13 cDNA transcripts comprise or consist of at least about 1000 to at least about 2000 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60.

The nucleic acid sequences for four HSD17B13 mRNA molecules encoding isoform proteins associated with the functional HSD17B13 protein are set forth in SEQ ID NO:3 (Transcript A), SEQ ID NO:4 (Transcript B), SEQ ID NO:7 (Transcript E), and SEQ ID NO:11 (Transcript I).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:3 (Transcript A). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:3 (Transcript A). In some embodiments, the HSD17B13 mRNA molecule encoding the isoform protein associated with the functional HSD17B13 protein comprises or consists of a nucleic acid sequence according to SEQ ID NO:3 (Transcript A).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4 (Transcript B). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:4 (Transcript B). In some embodiments, the HSD17B13 mRNA molecule encoding the isoform protein associated with the functional HSD17B13 protein comprises or consists of a nucleic acid sequence according to SEQ ID NO:4 (Transcript B).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:7 (Transcript E). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:7 (Transcript E). In some embodiments, the HSD17B13 mRNA molecule encoding the isoform protein associated with the functional HSD17B13 protein comprises or consists of a nucleic acid sequence according to SEQ ID NO:7 (Transcript E).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:11 (Transcript I). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:11 (Transcript I). In some embodiments, the HSD17B13 mRNA molecule encoding the isoform protein associated with the functional HSD17B13 protein comprises or consists of a nucleic acid sequence according to SEQ ID NO:11 (Transcript I).

The nucleic acid sequences for five HSD17B13 mRNA molecules encoding isoform proteins associated with a loss-of-function are set forth in SEQ ID NO:5 (Transcript C), SEQ ID NO:6 (Transcript D), SEQ ID NO:8 (Transcript F), SEQ ID NO:9 (Transcript G), and SEQ ID NO:10 (Transcript H).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:5 (Transcript C). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:5 (Transcript C). In some embodiments, the HSD17B13 mRNA molecule encoding the isoform protein associated with a loss-of-function comprises or consists of a nucleic acid sequence according to SEQ ID NO:5 (Transcript C).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6 (Transcript D). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:6 (Transcript D). In some embodiments, the HSD17B13 mRNA molecule encoding the isoform protein associated with a loss-of-function comprises or consists of a nucleic acid sequence according to SEQ ID NO:6 (Transcript D).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8 (Transcript F). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:8 (Transcript F). In some embodiments, the HSD17B13 mRNA molecule encoding the isoform protein associated with a loss-of-function comprises or consists of a nucleic acid sequence according to SEQ ID NO:8 (Transcript F).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:9 (Transcript G). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:9 (Transcript G). In some embodiments, the HSD17B13 mRNA molecule encoding the isoform protein associated with a loss-of-function comprises or consists of a nucleic acid sequence according to SEQ ID NO:9 (Transcript G).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:10 (Transcript H). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:10 (Transcript H). In some embodiments, the HSD17B13 mRNA molecule encoding the isoform protein associated with a loss-of-function comprises or consists of a nucleic acid sequence according to SEQ ID NO:10 (Transcript H).

In some embodiments, the HSD17B13 mRNA molecules comprise less nucleotides than the entire mRNA sequence. In some embodiments, the HSD17B13 mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, or at least about 900 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In some embodiments, the HSD17B13 mRNA molecules comprise or consist of at least about 200 to at least about 500 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In this regard, the longer mRNA molecules are preferred over the shorter ones. In some embodiments, the HSD17B13 mRNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In this regard, the longer mRNA molecules are preferred over the shorter ones.

The nucleic acid sequences for four HSD17B13 cDNA molecules encoding isoform proteins associated with the functional HSD17B13 protein are set forth in SEQ ID NO:12 (Transcript A), SEQ ID NO:13 (Transcript B), SEQ ID NO:16 (Transcript E), and SEQ ID NO:20 (Transcript I).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:12 (Transcript A). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:12 (Transcript A). In some embodiments, the HSD17B13 cDNA molecule encoding the isoform protein associated with the functional HSD17B13 protein comprises or consists of a nucleic acid sequence according to SEQ ID NO:12 (Transcript A).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:13 (Transcript B). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:13 (Transcript B). In some embodiments, the HSD17B13 cDNA molecule encoding the isoform protein associated with the functional HSD17B13 protein comprises or consists of a nucleic acid sequence according to SEQ ID NO:13 (Transcript B).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:16 (Transcript E). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:16 (Transcript E). In some embodiments, the HSD17B13 cDNA molecule encoding the isoform protein associated with the functional HSD17B13 protein comprises or consists of a nucleic acid sequence according to SEQ ID NO:16 (Transcript E).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:20 (Transcript I). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:20 (Transcript I). In some embodiments, the HSD17B13 cDNA molecule encoding the isoform protein associated with the functional HSD17B13 protein comprises or consists of a nucleic acid sequence according to SEQ ID NO:20 (Transcript I).

The nucleic acid sequences for five HSD17B13 cDNA molecules encoding isoform proteins associated with a loss-of-function are set forth in SEQ ID NO:14 (Transcript C), SEQ ID NO:15 (Transcript D), SEQ ID NO:17 (Transcript F), SEQ ID NO:18 (Transcript G), and SEQ ID NO:19 (Transcript H).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:14 (Transcript C). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:14 (Transcript C). In some embodiments, the HSD17B13 cDNA molecule encoding the isoform protein associated with a loss-of-function comprises or consists of a nucleic acid sequence according to SEQ ID NO:14 (Transcript C).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:15 (Transcript D). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:15 (Transcript D). In some embodiments, the HSD17B13 cDNA molecule encoding the isoform protein associated with a loss-of-function comprises or consists of a nucleic acid sequence according to SEQ ID NO:15 (Transcript D).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:17 (Transcript F). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:17 (Transcript F). In some embodiments, the HSD17B13 cDNA molecule encoding the isoform protein associated with a loss-of-function comprises or consists of a nucleic acid sequence according to SEQ ID NO:17 (Transcript F).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:18 (Transcript G). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:18 (Transcript G). In some embodiments, the HSD17B13 cDNA molecule encoding the isoform protein associated with a loss-of-function comprises or consists of a nucleic acid sequence according to SEQ ID NO:18 (Transcript G).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:19 (Transcript H). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:19 (Transcript H). In some embodiments, the HSD17B13 cDNA molecule encoding the isoform protein associated with a loss-of-function comprises or consists of a nucleic acid sequence according to SEQ ID NO:19 (Transcript H).

In some embodiments, the HSD17B13 cDNA molecules comprise less nucleotides than the entire cDNA sequence. In some embodiments, the HSD17B13 cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, or at least about 900 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In some embodiments, the HSD17B13 cDNA molecules comprise or consist of at least about 200 to at least about 500 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In this regard, the longer cDNA molecules are preferred over the shorter ones. In some embodiments, the HSD17B13 cDNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In this regard, the longer cDNA molecules are preferred over the shorter ones.

The probes and primers described herein can be used to hybridize to any of the functional or variant PNPLA3 genomic DNA molecules, mRNA molecules, or cDNA molecules derived from mRNA molecules described herein. The primers can be used, for example, to amplify portions of any of the functional or variant PNPLA3 genomic DNA molecules, mRNA molecules, or cDNA molecules derived from mRNA molecules described herein, so that the amplifications products can be, for example, detected or sequenced.

For example, the probes and primers can be used to hybridize to any of the wild type PNPLA3 genomic DNA molecules described herein, including the wild type PNPLA3 genomic DNA molecule comprising SEQ ID NO:30. The probes and primers can also be used to hybridize to any of the wild type PNPLA3 mRNA molecules described herein, including the wild type PNPLA3 mRNA molecules comprising SEQ ID NO:32 or SEQ ID NO:33. The probes and primers can also be used to hybridize to any of the wild type PNPLA3 cDNA molecules described herein, including the wild type PNPLA3 cDNA molecules comprising SEQ ID NO:36 or SEQ ID NO:37.

The probes and primers can also be used to hybridize to any of the variant PNPLA3 genomic DNA molecules described herein, including the variant PNPLA3 genomic DNA molecule comprising SEQ ID NO:31. The probes and primers can also be used to hybridize to any of the variant PNPLA3 mRNA molecules described herein, including the variant PNPLA3 mRNA molecules comprising SEQ ID NO:34 or SEQ ID NO:35. The probes and primers can also be used to hybridize to any of the variant PNPLA3 cDNA molecules described herein, including the variant PNPLA3 cDNA molecules comprising SEQ ID NO:38 or SEQ ID NO:39.

The probes can be used, for example, to detect any of the functional or variant HSD17B13 genomic DNA molecules, mRNA molecules, or cDNA molecules derived from mRNA molecules described herein. The primers can be used, for example, to amplify portions of any of the functional or variant HSD17B13 genomic DNA molecules, mRNA molecules, or cDNA molecules derived from mRNA molecules described herein, so that the amplifications products can be, for example, detected or sequenced.

For example, the probes and primers can be used to hybridize to any of the functional HSD17B13 genomic DNA molecules described herein, including the functional HSD17B13 genomic DNA molecule comprising SEQ ID NO:1. The probes and primers can also be used to hybridize to any of the functional HSD17B13 RNA transcripts described herein, including the functional HSD17B13 RNA transcripts comprising SEQ ID NO:44, SEQ ID NO:45, SEQ ID NO:48, or SEQ ID NO:52. The probes and primers can also be used to hybridize to any of the functional HSD17B13 DNA transcripts described herein, including the functional HSD17B13 DNA transcripts comprising SEQ ID NO:53, SEQ ID NO:54, SEQ ID NO:57, or SEQ ID NO:61. The probes and primers can also be used to hybridize to any of the functional HSD17B13 mRNA molecules described herein, including the functional HSD17B13 mRNA molecules comprising SEQ ID NO:3, SEQ ID NO:4, SEQ ID NO:7, or SEQ ID NO:11. The probes and primers can also be used to hybridize to any of the functional HSD17B13 cDNA molecules described herein, including the functional HSD17B13 cDNA molecules comprising SEQ ID NO:12, SEQ ID NO:13, SEQ ID NO:16, or SEQ ID NO:20.

The probes and primers can also be used to hybridize to any of the variant HSD17B13 genomic DNA molecules described herein, including the variant HSD17B13 genomic DNA molecule comprising SEQ ID NO:2. The probes and primers can also be used to hybridize to any of the variant HSD17B13 RNA transcripts described herein, including the variant HSD17B13 RNA transcripts comprising SEQ ID NO:46, SEQ ID NO:47, SEQ ID NO:49, SEQ ID NO:50, or SEQ ID NO:51. The probes and primers can also be used to hybridize to any of the variant HSD17B13 DNA transcripts described herein, including the variant HSD17B13 DNA transcripts comprising SEQ ID NO:55, SEQ ID NO:56, SEQ ID NO:58, SEQ ID NO:59, or SEQ ID NO:60. The probes and primers can also be used to hybridize to any of the variant HSD17B13 mRNA molecules described herein, including the variant HSD17B13 mRNA molecules comprising SEQ ID NO:5, SEQ ID NO:6, SEQ ID NO:8, SEQ ID NO:9, or SEQ ID NO:10. The probes and primers can also be used to hybridize to any of the HSD17B13 cDNA molecules described herein, including the HSD17B13 cDNA molecules comprising SEQ ID NO:14, SEQ ID NO:15, SEQ ID NO:17, SEQ ID NO:18, or SEQ ID NO:19.

In some embodiments, the probes and/or primers described herein comprise a nucleic acid sequence that specifically hybridizes to any of the nucleic acid molecules disclosed herein, or the complement thereof. In some embodiments, the probe or primer specifically hybridizes to any of the nucleic acid molecules disclosed herein under stringent conditions. The present disclosure also provides nucleic acid molecules having nucleic acid sequences that hybridize under moderate conditions to any of the nucleic acid molecules disclosed herein, or the complement thereof.

Appropriate stringency conditions which promote DNA hybridization include, for example, 6× sodium chloride/sodium citrate (SSC) at about 45° C., followed by a wash of 2×SSC at 50° C. (see, also *Current Protocols in Molecular Biology*, John Wiley & Sons, N.Y. (1989), 6.3.1-6.3.6). Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$, can be approximated from the equation of Meinkoth and Wahl, *Anal. Biochem.*, 1984, 138, 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7°

C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45'C (aqueous solution) or 32° C. (formamide solution), it is optimal to increase the SSC concentration so that a higher temperature can be used.

The probes described herein can be linked or fused to a label to aid in detection. The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The probe or primer can comprise any suitable length, non-limiting examples of which include at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides in length. In some embodiments, the probe or primer comprises at least about 18 nucleotides in length to about 25 nucleotides in length. The probe or primer can comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides in length. In some embodiments, the probe or primer is from about 18 to about 30 nucleotides in length. Alternately, in some embodiments, the probe comprises or consists of at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides.

In some embodiments, the probes and/or primers can hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to any of the wild type PNPLA3 or HSD17B13 nucleic acid molecules or variant PNPLA3 or HSD17B13 nucleic acid molecules described herein.

In some embodiments, the probe or primer comprises DNA. In some embodiments, the probe or primer comprises RNA.

The probes and primers described herein can also be alteration-specific probes and alteration-specific primers. The alteration-specific probe or alteration-specific primer can comprise a nucleic acid sequence which is complementary to and/or hybridizes, or specifically hybridizes, to a nucleic acid sequence encoding a variant PNPLA3 protein but which is not complementary to and/or hybridizes, or specifically hybridizes, to a nucleic acid sequence encoding a wild type PNPLA3 protein. In this context, "specifically hybridizes" means that the probe or primer (e.g., the alteration-specific probe or alteration-specific primer) does not hybridize to a nucleic acid molecule encoding a wild type PNPLA3 protein. Herein, the term "specifically hybridizes" means that the probe or primer exclusively hybridizes to the indicated nucleic acid molecule and not to another nucleic acid molecule. Accordingly, a probe or primer which specifically hybridizes to a nucleic acid molecule encoding a PNPLA3 protein comprising the I148M variation does not hybridize to a nucleic acid molecule encoding a PNPLA3 protein which does not comprise the I148M variation. The alteration-specific probe or alteration-specific primer can also comprise a nucleic acid sequence which is complementary to and/or hybridizes, or specifically hybridizes, to a nucleic acid sequence encoding a wild type PNPLA3 protein but which is not complementary to and/or hybridizes, or specifically hybridizes, to a nucleic acid sequence encoding a variant PNPLA3 protein. In this context, "specifically hybridizes" means that the probe or primer (e.g., the alteration-specific probe or alteration-specific primer) does not hybridize to a nucleic acid molecule encoding a variant PNPLA3 protein.

The alteration-specific probe or alteration-specific primer can also comprise a nucleic acid sequence which is complementary to and/or hybridizes, or specifically hybridizes, to a nucleic acid sequence encoding a variant HSD17B13 protein but which is not complementary to and/or hybridizes, or specifically hybridizes, to a nucleic acid sequence encoding a functional HSD17B13 protein. In this context, "specifically hybridizes" means that the probe or primer (e.g., the alteration-specific probe or alteration-specific primer) does not hybridize to a nucleic acid molecule encoding a functional HSD17B13 protein. For example, in this context "specifically hybridizes" means that the probe or primer does not hybridize to a nucleic acid molecule encoding a non-active/loss of function HSD17B13 protein. The alteration-specific probe or alteration-specific primer can also comprise a nucleic acid sequence which is complementary to and/or hybridizes, or specifically hybridizes, to a nucleic acid sequence encoding a functional HSD17B13 protein but which is not complementary to and/or hybridizes, or specifically hybridizes, to a nucleic acid sequence encoding a variant HSD17B13 protein. In this context, "specifically hybridizes" means that the probe or primer (e.g., the alteration-specific probe or alteration-specific primer) does not hybridize to a nucleic acid molecule encoding a variant HSD17B13 protein.

In some embodiments, the alteration-specific probe or alteration-specific primer comprises a nucleic acid sequence which is complementary to and/or hybridizes, or specifically hybridizes, to a portion of a PNPLA3 nucleic acid sequence that comprises a methionine at a position corresponding to position 148 according to SEQ ID NO:42, or comprises a methionine at a position corresponding to position 144 according to SEQ ID NO:43. In some embodiments, the alteration-specific probe or alteration-specific primer comprises a nucleic acid sequence which is complementary to and/or hybridizes, or specifically hybridizes, to the portion of the variant PNPLA3 genomic DNA that comprises an ATG codon at the positions corresponding to positions 5107 to 5109 according to SEQ ID NO:31. In some embodiments, the alteration-specific probe or alteration-specific primer comprises a nucleic acid sequence which is complementary to and/or hybridizes, or specifically hybridizes, to the portion of the variant PNPLA3 mRNA that comprises an AUG codon at the positions corresponding to positions 442 to 444 according to SEQ ID NO:34. In some embodiments, the alteration-specific probe or alteration-specific primer comprises a nucleic acid sequence which is complementary to and/or hybridizes, or specifically hybridizes, to the portion of the variant PNPLA3 mRNA that comprises an AUG codon at the positions corresponding to positions 430 to 432 according to SEQ ID NO:35. In some embodiments, the alteration-specific probe or alteration-specific primer comprises a nucleic acid sequence which is complementary to and/or hybridizes, or specifically hybridizes, to the portion of the variant PNPLA3 cDNA that comprises an ATG codon at the positions corresponding to positions 442 to 444 according to SEQ ID NO:38. In some embodiments, the alteration-specific probe or alteration-specific primer comprises a nucleic acid sequence which is complementary to and/or hybridizes, or specifically hybridizes, to the portion of the variant PNPLA3 cDNA that comprises an ATG codon at the positions corresponding to positions 430 to 432 according to SEQ ID NO:39.

In some embodiments, the alteration-specific probe or alteration-specific primer comprises a nucleic acid sequence which is complementary to and/or hybridizes, or specifically hybridizes, to the portion of the HSD17B13 genomic DNA that comprises an adenine at a position corresponding to position 12,667 according to SEQ ID NO:1. In some embodiments, the alteration-specific probe or alteration-specific primer comprises a nucleic acid sequence which is complementary to and/or hybridizes, or specifically hybridizes, to the portion of the HSD17B13 genomic DNA that comprises a thymine at a position corresponding to position 12,667 according to SEQ ID NO:2.

In some embodiments, the portion of the nucleic acid molecule to which the probe or primer is hybridized comprises from about 10 to about 200, from about 10 to about 150, from about 10 to about 100, from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein). In some preferred embodiments, the portion of the nucleic acid molecule to which the probe or primer is hybridized comprises from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein).

The kits described herein can comprise detection and/or amplification assay reagents that can be used for detecting and/or amplifying any of the wild type PNPLA3 and/or HSD17B13 nucleic acid molecules described herein and/or any of the variant PNPLA3 and/or HSD17B13 nucleic acid molecules described herein. In some embodiments, the kits for such detection and/or amplification can contain any of the reagents (e.g., probes and primers) described herein. In some embodiments, a basic kit can comprise a container having at least one probe or primer or at least two probes or primers, such as alteration-specific probes or alteration-specific primers, for a locus in any of the nucleic acid molecules disclosed herein. A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers. In some embodiments, the kits comprise at least one labeled probe (e.g., alteration-specific probe) for detection. In some embodiments, any of the kits disclosed herein can further comprise products and reagents required to carry out an annealing reaction, and instructions.

The present disclosure provides methods for detecting the presence of any of the wild type PNPLA3 proteins described herein. The present disclosure also provides methods for detecting the presence of any of the variant PNPLA3 proteins described herein. The present disclosure also provides methods for detecting the presence of any of the wild type PNPLA3 nucleic acid molecules described herein (e.g., genomic DNA molecules, mRNA molecules, and cDNA molecules) described herein. The present disclosure also provides methods for detecting the presence of any of the variant PNPLA3 nucleic acid molecules described herein (e.g., genomic DNA molecules, mRNA molecules, and cDNA molecules) described herein.

The present disclosure also provides methods for detecting the presence of any of the functional HSD17B13 proteins described herein. The present disclosure also provides methods for detecting the presence of any of the variant HSD17B13 proteins described herein. The present disclosure also provides methods for detecting the presence of any of the functional HSD17B13 nucleic acid molecules described herein (e.g., genomic DNA molecules, RNA transcripts, cDNA transcripts, mRNA molecules, and cDNA molecules) described herein. The present disclosure also provides methods for detecting the presence of any of the variant HSD17B13 nucleic acid molecules described herein (e.g., genomic DNA molecules, RNA transcripts, cDNA transcripts, mRNA molecules, and cDNA molecules) described herein.

In some embodiments of any of the methods described herein, a functional HSD17B13 protein, or nucleic acid molecule encoding the same, is detected or sought to be detected in a subject or patient. In some embodiments, the subject or patient comprises a functional HSD17B13 protein. In some embodiments, the functional HSD17B13 protein is one of the functional HSD17B13 proteins described herein (which can be encoded by any of the nucleic acid molecules described herein encoding the same). In some embodiments, a functional HSD17B13 protein has at least 90%, at least 80%, at least 70%, at least 60%, at least 50%, at least 40%, at least 30%, at least 20%, at least 10%, at least 5%, or at least 1% of the biological activity of the HSD17B13 protein having the amino acid sequence according to SEQ ID NO:40. In some embodiments, a functional HSD17B13 protein has at least 90%, at least 80%, at least 70%, at least 60%, or at least 50% of the biological activity of the HSD17B13 protein having the amino acid sequence according to SEQ ID NO:40. In some embodiments, a functional HSD17B13 protein has at least 90%, at least 80%, at least 70%, at least 60%, at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 70%, at least 60%, at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 30%, at least 20%, at least 10%, at least 5%, or at least 1% of the biological activity of HSD17B13 protein having SEQ ID NO:40. In some embodiments, a functional HSD17B13 protein has at least 90% of the biological activity of HSD17B13 protein having SEQ ID NO:40. In some embodiments, a functional HSD17B13 protein has at least 80% of the biological activity of HSD17B13 protein having SEQ ID NO:40. In some embodiments, a functional HSD17B13 protein has at least 70% of the biological activity of HSD17B13 protein having SEQ ID NO:40. In some embodiments, a functional HSD17B13 protein has at least 60% of the biological activity of HSD17B13 protein having SEQ ID NO:40. In some embodiments, a functional HSD17B13 protein has at least 50% of the biological activity of HSD17B13 protein having SEQ ID NO:40. In some embodiments, a functional HSD17B13 protein has at least 40% of the biological activity of HSD17B13 protein having SEQ ID NO:40. In some embodiments, a functional HSD17B13 protein has at least 30% of the biological activity of HSD17B13 protein having SEQ ID NO:40. In some embodiments, a functional HSD17B13 protein has at least 20% of the biological activity of HSD17B13 protein having SEQ ID NO:40. In some embodiments, a functional HSD17B13 protein has at least 10% of the biological activity of HSD17B13 protein having SEQ ID NO:40. In some embodiments, a functional HSD17B13 protein has at least 5% of the biological activity of HSD17B13 protein having SEQ ID NO:40. In some embodiments, a functional HSD17B13 protein has at least 1% of the biological activity of HSD17B13 protein having SEQ ID NO:40. In some embodiments, the activity of an HSD17B13 protein (e.g., functionality) can be determined by, for example, performing an oxidoreductase activity assay.

It is understood that gene sequences within a population and mRNAs and proteins encoded by such genes can vary due to polymorphisms such as single-nucleotide polymorphisms. The sequences provided herein are only exemplary sequences. Other sequences for the variant PNPLA3 and HSD17B13 genomic DNA, mRNA, cDNA, and polypeptide are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting a variant PNPLA3 nucleic acid molecule, preliminary processing designed to isolate or enrich the sample for the genomic DNA can be employed. A variety of techniques can be used for this purpose. When detecting the level of variant PNPLA3 mRNA, different techniques can be used enrich the biological sample with mRNA. Various methods to detect the presence or level of an mRNA or the presence of a particular variant genomic DNA locus can be used.

In some embodiments, the presence or absence of a particular PNPLA3 protein or HSD17B13 protein (e.g., functional or variant) is detected by sequencing at least a portion of the protein to determine whether the protein comprises an amino acid sequence encoding any of the variant PNPLA3 proteins or HSD17B13 proteins (e.g., functional or variant) described herein. In some embodiments, the presence or absence of a particular PNPLA3 protein or HSD17B13 protein (e.g., functional or variant) is detected by performing an immunoassay, such as an ELISA, to determine whether any of the variant PNPLA3 proteins or HSD17B13 proteins (e.g., functional or variant) described herein are present in the sample.

In some embodiments, the portion of the protein sequenced comprises from about 5 to about 100, from about 5 to about 50, from about 5 to about 40, from about 5 to about 30, from about 5 to about 20, or from about 5 to about 10 amino acids, and comprises the position corresponding to the position containing the variation (e.g., I148M of PNPLA3 or the portion of the variant HSD17B13 protein that is different from the corresponding wild type HSD17B13 protein). In some preferred embodiments, the portion of the protein sequenced comprises from about 5 to about 20, or from about 5 to about 10 amino acids, and comprises the position corresponding to the position containing the variation (e.g., I148M of PNPLA3 or the portion of the variant HSD17B13 protein that is different from the corresponding wild type HSD17B13 protein).

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various techniques (e.g., calorimetric, fluorescent, chemiluminescent, or radioactive) are suitable for use in the immunoassays.

In some embodiments, the presence or absence of a particular PNPLA3 nucleic acid molecule or HSD17B13 nucleic acid molecule (e.g., functional or variant genomic DNA, mRNA, cDNA, RNA transcript, or cDNA transcript) is detected by sequencing at least a portion of the nucleic acid molecule to determine whether the nucleic acid molecule comprises a nucleic acid sequence according to any of the variant PNPLA3 nucleic acid molecules or HSD17B13 nucleic acid molecules (e.g., functional or variant) described herein.

In some embodiments, the portion of the nucleic acid molecule sequenced comprises from about 10 to about 200, from about 10 to about 150, from about 10 to about 100, from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein). In some preferred embodiments, the portion of the nucleic acid molecule sequenced comprises from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein).

In some embodiments, the methods of detecting the presence or absence of any of the particular PNPLA3 nucleic acid molecules or HSD17B13 nucleic acid molecules (e.g., any of the functional or variant genomic DNA molecules, mRNA molecules, cDNA molecules, RNA transcripts, or cDNA transcripts) described herein in a subject, comprise: performing an assay on a biological sample obtained from the subject, which assay determines whether a nucleic acid molecule in the biological sample comprises any of the particular PNPLA3 nucleic acid molecules or HSD17B13 nucleic acid molecules (e.g., any of the functional or variant genomic DNA molecules, mRNA molecules, cDNA molecules, RNA transcripts, or cDNA transcripts) described herein. In some embodiments, the biological sample comprises a cell or cell lysate. Such methods can further comprise, for example, obtaining a biological sample from the subject, optionally reverse transcribing the mRNA into cDNA, and performing the assay. Such assays can comprise, for example, determining the identity of particular positions of the particular nucleic acid molecules described herein.

For example, the assay can comprise the use of alteration-specific probes or alteration-specific primers that comprise a nucleic acid sequence which is complementary to and/or hybridizes, or specifically hybridizes, to a portion of a PNPLA3 nucleic acid sequence that comprises a methionine at a position corresponding to position 148 according to SEQ ID NO:42, or comprises a methionine at a position corresponding to position 144 according to SEQ ID NO:43, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 genomic DNA that comprises an ATG codon at the positions corresponding to positions 5107 to 5109 according to SEQ ID NO:31, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 mRNA that comprises an AUG codon at the positions corresponding to positions 442 to 444 according to SEQ ID NO:34, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 mRNA that comprises an AUG codon at the positions corresponding to positions 430 to 432 according to SEQ ID NO:35, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 cDNA that comprises an ATG codon at the positions corresponding to positions 442 to 444 according to SEQ ID NO:38, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 cDNA that comprises an ATG codon at the positions corresponding to positions 430 to 432 according to SEQ ID NO:39, or a portion adjacent thereto.

In some embodiments, the assay can comprise the use of alteration-specific probes or alteration-specific primers that comprise a nucleic acid sequence which is complementary to and/or hybridizes, or specifically hybridizes, to the portion of the HSD17B13 genomic DNA that comprises an adenine at a position corresponding to position 12,667 according to SEQ ID NO:1, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the HSD17B13 genomic DNA that comprises a thymine at a position corresponding to position 12,667 according to SEQ ID NO:2, or a portion adjacent thereto.

In some embodiments, the assay comprises: sequencing at least a portion of the nucleic acid molecules described herein present in the biological sample from the subject, wherein the portion sequenced includes the positions disclosed herein. For example, the portion sequenced can be a portion of a PNPLA3 nucleic acid sequence that comprises a methionine at a position corresponding to position 148 according to SEQ ID NO:42, or comprises a methionine at a position corresponding to position 144 according to SEQ ID NO:43. In some embodiments, the portion sequenced can be portion of the variant PNPLA3 genomic DNA that comprises an ATG codon at the positions corresponding to positions 5107 to 5109 according to SEQ ID NO:31. In some embodiments, the portion sequenced can be a portion of the variant PNPLA3 mRNA that comprises an AUG codon at the positions corresponding to positions 442 to 444 according to SEQ ID NO:34. In some embodiments, the portion sequenced can be a portion of the variant PNPLA3 mRNA that comprises an AUG codon at the positions corresponding to positions 430 to 432 according to SEQ ID NO:35. In some embodiments, the portion sequenced can be a portion of the variant PNPLA3 cDNA that comprises an ATG codon at the positions corresponding to positions 442 to 444 according to SEQ ID NO:38. In some embodiments, the portion sequenced can be a portion of the variant PNPLA3 cDNA that comprises an ATG codon at the positions corresponding to positions 430 to 432 according to SEQ ID NO:39.

In some embodiments, the portion sequenced can be a portion of the HSD17B13 genomic DNA that comprises an adenine at a position corresponding to position 12,667 according to SEQ ID NO:1. In some embodiments, the portion sequenced can be a portion of the HSD17B13 genomic DNA that comprises a thymine at a position corresponding to position 12,667 according to SEQ ID NO:2.

In some embodiments, the assay comprises: a) contacting the biological sample with a primer (or alteration-specific primer) hybridizing to the regions adjacent to the portions of the nucleic acid molecules identified herein (e.g., adjacent to a portion of a PNPLA3 nucleic acid sequence that comprises a methionine at a position corresponding to position 148 according to SEQ ID NO:42, or comprises a methionine at a position corresponding to position 144 according to SEQ ID NO:43; adjacent to a portion of the variant PNPLA3 genomic DNA that comprises an ATG codon at the positions corresponding to positions 5107 to 5109 according to SEQ ID NO:31; adjacent to a portion of the variant PNPLA3 mRNA that comprises an AUG codon at the positions corresponding to positions 442 to 444 according to SEQ ID NO:34; adjacent to a portion of the variant PNPLA3 mRNA that comprises an AUG codon at the positions corresponding to positions 430 to 432 according to SEQ ID NO:35; adjacent to a portion of the variant PNPLA3 cDNA that comprises an ATG codon at the positions corresponding to positions 442 to 444 according to SEQ ID NO:38; adjacent to a portion of the variant PNPLA3 cDNA that comprises an ATG codon at the positions corresponding to positions 430 to 432 according to SEQ ID NO:39; adjacent to a portion of the HSD17B13 genomic DNA that comprises an adenine at a position corresponding to position 12,667 according to SEQ ID NO:1; or adjacent to a portion of the HSD17B13 genomic DNA that comprises a thymine at a position corresponding to position 12,667 according to SEQ ID NO:2); b) extending the primer at least through the position of the nucleic acid molecules corresponding to nucleotide positions beyond the altered site (e.g., the portion of a PNPLA3 nucleic acid sequence that comprises a methionine at a position corresponding to position 148 according to SEQ ID NO:42, or comprises a methionine at a position corresponding to position 144 according to SEQ ID NO:43; the portion of the variant PNPLA3 genomic DNA that comprises an ATG codon at the positions corresponding to positions 5107 to 5109 according to SEQ ID NO:31; the portion of the variant PNPLA3 mRNA that comprises an AUG codon at the positions corresponding to positions 442 to 444 according to SEQ ID NO:34; the portion of the variant PNPLA3 mRNA that comprises an AUG codon at the positions corresponding to positions 430 to 432 according to SEQ ID NO:35; the portion of the variant PNPLA3 cDNA that comprises an ATG codon at the positions corresponding to positions 442 to 444 according to SEQ ID NO:38; the portion of the variant PNPLA3 cDNA that comprises an ATG codon at the positions corresponding to positions 430 to 432 according to SEQ ID NO:39; the portion of the HSD17B13 genomic DNA that comprises an adenine at a position corresponding to position 12,667 according to SEQ ID NO:1; or the portion of the HSD17B13 genomic DNA that comprises a thymine at a position corresponding to position 12,667 according to SEQ ID NO:2); and c) determining whether the extension product of the primer comprises the nucleic acid sequence of any of the variant or wild type PNPLA3 or HSD17B13 nucleic acid molecules described herein.

In some embodiments, only PNPLA3 genomic DNA is analyzed. In some embodiments, only PNPLA3 mRNA is analyzed. In some embodiments, only PNPLA3 cDNA obtained from PNPLA3 mRNA is analyzed. In some embodiments, only HSD17B13 genomic DNA is analyzed. In some embodiments, only HSD17B13 mRNA is analyzed. In some embodiments, only HSD17B13 cDNA obtained from HSD17B13 mRNA is analyzed. In some embodiments, only HSD17B13 RNA transcripts is analyzed. In some embodiments, only HSD17B13 cDNA obtained from HSD17B13 RNA transcripts is analyzed.

In some embodiments, the assay comprises contacting the biological sample with a primer or probe that specifically hybridizes to any of the particular variant PNPLA3 nucleic acid molecules or variant HSD17B13 nucleic acid molecules (e.g., any of the variant genomic DNA molecules, mRNA molecules, cDNA molecules, RNA transcripts, or cDNA transcripts) described herein and not the corresponding functional nucleic acid molecules under stringent conditions, and determining whether hybridization has occurred.

In some embodiments, the assay comprises contacting the biological sample with a primer or probe that specifically hybridizes to any of the particular variant PNPLA3 nucleic acid molecules (e.g., any of the variant genomic DNA molecules, mRNA molecules, cDNA molecules, RNA transcripts, or cDNA transcripts) or nucleic acid molecules encoding a functional HSD17B13 protein (e.g., any of the genomic DNA molecules, mRNA molecules, cDNA molecules, RNA transcripts, or cDNA transcripts encoding a functional HSD17B13 protein) described herein and not to the corresponding nucleic acid molecules encoding wild type PNPLA3 or variant HSD17B13, respectively, under stringent conditions, and determining whether hybridization has occurred.

In some embodiments, the assay comprises RNA sequencing (RNA-Seq). In some embodiments, the assays also comprise reverse transcribing mRNA into cDNA via the reverse transcriptase polymerase chain reaction (RT-PCR).

Such probes and primers can hybridize specifically to a target sequence under high stringency hybridization conditions. Probes and primers may have complete nucleic acid sequence identity of contiguous nucleotides with the target sequence, although probes differing from the target nucleic acid sequence and that retain the ability to specifically detect and/or identify a target nucleic acid sequence may be designed by conventional methods. Accordingly, probes and primers can share at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity or complementarity to the target nucleic acid molecule.

When a probe is hybridized with a nucleic acid molecule in a biological sample under conditions that allow for the binding of the probe to the nucleic acid molecule, this binding can be detected and allow for an indication of the presence of the particular variant or wild type PNPLA3 or variant or functional HSD17B13 locus or the presence or the level of the particular variant or wild type PNPLA3 or variant or functional HSD17B13 mRNA or cDNA in the biological sample. Such identification of a bound probe has been described. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 gene. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 mRNA. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 cDNA.

In some embodiments, to determine whether a particular nucleic acid complement of a biological sample comprises a nucleic acid sequence encoding a particular functional or variant PNPLA3 protein or HSD17B13 protein, the biological sample may be subjected to a nucleic acid amplification method using a primer pair that includes a first primer derived from the 5' flanking sequence adjacent to positions encoding a site of interest (e.g., any of the positions described herein), and a second primer derived from the 3' flanking sequence adjacent to positions encoding the same site of interest, to produce an amplicon that is diagnostic for the presence of the particular functional or variant PNPLA3 protein or HSD17B13 protein. For example, with regard to PNPLA3 the amplicon may comprise a nucleotide sequence encoding the position which corresponds to position 148 according to SEQ ID NO: 42. With regard to HSD17B13 the amplicon may comprise a nucleotide sequence which corresponds to positions 5107 to 5109 according to SEQ ID NO: 31. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding the site of interest and at least 1, 2, 3, 4, 5, 6, 7, 8, 9, 10, or more nucleotides on each side of positions encoding the site of interest. Similar amplicons can be generated from the mRNA and/or cDNA sequences.

Representative methods for preparing and using probes and primers are described, for example, in *Molecular Cloning: A Laboratory Manual*, 2nd Ed., Vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990). PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using guidelines.

Any nucleic acid hybridization or amplification or sequencing method can be used to specifically detect the presence of the functional or variant PNPLA3 or HSD17B13 gene locus and/or the level of functional or variant PNPLA3 or HSD17B13 mRNA or cDNA produced from mRNA. In some embodiments, the nucleic acid molecule can be used either as a primer to amplify a region of the functional or variant PNPLA3 or HSD17B13 nucleic acid or the nucleic acid molecule can be used as a probe that specifically hybridizes, for example, under stringent conditions, to a nucleic acid molecule comprising the functional or variant PNPLA3 or HSD17B13 gene locus or a nucleic acid molecule comprising a functional or variant PNPLA3 or HSD17B13 mRNA or cDNA produced from mRNA.

A variety of techniques are available in the art including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example, Hybridization Protection Assay (HPA), quantitative evaluation of the amplification process in real-time, and determining the quantity of target sequence initially present in a sample, but which is not based on a real-time amplification.

Also provided are methods for identifying nucleic acids which do not necessarily require sequence amplification and are based on, for example, the methods of Southern (DNA: DNA) blot hybridizations, in situ hybridization (ISH), and fluorescence in situ hybridization (FISH) of chromosomal material. Southern blotting can be used to detect specific nucleic acid sequences. In such methods, nucleic acid that is extracted from a sample is fragmented, electrophoretically separated on a matrix gel, and transferred to a membrane filter. The filter bound nucleic acid is subject to hybridization with a labeled probe complementary to the sequence of interest. Hybridized probe bound to the filter is detected. In any such methods, the process can include hybridization using any of the probes described or exemplified herein.

In hybridization techniques, stringent conditions can be employed such that a probe or primer will specifically hybridize to its target. In some embodiments, a polynucleotide primer or probe under stringent conditions will hybridize to its target sequence (e.g., the functional or variant PNPLA3 or HSD17B13 locus, functional or variant PNPLA3 or HSD17B13 mRNA, or functional or variant PNPLA3 or HSD17B13 cDNA) to a detectably greater degree than to other sequences (e.g., the corresponding functional or variant PNPLA3 or HSD17B13 locus, functional or variant PNPLA3 or HSD17B13 mRNA, or functional or variant PNPLA3 or HSD17B13 cDNA), such as, at least 2-fold, at least 3-fold, at least 4-fold, or more over background, including over 10-fold over background. In some embodiments, a polynucleotide primer or probe under stringent conditions will hybridize to its target sequence to a detectably greater degree than to other sequences by at least 2-fold. In some embodiments, a polynucleotide primer or probe under stringent conditions will hybridize to its target sequence to a detectably greater degree than to other sequences by at least 3-fold. In some embodiments, a polynucleotide primer or probe under stringent conditions will hybridize to its target sequence to a detectably greater degree than to other sequences by at least 4-fold. In some embodiments, a polynucleotide primer or probe under stringent conditions will hybridize to its target sequence to a detectably greater degree than to other sequences by over 10-fold over background. Stringent conditions are sequence-dependent and will be different in different circumstances. By controlling the stringency of the hybridization and/or washing conditions, target sequences that are 100% complementary to the probe can be identified (homologous probing). Alternately, stringency conditions can be adjusted to allow some mismatching in sequences so that lower degrees of identity are detected (heterologous probing).

In some embodiments, the detecting step comprises: amplifying at least a portion of the nucleic acid molecule that encodes a site of interest (e.g., any of the positions described herein); labeling the nucleic acid molecule with a detectable label; contacting the labeled nucleic acid with a support comprising a probe, wherein the probe comprises a nucleic acid sequence which hybridizes under stringent conditions to a nucleic acid sequence encoding the a site of interest (e.g., any of the positions described herein); and detecting the detectable label.

In some embodiments, the detecting step comprises: amplifying at least a portion of the nucleic acid molecule that encodes a PNPLA3 or HSD17B13 protein, wherein the amplified nucleic acid molecule encodes an amino acid sequence which comprises a site of interest (e.g., any of the positions described herein); labeling the nucleic acid molecule with a detectable label; contacting the labeled nucleic acid with a support comprising a probe, wherein the probe comprises a nucleic acid sequence which hybridizes under stringent conditions to a nucleic acid sequence encoding a site of interest (e.g., any of the positions described herein); and detecting the detectable label. Any of the nucleic acid molecules disclosed herein can be amplified. For example, any of the genomic DNA, cDNA, or mRNA molecules disclosed herein can be amplified. In some embodiments, the nucleic acid molecule is mRNA and the method further comprises reverse-transcribing the mRNA into a cDNA prior to the amplifying step.

In some embodiments, the detecting step comprises: contacting the nucleic acid molecule that encodes a PNPLA3 or HSD17B13 protein with a probe comprising a detectable label, wherein the probe comprises a nucleic acid sequence which hybridizes under stringent conditions to a nucleic acid sequence encoding the variant PNPLA3 or HSD17B13 protein, and detecting the detectable label. In some embodiments, the detecting step comprises: contacting the nucleic acid molecule that encodes a PNPLA3 or HSD17B13 protein with a probe comprising a detectable label, wherein the probe comprises a nucleic acid sequence which hybridizes under stringent conditions to a nucleic acid sequence encoding a site of interest (e.g., any of the positions described herein), and detecting the detectable label. In some embodiments, the nucleic acid molecule is present within a cell obtained from the human subject, such that the detection is according to an in situ hybridization technique.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by detection of the presence and quantity of variant mRNA or cDNA in the biological sample.

In some embodiments, the detecting step comprises amplifying at least a portion of the nucleic acid molecule that encodes a particular PNPLA3 or HSD17B13 protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding the particular PNPLA3 or HSD17B13 protein, and detecting the detectable label. In some embodiments, the detecting step comprises amplifying at least a portion of the nucleic acid molecule that encodes a particular PNPLA3 or HSD17B13 protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding a site of interest (e.g., the portion of a PNPLA3 nucleic acid sequence that encodes a methionine at a position corresponding to position 148 according to SEQ ID NO:42, or encodes a methionine at a position corresponding to position 144 according to SEQ ID NO:43; the portion of the variant PNPLA3 genomic DNA that comprises an ATG codon at the positions corresponding to positions 5107 to 5109 according to SEQ ID NO:31; the portion of the variant PNPLA3 mRNA that comprises an AUG codon at the positions corresponding to positions 442 to 444 according to SEQ ID NO:34; the portion of the variant PNPLA3 mRNA that comprises an AUG codon at the positions corresponding to positions 430 to 432 according to SEQ ID NO:35; the portion of the variant PNPLA3 cDNA that comprises an ATG codon at the positions corresponding to positions 442 to 444 according to SEQ ID NO:38; the portion of the variant PNPLA3 cDNA that comprises an ATG codon at the positions corresponding to positions 430 to 432 according to SEQ ID NO:39; the portion of the HSD17B13 genomic DNA that comprises an adenine at a position corresponding to position 12,667 according to SEQ ID NO:1; or the portion of the HSD17B13 genomic DNA that comprises a thymine at a position corresponding to position 12,667 according to SEQ ID NO:2), and detecting the detectable label. If the nucleic acid includes mRNA, the method may further comprise reverse-transcribing the mRNA into a cDNA prior to the amplifying step. In some embodiments, the determining step comprises contacting the nucleic acid molecule that encodes a particular PNPLA3 or HSD17B13 protein with a probe comprising a detectable label and detecting the detectable label.

The disclosure provides methods for identifying a human subject as a candidate for treating or inhibiting a liver disease by inhibiting hydroxysteroid 17-beta dehydrogenase 13 (HSD17B13), the method comprising determining whether or not a sample from the subject comprises a first nucleic acid encoding a patatin like phospholipase domain containing 3 (PNPLA3) protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or both of the proteins are detected. In some embodiments, the subject is obese. In some embodiments, the subject has a fatty liver. In some embodiments, the first nucleic acid molecule comprises genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the first nucleic acid molecule comprises mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the first nucleic acid molecule comprises a cDNA obtained from mRNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, detecting the first nucleic acid comprises sequencing at least a portion of the first nucleic acid and the portion comprises the codon which encodes the I148M variation. In some embodiments, detecting the first nucleic acid comprises hybridizing the first nucleic acid with a probe or primer that specifically hybridizes to a portion of the first nucleic acid, wherein the portion comprises the codon encoding the I148M variation. In some embodiments, the probe or primer is an allele-specific probe or primer. In some embodiments, the probe or primer comprises a label. In some embodiments, the methods further comprise determining whether the subject is homozygous or heterozygous for the 1148M variation.

In some embodiments, the second nucleic acid comprises genomic DNA. In some embodiments, the genomic DNA comprises an adenine at a position corresponding to position 12,667 according to SEQ ID NO:1. In some embodiments, the genomic DNA comprises SEQ ID NO:1. In some embodiments, the second nucleic acid molecule comprises mRNA. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the second nucleic acid molecule comprises cDNA obtained from mRNA. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, detecting the second nucleic acid comprises sequencing the second nucleic acid. In some embodiments, detecting the second nucleic acid comprises hybridizing the second nucleic acid with a probe or primer that specifically hybridizes to the second nucleic acid. In some embodiments, the probe or primer is an allele-specific probe or primer. In some embodiments, the probe or primer comprises a label. In some embodiments, the methods further comprise determining whether the subject is homozygous or heterozygous for the second nucleic acid encoding a functional HSD17B13 protein in the sample.

The present disclosure provides methods of identifying a subject who is a candidate for HSD17B13 inhibition, the method comprising determining whether or not a sample from the subject comprises a nucleic acid encoding a PNPLA3 Ile148Met variant or PNPLA3 Ile144Met variant. The present disclosure also provides methods for identifying a human subject as a candidate for treating or inhibiting a liver disease by inhibiting HSD17B13, the method comprising determining whether or not a sample from the subject comprises a first nucleic acid encoding a PNPLA3 protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or when both proteins are detected.

The present disclosure also provides methods of classifying a subject who is a candidate for HSD17B13 inhibition, the method comprising determining whether or not a sample from the subject comprises a nucleic acid encoding a PNPLA3 Ile148Met variant or PNPLA3 Ile144Met variant. The present disclosure also provides methods for classifying a human subject as a candidate for treating or inhibiting a liver disease by inhibiting HSD17B13, the method comprising determining whether or not a sample from the subject comprises a first nucleic acid encoding a PNPLA3 protein comprising an I148M variation and a second nucleic acid encoding a functional HSD17B13 protein, and/or a PNPLA3 protein comprising an I148M variation and a functional HSD17B13 protein, and classifying the subject as a candidate for treating or inhibiting a liver disease by inhibiting HSD17B13 when both the first and second nucleic acids are detected and/or when both proteins are detected.

The variant PNPLA3 Ile148Met variant or PNPLA3 Ile144Met variant can be any of the variant PNPLA3 Ile148Met variants and PNPLA3 Ile144Met variants described herein. The variant PNPLA3 Ile148Met variant or PNPLA3 Ile144Met variant can be detected by any of the methods described herein. In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In preferred embodiments, the subject does not comprise any genes encoding loss of function variations in the HSD17B13 protein. It is believed that loss of function variations in the HSD17B13 protein, including those described or exemplified herein, confer a liver disease-protective effect and it is further believed that this protective effect is enhanced in the presence of the variant PNPLA3 Ile148M variation. Thus, it is believed that subjects (e.g., subjects comprising the 1148M variation in PNPLA3) in whom both copies of the genes (from each chromosome) encoding the HSD17B13 protein encode a loss of function variation are unlikely to benefit from HSD17B13 inhibition therapy. Nevertheless, it is believed that subjects who express at least a partially functional HSD17B13 protein will benefit from HSD17B13 inhibition therapy. Thus, the methods may comprise classifying the status of the gene (in one or both chromosomes) encoding HSD17B13, including whether the gene encodes a loss of function variation in the HSD17B13 protein, as well as whether the subject is homozygous or heterozygous.

In some embodiments, the methods further comprise detecting the presence of a nucleic acid molecule or gene encoding a functional HSD17B13 protein in a sample from the subject. The nucleic acid molecule can encode any of the functional HSD17B13 proteins described herein. The HSD17B13 nucleic acid molecule can be detected by any of the methods described herein. In some embodiments, the methods further comprise determining whether the subject is homozygous or heterozygous for a gene encoding a functional HSD17B13 protein. In some embodiments, the subject is homozygous for a gene encoding a functional HSD17B13 protein. In some embodiments, the subject is heterozygous for a gene encoding a functional HSD17B13.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A form for a solid-state substrate is a microtiter dish, such as a standard 96-well type. In some embodiments, a multi-well glass slide can be employed that normally contain one array per well. This feature allows for greater control of assay reproducibility, increased throughput and sample handling, and ease of automation. In some embodiments, the support is a microarray.

In some embodiments, the methods further comprises determining whether the subject is obese. In some embodiments, a subject is obese if their body mass index (BMI) is over 30 kg/m$^2$. Obesity is can be a characteristic of a subject having or at risk of developing a liver disease. In some embodiments, the methods further comprises determining whether the subject has a fatty liver. A fatty liver can be a characteristic of a subject having or at risk of developing a liver disease. In some embodiments, the methods further comprises determining whether the subject is obese and has a fatty liver.

In some embodiments, the methods further comprise administering an inhibitor of HSD17B13 to the subject. Methods of administering an inhibitor of HSD17B13 to the subject are described herein.

In some embodiments, the nucleic acid molecule encoding the variant PNPLA3 Ile148Met protein or PNPLA3 Ile144Met protein is any of the nucleic acid molecules described herein. In some embodiments, the nucleic acid molecule encoding the variant PNPLA3 Ile148Met protein or PNPLA3 Ile144Met protein is genomic DNA. In some embodiments, the genomic DNA encoding the variant PNPLA3 Ile148Met protein or PNPLA3 Ile144Met protein is any of the genomic DNA molecules described herein. In some embodiments, the nucleic acid molecule encoding the variant PNPLA3 Ile148Met protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein is detected by nucleic acid sequencing or hybridization of a probe, as described herein. In some embodiments, the genomic DNA encoding the variant PNPLA3 protein that comprises the ATG codon is detected by nucleic acid sequencing or hybridization of a probe, as described herein.

In some embodiments, the nucleic acid molecule encoding the variant PNPLA3 Ile148Met protein or PNPLA3 Ile144Met protein is mRNA. In some embodiments, the mRNA encoding the variant PNPLA3 Ile148Met protein or PNPLA3 Ile144Met protein is any of the mRNA molecules described herein. In some embodiments, the nucleic acid molecule encoding the variant PNPLA3 Ile148Met protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein is detected by nucleic acid sequencing or hybridization of a probe, as described herein. In some embodiments, the mRNA encoding the variant PNPLA3 protein that comprises the AUG codon is identified by nucleic acid sequencing or hybridization of a probe, as described herein.

In some embodiments, the nucleic acid molecule encoding the variant PNPLA3 Ile148Met protein or PNPLA3 Ile144Met protein is cDNA. In some embodiments, the cDNA encoding the variant PNPLA3 Ile148Met protein or PNPLA3 Ile144Met protein is any of the cDNA molecules described herein. In some embodiments, the nucleic acid molecule encoding a PNPLA3 Ile148Met protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein is identified by nucleic acid sequencing or hybridization of a probe. In some embodiments, the cDNA encoding the variant PNPLA3 protein that comprises the ATG codon is identified by nucleic acid sequencing or hybridization of a probe, as described herein.

In some embodiments, the nucleic acid molecule encoding the functional HSD17B13 protein is any of the nucleic acid molecules described herein. In some embodiments, the nucleic acid molecule encoding the functional HSD17B13 protein is genomic DNA. In some embodiments, the genomic DNA encoding the functional HSD17B13 protein is any of the genomic DNA molecules described herein. In some embodiments, the genomic DNA comprises an adenine at a position corresponding to position 12,667 according to SEQ ID NO:1. In some embodiments, the genomic DNA comprises SEQ ID NO:1. In some embodiments, the presence of the functional HSD17B13 genomic DNA is determined by nucleic acid sequencing or hybridization of a probe, as described herein.

In some embodiments, the nucleic acid molecule encoding the functional HSD17B13 protein is mRNA. In some embodiments, the mRNA encoding the functional HSD17B13 protein is any of the mRNA molecules described herein. In some embodiments, the functional HSD17B13 nucleic acid molecule is mRNA. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the presence of the functional HSD17B13 mRNA is determined by nucleic acid sequencing or hybridization of a probe, as described herein.

In some embodiments, the nucleic acid molecule encoding the functional HSD17B13 protein is cDNA. In some embodiments, the cDNA encoding the functional HSD17B13 protein is any of the cDNA molecules described herein. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, the presence of the functional HSD17B13 cDNA is determined by nucleic acid sequencing or hybridization of a probe, as described herein.

In some embodiments, the methods further comprising obtaining the sample from the subject. In some embodiments, the subject who is a candidate for HSD17B13 inhibition has a liver disease or is susceptible to developing a liver disease. In some embodiments, the liver disease is a chronic liver disease. In some preferred embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some preferred embodiments, the chronic liver disease is nonalcoholic fatty liver disease (NAFLD), alcoholic liver disease (ALD), non-alcoholic steatohepatitis (NASH), cirrhosis, or steatosis. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods of detecting a PNPLA3 Ile148Met variant, or a PNPLA3 Ile144Met variant, and functional HSD17B13 in a subject comprising: detecting the presence of a PNPLA3 Ile148Met protein, or a nucleic acid molecule encoding a PNPLA3 Ile148Met protein, in a sample from the subject, or detecting the presence of a PNPLA3 Ile144Met protein, or a nucleic acid molecule encoding a PNPLA3 Ile144Met protein, in a sample from the subject; and detecting the presence of a functional HSD17B13 protein, or a nucleic acid molecule encoding a functional HSD17B13 protein, in a sample from the subject. The variant PNPLA3 Ile148Met variant protein or nucleic acid molecule can be any of the variant PNPLA3 Ile148Met variant proteins or nucleic acid molecules described herein. The variant PNPLA3 Ile144Met variant protein or nucleic acid molecule can be any of the variant PNPLA3 Ile144Met variant proteins or nucleic acid molecules described herein. The functional HSD17B13 protein or nucleic acid molecule can be any of the functional HSD17B13 proteins or nucleic acid molecules described herein.

In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In some embodiments, the methods further comprise determining whether the subject is homozygous or heterozygous for functional HSD17B13. In some embodiments, the subject is homozygous for functional HSD17B13. In some embodiments, the subject is heterozygous for functional HSD17B13.

In some embodiments, the presence of a functional HSD17B13 protein is detected in the sample. The functional HSD17B13 protein can be any of the functional HSD17B13 proteins described herein. In some embodiments, the functional HSD17B13 protein comprises an amino acid sequence according to SEQ ID NO:21, SEQ ID NO:22, SEQ ID NO:25, or SEQ ID NO:29. In some embodiments, the functional HSD17B13 protein is detected by amino acid sequencing or immunoassay, as described herein.

In some embodiments, the presence of a functional HSD17B13 nucleic acid molecule is detected in the sample. The functional HSD17B13 nucleic acid molecule can be any of the functional HSD17B13 nucleic acid molecules described herein. In some embodiments, the functional HSD17B13 nucleic acid molecule is genomic DNA. The functional HSD17B13 genomic DNA molecule can be any of the functional HSD17B13 genomic DNA molecules described herein. In some embodiments, the genomic DNA comprises an adenine at a position corresponding to position 12,667 according to SEQ ID NO:1. In some embodiments, the genomic DNA comprises SEQ ID NO:1. In some embodiments, the genomic DNA is detected by nucleic acid sequencing or hybridization of a probe, as described herein.

In some embodiments, the functional HSD17B13 nucleic acid molecule is mRNA. The functional HSD17B13 mRNA molecule can be any of the functional HSD17B13 mRNA molecules described herein. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the mRNA is detected by nucleic acid sequencing or hybridization of a probe, as described herein.

In some embodiments, the functional HSD17B13 nucleic acid molecule is cDNA. The functional HSD17B13 cDNA molecule can be any of the functional HSD17B13 cDNA molecules described herein. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, the cDNA is detected by nucleic acid sequencing or hybridization of a probe, as described herein.

In some embodiments, the presence of a PNPLA3 Ile148Met protein or PNPLA3 Ile144Met protein is detected in the sample. The variant PNPLA3 Ile148Met protein or PNPLA3 Ile144Met protein can be any of the variant PNPLA3 Ile148Met proteins or PNPLA3 Ile144Met proteins described herein. In some embodiments, the variant PNPLA3 Ile148Met protein comprises a methionine at a position corresponding to position 148 according to SEQ ID NO:42, or comprises a methionine at a position corresponding to position 144 according to SEQ ID NO:43. In some embodiments, the variant PNPLA3 Ile148Met protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 Ile148Met protein comprises a methionine at a position corresponding to position 144 according to SEQ ID NO:43. In some embodiments, the variant PNPLA3 protein in the sample comprises the amino acid sequence according to SEQ ID NO:43. In some embodiments, the variant PNPLA3 Ile148Met protein or PNPLA3 Ile144Met protein is detected by amino acid sequencing or immunoassay, as described herein.

In some embodiments, the presence of a nucleic acid molecule encoding a PNPLA3 Ile148Met protein or PNPLA3 Ile148Met protein is detected in the sample. The nucleic acid molecule encoding a PNPLA3 Ile148Met protein or PNPLA3 Ile148Met protein can be any of the nucleic acid molecules encoding a PNPLA3 Ile148Met protein or PNPLA3 Ile148Met protein described herein.

In some embodiments, the nucleic acid molecule encoding a PNPLA3 Ile148Met protein or PNPLA3 Ile144Met protein is genomic DNA. The genomic DNA encoding a PNPLA3 Ile148Met protein or PNPLA3 Ile144Met protein can be any of the genomic DNA molecules described herein. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is detected by nucleic acid sequencing or hybridization of a probe, as described herein.

In some embodiments, the nucleic acid molecule encoding a PNPLA3 Ile148Met protein or PNPLA3 Ile148Met protein is mRNA. The mRNA molecule encoding a PNPLA3 Ile148Met protein or PNPLA3 Ile148Met protein can be any of the mRNA molecules described herein. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, nucleic acid molecule encoding a PNPLA3 Ile148Met protein or PNPLA3 Ile144Met protein is cDNA. The cDNA encoding a PNPLA3 Ile148Met protein or PNPLA3 Ile144Met protein can be any of the cDNA molecules described herein. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

In some embodiments, the method further comprises obtaining the sample from the subject.

The present disclosure also provides methods of identifying a subject having a protective effect against liver disease, comprising: detecting the presence of a PNPLA3 Ile148Met variant or PNPLA3 Ile144Met variant in a sample from the subject; and detecting the presence of an HSD17B13 loss-of-function variant in a sample from the subject. The present disclosure also provides methods of classifying a subject having a protective effect against liver disease, comprising: detecting the presence of a PNPLA3 Ile148Met variant or PNPLA3 Ile144Met variant in a sample from the subject; and detecting the presence of an HSD17B13 loss-of-function variant in a sample from the subject. The variant PNPLA3 Ile148Met variant and PNPLA3 Ile144Met variant can be any of the variant PNPLA3 Ile148Met variants and PNPLA3 Ile144Met variants described herein. The HSD17B13 loss-of-function variant can be any of the HSD17B13 loss-of-function variants described herein.

In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In some embodiments, the methods further comprise determining whether the subject is homozygous or heterozygous for functional HSD17B13. In some embodiments, the subject is homozygous for functional HSD17B13. In some embodiments, the subject is heterozygous for functional HSD17B13.

In some embodiments, the variant PNPLA3 Ile148Met variant or PNPLA3 Ile144Met variant is detected in the subject by detecting a PNPLA3 Ile148Met protein, or a nucleic acid molecule encoding a PNPLA3 Ile148Met protein, in a sample from the subject, or detecting a PNPLA3 Ile144Met protein, or a nucleic acid molecule encoding a PNPLA3 Ile144Met protein, in a sample from the subject; and the HSD17B13 loss-of-function is detected in the subject by detecting an HSD17B13 loss-of-function variant protein, or a nucleic acid molecule encoding an HSD17B13 loss-of-function variant protein, in a sample from the subject. In some embodiments, the variant PNPLA3 Ile148Met variant or PNPLA3 Ile144Met variant is detected in the subject by detecting a PNPLA3 Ile148Met protein, or a nucleic acid molecule encoding a PNPLA3 Ile148Met protein, in a sample from the subject; and the HSD17B13 loss-of-function is detected in the subject by detecting an HSD17B13 loss-of-function variant protein, or a nucleic acid molecule encoding an HSD17B13 loss-of-function variant protein, in a sample from the subject.

In some embodiments, the presence of a PNPLA3 Ile148Met protein or PNPLA3 Ile144Met protein is detected in the sample. The variant PNPLA3 Ile148Met protein and PNPLA3 Ile144Met protein can be any of the variant PNPLA3 Ile148Met proteins and PNPLA3 Ile144Met proteins described herein. In some embodiments, the variant PNPLA3 Ile148Met protein comprises a methionine at a position corresponding to position 148 according to SEQ ID NO:42, or comprises a methionine at a position corresponding to position 144 according to SEQ ID NO:43. In some embodiments, the variant PNPLA3 Ile148Met protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 Ile148Met protein comprises a methionine at a position corresponding to position 144 according to SEQ ID NO:43. In some embodiments, the variant PNPLA3 protein in the sample comprises the amino acid sequence according to SEQ ID NO:43. In some embodiments, the variant PNPLA3 Ile148Met protein is detected by amino acid sequencing or immunoassay, as described herein.

In some embodiments, the presence of a nucleic acid molecule encoding a PNPLA3 Ile148Met protein or PNPLA3 Ile144Met protein is detected in the sample. The nucleic acid molecule encoding the variant PNPLA3 Ile148Met protein or PNPLA3 Ile144Met protein can be any of the nucleic acid molecules encoding the variant PNPLA3 Ile148Met proteins and PNPLA3 Ile144Met proteins described herein.

In some embodiments, wherein the nucleic acid molecule encoding a PNPLA3 Ile148Met protein or PNPLA3 Ile144Met protein is genomic DNA. The genomic DNA encoding the variant PNPLA3 Ile148Met protein or PNPLA3 Ile144Met protein can be any of the variant PNPLA3 Ile148Met proteins and PNPLA3 Ile144Met proteins described herein. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is detected by nucleic acid sequencing or hybridization of a probe.

In some embodiments, the nucleic acid molecule encoding the variant PNPLA3 Ile148Met protein or PNPLA3 Ile144Met protein is mRNA. The mRNA molecule encoding the variant PNPLA3 Ile148Met proteins and PNPLA3 Ile144Met proteins can be any of the variant PNPLA3 Ile148Met proteins and PNPLA3 Ile144Met proteins described herein. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, the nucleic acid molecule encoding a PNPLA3 Ile148Met protein or PNPLA3 Ile148Met protein is cDNA. The cDNA encoding the variant PNPLA3 Ile148Met protein and PNPLA3 Ile148Met protein can be any of the variant PNPLA3 Ile148Met proteins and PNPLA3 Ile148Met proteins described herein. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

In some embodiments, the presence of an HSD17B13 loss-of-function variant protein is detected in the sample. The HSD17B13 loss-of-function variant can be any of the HSD17B13 loss-of-function variant proteins described herein. In some embodiments, the HSD17B13 loss-of-function variant protein comprises an amino acid sequence according to SEQ ID NO:23. In some embodiments, the HSD17B13 loss-of-function variant protein comprises an amino acid sequence according to SEQ ID NO:24. In some embodiments, the HSD17B13 loss-of-function variant protein comprises an amino acid sequence according to SEQ ID NO:26. In some embodiments, the HSD17B13 loss-of-function variant protein comprises an amino acid sequence according to SEQ ID NO:27. In some embodiments, the HSD17B13 loss-of-function variant protein comprises an amino acid sequence according to SEQ ID NO:28. In some embodiments, the HSD17B13 loss-of-function variant protein is detected by amino acid sequencing or immunoassay, as described herein.

In some embodiments, the presence of a nucleic acid molecule encoding an HSD17B13 loss-of-function variant protein is detected in the sample. The nucleic acid molecule encoding an HSD17B13 loss-of-function variant protein can be any of the nucleic acid molecules encoding the HSD17B13 loss-of-function variant protein described herein.

In some embodiments, the nucleic acid molecule encoding the HSD17B13 loss-of-function variant protein is genomic DNA. The genomic DNA molecule encoding the HSD17B13 loss-of-function variant protein can be any of the HSD17B13 loss-of-function variant proteins described herein. In some embodiments, the genomic DNA encoding an HSD17B13 loss-of-function variant protein which comprises a thymine at a position corresponding to position 12,667 according to SEQ ID NO:2. In some embodiments, the genomic DNA encoding an HSD17B13 loss-of-function variant protein comprises SEQ ID NO:2. In some embodiments, the genomic DNA encoding the HSD17B13 loss-of-function variant protein is detected by nucleic acid sequencing or hybridization of a probe, as described herein.

In some embodiments, the nucleic acid molecule encoding the HSD17B13 loss-of-function variant protein is mRNA. The mRNA molecule encoding the HSD17B13 loss-of-function variant protein can be any of the mRNA molecules encoding the HSD17B13 loss-of-function variant proteins described herein. In some embodiments, the mRNA encoding an HSD17B13 loss-of-function variant protein comprises SEQ ID NO:5. In some embodiments, the mRNA encoding an HSD17B13 loss-of-function variant protein comprises SEQ ID NO:6. In some embodiments, the mRNA encoding an HSD17B13 loss-of-function variant protein comprises SEQ ID NO:8. In some embodiments, the mRNA encoding an HSD17B13 loss-of-function variant protein comprises SEQ ID NO:9. In some embodiments, the mRNA encoding an HSD17B13 loss-of-function variant protein comprises SEQ ID NO:10. In some embodiments, the mRNA encoding the HSD17B13 loss-of-function variant protein is detected by nucleic acid sequencing or hybridization of a probe, as described herein.

In some embodiments, the nucleic acid molecule encoding the HSD17B13 loss-of-function variant protein is cDNA. The cDNA molecules encoding the HSD17B13 loss-of-function variant protein can be any of the cDNA molecules encoding the HSD17B13 loss-of-function variant protein described herein. In some embodiments, the cDNA encoding an HSD17B13 loss-of-function variant protein comprises SEQ ID NO:5. In some embodiments, the cDNA encoding an HSD17B13 loss-of-function variant protein comprises SEQ ID NO:6. In some embodiments, the cDNA encoding an HSD17B13 loss-of-function variant protein comprises SEQ ID NO:8. In some embodiments, the cDNA encoding an HSD17B13 loss-of-function variant protein comprises SEQ ID NO:9. In some embodiments, the cDNA encoding an HSD17B13 loss-of-function variant protein comprises SEQ ID NO:10. In some embodiments, the cDNA encoding the HSD17B13 loss-of-function variant protein is detected by nucleic acid sequencing or hybridization of a probe, as described herein.

In some embodiments, the methods further comprises obtaining the sample from the subject. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides any of the methods described herein further comprising administering to the subject an inhibitor of HSD17B13. In some embodiments, the inhibitor of HSD17B13 comprises a functional polypeptide, an antisense DNA, RNA, an siRNA, or an shRNA that hybridizes to the endogenous HSD17B13 genomic DNA or mRNA and decreases expression of HSD17B13 polypeptide in a cell in the subject. In some embodiments, the HSD17B13 inhibitor can also inhibit one or more additional members of the short-chain dehydrogenases/reductases (SDR) family, of which HSD17B13 is a member. Such other members include, but are not limited to, HSD17B1, HSD17B2, HSD17B3, HSD17B4, HSD17B6, HSD17B7, HSD17B8, HSD17B10, HSD17B11, HSD17B12, HSD17B13, HSD17B14, HSD11B1, HSD11B2, HSD3B1, HSD3B2, and HSD3B7, as well as close homologs dehydrogenase/reductase 3 (DHRS3) and retinol dehydrogenase 10 (RDH10). In some embodiments, the inhibitor of HSD17B13 is administered to inhibit liver disease in the subject. In some embodiments, the inhibitor of HSD17B13 is administered to treat liver disease in the subject. In some embodiments, the liver disease is a chronic liver disease. In some embodiments, the chronic liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the subject is homozygous for the gene encoding the I148M variation. In some embodiments, the subject is heterozygous for the gene encoding the I148M variation. In some embodiments, the subject further is homozygous for the gene encoding the functional HSD17B13 protein. In some embodiments, the subject further is heterozygous for the gene encoding the functional HSD17B13 protein and a gene encoding a loss of function variant of HSD17B13.

The disclosure also provides methods of treating or inhibiting liver disease, comprising administering an inhibitor of hydroxysteroid 17-beta dehydrogenase 13 (HSD17B13) to a human liver disease patient expressing a patatin like phospholipase domain containing 3 (PNPLA3) protein comprising an I148M variation such that liver disease is treated or inhibited in the patient. In some embodiments, the liver disease is a chronic liver disease. In some embodiments, the liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the patient is obese. In some embodiments, the patient has a fatty liver. In some embodiments, the patient has been determined to express the variant PNPLA3 protein (e.g., a PNPLA3 protein comprising the I148M or I144M variation) by detection of the variant PNPLA3 protein in a sample from the subject. In some embodiments, the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 protein is detected by amino acid sequencing or by an immunoassay. In some embodiments, the subject has been determined to express the variant PNPLA3 protein by detection of a nucleic acid molecule encoding the variant PNPLA3 protein (e.g., a variant PNPLA3 nucleic acid molecule encoding a PNPLA3 protein comprising the I148M or I144M variation) in a sample from the subject. In some embodiments, the variant PNPLA3 protein comprises a methionine at a position corresponding to position 148 according to SEQ ID NO:42. In some embodiments, the variant PNPLA3 protein comprises the amino acid sequence according to SEQ ID NO:42. In some embodiments, the nucleic acid molecule encoding the variant PNPLA3 protein comprises genomic DNA, mRNA, or cDNA obtained from mRNA. In some embodiments, the nucleic acid molecule comprises genomic DNA comprising an ATG codon at the positions corresponding to positions 5107 to 5109 according to SEQ ID NO:31. In some embodiments, the genomic DNA comprises the nucleotide sequence according to SEQ ID NO:31. In some embodiments, the nucleic acid molecule comprises mRNA comprising an AUG codon at the positions corresponding to positions 442 to 444 according to SEQ ID NO:34. In some embodiments, the mRNA comprises the nucleotide sequence according to SEQ ID NO:34. In some embodiments, the nucleic acid molecule comprises mRNA comprising an AUG codon at the positions corresponding to positions 430 to 432 according to SEQ ID NO:35. In some embodiments, the mRNA comprises the nucleotide sequence according to SEQ ID NO:35. In some embodiments, the nucleic acid molecule comprises cDNA obtained from mRNA, the cDNA comprising an ATG codon at the positions corresponding to positions 442 to 444 according to SEQ ID NO:38. In some embodiments, the cDNA comprises the nucleotide sequence according to SEQ ID NO:38. In some embodiments, the nucleic acid molecule comprises cDNA obtained from mRNA, the cDNA comprising an ATG codon at the positions corresponding to positions 430 to 432 according to SEQ ID NO:39. In some embodiments, the cDNA comprises the nucleotide sequence according to SEQ ID NO:39. In some embodiments, the nucleic acid is detected by sequencing at least a portion of the nucleic acid, the portion encoding the I148M variation. In some embodiments, the nucleic acid is detected by hybridization of a probe or primer that specifically hybridizes to a portion of the nucleic acid, wherein the portion comprises the codon encoding the I148M variation. In some embodiments, the probe or primer is an allele-specific probe or primer. In some embodiments, the probe or primer comprises a label. In some embodiments, the patient is homozygous for a gene encoding the variant PNPLA3 protein. In some embodiments, the patient is heterozygous for a gene encoding the variant PNPLA3 protein. In some embodiments, patient is homozygous for a gene encoding a functional HSD17B13 protein. In some embodiments, the patient is heterozygous for a gene encoding a functional HSD17B13 protein. In some embodiments, the patient is heterozygous for the gene encoding the functional HSD17B13 protein and a gene encoding a loss of function variant of HSD17B13.

Inhibitors of HSD17B13 can be used as described herein for treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether or not the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the method as defined herein. In some embodiments, the variant PNPLA3 protein comprises a methionine at the position corresponding to position 148 according to SEQ ID NO:42. In some embodiments, the variant PNPLA3 protein comprises the amino acid sequence according to SEQ ID NO:42, or an amino acid sequence having at least 90% sequence identity to SEQ ID NO:42 and comprising the I148M variation. In some embodiments, the variant PNPLA3 protein comprises a methionine at the position corresponding to position 144 according to SEQ ID NO:43. In some embodiments, the variant PNPLA3 protein comprises the amino acid sequence according to SEQ ID NO:43, or an amino acid sequence having at least 90% sequence identity to SEQ ID NO:43 and comprising the I144M variation. In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34, or a nucleotide sequence having at least 90% sequence identity to SEQ ID NO:34 and encoding a PNPLA3 protein which comprises the I148M variation. In some embodiments, the mRNA comprises an AUG codon at the positions corresponding to positions 430 to 432 according to SEQ ID NO:35. In some embodiments, the mRNA comprises the nucleotide sequence according to SEQ ID NO:35, or a nucleotide sequence having at least 90% sequence identity to SEQ ID NO:35 and encoding a PNPLA3 protein which comprises the I144M variation. In some embodiments, the nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38, or a nucleotide sequence having at least 90% sequence identity to SEQ ID NO:38 and encoding a PNPLA3 protein which comprises the I148M variation. In some embodiments, the cDNA comprises an ATG codon at the positions corresponding to positions 430 to 432 according to SEQ ID NO:39. In some embodiments, the cDNA comprises the nucleotide sequence according to SEQ ID NO:39, or a nucleotide sequence having at least 90% sequence identity to SEQ ID NO:39 and encoding a PNPLA3 protein which comprises the I144M variation. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or nonalcoholic steatohepatitis (NASH). In some embodiments, the non-alcoholic liver disease comprises one or more of cirrhosis, steatosis, or hepatocellular carcinoma not caused by alcohol consumption. In some embodiments, the human subject is homozygous or heterozygous for functional HSD17B13.

In some embodiments, inhibitors of HSD17B13 reduce or inhibit HSD17B13 gene expression or the function of HSD17B13 protein. Inhibitors of HSD17B13 include, but are not limited to, naturally occurring and synthetic ligands, antagonists, agonists, antibodies, peptides, cyclic peptides, nucleic acids, functional polynucleotides, small organic molecules, and the like. Functional polynucleotides are nucleic acid molecules that have a specific function, such as binding a target molecule or catalyzing a specific reaction. Examples of functional polynucleotides include, but are not limited to, antisense molecules, aptamers, ribozymes, and triplex forming molecules. The functional polynucleotides can act as inhibitors of a specific activity possessed by a target molecule. Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant (kd) less than or equal to about 10-6, less than or equal to about 10-8, less than or equal to about 10-10, or less than or equal to about 10-12. A representative sample of methods and techniques which aid in the design and use of antisense molecules, and antisense molecules, can be found in the following non-limiting list of U.S. Patents and applications: U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; 6,057,437; and U.S. Ser. No. 62/645,941 filed Mar. 21, 2018, each of which is incorporated herein by reference in its entirety. Examples of antisense molecules include, but are not limited to, antisense RNAs, small interfering RNAs (siRNAs), and short hairpin RNAs (shRNAs). For example, the antisense RNAs, siRNAs, or shRNAs can be designed to target a region unique of the HSD17B13 genomic DNA or mRNA. In some embodiments, the inhibitor of HSD17B13 is an antisense molecule. In some embodiments, the inhibitor of HSD17B13 is an shRNA molecule. In some embodiments, the inhibitor of HSD17B13 is an siRNA molecule.

In any of the methods described herein, administration of an inhibitor of HSD17B13 can result in the reduction or elimination of particular characteristics of liver disease. In some embodiments, the characteristics of liver disease include, but are not limited to inflammation and fibrosis.

The present disclosure also provides methods of treating a subject who is PNPLA3 Ile148Met positive (i.e., "PNPLA3 Ile148Met+") or PNPLA3 Ile144Met positive (i.e., "PNPLA3 Ile144Met+"), comprising administering an inhibitor of HSD17B13 to the subject. The present disclosure also provides methods of treating or inhibiting liver disease comprising administering an inhibitor of HSD17B13 to a human liver disease patient expressing a PNPLA3 protein comprising an I148M variation such that liver disease is treated or inhibited in the patient.

The variant PNPLA3 Ile148Met positive or PNPLA3 Ile144Met positive subject can have any of the variant PNPLA3 proteins described herein. In some embodiments, the subject is also homozygous or heterozygous for functional HSD17B13. In some embodiments, the subject is homozygous for functional HSD17B13. In some embodiments, the subject is heterozygous for functional HSD17B13. In some embodiments, the subject is homozygous for the HSD17B13 loss-of-function variant. The subject can have any of the functional HSD17B13 proteins described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a PNPLA3 protein in a sample from the subject, wherein the variant PNPLA3 protein comprises a methionine at a position corresponding to position 148 according to SEQ ID NO:42, or comprises a methionine at a position corresponding to position 144 according to SEQ ID NO:43. The variant PNPLA3 Ile148Met positive or PNPLA3 Ile144Met positive subject can have any of the variant PNPLA3 proteins described herein.

In some embodiments, the subject who is PNPLA3 Ile148Met+ has been determined to be PNPLA3 Ile148Met+ by detection of a PNPLA3 protein in a sample from the subject, wherein the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42.

In some embodiments, the subject who is PNPLA3 Ile144Met+ has been determined to be PNPLA3 Ile144Met+ by detection of a PNPLA3 protein in a sample from the subject, wherein the variant PNPLA3 protein comprises a methionine at a position corresponding to position 144 according to SEQ ID NO:43. In some embodiments, the variant PNPLA3 protein in the sample comprises the amino acid sequence according to SEQ ID NO:43.

In some embodiments, the variant PNPLA3 protein that comprises the methionine at the position corresponding to position 148 according to SEQ ID NO:42, or that comprises the methionine at the position corresponding to position 144 according to SEQ ID NO:43 is identified by amino acid sequencing or immunoassay as described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a nucleic acid molecule encoding a PNPLA3 protein in a sample from the subject, wherein the variant PNPLA3 protein comprises a methionine at a position corresponding to position 148 according to SEQ ID NO:42, or comprises a methionine at a position corresponding to position 144 according to SEQ ID NO:43. The variant PNPLA3 Ile148Met positive or PNPLA3 Ile144Met positive subject can have any of the variant PNPLA3 nucleic acid molecules described herein.

In some embodiments, the subject who is PNPLA3 Ile148Met+ has been determined to be PNPLA3 Ile148Met+ by detection of a nucleic acid molecule encoding a PNPLA3 protein in a sample from the subject, wherein the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42.

In some embodiments, the subject who is PNPLA3 Ile144Met+ has been determined to be PNPLA3 Ile144Met+ by detection of a nucleic acid molecule encoding PNPLA3 protein in a sample from the subject, wherein the variant PNPLA3 protein comprises a methionine at a position corresponding to position 144 according to SEQ ID NO:43. In some embodiments, the variant PNPLA3 protein in the sample comprises the amino acid sequence according to SEQ ID NO:43.

In some embodiments, the nucleic acid molecule encoding the variant PNPLA3 protein is genomic DNA, mRNA, or cDNA derived from mRNA.

In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is identified by nucleic acid sequencing or hybridization of a probe, as described herein.

In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

Administration of the inhibitor of HSD17B13 can be by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In some embodiments, the subject has a liver disease or is susceptible to developing a liver disease. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods for treating a patient with a liver disease therapeutic agent, wherein the patient is suffering from a liver disease. The methods comprise determining whether or not a sample from the subject comprises: i) a first nucleic acid encoding a PNPLA3 protein comprising an I148M variation and a second nucleic acid encoding a functional HSD17B13 protein, and/or ii) a PNPLA3 protein comprising an I148M variation and a functional HSD17B13 protein. In some embodiments, the methods comprise determining whether or not a sample from the subject comprises a first nucleic acid encoding a PNPLA3 protein comprising an I148M variation and a second nucleic acid encoding a functional HSD17B13 protein. In some embodiments, the methods comprise determining whether or not a sample from the subject comprises a PNPLA3 protein comprising an I148M variation and a functional HSD17B13 protein.

In some embodiments, this determination is carried out by obtaining or having obtained a biological sample from the patient. In some embodiments, the methods further comprise performing or having performed a genotyping assay on the biological sample to determine if the patient has a first nucleic acid encoding a PNPLA3 protein comprising an I148M variation and a second nucleic acid encoding a functional HSD17B13 protein. In some embodiments, the methods further comprise performing or having performed an assay on the biological sample to determine if the patient has a PNPLA3 protein comprising an I148M variation and a functional HSD17B13 protein.

In some embodiments, when the patient has a nucleic acid encoding a PNPLA3 protein comprising an I148M variation and/or has a PNPLA3 protein comprising an I148M variation, and has a nucleic acid encoding a functional HSD17B13 protein and/or has a functional HSD17B13 protein, then the method further comprises administering an inhibitor of HSD17B13 to the patient. In some embodiments, when the patient has a nucleic acid encoding a PNPLA3 protein comprising an I148M variation and/or has a PNPLA3 protein comprising an I148M variation, and has a nucleic acid encoding a functional HSD17B13 protein and/or has a functional HSD17B13 protein, then the method further comprises administering an inhibitor of HSD17B13 to the patient and administering a liver disease therapeutic agent to the patient. In some embodiments, when the patient has a nucleic acid encoding a PNPLA3 protein comprising an I148M variation and/or has a PNPLA3 protein comprising an I148M variation, but does not have a nucleic acid encoding a functional HSD17B13 protein and/or has a functional HSD17B13 protein, then the method further comprises administering a liver disease therapeutic agent to the patient.

Examples of liver disease therapeutic agents include, but are not limited to, Disulfiram, Naltrexone, Acamprosate, Prednisone, Prednisone, Azathioprine, Penicillamine, Trientine, Deferoxamine, Ciprofloxacin, Norofloxacin, Ceftriaxone, Ofloxacin, Amoxicillin-clavulanate, Phytonadione, Bumetanide, Furosemide, Hydrochlorothiazide, Chlorothiazide, Amiloride, Triamterene, Spironolactone, Octreotide, Atenolol, Metoprolol, Nadolol, Propranolol, Timolol, and Carvedilol.

Additional examples of liver disease therapeutic agents (e.g., for use in chronic hepatitis C treatment) include, but are not limited to, ribavirin, paritaprevir, simeprevir (Olysio), grazoprevir, ledipasvir, ombitasvir, elbasvir, daclatasvir (Daklinza), dasabuvir, ritonavir, sofosbuvir, velpatasvir, voxilaprevir, glecaprevir, pibrentasvir, peginterferon alfa-2a, peginterferon alfa-2b, and interferon alfa-2b.

Additional examples of liver disease therapeutic agents (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; antioxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA). Other suitable treatments include ACE inhibitors/ARBs, oligofructose, and Incretin analogs.

Additional examples of liver disease therapeutic agents (e.g., for use in NASH) include, but are not limited to, obeticholic acid (Ocaliva®), Selonsertib, Elafibranor, Ceniviroc, GR_MD_02, MGL_3196, IMM124E, arachidyl amido cholanoic acid (Aramchol™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

The present disclosure also provides inhibitors of HSD17B13 for use in the manufacture of a medicament for the treatment of liver disease in a human subject who is PNPLA3 Ile148Met positive or PNPLA3 Ile144Met positive and who is also homozygous or heterozygous for functional HSD17B13. In some embodiments, the subject is homozygous for PNPLA3 Ile148Met variant or PNPLA3 Ile144Met variant. In some embodiments, the subject is heterozygous for PNPLA3 Ile148Met variant or PNPLA3 Ile144Met variant. In some embodiments, the subject is homozygous for functional HSD17B13. In some embodiments, the subject is heterozygous for functional HSD17B13.

In some embodiments, the inhibitor of HSD17B13 is for use in the treatment of a liver disease in a human subject having a PNPLA3 protein comprising a methionine at a position corresponding to position 148 according to SEQ ID NO:42, or a nucleic acid molecule encoding a PNPLA3 protein comprising a methionine at a position corresponding to position 148 according to SEQ ID NO:42, or comprising a methionine at a position corresponding to position 144 according to SEQ ID NO:43, or a nucleic acid molecule encoding a PNPLA3 protein comprising a methionine at a position corresponding to position 148 according to SEQ ID NO:43. In some embodiments, the variant PNPLA3 protein comprises a methionine at a position corresponding to position 148 according to SEQ ID NO:42. In some embodiments, the variant PNPLA3 protein comprises the amino acid sequence according to SEQ ID NO:42. In some embodiments, the variant PNPLA3 protein comprises a methionine at a position corresponding to position 144 according to SEQ ID NO:43. In some embodiments, the variant PNPLA3 protein comprises the amino acid sequence according to SEQ ID NO:43.

In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31.

In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35.

In some embodiments, nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39.

In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

In some embodiments, the human subject is homozygous or heterozygous for functional HSD17B13. In some embodiments, the subject is homozygous for functional HSD17B13. In some embodiments, the subject is heterozygous for functional HSD17B13.

In any of the methods described herein, a probe or primer or an alteration-specific probe or an alteration-specific primer can be specifically complementary to or specifically hybridize with a single nucleic acid species. For example, a probe or primer or an alteration-specific probe or an alteration-specific primer specifically complementary to or specifically hybridizing with a nucleic acid molecule for HSD17B13 transcript A, transcript B, transcript E, or transcript I (e.g., any of the mRNA, cDNA, RNA transcript, or cDNA transcript for functional HSD17B13 described herein) is not complementary to or does not hybridize with any of the nucleic acid molecules for a variant HSD17B13 (e.g., any of the mRNA, cDNA, RNA transcripts, or cDNA transcripts for variants C, D, F, G, H of HSD17B13).

The present disclosure also provides an inhibitor of HSD17B13 for use in the treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether or not the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the methods as defined herein.

In some embodiments, the variant PNPLA3 protein comprises a methionine at the position corresponding to position 148 according to SEQ ID NO:42. In some embodiments, the variant PNPLA3 protein comprises the amino acid sequence according to SEQ ID NO:42, or an amino acid sequence having at least 90% sequence identity to SEQ ID NO:42 and comprising the I148M variation. In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34, or a nucleotide sequence having at least 90% sequence identity to SEQ ID NO:34 and encoding a PNPLA3 protein which comprises the I148M variation. In some embodiments, the mRNA comprises an AUG codon at the positions corresponding to positions 430 to 432 according to SEQ ID NO:35. In some embodiments, the mRNA comprises the nucleotide sequence according to SEQ ID NO:35, or a nucleotide sequence having at least 90% sequence identity to SEQ ID NO:35 and encoding a PNPLA3 protein which comprises the I148M variation. In some embodiments, the nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38, or a nucleotide sequence having at least 90% sequence identity to SEQ ID NO:38 and encoding a PNPLA3 protein which comprises the I148M variation. In some embodiments, the cDNA comprises an ATG codon at the positions corresponding to positions 430 to 432 according to SEQ ID NO:39. In some embodiments, the cDNA comprises the nucleotide sequence according to SEQ ID NO:39, or a nucleotide sequence having at least 90% sequence identity to SEQ ID NO:39 and encoding a PNPLA3 protein which comprises the I148M variation.

In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

In some embodiments, the human subject is homozygous or heterozygous for functional HSD17B13.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of what the inventors regard as their subject matter. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Genetic Interaction Between PNPLA3 rs738409 (p.I148M) And HSD17B13 rs72613567—Study Design In this study, exome sequencing was used to identify variants associated with serum alanine aminotransferase (ALT) and aspartate aminotransferase (AST) levels, which are markers of hepatocyte injury, in the DiscovEHR human genetics study, a cohort that links exome sequence data to electronic health records (EHR), and in three additional studies. The associations between implicated genetic variants and clinical diagnoses of chronic liver disease in DiscovEHR and two independent cohorts was also studied. The association between one of these variants and the histopathological severity of liver disease in an independent cohort of bariatric surgery patients who underwent liver biopsy was also studied.

Study Design and Participants

Human genetics studies were conducted using genomic DNA samples and data from six cohorts. These studies included two Regeneron Genetics Center and the Geisinger Health System (GHS) DiscovEHR study populations originating from the first 50,726 adult consented participants from the MyCode® Community Health Initiative of GHS20. The GHS discovery cohort consisted of 46,544 European individuals recruited from outpatient primary care and specialty clinics between 2007 and 2016, excluding all those recruited to the bariatric surgery cohort. The GHS bariatric surgery cohort consisted of 2,644 European individuals who had been referred for bariatric surgery. Replication studies of associations with liver transaminases were performed in the Dallas Heart Study and the Penn Medicine Biobank, which included 1,357 and 8,527 individuals of European ancestry, respectively. Replication studies of the associations with chronic liver disease included 517 individuals from the Dallas Liver Study (DLS) and 439 individuals from the Dallas Pediatric Liver Study (DPLS). Full study descriptions and clinical phenotype and disease definitions are described the Methods section in the Supplementary Appendix.

Baseline characteristics of genotyped multi-ethnic cases and controls from the Dallas Liver and Pediatric Liver Studies are shown in FIG. 5.

Sample Preparation, Sequencing, and Genotyping

DNA sample preparation and whole exome sequencing for the participants in the DiscovEHR study, the Dallas Heart Study, and the Penn Medicine Biobank were performed at the Regeneron Genetics as previously described (Dewey et al., Science, 2016, In Press). HSD17B13 rs72613567 was genotyped by Taqman assay (and verified by Sanger sequencing in 5 individuals of each genotype) in the Dallas Liver Study and Dallas Pediatric Liver Study.

Clinical Measurements and Chronic Liver Disease Definitions in the Discovery Cohort Clinical laboratory measurements for alanine aminotransferase (ALT) and aspartate aminotransferase (AST) were extracted from EHRs of participants from the GHS discovery cohort and bariatric surgery cohort. Median ALT and AST values were calculated for all participants with two or more measurements, and were $log_{10}$-transformed to normalize the distribution prior to association analyses.

International Classification of Diseases, Ninth Revision (ICD-9) disease diagnosis codes were extracted from EHRs and collapsed into clinical disease categories for non-viral, nonalcoholic (ICD-9 571.40, 571.41, 571.49, 571.5, 571.8, 571.9) or alcoholic (ICD-9 571.0, 571.1, 571.2, 571.3) liver disease case definitions. Additional case definitions based on single diagnosis codes included: alcoholic cirrhosis (ICD-9 571.2), nonalcoholic cirrhosis (ICD-9 571.5), and HCC (ICD-9 155.0). For these case definitions, a common control group without liver disease ("no liver disease") was defined as participants with no case criteria or single-encounter or problem-list diagnosis code indicating any type of liver disease.

Regional association plots for alanine aminotransferase (ALT; A) and aspartate aminotransferase (AST; B) levels in the GHS discovery cohort in the region around HSD17B13 are shown in FIG. 6 (panels A and B). Purple diamonds indicate the splice variant rs72613567. Each circle indicates a single nucleotide variant with the color of the circle indicating the linkage disequilibrium (r2 calculated in the DiscovEHR cohort) between that variant and rs72613567. Blue lines indicate estimated recombination rates in Hap-Map. The bottom portion of the panels show the relative position and the transcribed strand of each gene in the locus. There were no significant associations between AST or ALT and coding or splice region variants in the neighboring gene HSD17B11 (most significant P-values $1.4 \times 10^{-1}$ and $4.3 \times 10^{-2}$ for ALT and AST, respectively).

Liver Histopathologic Phenotype Definitions in the Bariatric Surgery Cohort

The GHS bariatric surgery cohort consisted of 2,644 individuals of European descent, with intra-operative liver biopsy specimens available from 2,391 of these individuals. Liver biopsy specimens were formalin-fixed and stained with hematoxylin and eosin for histology, and Masson's trichrome stain for assessment of fibrosis, as previously described (Gerhard et al., Patient Saf. Surg., 2011, 5, 1). Histologic diagnoses were determined by hepatopathologists using previously established criteria (Brunt et al., Am. J. Gastroenterol., 1999, 94, 2467-74). Histologic diagnoses were used to defined the following phenotypes: 1) Normal: no evidence of steatosis, NASH, or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage).

Baseline characteristics of sequenced European-ancestry individuals from the discovery and replication cohorts are shown in FIG. 1. Single nucleotide variants associated with serum transaminase levels at $P<1.0 \times 10^{-7}$ in the discovery cohort are shown in FIG. 2.

DNA Sample Preparation and Sequencing

In brief, exome capture was performed using NimbleGen probes according to the manufacturer's recommended protocol (Roche NimbleGen). The captured DNA was PCR amplified and quantified by qRT-PCR (Kapa Biosystems). The multiplexed samples were sequenced using 75 bp paired-end sequencing on an Illumina v4 HiSeq 2500 to a coverage depth sufficient to provide greater than 20× haploid read depth of over 85% of targeted bases in 96% of samples (approximately 80× mean haploid read depth of targeted bases). Raw sequence data from each Illumina Hiseq 2500 run were uploaded to the DNAnexus platform (Reid et al., BMC Bioinformatics, 2014, 15, 30) for sequence read alignment and variant identification. In brief, raw sequence data were converted from BCL files to sample-specific FASTQ-files, which were aligned to the human reference build GRCh37.p13 with BWA-mem (Li et al., Bioinformatics, 2009, 25, 1754-60). Single nucleotide variants (SNV) and insertion/deletion (indel) sequence variants were identified using the Genome Analysis Toolkit (McKenna et al., Genome Res., 2010, 20, 1297-303).

Exome-Wide Association Analysis of Liver Enzymes and Chronic Liver Disease Phenotypes 502,219 biallelic variants with missing data rate <1%, Hardy-Weinberg equilibrium P-value >$1.0\times10^{-6}$, and minor allele frequency >0.1%, were examined for association with transaminase levels. $Log_{10}$-transformed median ALT and AST were adjusted for age, $age^2$, sex, BMI, and the first four principal components of ancestry. To account for relatedness among study participants, a genetic relatedness matrix was fit as a random-effects covariate. Both principal components and the genetic relatedness matrix were constructed from 39,858 non-MHC markers in approximate linkage equilibrium and with minor allele frequency >0.1%. A linear mixed models was used as implemented in the GCTA package (Yang et al., Am. J. Hum. Genet., 2011, 88, 76-82) to test for association between trait residuals and single nucleotide variants. All P-values reported in the text correspond to the allelic model.

Replication of associations in the GHS discovery cohort was attempted in three separate European-ancestry cohorts: the GHS bariatric surgery cohort, the Dallas Heart Study, and the Penn Medicine Biobank (described above). ALT and AST measures from the GHS bariatric surgery cohort and from Penn Medicine Biobank were $log_{10}$-transformed and adjusted for age, $age^2$, sex, BMI, and the first four principal components of ancestry. Genetic relatedness matrices were included as random-effects covariates, and analysis was performed using linear mixed models in GCTA. In the Dallas Heart study, $log_{10}$-transformed ALT and AST measures were adjusted for age, $age^2$, sex, BMI, and the first ten principal components of ancestry, and analysis was performed using linear regression implemented in PLINK. Summary statistics for the three replication cohorts were meta-analyzed using METAL (Willer et al., Bioinformatics, 2010, 26, 2190-1) (replication meta-analysis). Summary statistics for the discovery cohort and the three replication cohorts were meta-analyzed similarly (joint meta-analysis).

Replication and joint meta-analysis of 35 exome-wide significant single nucleotide variants from the discovery cohort in three separate European-ancestry cohorts is shown in FIG. 3.

For variants with exome wide significant associations with transaminases ($p<1\times10^{-7}$) in the GHS discovery cohort, association analyses and meta-analysis were performed, as described herein, in the European-ancestry replication studies described herein. A Bonferroni significance threshold determined by the number of variants tested was used to define replicated associations. Meta-analysis of discovery and replication studies was also performed. All P-values reported in the text correspond to the allelic model.

Transaminase-associated single nucleotide variants was also examined for associations with chronic liver disease phenotypes (defined and analyzed as described herein). A Bonferroni significance threshold determined by the number of variants and broad chronic liver disease categories tested was used to determine significance of associations. Replicated novel variants were also examined for association with histopathologically defined liver phenotypes from the GHS bariatric surgery cohort.

Association Analysis with Chronic Liver Disease Phenotypes

Thirteen significant and replicated single nucleotide variants from the liver enzyme ExWAS were analyzed for associations with chronic liver disease phenotypes defined from the GHS discovery cohort, as described above. A Bonferroni significance threshold of P<0.05/26 ($P<1.92\times10^{-3}$) was used to account for the thirteen variants and two broad chronic liver disease categories (alcoholic and nonalcoholic) tested. The HSD17B13 rs72613567 variant was further tested for association with histopathologically defined liver phenotypes from the GHS bariatric surgery cohort, as described above. Odds ratios were estimated with the use of Firth's penalized likelihood method of logistic regression after adjustment for age, $age^2$, sex, BMI, and the first four principal components of ancestry. Genotypic odds ratios were estimated for HSD17B13 rs72613567 using the same covariates.

Odds ratios for liver disease in the DLS were estimated by logistic regression, adjusted for age, $age^2$, sex, BMI, and self-reported ethnicity. Participants from the Dallas Heart Study with available rs72613567 genotypes were used as normal controls (n=4,279). Odds ratios in the DPLS were estimated by logistic regression.

Association of thirteen exome-wide significant and replicating single nucleotide variants with liver disease phenotypes in the discovery cohort is shown in FIG. 4.

Genetic Interaction Between PNPLA3 rs738409 (p.I148M) and HSD17B13 rs72613567—Analysis To evaluate the combined effect of PNPLA3 rs738409 and HSD17B13 rs72613567, association analyses for quantitative (ALT and AST) and binary (nonalcoholic liver disease and alcoholic liver disease) traits were conducted using linear and logistic regression, respectively, modeling main effects for both genetic variants as well as an interaction term, assuming an additive genetic model. All models were adjusted for age, $age^2$, sex, BMI, and the first four principal components of ancestry. Statistical analyses were performed using the glm function in base R.

Software

Genetic association analyses were performed using GCTA software, version 1.25.0 (Yang et al., Am. J. Hum. Genet., 2011, 88, 76-82) and PLINK, version 1.9.0. Quantile-quantile and Manhattan plots were generated using R software, version 3.2.1 (R Project for Statistical Computing). Regional association plots were generated using LocusZoom (Pruim et al., Bioinformatics, 2010, 26, 2336-7).

RNA Sequencing Studies

RNA quality and concentration was evaluated by running total RNA on an Agilent RNA Nano Bioanalyzer chip; all samples had an RNA integrity number (RIN) greater than 8. Polyadenylated RNA transcripts were isolated using two rounds of enrichment with oligo(dT)25 beads (Thermo Fisher Scientific). Samples were purified and concentrated with RNAclean XP beads (Beckman Coulter) and heat-fragmented to approximately 140 base pairs. First-strand synthesis was completed with SuperScript III reverse transcriptase (Thermo Fisher Scientific) using random hexamers; dTTP was replaced with dUTP during second-strand synthesis. Samples were processed according to the standard DNA library preparation method referenced above for exomes with the addition of a uracil DNA-glycosylase step to generate strand-specific sequencing libraries. Samples were pooled and sequenced using 75 bp paired-end sequencing on an Illumina v4 HiSeq 2500.

Identification and Validation of Novel HSD17B13 Transcripts

Reads were mapped to the Human.B38 using ArrayStudio® software (OmicSoft®, Cary, N.C.) allowing two mismatches. Two approaches were employed to identify novel HSD17B13 transcripts. Novel exon junctions were discovered based on Gencode v24 using ArrayStudio. De novo transcript assembly was performed using Trinity (v2.2.0) in default setting. Custom gene models were built to incorporate novel transcripts of HSD17B13, and transcript quantification was estimated by read alignment to the custom gene model. Protein sequence alignment of all identified HSD17B13 isoforms was determined. RT-PCR was performed on total RNA from human liver samples using the SuperScript™ One-Step RT-PCR System with Platinum™ Taq DNA Polymerase (Thermofisher). Each 50 µL RT-PCR reaction contained 1× Reaction Mix, 500 nM each forward and reverse primers (PST516: ATGAACATCATCCTAGAAATCCTTC; SEQ ID NO:62) and PST517: ATCATGCATACATCTCTGGCT GGAG; SEQ ID NO:63), 1 µL of RT/Platinum Taq, and 75 ng RNA. Cycling conditions were: one cycle of 45° C. for 30 minutes; one cycle of 94° C. for 2 minutes; 40 cycles of 94° C. for 20 seconds, 53° C. for 30 seconds, and 72° C. for 90 seconds; one cycle of 72° C. for 5 minutes; then a 10° C. hold. Products were purified using the QIAquick PCR Purification Kit (Qiagen) and submitted for direct Sanger sequencing using the primer DE002 (ATCAGAACTTC AGGCCTTGG; SEQ ID NO:64). To identify the B and C transcripts, the RT-PCR products were run out on a 2% agarose gel stained with SYBR GoldSYBR® Gold Nucleic Acid Gel Stain (Thermofisher), and bands of the expected molecular weight were excised and purified using the QIAquick Gel Extraction Kit (Qiagen), then subjected to cloning with the TOPO® TA Cloning Kit (Thermofisher). Sequencing of the TOPO clones was performed using, M13F and M13R sequencing primers. Sequence analysis was performed using the Sequencher DNA analysis software (Gene Codes Corporation).

Full-length HSD17B13 transcripts were amplified directly from 50 ng of total RNA with the SuperScript III One-step RT-PCR System with Platinum Taq High Fidelity (Thermo Fisher Scientific) using gene-specific primers in the first (GCAAAGCCATGAACATCATCC; SEQ ID NO:65) and last exons (TCTTGATGTAGTGGGAGTCGGATT; SEQ ID NO:66) to generate an amplicon of about 2.2 kb (maximum predicted size transcript). Amplicons were verified on an Agilent Bioanalyzer. PacBio-compatible barcoded adapters were ligated to the amplicons and cleaned with PacBio PB beads (Pacific Biosciences). Libraries were pooled in equal amounts and sequenced on one SMRT cell for 180 minutes on the PacBio RSII platform. The data was demultiplexed using PacBio software smrtanalysis v2.3 tool labelzmw and then analyzed with ConsensusTools AmpliconAnalysis. Resulting amplicons were compared to HSD17B13 RefSeq genes to determine isoform and genotype status.

Subcellular Localization of HSD1713 Isoforms HepG2 cells were infected with lentivirus carrying the HSD17B13 A and D transcripts, stable cell lines were selected, and HSD17B13 isoforms, lipid droplets, and endoplasmic reticulum were visualized using immunofluorescence. Briefly, HepG2 cells were cultured in Eagle's Minimum Essential Medium supplemented with 10% fetal bovine serum. HSD1713 transcripts A and D were sub-cloned into Myc-DDK backbone lentivirus constructs, and lentivirus were generated. HepG2 cells were infected with lentivirus carrying the HSD1713 transcripts. Stable cell lines expressing each HSD1713 transcript were selected with 1-3 mg/ml Geneticin G-418 sulfate in complete culture medium for two weeks. Following fixation, HSD17B13 isoforms were detected with mouse anti-Myc antibody. Lipid droplets were labeled with BODIPY FL dye (Sigma). Lipid coat protein and endoplasmic reticulum were labeled with rabbit anti-PLIN antibody (Sigma) and rabbit anti-calnexin antibody (Cell Signaling Technology). Secondary antibodies for immunofluorescence were Alexa Fluor 488 donkey anti-rabbit IgG and Alexa Fluor 594 donkey anti-mouse IgG (Jackson ImmunoResearch).

Quantification of HSD171B3 Protein Expression in Human Liver Biopsy Tissue

Human liver and cell pellet samples were homogenized in ice-cold 1×RIPA lysis buffer (EMD Millipore) in the presence of protease and phosphatase inhibitor mixtures (Thermo-Fisher). Supernatant was collected and used for protein concentration using BCA protein assay (Thermo-Fisher). Human tissue lysates were loaded at 30 µg/well and stable cell lines were loaded 9 µg/well and separated on SDS/PAGE gels (Bio-Rad) and transferred to PVDF membranes (Bio-Rad). The membranes were blocked for 1 hour with 5% (wt/vol) milk in 1×TBS supplemented with 0.1% Tween20 (Bio-Rad). Membranes were incubated with antibody at 4° C. overnight against HSD17B13 (1:200, Thermo-Fisher) and B-Actin (1:500, Cell Signaling Technology). Bound antibody was detected using HRP-conjugated anti-rabbit antibody (1:10,000, Jackson ImmunoResearch) and enhanced using chemiluminescence reagent (Thermo-Fisher). Band intensities were quantified using Image J software.

In Vitro and Cellular Characterization of HSD17B13 Enzymatic Activity

Recombinant human HSD17B13 protein was purified from E. coli (Genscript) transformed with plasmid DNA harboring HSD17B13 transcript A or transcript D. The HSD17B13 variants contained a 10×His tag at the C terminus and were purified from soluble fraction using a $Ni^{2+}$ affinity purification. Enzymatic activity was determined through measurement of NADH production using the NAD(P)H-Glo Detection System (Promega). Reactions were performed for 3 hours at 25° C. in 0.2 M tris-HCl, pH 7.5, 0.5 mM $NAD^+$, 75 µM of substrate (Sigma) and 500 ng purified enzyme in a final volume of 100 µL. After incubation, 20 µl of the reaction was combined with 20 µl luciferase reagent (Promega), incubated at room temperature for 1 hour and read on an Envision Plate Reader (Perkin Elmer).

HEK293 cells overexpressing HSD17B13 transcript A, transcript D or green fluorescent protein (GFP, control) were used to investigate the activity of HSD17B13 against estradiol in a cell-based assay. Estradiol was fed to each cell type. After 48 hours, the media was collected and the concentration of estradiol and its converted product estrone were identified and quantified by LC-MS. Hydroxyestradiol (metabolite from estradiol) and hydroxyestrone (metablolite from estrone) were identified by LC-MS.

Example 2: Gene Expression Analysis of HSD17B13 and PNPLA3 in 66 Human Liver Samples Gene expression of HSD17B13 and PNPLA3 were analyzed with 66 human liver samples. All the samples were from control donors without steatosis, lobular inflammation, or fibrosis. The distribution of HSD17B13 rs72613567 (T/T, T/TA, and TA/TA) and PNPLA3 rs738409 (C/C, C/G, and G/G) genotypes is shown in Table 1.

| Genotype | C/C | C/G | G/G | ND |
|---|---|---|---|---|
| T/T | 12 | 8 | 1 | 0 |
| T/TA | 15 | 12 | 0 | 2 |
| TA/TA | 12 | 4 | 0 | 0 |

Figure 7:
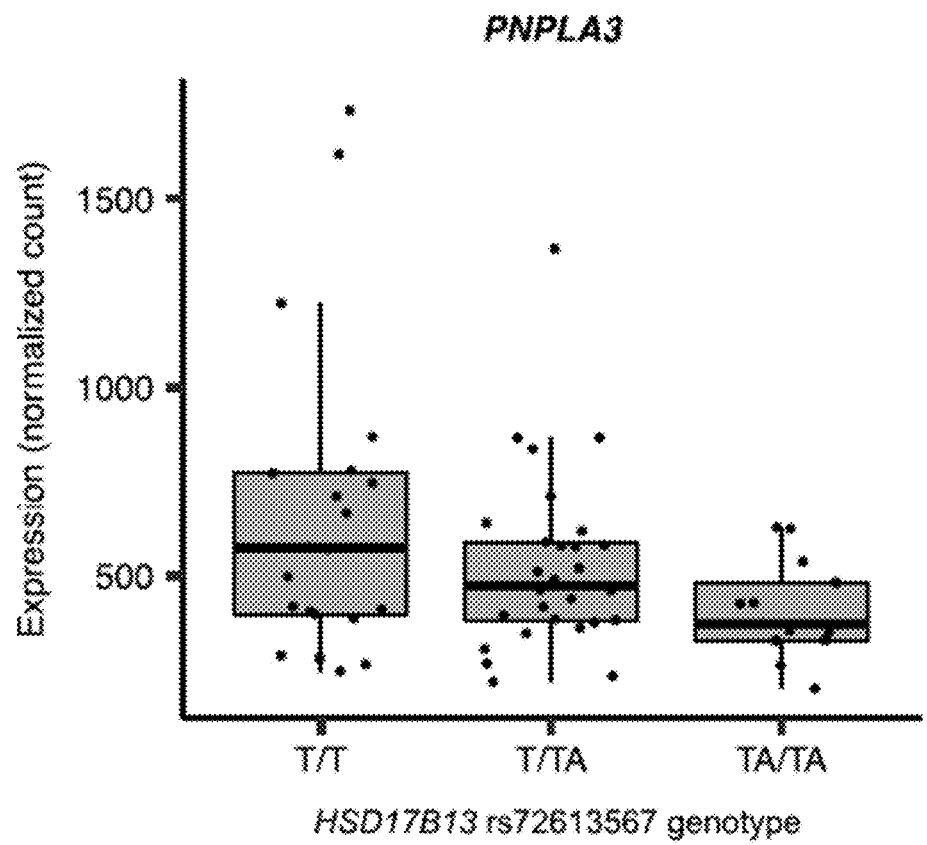
FIG. 7 shows the expression of PNPLA3 in homozygous reference (T/T), heterozygous (T/TA), and homozygous alternate (TA/TA) carriers of the HSD17B13 rs72613567 splice variant.
Figure 8:
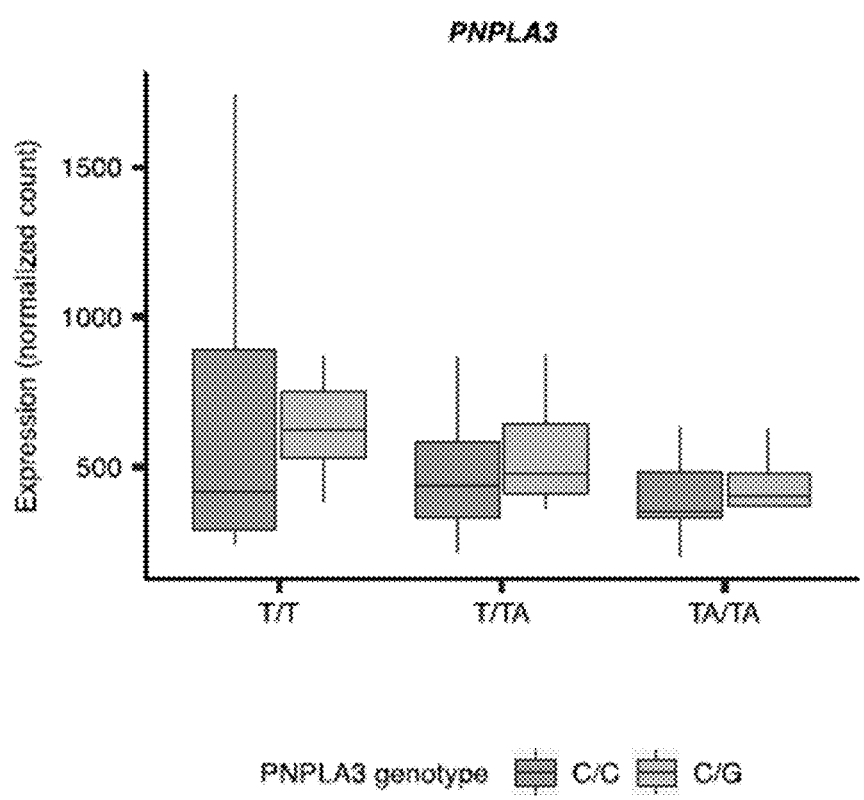
FIG. 8 shows the expression difference of the 63 PNPLA3 rs738409 carriers (C/C and C/G) in the three HSD17B13 rs72613567 genotypes (T/T, T/TA, TA/TA).

The expression of PNPLA3 was significantly reduced in homozygous alternate carriers of the HSD17B13 rs72613567 splice variant (see, FIG. 7). mRNA expression is displayed in FPKM units. A 1.6-fold decrease compared to T/T with FDR 0.0071 was observed. The variant PNPLA3 C/C carries with the HSD17B13 TA/TA genotype had significantly decreased expression when compared with HSD17B13 T/T carries: 1.7-fold (FDR 0.017) decrease. The variant PNPLA3 C/G carriers with TA/TA genotype showed decrease in expression but not statistically significant (1.4-fold, FDR 1). FIG. 8 shows the expression difference of the 63 PNPLA3 rs738409 carriers (C/C and C/G, see Table 1) in the three HSD17B13 rs72613567 genotypes (T/T, T/TA, TA/TA).

Figure 10:
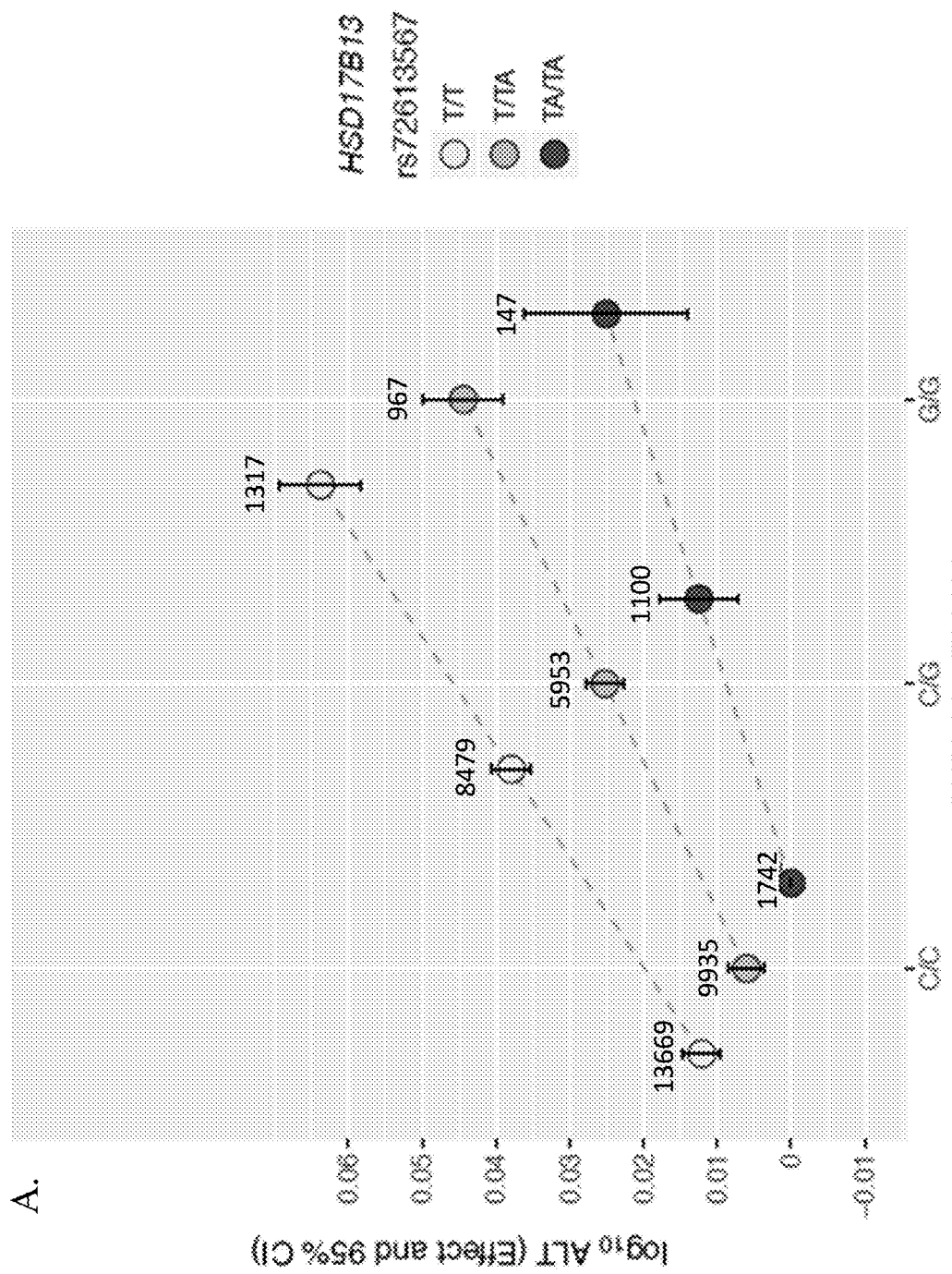
FIG. 10 (panels A and B) shows HSD17B13 rs72613567:TA mitigates the risk of liver injury associated with PNPLA3 p.I148M.
Figure 10:
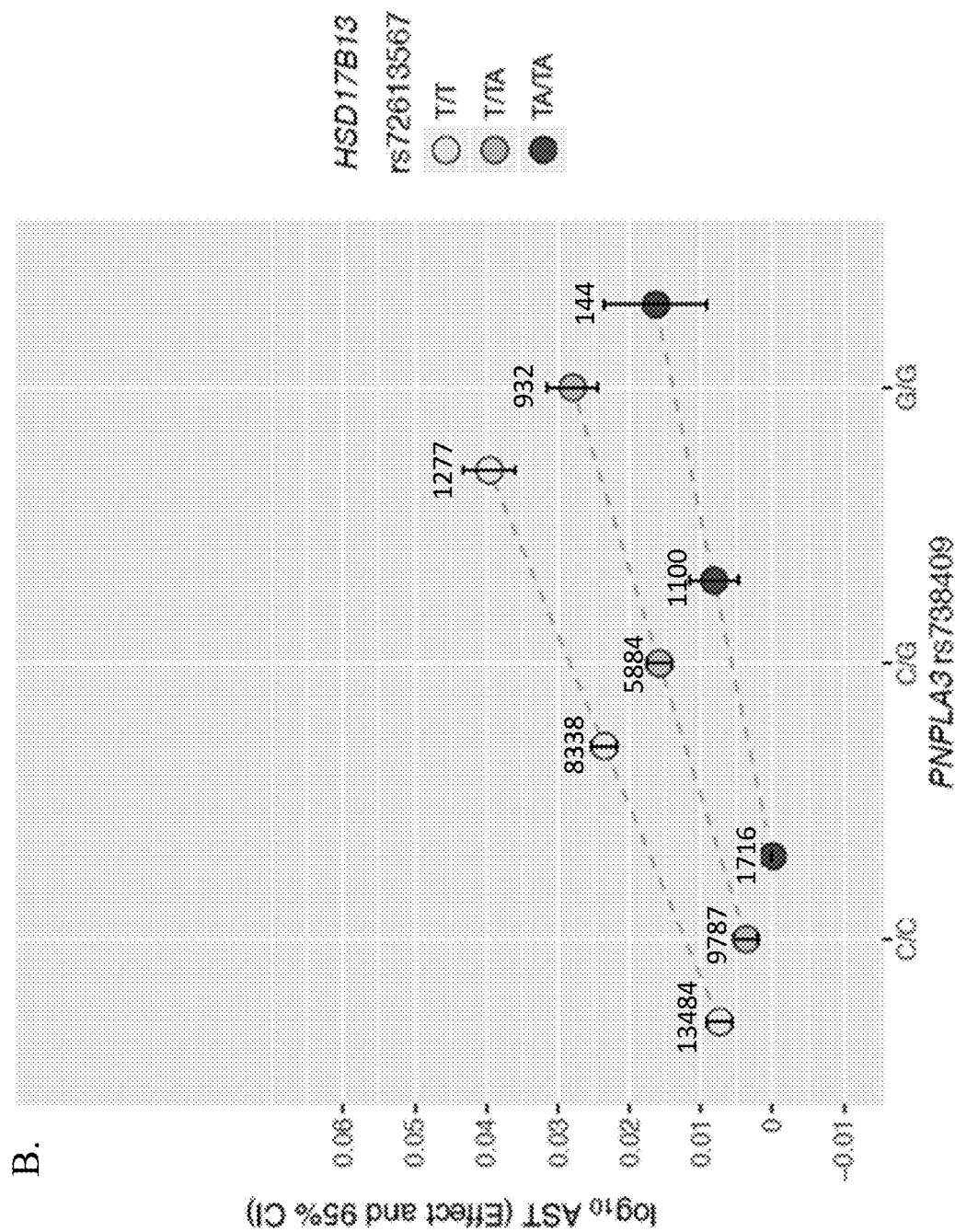
Figure 11:
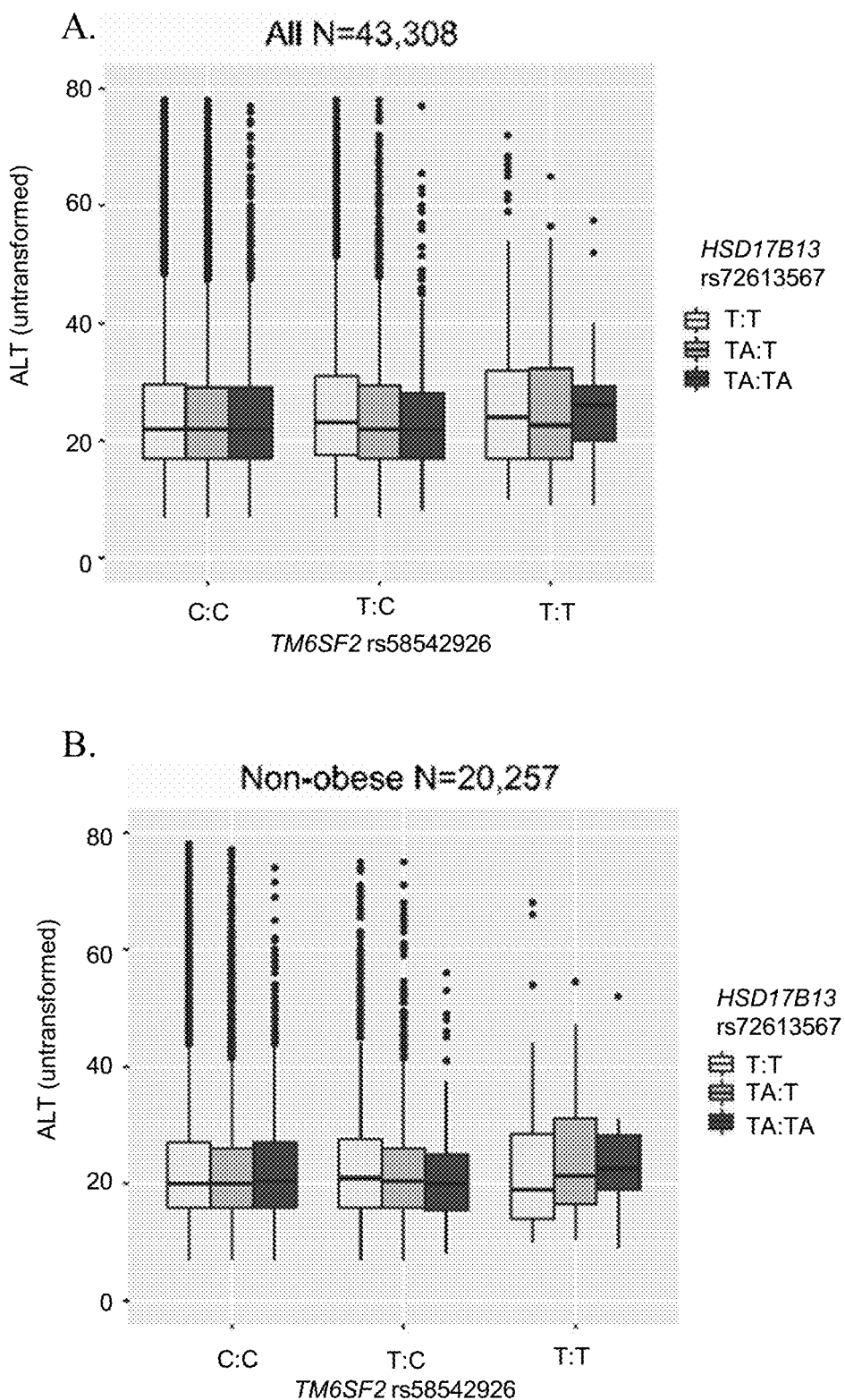
FIG. 11 (panels A through F) shows raw and residualized ALT levels by PNPLA3 rs738409 (p.I148M) and HSD17B13 rs72613567 genotype.
Figure 11:
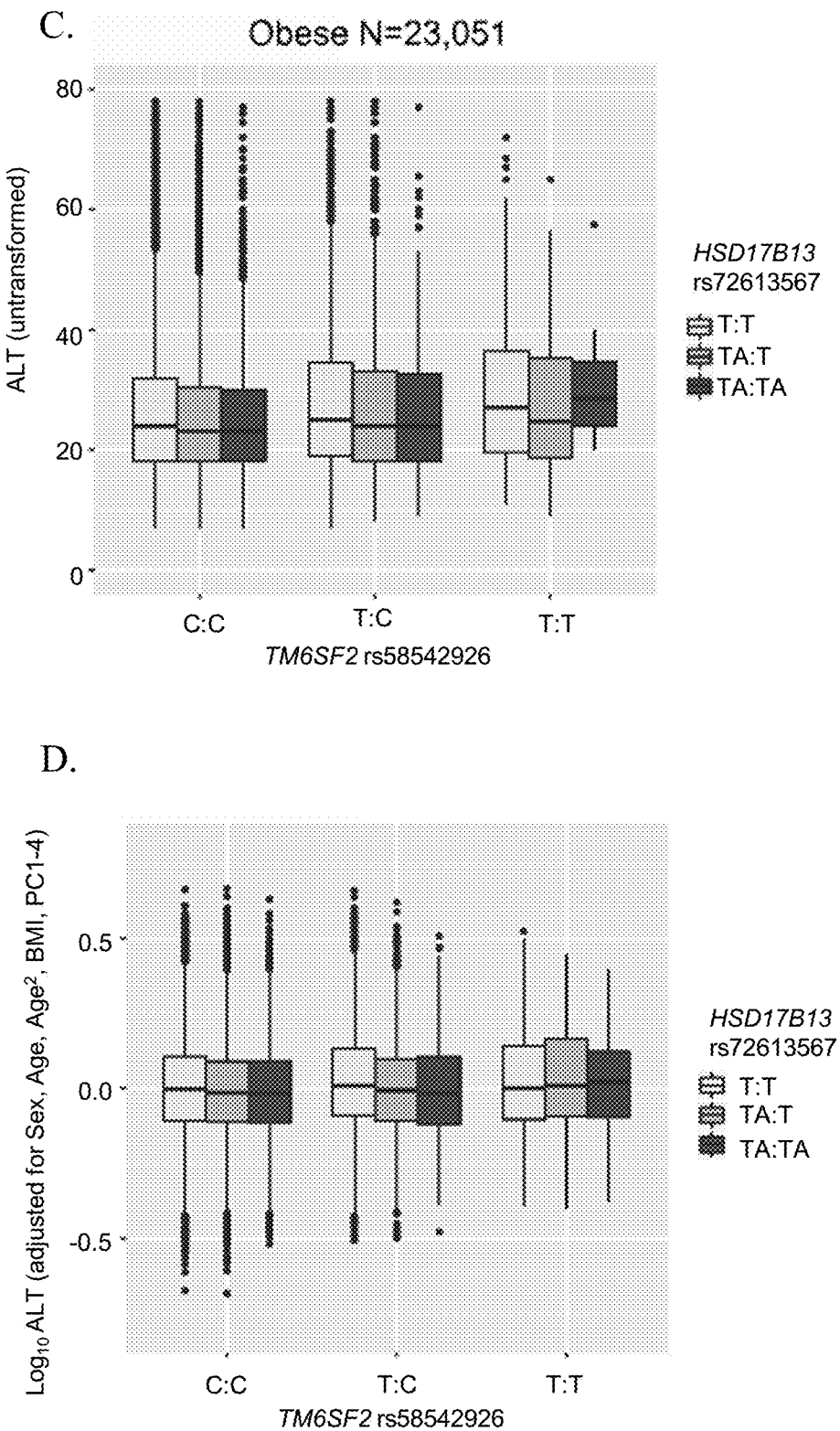
Figure 12:
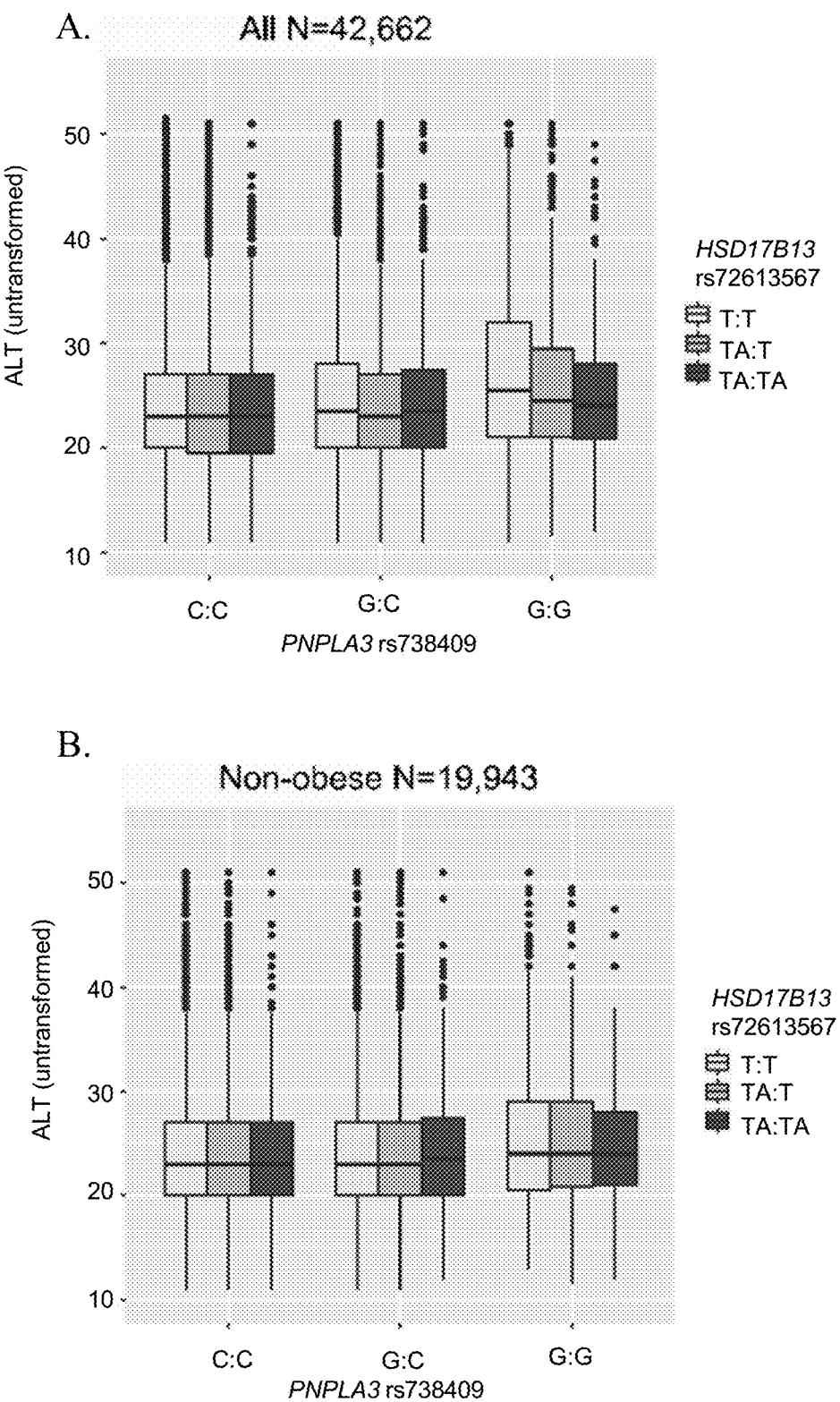
FIG. 12 (panels A through F) shows raw and residualized AST levels by PNPLA3 rs738409 (p.I148M) and HSD17B13 rs72613567 genotype.
Figure 13:
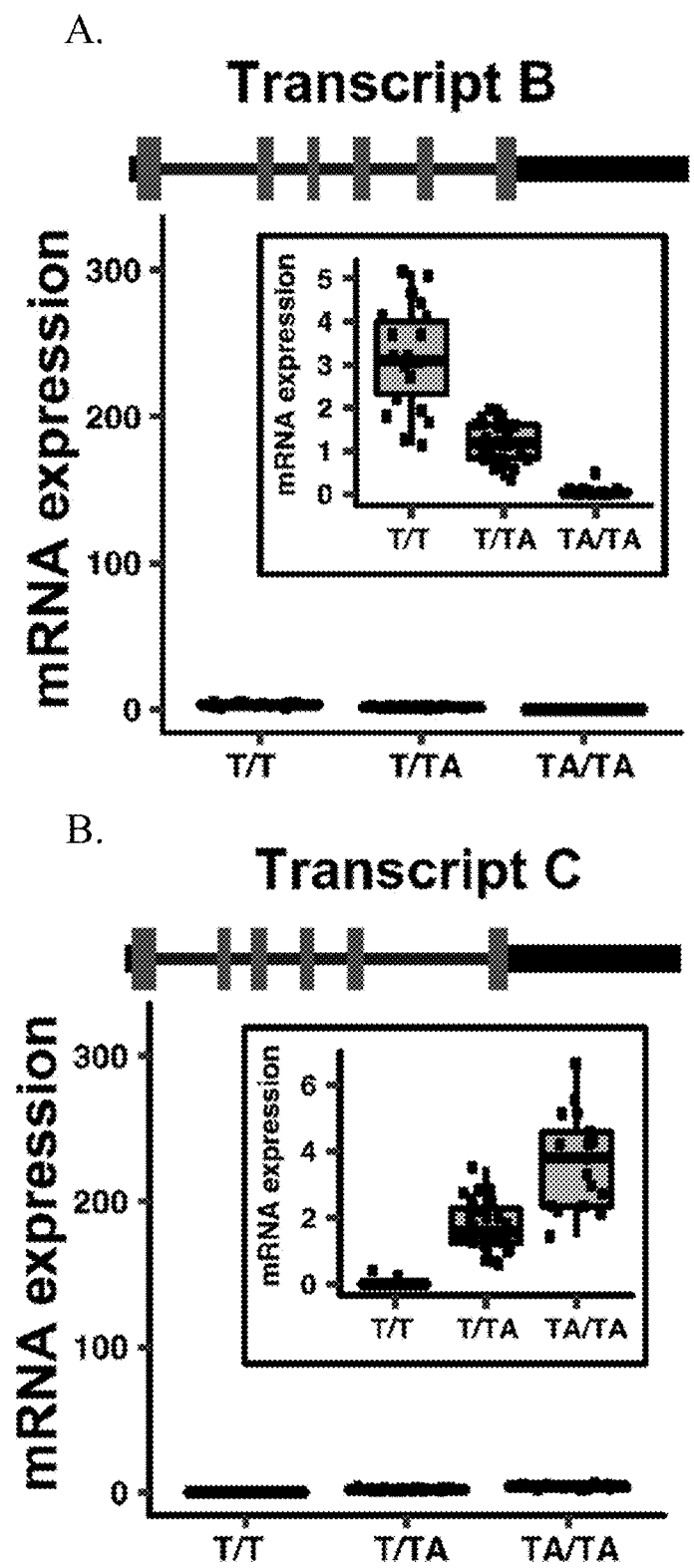
FIG. 13 (panels A through F) show mRNA expression of four additional novel HSD17B13 transcripts (E-H) in homozygous reference (T/T), heterozygous (T/TA), and homozygous alternate (TA/TA) carriers of the HSD17B13 splice variant.

The variant PNPLA3 p.I148M variant is the most well validated genetic risk factor for NAFLD, and the 148M allele exists in homozygous state in 5-25% of individuals, depending on ancestry. To understand whether the HSD17B13 rs72613567:TA modifies the risk of liver injury associated with PNPLA3 p.I148M, analyses of interaction between the two variants in association with ALT, AST, and chronic liver disease phenotypes in DiscovEHR was performed. These analyses were performed in all participants, as well as in obese (body mass index (BMI) >30 kg/m2) and non-obese (BMI ≤30 kg/m2) subpopulations. There was nominally significant interaction between HSD17B13 rs72613567:TA and PNPLA3 p.I148M in association analyses of ALT (P=1.8×10-3 for interaction) and AST (P=4.5×10-3 for interaction) levels; these associations were primarily driven by associations in obese individuals (see, FIG. 9). In these analyses, the rs72613567:TA allele mitigated the allele dosage-dependent associations of PNPLA3 148M allele with increased ALT and AST (see, FIG. 10). Referring to FIG. 10, panel A shows the association of HSD17B13 rs72613567 with ALT in individuals with each PNPLA3 p.I148M genotype, and panel B shows the association of HSD17B13 rs72613567 with AST in individuals with each PNPLA3 p.I148M genotype. Effect estimates (beta and 95% CI) were calculated using linear regression, with adjustment for age, age2, sex, BMI, and four principal components of ancestry. FIG. 11 (panels A through F) show raw and residualized ALT levels by PNPLA3 rs738409 (p.I148M) and HSD17B13 rs72613567 genotype. Residuals were calculated by linear regression adjusted for age, age2, sex, BMI, and four principal components 1-4. FIG. 12 (panels A through F) show raw and residualized AST levels by PNPLA3 rs738409 (p.I148M) and HSD17B13 rs72613567 genotype. Residuals were calculated by linear regression adjusted for age, age2, sex, BMI, and four principal components 1-4. FIG. 13 (panels A through F) show mRNA expression of four additional novel HSD17B13 transcripts (E-H) in homozygous reference (T/T), heterozygous (T/TA), and homozygous alternate (TA/TA) carriers of the HSD17B13 splice variant. Coding regions in gene models are indicated in blocks and untranslated regions in lines. Transcripts E and H contain an additional exon between exons 3 and 4. Transcript F involves read-through from exon 6 to intron 6. The arrow (see, Panel D) indicates the A insertion from rs72613567. Transcript G lacks exon 2. The asterisk in transcripts G and H illustrates insertion of G at the 3'-end of exon 6, which leads to premature truncation of the protein (similar to transcript D). Transcripts are differentially expressed according to HSD17B13 genotype, as shown in the box plots. mRNA expression is displayed in FPKM units.

Figure 14:
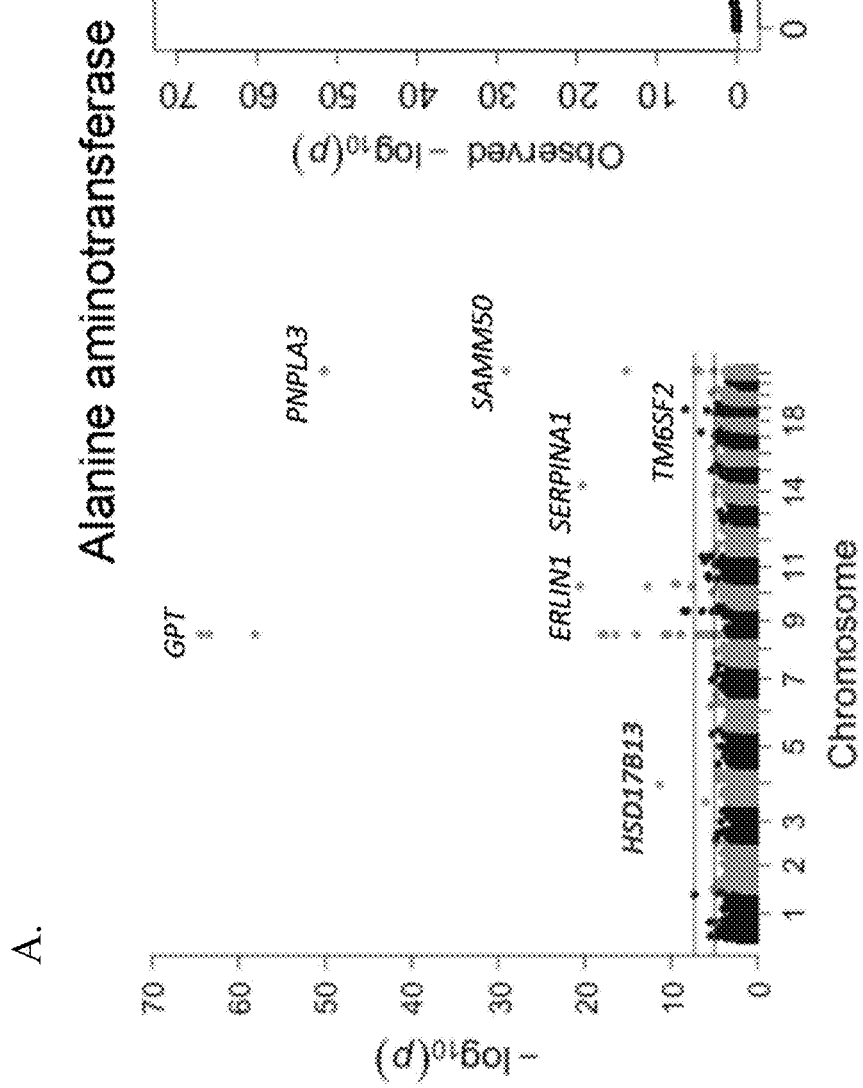
FIG. 14 (panels A and B) shows Manhattan plots (left) and quantile-quantile plots (right) of single nucleotide variant associations with serum transaminase levels in the GHS discovery cohort.
Figure 14:
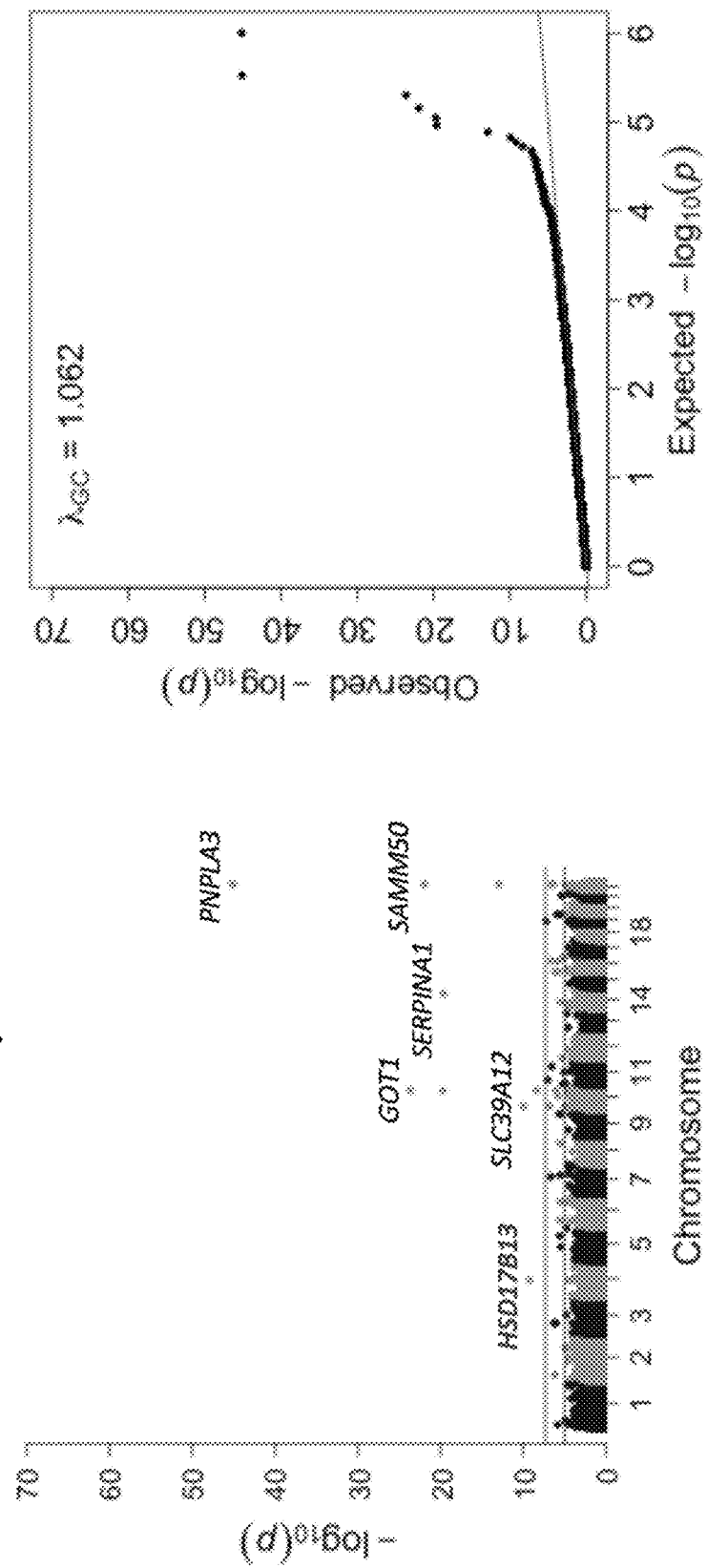

Example 3: Gene Expression Analysis of HSD17B13 and PNPLA3 in 66 Human Liver Samples Association of Exonic Variants with Asparatate and Alanine Aminotransferases 502,219 biallelic single genetic variants were examined for association with serum ALT or AST levels in 46,544 individuals of European descent from the DiscovEHR study ("GHS discovery cohort"; basic demographics in FIG. 1). A total of 35 variants in 19 genes were found to be associated with ALT or AST at $P<1.0\times10^{-7}$ (see, FIG. 14 and FIG. 2). Referring to FIG. 14, Manhattan plots (left) and quantile-quantile plots (right) of single nucleotide variant associations with serum transaminase levels in the GHS discovery cohort are shown. There were 31 variants in 16 genes significantly associated with alanine aminotransferase (ALT) levels at $P<1.0\times10^{-7}$ (see, Panel A). There were 12 variants in 10 genes significantly associated with aspartate aminotransferase (AST) levels at $P<1.0\times10^{-7}$ (see, Panel B). All significant associations are shown in FIG. 2. There were thirteen variants in nine genes (indicated here by their gene name), including HSD17B13, that remained significantly associated with ALT or AST in a replication meta-analysis of three separate European-ancestry cohorts (see, FIG. 3). The association tests were well calibrated, as shown by exome-wide quantile-quantile plots and genomic control lambda values.

Replication studies were performed in three cohorts of European-ancestry individuals: 1) bariatric surgery patients (n=2,644) from DiscovEHR ("GHS bariatric surgery cohort"); 2) 1,357 individuals from the Dallas Heart Study; and 3) 8,526 individuals from the Penn Medicine Biobank. In meta-analysis of the replication cohorts, thirteen variants in nine genes were significantly associated with serum levels of ALT or AST (Bonferroni significance threshold of $P<1.43\times10^{-3}$ for 35 variants tested; see, FIG. 3). These included variants that were previously reported to be associated with elevated transaminase levels, such as PNPLA3 (Romeo et al., Nat. Genet., 2008, 40, 1461-5), TM6SF2 (Kozlitina et al., Nat. Genet. 2014, 46, 352-6), SERPINA1 (Brantly et al., Am. J. Med., 1988, 84, 13-31), SAMM50 (Kitamoto et al., Hum. Genet., 2013, 132, 783-92), and ERLIN1 (Feitosa et al., Atherosclerosis, 2013, 228, 175-80). SERPINA1 encodes alpha-1-antitrypsin, whose functional deficiency causes liver disease; the association with SAMM50 is mediated via linkage disequilibrium with variation in PNPLA3, and ERLIN1 has been implicated in liver fat deposition. Variants that were not previously reported to be associated with liver disease were also identified. These included several variants in GPT and GOT1, the genes encoding ALT and AST, respectively, and SLC39A12, which encodes solute carrier family 39 member 12.

A reproducible association between a variant in HSD1713, the gene encoding hydroxysteroid 17-beta dehydrogenase 13, an uncharacterized member of the 17-beta hydroxysteroid dehydrogenase family, and decreased levels of ALT (discovery $P=4.2\times10^{-12}$, replication $P=1.7\times10^{-4}$)

and AST (discovery $P=6.2\times10^{-10}$, replication $P=1.7\times10^{-4}$, see, FIG. 3) was also identified. The associated variant, rs72613567, is an insertion of an adenine adjacent to the donor splice site of exon six (TA allele), and had an allele frequency of 26.0% in the GHS discovery cohort. Previously, Chambers, et al identified a nearby locus at 4q22 (r56834314) associated with ALT levels (Chambers et al., Nat. Genet., 2011, 43, 1131-8); rs72613567 has not heretofore been reported to be associated with transaminase levels. HSD1713 is 30 kb upstream of HSD17B11, another member of the same gene family. No exome-wide significant associations were observed between coding or splice variants in HSD17B11 and transaminase levels in the discovery cohort (see, FIG. 6) or in the joint meta-analysis of the discovery cohort and three replication cohorts. Furthermore, linkage disequilibrium of rs72613567 with variants in HSD17B11 was modest across all ancestry groups ($r^2<0.4$ with all ascertained variants in HSD17B11 in all ancestry groups; data not shown). Collectively, these findings suggest HSD1713 as the gene in the genomic region that is most likely to be functionally related to transaminase levels.

Association of Exonic Variants with Clinical Diagnoses of Chronic Liver Disease

The relationship between the thirteen transaminase-associated variants in the nine genes found in the discovery and replication cohorts and chronic liver disease, including alcoholic and nonalcoholic (non-viral) liver disease, as well as the most advanced forms of chronic liver disease: alcoholic cirrhosis, nonalcoholic cirrhosis, and hepatocellular carcinoma (HCC), was also analyzed. Using a Bonferroni significance threshold of $P<1.92\times10^{-3}$ for the thirteen variants tested, significant associations were found between six variants in five genes (HSD1713, SERPINA1, TM6SF2, PNPLA3, and SAMM50) and chronic liver disease phenotypes (see, FIG. 4). The SERPINA1, TM6SF2, PNPLA3, and SAMM50 associations confirm previously reported associations. In the discovery cohort, HSD1713 rs72613567:TA was associated with lower odds of all EHR-derived categories of both alcoholic and nonalcoholic liver disease in an allele dosage-dependent manner (see, FIG. 15, panel A): all categories of alcoholic liver disease, heterozygous odds ratio ($OR_{het}$) (95% confidence interval) 0.58 (0.42-0.80), homozygous OR ($OR_{hom}$) 0.47 (0.23-0.97), allelic OR ($OR_{allelic}$) 0.62 (0.48-0.81), $P=1.8\times10^{-4}$; all categories of nonalcoholic liver disease, $OR_{het}$ 0.83 (0.75-0.92), $OR_{hom}$ 0.70 (0.57-0.87), $OR_{allelic}$ 0.84 (0.78-0.91), $P=1.3\times10^{-5}$. HSD1713 rs72613567:TA was also associated with lower odds alcoholic and nonalcoholic cirrhosis, with 42% and 73% lower odds of alcoholic cirrhosis for heterozygotes and homozygotes, respectively, ($OR_{het}$ 0.58 (0.39-0.86), $OR_{hom}$ 0.27 (0.09-0.85), $OR_{allelic}$ 0.56 (0.41-0.78), $P=3.4\times10^{-4}$) and 26% and 49% lower odds of nonalcoholic cirrhosis for heterozygotes and homozygotes, respectively ($OR_{het}$ 0.74 (0.60-0.93), $OR_{hom}$ 0.51 (0.31-0.85), $OR_{allelic}$ 0.74 (0.62-0.88), $P=4.5\times10^{-4}$). HSD1713 rs72613567:TA was also nominally associated with lower odds of HCC.

These findings were confirmed and extended in the multi-ethnic Dallas Liver Study (DLS) and the Dallas Pediatric Liver Study (DPLS) (see, FIG. 5). In the DLS, the TA allele was associated with lower odds of any liver disease in an allele-dosage dependent manner ($OR_{het}$ 0.74 (0.57-0.97), $OR_{hom}$ 0.41 (0.21-0.83), $OR_{allelic}$ 0.70 (0.5-0.88), $P=1.8\times10^{-3}$, see FIG. 15, panel B). Similar effects were observed across EHR-derived liver disease subtypes, including protective associations with advanced, cirrhotic forms of alcoholic ($OR_{allelic}$ 0.72 (0.53-0.99), $P=4.4\times10^{-2}$) and nonalcoholic ($OR_{allelic}$ 0.65 (0.40-1.07), $P=9.0\times10^{-2}$) liver disease. In subset analyses of individuals grouped by self-reported ethnicity, the association with liver disease was significant in Hispanic Americans (n=326 cases and 722 controls, $OR_{allelic}$ 0.51 (0.35-0.74), $P=4.0\times10^{-4}$); similar numerical trends, which did not achieve statistical significance, were also noted in the African American (n=33 cases and 2,291 controls, $OR_{allelic}$ 0.74 (0.25-2.47), $P=0.67$) and European American (n=158 cases and 1,266 controls, $OR_{allelic}$ 0.87 (0.65-1.15), $P=0.32$) subsets of the DLS. In the DPLS, a separate study of Hispanic American pediatric liver disease patients and obese controls, the TA allele was also associated with lower odds of liver disease ($OR_{allelic}$ 0.61 (0.37-0.99), $P=4.6\times10^{-2}$). Thus, HSD17B13 rs72613567:TA was associated with reduced odds of multiple forms of chronic liver disease, including cirrhosis, in adults and children in three independent populations.

Figure 15:
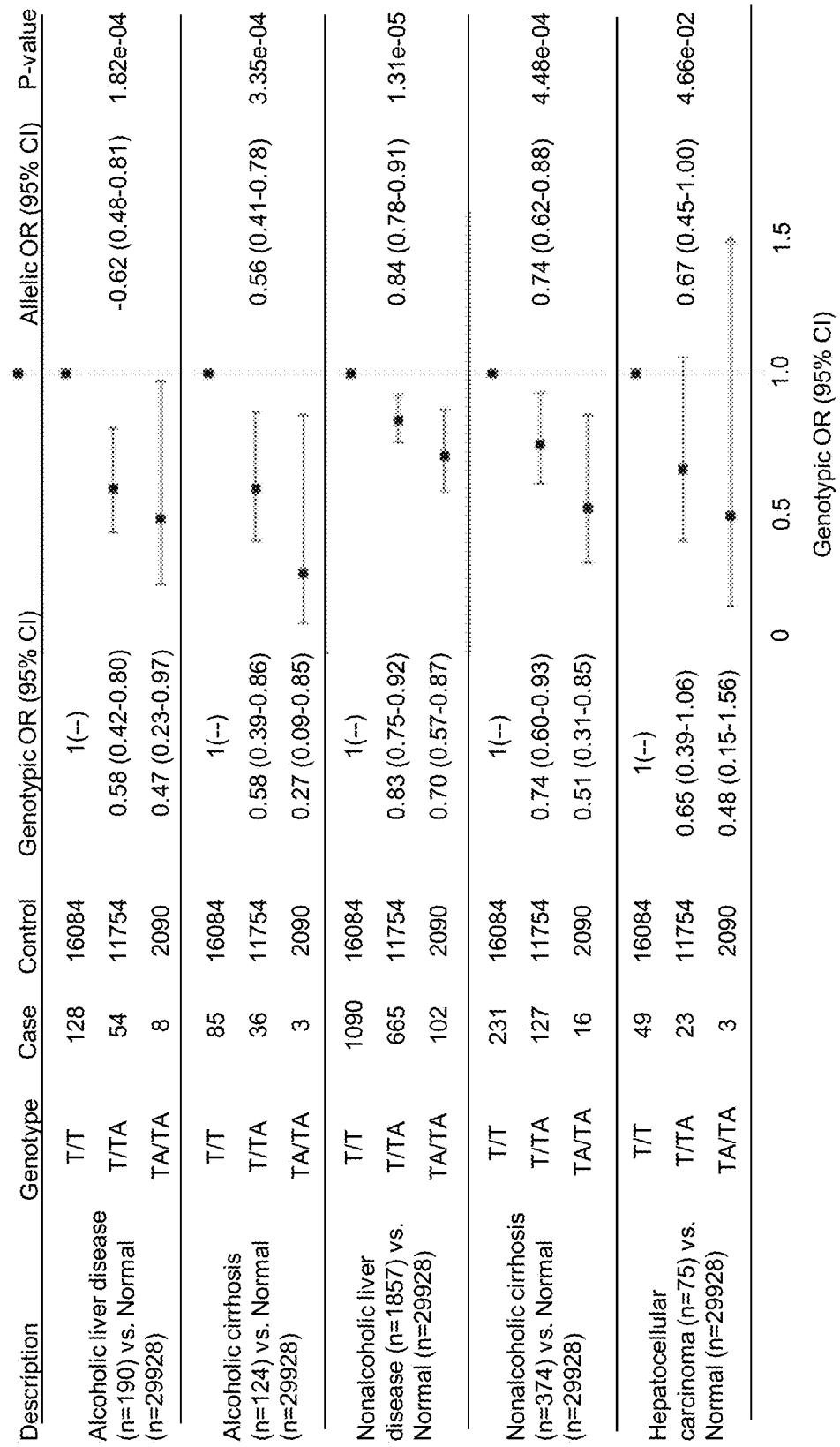
FIG. 15 (panels A and B) shows HSD17B13 rs72613567:TA is associated with reduced risk of alcoholic and nonalcoholic liver disease phenotypes.
Figure 15:
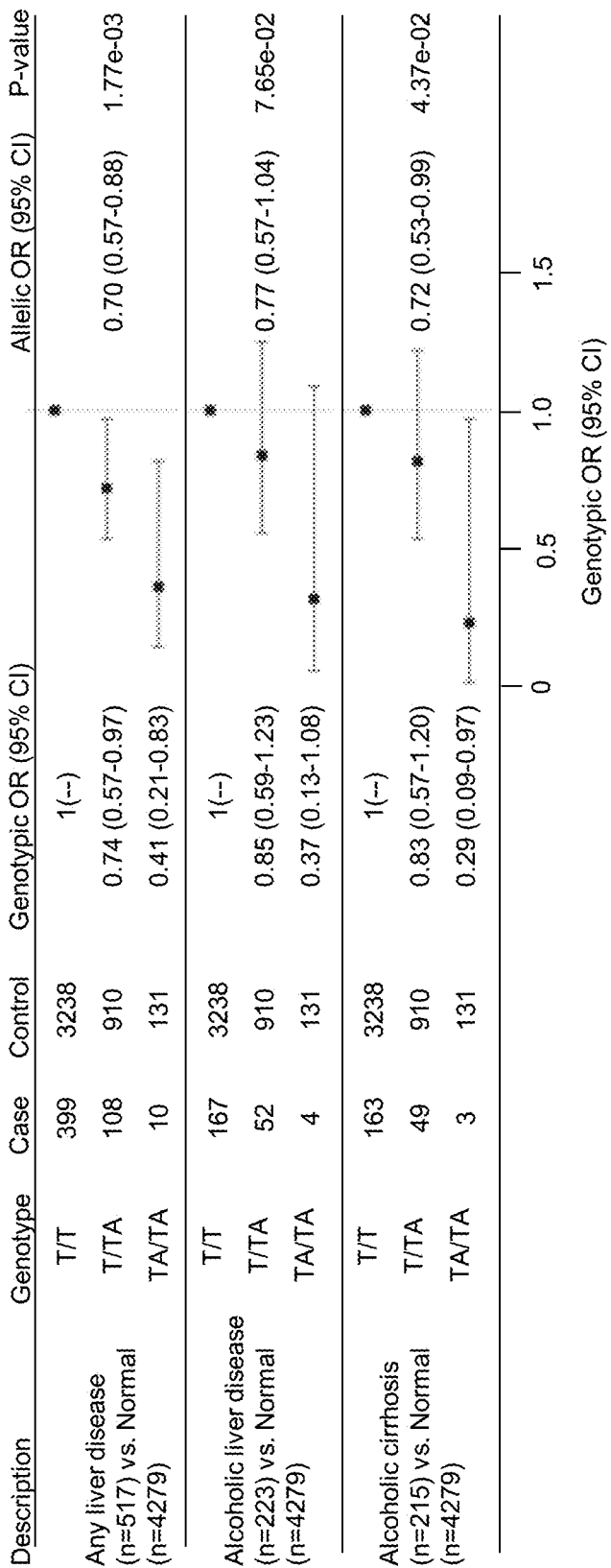
Figure 15:
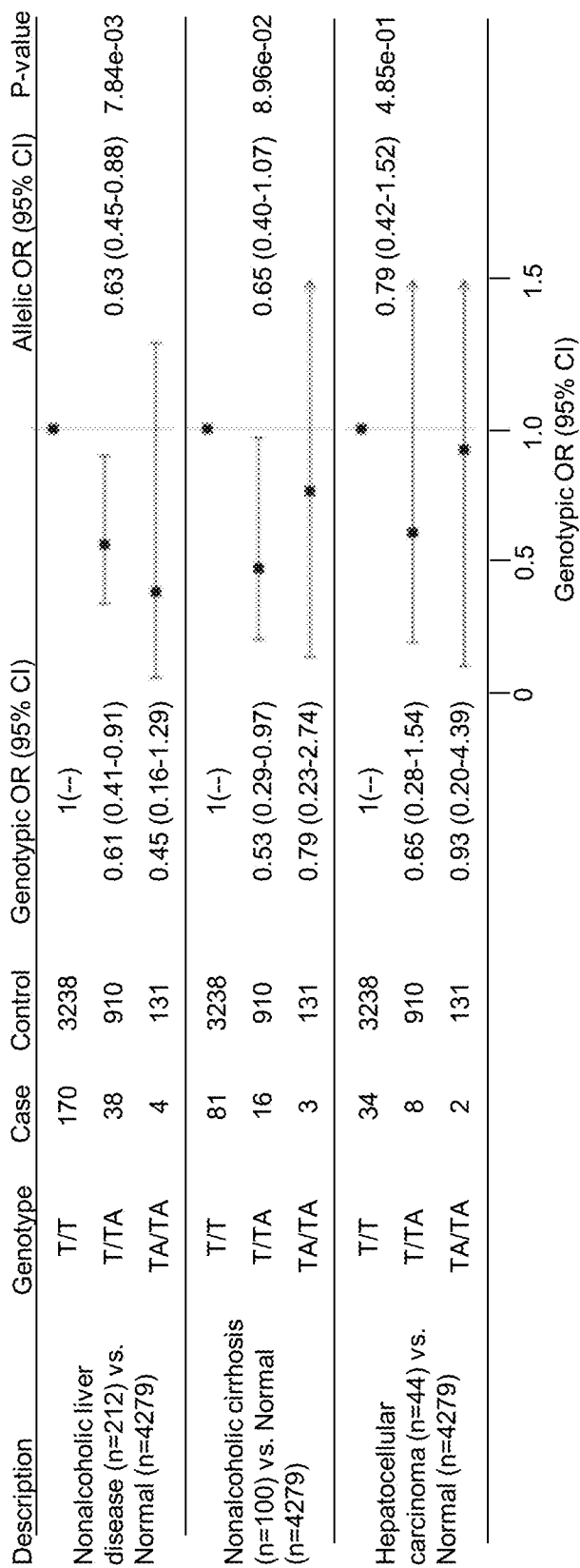

Referring to FIG. 15, HSD17B13 rs72613567:TA is associated with reduced risk of alcoholic and nonalcoholic liver disease phenotypes is shown. In the GHS discovery cohort, HSD17B13 rs72613567 was associated with lower odds of nonalcoholic and alcoholic liver disease, cirrhosis, and hepatocellular carcinoma in an allele dosage-dependent manner (see, Panel A). Odds ratios were calculated using logistic regression, with adjustment for age, $age^2$, sex, BMI, and principal components of ancestry. Genotypic odds ratios for heterozygous (Het OR) and homozygous (Hom OR) carriers are also shown. In the Dallas Liver Study, HSD17B13 rs72613567 was associated with lower odds of any liver disease in an allele dosage-dependent manner (see, Panel B). Similar allele dosage-dependent effects were observed across liver disease subtypes. Odds ratios were calculated using logistic regression, with adjustment for age, $age^2$, sex, BMI, and self-reported ethnicity.

Genetic Interaction Between PNPLA3 rs738409 (p.I148M) and HSD17B13 rs72613567

The variant PNPLA3 p.I148M variant is the most well validated genetic risk factor for NAFLD, and the 148M allele exists in homozygous state in 5-25% of individuals, depending on ancestry. To understand whether the HSD17B13 rs72613567:TA modifies the risk of liver injury associated with PNPLA3 p.I148M, analyses of interaction between the two variants in association with ALT, AST, and chronic liver disease phenotypes in DiscovEHR was performed. These analyses were performed in all participants, as well as in obese (body mass index [BMI]≥30 kg/m$^2$) and non-obese (BMI<30 kg/m$^2$) subpopulations. There was nominally significant interaction between HSD17B13 rs72613567:TA and PNPLA3 p.I148M in association analyses of ALT ($P=1.8\times10^{-3}$ for interaction) and AST ($P=4.5\times10^{-3}$ for interaction) levels; these associations were primarily driven by associations in obese individuals (see, FIG. 9). In these analyses, the rs72613567:TA allele mitigated the allele dosage-dependent associations of PNPLA3 148M allele with increased ALT and AST (see, FIG. 16, FIG. 11, and FIG. 12). RNA sequencing-based expression analysis revealed that HSD1713 rs72613567:TA was associated with decreased PNPLA3 mRNA expression in an allele dosage-dependent manner (see, FIG. 7). These data suggest the HSD1713 rs72613567:TA variant mitigates the risk of liver injury in individuals genetically predisposed to steatotic liver disease by the variant PNPLA3 p.I148M variant.

Figure 16:
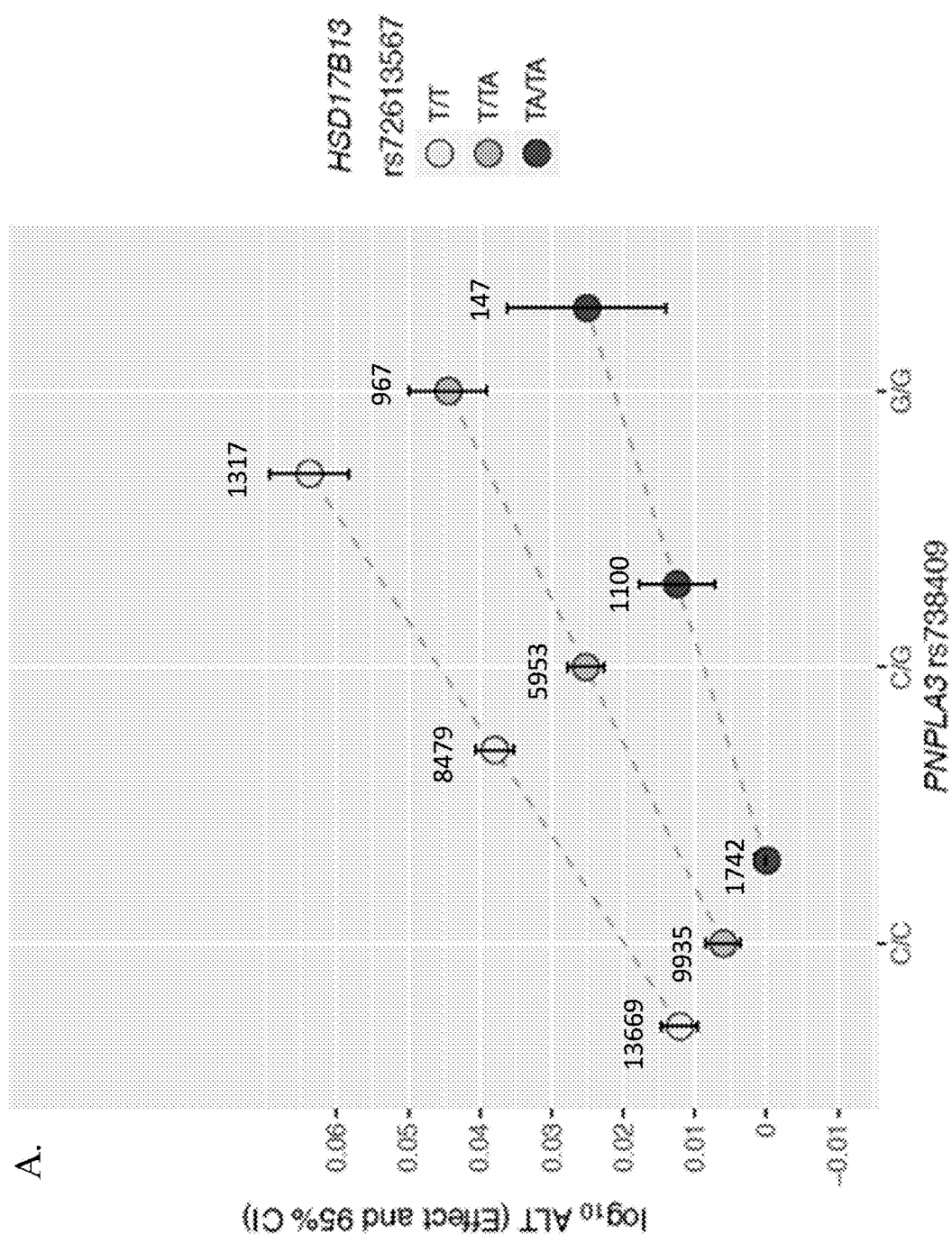
FIG. 16 (panels A and B) shows HSD17B13 rs72613567:TA mitigates the risk of liver injury associated with PNPLA3 p.I148M.
Figure 16:
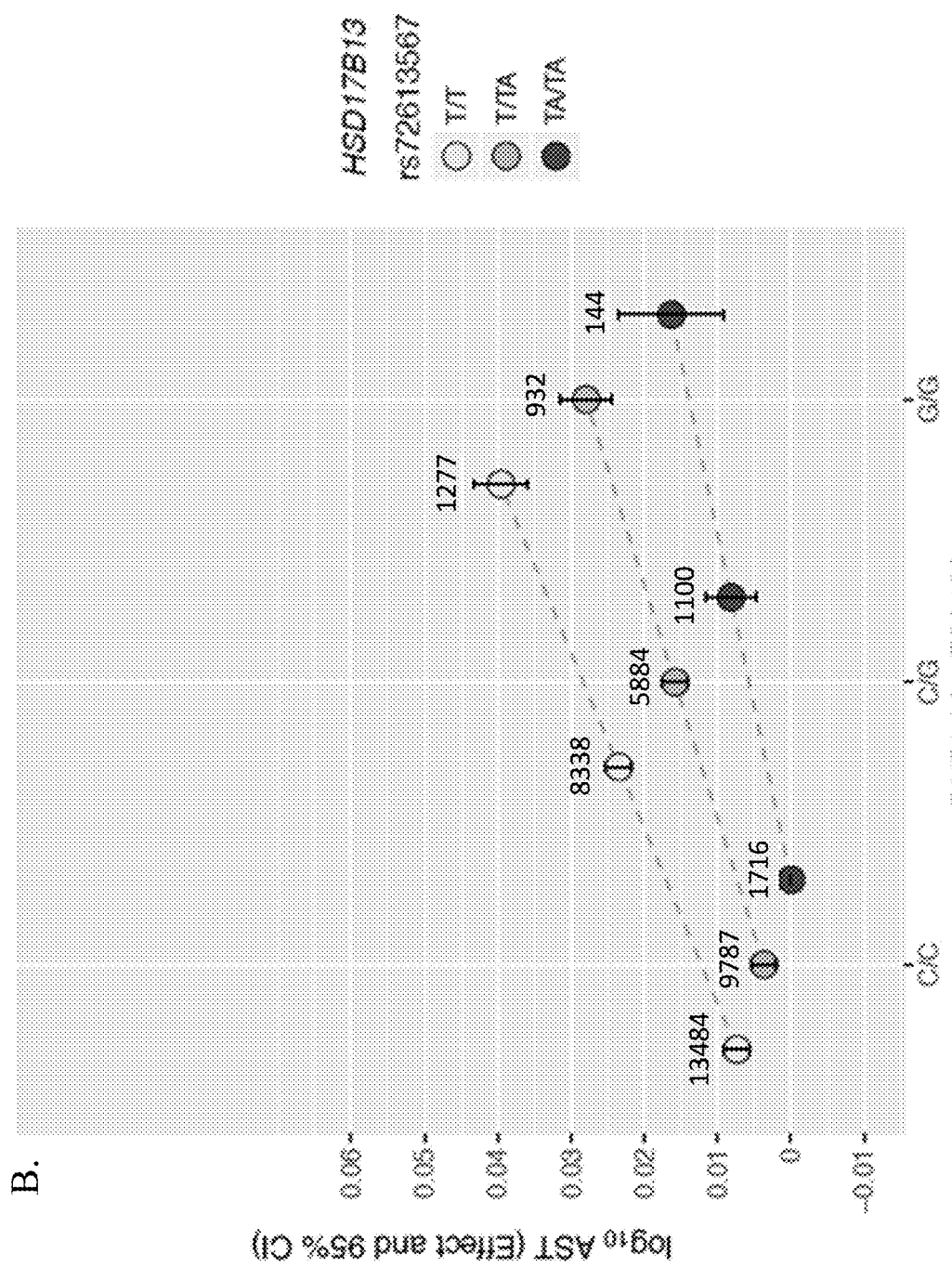

Referring to FIG. 16, HSD17B13 rs72613567:TA mitigates the risk of liver injury associated with PNPLA3 p.I148M is shown. Association of HSD17B13 rs72613567 with ALT in individuals with each PNPLA3 p.I148M genotype (see, Panel A). Association of HSD17B13 rs72613567 with AST in individuals with each PNPLA3 p.I148M genotype (see, Panel B). Effect estimates (beta and 95% CI) were calculated using linear regression, with adjustment for age, age$^2$, sex, BMI, and four principal components of ancestry. The P values for interaction between HSD17B13 rs72613567:TA and PNPLA3 p.I148M in association analyses of ALT and AST levels were P=1.8×10$^{-3}$ and P=4.5× 10$^{-3}$, respectively.

Association of HSD17B3 rs72613567:TA with Liver Pathology

NAFLD describes a disease spectrum ranging from liver fat accumulation without evidence of significant inflammation (simple steatosis), to more clinically impactful NASH. To confirm the association between the HSD17B3 rs72613567:TA and EHR-derived liver disease diagnoses codes, and to further understand its association with histopathological progression of steatosis to NASH, tests of association in the GHS bariatric surgery cohort were performed. In this cohort of 2,391 of the whole exome sequenced individuals assessed by liver biopsy at the time of bariatric surgery, a total of 555 (23%) individuals had no evidence of steatosis, steatohepatitis, or fibrosis ("normal"), 830 (35%) had simple steatosis, and 1006 (42%) had NASH. When comparing prevalence of normal liver, simple steatosis, and NASH by genotype, it was observed that the prevalence of normal liver did not appear to differ by genotype (23%, 24%, and 23% for T/T, T/TA, and TA/TA carriers, respectively, P=0.5 by Chi-squared test for trend in proportions), but that the prevalence of NASH decreased (45%, 40%, and 31% for T/T, T/TA, and TA/TA carriers, respectively, P=1.6×10$^{-4}$) and that of simple steatosis increased (33%, 35%, and 47% for T/T, T/TA, and TA/TA carriers, respectively, P=1.1×10$^{-3}$) with each TA allele (see, FIG. 17, Panel A). Among individuals with steatosis, the TA allele was associated with statistically significantly lower odds of NASH, as compared to simple steatosis, in an allele dosage-dependent manner (OR$_{het}$ 0.87 (0.714.06), OR$_{hom}$ 0.48 (0.33-0.70), OR$_{allelic}$ 0.77 (0.66-0.90), P=6.5×10$^{-4}$) (see, FIG. 17, Panel B). Altogether, these data suggest a role for HSD17B3 in mediating NAFLD progression from simple steatosis to more advanced stages of NASH and fibrosis.

Figure 17:
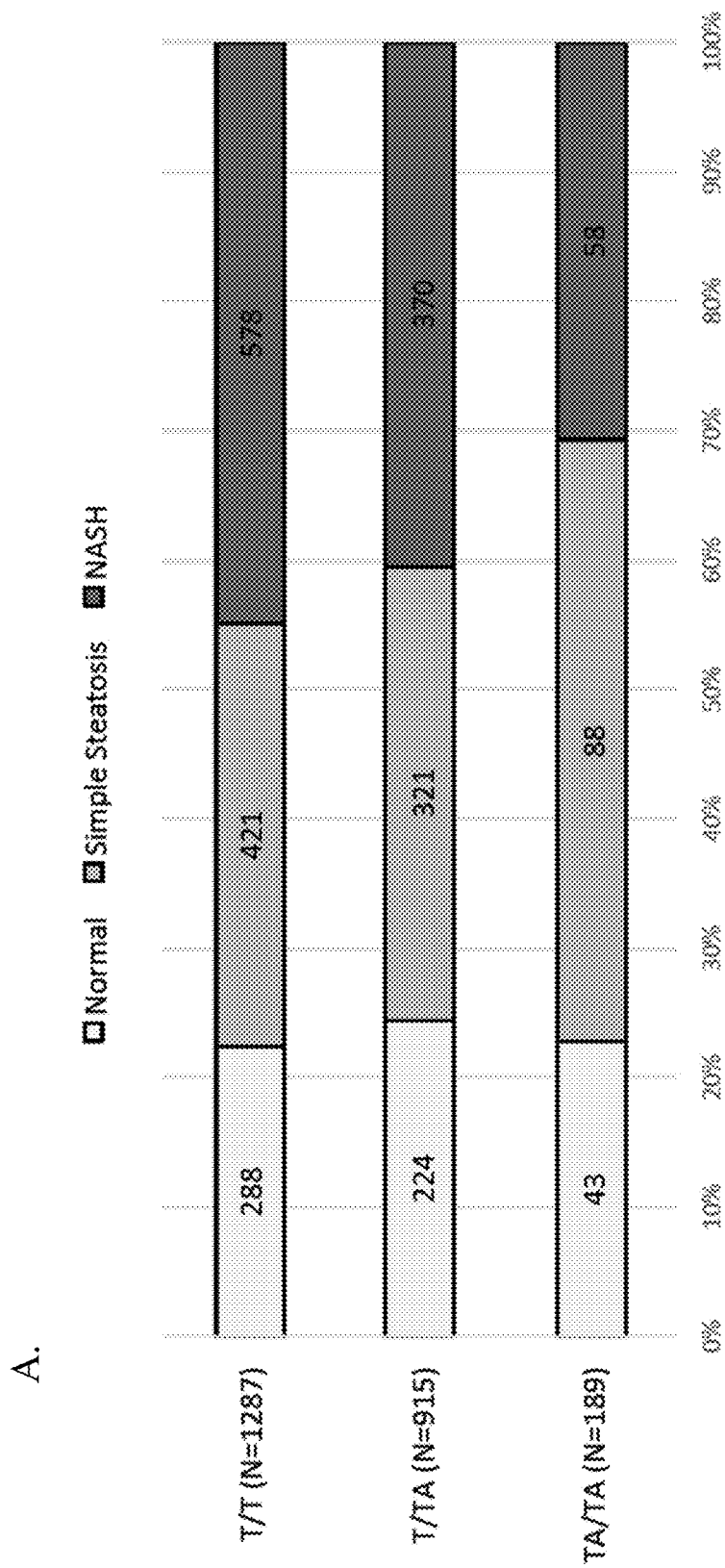
FIG. 17 (panels A and B) shows HSD17B13 rs72613567:TA is associated with reduced risk of progression from simple steatosis to steatohepatitis and fibrosis.
Figure 17:
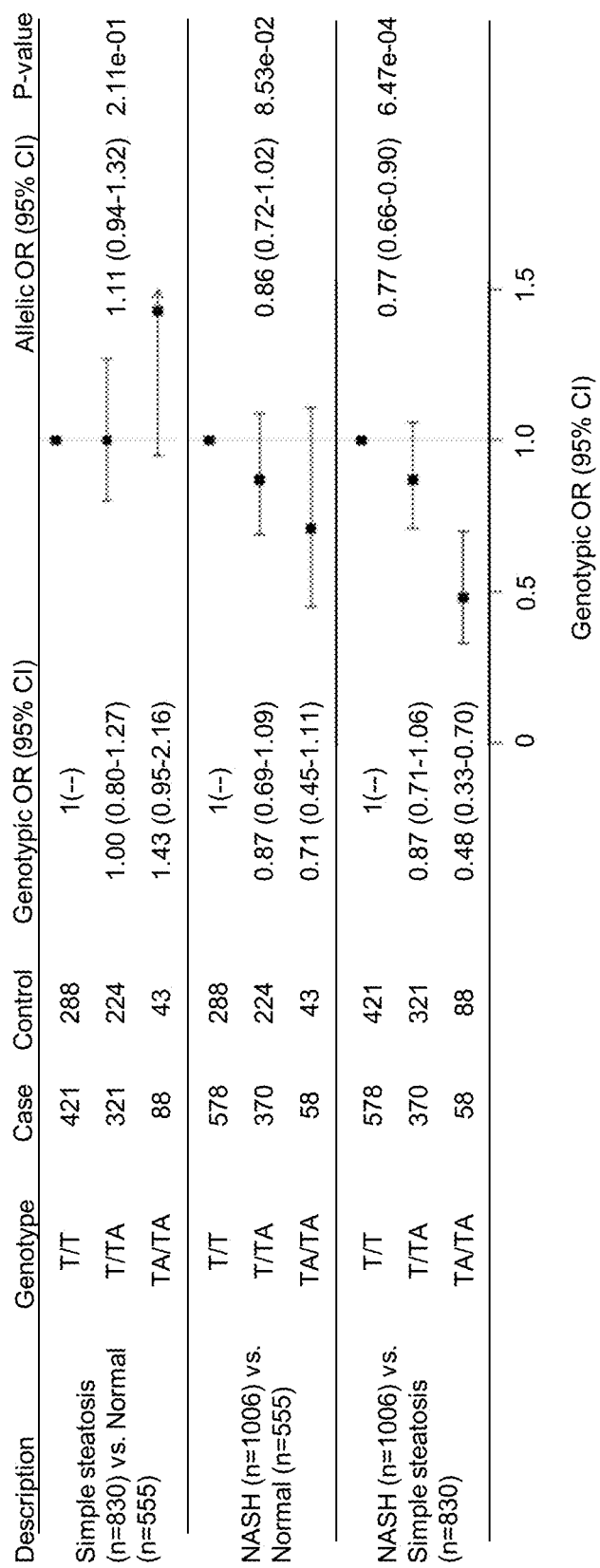

Referring to FIG. 17, HSD17B13 rs72613567:TA is associated with reduced risk of progression from simple steatosis to steatohepatitis and fibrosis is shown. Prevalence of histopathologically-characterized liver disease according to HSD17B13 rs72613567 genotype in 2,391 individuals with liver biopsies from the GHS bariatric surgery cohort (see, Panel A). The prevalence of normal liver did not appear to differ by genotype (P=0.5 by Chi-squared test for trend in proportions), but the prevalence of NASH decreased (P=1.6×10$^{-4}$) and that of simple steatosis increased (P=1.1× 10$^{-3}$) with each TA allele. In the GHS bariatric surgery cohort, HSD17B13 rs72613567 was associated with 13% and 52% lower odds of NASH in heterozygous and homozygous TA carriers, respectively (see, Panel B). Odds ratios were calculated using logistic regression, with adjustment for age, age$^2$, sex, BMI, and principal components of ancestry. Genotypic odds ratios for heterozygous (Het OR) and homozygous (Hom OR) carriers are also shown.

Effect of rs72613567:TA on HSD1713 mRNA and HSD1713 Protein Expression

The effect of the HSD1713 rs72613567:TA allele on expression of known and novel transcripts of the gene was examined. RNA sequencing was used to assess HSD1713 mRNA expression in histologically normal liver samples from 22 T/T homozygous, 30 T/TA heterozygous, and 17 TA/TA homozygous carriers of the HSD1713 rs72613567 splice variant. In addition to the two HSD1713 transcripts, A and B, two novel transcripts were identified: transcript C, which lacked exon 6, and transcript D which contained an insertion of a guanine nucleotide at the 3' end of exon 6, which would be predicted to result in premature truncation of the protein. Four additional transcripts (E-H) were expressed at very low levels (see, FIG. 13). The transcripts were validated by RT-PCR and Sanger sequencing (data not shown). The D transcript was also validated using long read cDNA sequencing. The expression levels of these transcripts varied according to HSD1713 rs72613567 genotype; levels of transcripts A and B decreased, while those of transcripts C and D increased in an allele dosage-dependent manner with each TA allele (see, FIG. 18, Panels A and B). Transcript A, which encodes the full-length 300 amino acid protein, was the predominant transcript in T/T homozygotes, while transcript D, which encodes the prematurely truncated protein, was the predominant transcript in TA/TA homozygotes. In human liver biopsy tissue, the truncated isoform D protein was minimally present in heterozygotes and TA/TA homozygotes, and isoform A protein abundance was reduced in an allele dosage-dependent manner (see, FIG. 18, Panels C and D). These data are consistent with HSD1713 rs72613567 altering mRNA splicing, resulting in the synthesis of a truncated form of the protein with substantially reduced expression in human liver.

Figure 18:
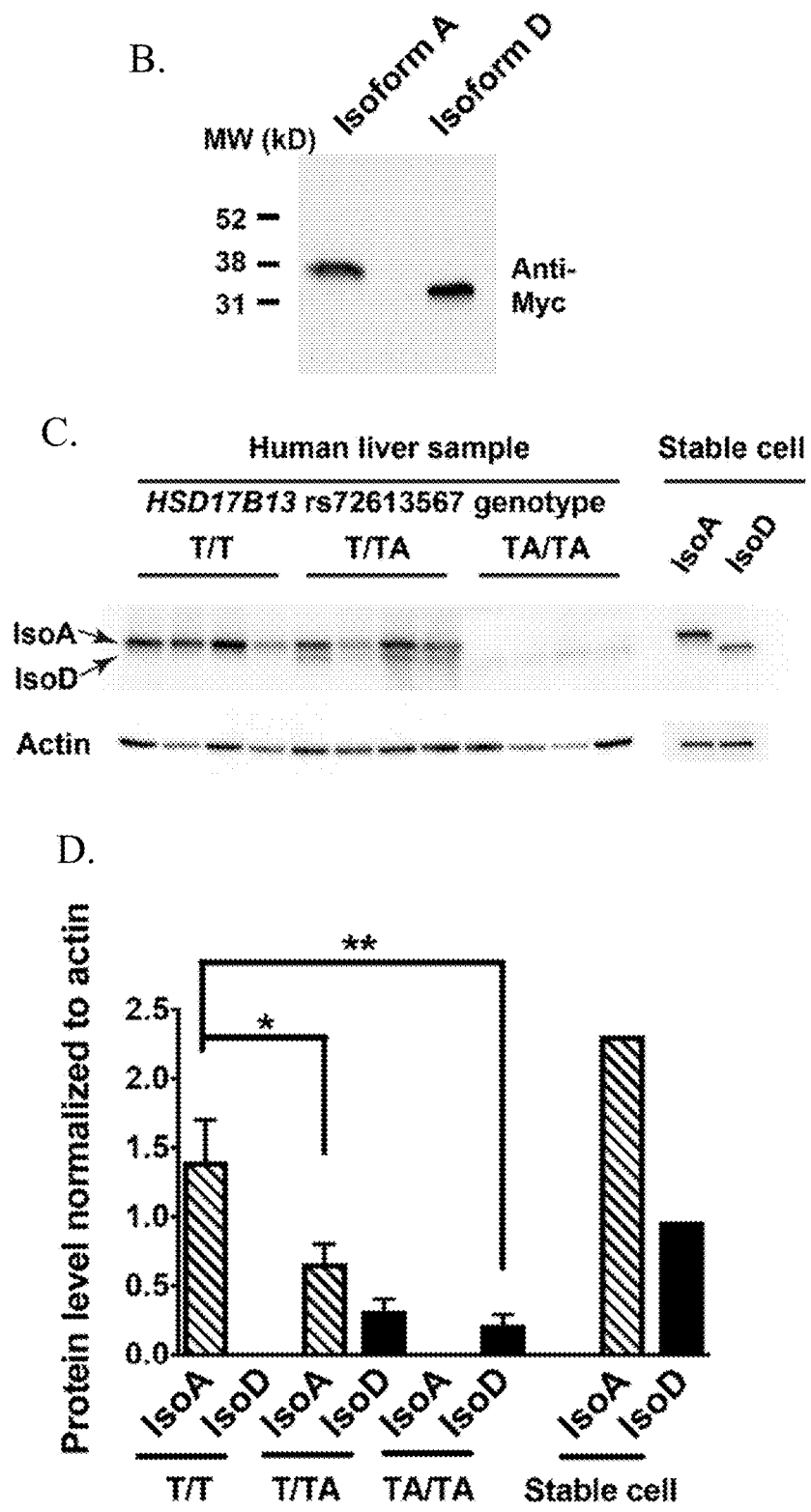
FIG. 18 (panels A through G) shows Expression, subcellular localization, and enzymatic activity of a novel HSD17B13 transcript.
Figure 18:
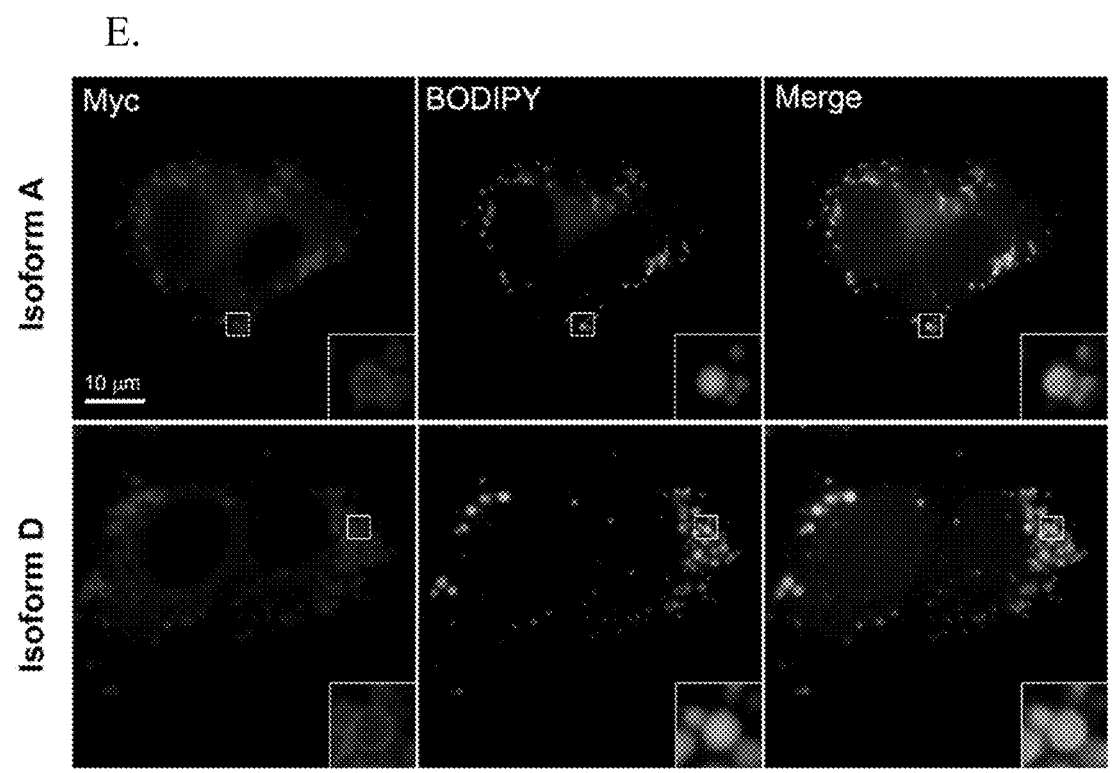

Referring to FIG. 18, expression, subcellular localization, and enzymatic activity of a novel HSD17B13 transcript is shown. Expression of HSD17B13 transcripts A and D in homozygous reference (T/T), heterozygous (T/TA), and homozyous alternate (TA/TA) carriers of the HSD17B13 rs72613567 splice variant (see, Panel A). Coding regions in HSD17B13 gene are indicated in red, untranslated regions as thick black lines, and introns as thin black lines. The asterisk in transcript D indicates the A insertion from rs72613567. mRNA expression is displayed in FPKM units (Fragments Per Kilobase of transcript per Million mapped reads). Western blot from HepG2 cells overexpressing HSD17B13 transcripts A and D. HSD17B13 transcript D was translated to a truncated protein with lower molecular weight compared to HSD17B13 transcript A (see, Panel B). HSD17B13 western blot from fresh frozen human liver and HEK293 cell samples (see, Panel C). Human liver samples are from homozygous reference (T/T), heterozygous (T/TA), and homozygous alternate (TA/TA) carriers of the HSD17B13 rs72613567 splice variant. Cell samples are from HEK293 cells overexpressing non-tagged HSD17B13 transcripts A and D. HSD17B13 transcript D was translated to a truncated protein IsoD with lower molecular weight than HSD17B13 IsoA. HSD17B13 IsoD protein levels were lower than IsoA protein levels from both human liver (left) and cell (right) samples (see, Panel D). Protein level normalized to Actin was shown in the bar columns; ** P<0.001, *P<0.05. Both HSD17B13 isoforms A and D were localized on lipid droplet membrane (see, Panel E). HepG2 stably overexpressing HSD17B13 transcripts A or D were labelled with BODIPY to show lipid droplets and anti-Myc to show HSD17B13 localization. All figures are magnified to the same extent. Scale bar indicates 10 μm. Insets represent 4× amplification of the original images. Enzymatic activity of HSD17B13 isoforms A and D to 17-beta estradiol (estradiol), leukotriene B4 (LTB4), and 13-Hydroxyoctadecadienoic acid (13(S)-HODE (see, Panel F). HSD17B13 isoform D show <10% enzymatic activity of the corresponding values for isoform A. G, HSD17B13 isoform D when overexpressed in HEK293 cells did not show much conversion of estradiol (substrate) to estrone (product) when measured in the culture media, while overexpressed HSD17B13 isoform A showed robust conversion.

Expression of HSD1713 in Human Liver Cells

HSD17B13 is expressed primarily in the liver (Liu et al., Acta Biochim. Pol., 2007, 54, 213-8), where it localizes to lipid droplets (Su et al., Proc. Natl. Acad. Sci. USA, 2014, 111, 11437-42), consistent with a role in the pathogenesis of fatty liver disease. The expression of HSD171B3 and its localization was evaluated in an immortalized human liver cell line stably transduced with lentivirus expressing HSD1713 transcripts A and D. HSD17B13 isoform A was mainly detected on membranes surrounding BODIPY-labeled lipid droplets (see, FIG. 18, Panel E). Similar subcellular localization was observed for HSD17B13 isoform D at the lipid droplet surface (see, FIG. 18, Panel F).

Effect of rs72613567:TA on HSD1713 Activity In Vitro and in Cellular Models

To understand the functional consequences of premature truncation of HSD17B13 protein due to rs72613567:TA, the enzymatic activity of isoforms A and D was evaluated in vitro using recombinant protein. Greater than 300 putative substrates were examined, of which estradiol, leukotriene B4, and 13-Hydroxyoctadecadienoic acid were enzymatically converted by HSD17B13, resulting in oxidation of a hydroxyl to a ketone group. HSD17B13 isoform D showed greatly reduced activity towards the 3 substrates (see, FIG. 18, Panel F).

Compared to GFP control, HSD17B13 transcript A overexpressing cells had lower concentration of estradiol as well as higher concentration of estrone in the cell culture medium, suggesting enzyme activity against estradiol (see, FIG. 18, Panel G). HSD17B13 transcript D overexpressing cells had similar ratio of estrone/estadiol vs GFP control cells, suggesting that HSD17B13 transcript D has significant loss of function. The mass spec analysis revealed rapid conversion of estrone into hydroxyestrone and other products accounting for the low accumulation of estrone compared to consumed estradiol.

Through large-scale exome sequencing, a novel association was identified between a splice variant in HSD1713 and decreased serum transaminase levels, as well as reduced risk of nonalcoholic and alcoholic forms of liver disease, including advanced cirrhotic forms of liver disease and HCC. To our knowledge, this is the first report of a protein-altering variant that has a protective association with liver disease. The HSD1713 rs72613567:TA allele was not associated with simple steatosis, but reduced the risk of progression to NASH. The consistency of the dosage-dependent protective associations in four independent cohorts (DiscovEHR, an independent bariatric surgery cohort in DiscovEHR, DLS, and DPLS) across several different liver disease categories and ethnicities support the notion that the reported HSD1713 variant protects from progression to more clinically advanced stages of chronic liver disease. The observed allele dosage-dependence also argues that more profound regulation of HSD17B13 function may result in more profound effects on disease risk and progression. The HSD1713 rs72613567:TA allele also mitigated the risk of liver injury in individuals genetically predisposed to steatotic liver disease by the variant PNPLA3 p.I148M variant. This finding may suggest an important subpopulation for therapeutic modulation of HSD17B13—individuals heterozygous or homozygous for the variant PNPLA3 148M allele.

The association findings described herein were primarily based on observations in European and Hispanic Americans who have elevated BMI. HSD1713 is in close proximity with HSD17B11, a member of the same gene family with high sequence similarity to HSD1713 but broader tissue distribution. Overall, the data presented herein support the position that HSD1713 is a potential therapeutic target for prevention and treatment of fatty liver disease in humans. The data presented herein indicate that targeting of HSD17B13 could reduce progression of liver disease from steatosis to later stages of NASH, fibrosis, and cirrhosis, which are associated with significant morbidity and mortality, and for which there are currently no effective treatments.

Figure 19:
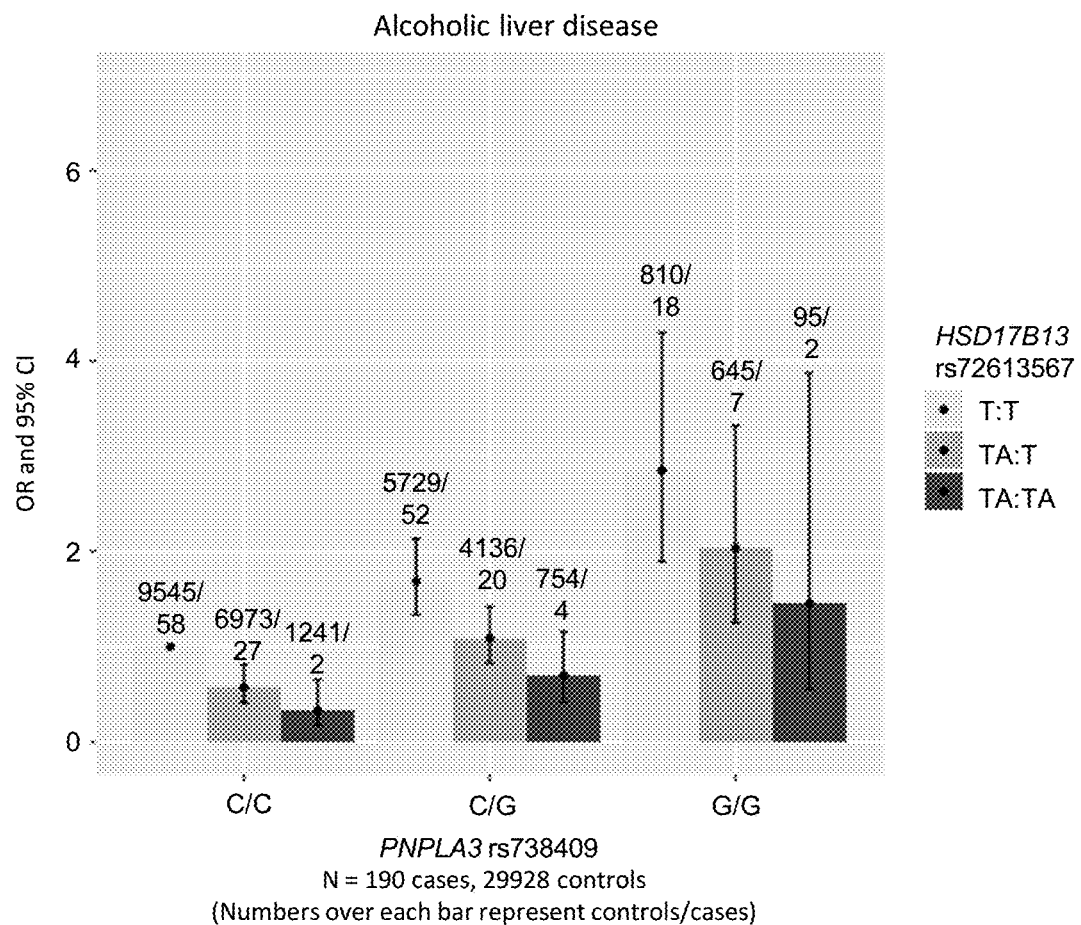
FIG. 19 (panels A and B) shows HSD17B13 rs72613567:TA mitigates the risk of alcoholic and nonalcoholic liver disease associated with PNPLA3 I148M. The numbers over each bar represent controls/cases.
Figure 19:
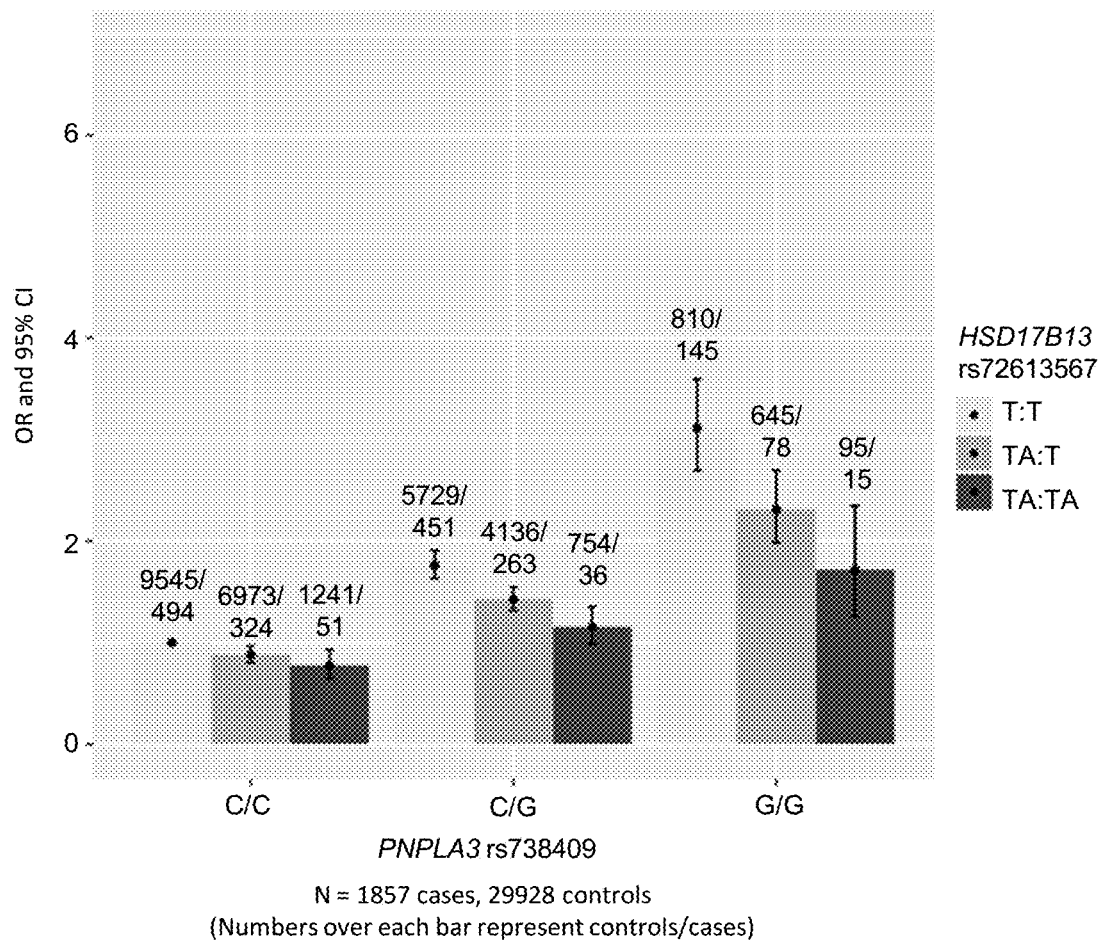

Example 4: HSD17B13 rs72613567:TA Mitigates the Risk of Alcoholic and Nonalcoholic Liver Disease Associated with PNPLA3 I148M Association of HSD17B13 and PNPLA3 genotypes with liver disease was analyzed by comparing HSD17B13 and PNPLA3 genotypes of 29,928 human liver samples from control donors without steatosis, lobular inflammation, or fibrosis with either 190 samples from patients having alcoholic liver disease, or with 1857 patients having nonalcoholic liver disease. The odds ratio was calculated by the equation of (incidence rate of a group having disease)/(incidence rate of the control group) for each combination of HSD17B13 and PNPLA3 genotype with 95% confidence intervals. Referring to FIG. 19, panel A shows the association of HSD17B13 rs72613567 with alcoholic liver disease in individuals with each PNPLA3 p.I148M genotype, and panel B shows the association of HSD17B13 rs72613567 with nonalcoholic liver disease in individuals with each PNPLA3 p.I148M genotype. The data demonstrate that PNPLA3 p.I148M is associated with higher incidence of both alcoholic and nonalcoiholic liver disease in a dosage-dependent manner. The HSD17B13 rs72613567:TA genotype was associated with a reduced risk for both alcoholic and nonalcoholic liver disease in an allele dosage-dependent manner.

What is claimed:

1. A method for treating a human subject having a non-alcoholic liver disease, the method comprising:
    performing or having performed an assay on a biological sample from the subject to identify if the subject as having:
        i) a first nucleic acid encoding a patatin like phospholipase domain containing 3 (PNPLA3) protein comprising an I148M variation and a second nucleic acid encoding a functional HSD17B13 protein; and/or
        ii) a PNPLA3 protein comprising an I148M variation and a functional HSD17B13 protein; and
    administering an inhibitor of HSD17B13 to the subject having both the first and second nucleic acids as defined in i) and/or both of the proteins as defined in ii);
    wherein the presence of both the first and second nucleic acids as defined in i) and/or both of the proteins as defined in ii) indicates that the subject is a candidate for treating the non-alcoholic liver disease by inhibiting HSD17B13;
    wherein the non-alcoholic liver disease is nonalcoholic fatty liver disease (NAFLD) or non-alcoholic steatohepatitis (NASH);
    wherein the inhibitor of HSD17B13 is an inhibitory nucleic acid molecule; and
    wherein the functional HSD17B13 protein comprises oxidoreductase activity.

2. The method according to claim 1 wherein the first nucleic acid molecule comprises genomic DNA, mRNA, or a cDNA obtained from mRNA.

3. The method according to claim 2, wherein:
    the genomic DNA comprises an ATG codon at the positions corresponding to positions 5107 to 5109 according to SEQ ID NO:31;
    the mRNA comprises an AUG codon at the positions corresponding to positions 442 to 444 according to SEQ ID NO:34;
    the mRNA comprises an AUG codon at the positions corresponding to positions 430 to 432 according to SEQ ID NO:35;
    the cDNA comprises an ATG codon at the positions corresponding to positions 442 to 444 according to SEQ ID NO:38; or
    the cDNA comprises an ATG codon at the positions corresponding to positions 430 to 432 according to SEQ ID NO:39.

4. The method according to claim 2, wherein:
    the genomic DNA comprises the nucleotide sequence according to SEQ ID NO:31, or a nucleotide sequence having at least 90% sequence identity to SEQ ID NO:31 and encoding a PNPLA3 protein which comprises the I148M variation;
    the mRNA comprises the nucleotide sequence according to SEQ ID NO:34, or a nucleotide sequence having at least 90% sequence identity to SEQ ID NO:34 and encoding a PNPLA3 protein which comprises the I148M variation;
    the mRNA comprises the nucleotide sequence according to SEQ ID NO:35, or a nucleotide sequence having at least 90% sequence identity to SEQ ID NO:35 and encoding a PNPLA3 protein which comprises the I148M variation;
    the cDNA comprises the nucleotide sequence according to SEQ ID NO:38, or a nucleotide sequence having at least 90% sequence identity to SEQ ID NO:38 and encoding a PNPLA3 protein which comprises the I148M variation; or
    the cDNA comprises the nucleotide sequence according to SEQ ID NO:39, or a nucleotide sequence having at least 90% sequence identity to SEQ ID NO:39 and encoding a PNPLA3 protein which comprises the I148M variation.

5. The method according to claim 1, wherein the assay comprises:
sequencing at least a portion of the first nucleic acid, wherein the portion comprises the codon which encodes the I148M variation; or
hybridizing the first nucleic acid with a probe or primer that specifically hybridizes to a portion of the first nucleic acid, wherein the portion comprises the codon encoding the I148M variation.

6. The method according to claim 5, wherein the probe or primer is an allele-specific probe or primer, and wherein the probe or primer optionally comprises a label.

7. The method according to claim 1, further comprising determining whether the subject is homozygous or heterozygous for the I148M variation.

8. The method according to claim 1, wherein the second nucleic acid comprises genomic DNA, mRNA, or a cDNA obtained from mRNA.

9. The method according to claim 8, wherein:
the genomic DNA comprises an adenine at the position corresponding to position 12,667 according to SEQ ID NO:1;
the genomic DNA comprises the nucleotide sequence according to SEQ ID NO:1, or a nucleotide sequence having at least 90% sequence identity to SEQ ID NO:1 and encoding a functional HSD17B13 protein
the mRNA comprises the nucleotide sequence according to SEQ ID NO:3, or a nucleotide sequence having at least 90% sequence identity to SEQ ID NO:3 and encoding a functional HSD17B13 protein;
the mRNA comprises the nucleotide sequence according to SEQ ID NO:4 or a nucleotide sequence having at least 90% sequence identity to SEQ ID NO:4 and encoding a functional HSD17B13 protein;
the mRNA comprises the nucleotide sequence according to SEQ ID NO:7 or a nucleotide sequence having at least 90% sequence identity to SEQ ID NO:7 and encoding a functional HSD17B13 protein;
the mRNA comprises the nucleotide sequence according to SEQ ID NO:11 or a nucleotide sequence having at least 90% sequence identity to SEQ ID NO:11 and encoding a functional HSD17B13 protein;
the cDNA comprises the nucleotide sequence according to SEQ ID NO:12 or a nucleotide sequence having at least 90% sequence identity to SEQ ID NO:12 and encoding a functional HSD17B13 protein;
the cDNA comprises the nucleotide sequence according to SEQ ID NO:13 or a nucleotide sequence having at least 90% sequence identity to SEQ ID NO:13 and encoding a functional HSD17B13 protein;
the cDNA comprises the nucleotide sequence according to SEQ ID NO:16 or a nucleotide sequence having at least 90% sequence identity to SEQ ID NO:16 and encoding a functional HSD17B13 protein; or
the cDNA comprises the nucleotide sequence according to SEQ ID NO:20 or a nucleotide sequence having at least 90% sequence identity to SEQ ID NO:20 and encoding a functional HSD17B13 protein.

10. The method according to claim 1, wherein the assay comprises:
sequencing the second nucleic acid; or
hybridizing the second nucleic acid with a probe or primer that specifically hybridizes to a portion of the second nucleic acid, wherein the portion comprises an adenine at the position corresponding to position 12,667 according to SEQ ID NO:1.

11. The method according to claim 10, wherein the probe or primer is an allele-specific probe or primer, and wherein the probe or primer optionally comprises a label.

12. The method according to claim 1, further comprising determining whether the subject is homozygous or heterozygous for the second nucleic acid encoding a functional HSD17B13 protein in the sample.

13. The method according to claim 1, wherein the non-alcoholic liver disease is NAFLD.

14. The method according to claim 1, wherein the non-alcoholic liver disease is NASH.

15. The method according to claim 1, wherein the inhibitory nucleic acid molecule comprises an antisense RNA.

16. The method according to claim 1, wherein the inhibitory nucleic acid molecule comprises a small interfering RNA (siRNA).

17. The method according to claim 1, wherein the inhibitory nucleic acid molecule comprises a short hairpin RNA (shRNA).

18. A method for treating a human subject having non-alcoholic steatohepatitis (NASH), the method comprising:
performing or having performed an assay on a biological sample from the subject to identify the subject as having:
i) a first nucleic acid encoding a patatin like phospholipase domain containing 3 (PNPLA3) protein comprising an I148M variation and a second nucleic acid encoding a functional HSD17B13 protein; and/or
ii) a PNPLA3 protein comprising an I148M variation and a functional HSD17B13 protein; and
administering an inhibitor of HSD17B13 to the subject having both the first and second nucleic acids as defined in i) and/or both of the proteins as defined in ii);
wherein the presence of both the first and second nucleic acids as defined in i) and/or both of the proteins as defined in ii) indicates that the subject is a candidate for treating NASH by inhibiting HSD17B13;
wherein the inhibitor of HSD17B13 is a small interfering RNA (siRNA); and
wherein the functional HSD17B13 protein comprises oxidoreductase activity.

19. The method according to claim 18 wherein the first nucleic acid molecule comprises genomic DNA, mRNA, or a cDNA obtained from mRNA.

20. The method according to claim 19, wherein:
the genomic DNA comprises an ATG codon at the positions corresponding to positions 5107 to 5109 according to SEQ ID NO:31;
the mRNA comprises an AUG codon at the positions corresponding to positions 442 to 444 according to SEQ ID NO:34;
the mRNA comprises an AUG codon at the positions corresponding to positions 430 to 432 according to SEQ ID NO:35;
the cDNA comprises an ATG codon at the positions corresponding to positions 442 to 444 according to SEQ ID NO:38; or
the cDNA comprises an ATG codon at the positions corresponding to positions 430 to 432 according to SEQ ID NO:39.

21. The method according to claim 19, wherein:
the genomic DNA comprises the nucleotide sequence according to SEQ ID NO:31, or a nucleotide sequence having at least 90% sequence identity to SEQ ID NO:31 and encoding a PNPLA3 protein which comprises the I148M variation;

the mRNA comprises the nucleotide sequence according to SEQ ID NO:34, or a nucleotide sequence having at least 90% sequence identity to SEQ ID NO:34 and encoding a PNPLA3 protein which comprises the I148M variation;

the mRNA comprises the nucleotide sequence according to SEQ ID NO:35, or a nucleotide sequence having at least 90% sequence identity to SEQ ID NO:35 and encoding a PNPLA3 protein which comprises the I148M variation;

the cDNA comprises the nucleotide sequence according to SEQ ID NO:38, or a nucleotide sequence having at least 90% sequence identity to SEQ ID NO:38 and encoding a PNPLA3 protein which comprises the I148M variation; or the cDNA comprises the nucleotide sequence according to SEQ ID NO:39, or a nucleotide sequence having at least 90% sequence identity to SEQ ID NO:39 and encoding a PNPLA3 protein which comprises the I148M variation.

22. The method according to claim 18, wherein the assay comprises:

sequencing at least a portion of the first nucleic acid, wherein the portion comprises the codon which encodes the I148M variation; or hybridizing the first nucleic acid with a probe or primer that specifically hybridizes to a portion of the first nucleic acid, wherein the portion comprises the codon encoding the I148M variation.

23. The method according to claim 22, wherein the probe or primer is an allele-specific probe or primer, and wherein the probe or primer optionally comprises a label.

24. The method according to claim 18, further comprising determining whether the subject is homozygous or heterozygous for the I148M variation.

25. The method according to claim 18, wherein the second nucleic acid comprises genomic DNA, mRNA, or a cDNA obtained from mRNA.

26. The method according to claim 25, wherein:

the genomic DNA comprises an adenine at the position corresponding to position 12,667 according to SEQ ID NO:1;

the genomic DNA comprises the nucleotide sequence according to SEQ ID NO:1, or a nucleotide sequence having at least 90% sequence identity to SEQ ID NO:1 and encoding a functional HSD17B13 protein the mRNA comprises the nucleotide sequence according to SEQ ID NO:3, or a nucleotide sequence having at least 90% sequence identity to SEQ ID NO:3 and encoding a functional HSD17B13 protein;

the mRNA comprises the nucleotide sequence according to SEQ ID NO:4 or a nucleotide sequence having at least 90% sequence identity to SEQ ID NO:4 and encoding a functional HSD17B13 protein;

the mRNA comprises the nucleotide sequence according to SEQ ID NO:7 or a nucleotide sequence having at least 90% sequence identity to SEQ ID NO:7 and encoding a functional HSD17B13 protein;

the mRNA comprises the nucleotide sequence according to SEQ ID NO:11 or a nucleotide sequence having at least 90% sequence identity to SEQ ID NO:11 and encoding a functional HSD17B13 protein;

the cDNA comprises the nucleotide sequence according to SEQ ID NO:12 or a nucleotide sequence having at least 90% sequence identity to SEQ ID NO:12 and encoding a functional HSD17B13 protein;

the cDNA comprises the nucleotide sequence according to SEQ ID NO:13 or a nucleotide sequence having at least 90% sequence identity to SEQ ID NO:13 and encoding a functional HSD17B13 protein;

the cDNA comprises the nucleotide sequence according to SEQ ID NO:16 or a nucleotide sequence having at least 90% sequence identity to SEQ ID NO:16 and encoding a functional HSD17B13 protein; or the cDNA comprises the nucleotide sequence according to SEQ ID NO:20 or a nucleotide sequence having at least 90% sequence identity to SEQ ID NO:20 and encoding a functional HSD17B13 protein.

27. The method according to claim 18, wherein the assay comprises:

sequencing the second nucleic acid; or hybridizing the second nucleic acid with a probe or primer that specifically hybridizes to a portion of the second nucleic acid, wherein the portion comprises an adenine at the position corresponding to position 12,667 according to SEQ ID NO:1.

28. The method according to claim 27, wherein the probe or primer is an allele-specific probe or primer, and wherein the probe or primer optionally comprises a label.

29. The method according to claim 18, further comprising determining whether the subject is homozygous or heterozygous for the second nucleic acid encoding a functional HSD17B13 protein in the sample.

\* \* \* \* \*